US012703762B2

(12) United States Patent
Ewert et al.

(10) Patent No.: US 12,703,762 B2
(45) Date of Patent: Aug. 11, 2026

(54) REVERSAL BINDING AGENTS FOR ANTI-FACTOR XI/XIa ANTIBODIES AND USES THEREOF

(71) Applicant: NOVARTIS AG, Basel (CH)

(72) Inventors: Stefan Ewert, Basel (CH); Andrew Green, Basel (CH); Alexander Wolfgang Koch, Cambridge, MA (US)

(73) Assignee: Novartis AG, Basel (CH)

( * ) Notice: Subject to any disclaimer, the term of this patent is extended or adjusted under 35 U.S.C. 154(b) by 1134 days.

(21) Appl. No.: 17/309,713

(22) PCT Filed: Dec. 17, 2019

(86) PCT No.: PCT/US2019/066949
§ 371 (c)(1),
(2) Date: Jun. 16, 2021

(87) PCT Pub. No.: WO2020/131935
PCT Pub. Date: Jun. 25, 2020

(65) Prior Publication Data

US 2022/0025070 A1 Jan. 27, 2022

Related U.S. Application Data

(60) Provisional application No. 62/781,236, filed on Dec. 18, 2018.

(51) Int. Cl.
*C07K 16/42* (2006.01)

(52) U.S. Cl.
CPC ...... *C07K 16/4241* (2013.01); *C07K 2317/21* (2013.01); *C07K 2317/55* (2013.01); *C07K 2317/76* (2013.01); *C07K 2317/92* (2013.01)

(58) Field of Classification Search
CPC ............ C07K 16/4241; C07K 2317/21; C07K 2317/55; C07K 2317/76; C07K 2317/92
See application file for complete search history.

(56) References Cited

U.S. PATENT DOCUMENTS 4,399,216 A 8/1983 Axel et al.
4,439,196 A 3/1984 Higuchi
4,447,224 A 5/1984 DeCant, Jr. et al.
4,447,233 A 5/1984 Mayfield
4,486,194 A 12/1984 Ferrara
4,487,603 A 12/1984 Harris
4,596,556 A 6/1986 Morrow et al.
4,634,665 A 1/1987 Axel et al.
4,790,824 A 12/1988 Morrow et al.
4,816,397 A 3/1989 Boss et al.
4,816,567 A 3/1989 Cabilly et al.
4,941,880 A 7/1990 Burns
4,946,778 A 8/1990 Ladner et al.
4,963,657 A 10/1990 Pixley
5,064,413 A 11/1991 McKinnon et al.
5,179,017 A 1/1993 Axel et al.
5,223,409 A 6/1993 Ladner et al.
5,225,539 A 7/1993 Winter
5,312,335 A 5/1994 McKinnon et al.
5,383,851 A 1/1995 McKinnon, Jr. et al.
5,399,163 A 3/1995 Peterson et al.
5,403,484 A 4/1995 Ladner et al.
5,545,806 A 8/1996 Lonberg et al.
5,569,825 A 10/1996 Lonberg et al.
5,571,698 A 11/1996 Ladner et al.
5,585,089 A 12/1996 Queen et al.
5,624,821 A 4/1997 Winter et al.
5,625,126 A 4/1997 Lonberg et al.
5,633,425 A 5/1997 Lonberg et al.
5,648,260 A 7/1997 Winter et al.
5,661,016 A 8/1997 Lonberg et al.
5,959,083 A 9/1999 Bosslet et al.
6,005,091 A 12/1999 Blackburn et al.
6,180,370 B1 1/2001 Queen et al.
7,217,794 B2 5/2007 Abdel-Neguid et al.
7,300,922 B2 11/2007 Sullenger et al.
7,459,564 B2 12/2008 Corte et al.
7,501,404 B2 3/2009 Bannister et al.
7,544,699 B2 6/2009 Mjalli et al.
7,626,039 B2 12/2009 Pinto et al.
7,645,799 B2 1/2010 Corte et al.
(Continued)

FOREIGN PATENT DOCUMENTS

CN 1390258 A 1/2003
CN 105073775 A 11/2015
(Continued)

OTHER PUBLICATIONS

Ahmed (Postgrad Med J (2007) 83: 575-582) (Year: 2007).*
Greinacher (N Engl J Med (2015) 373: 252-261) (Year: 2015).*
"Efficacy and Safety of MAA868 in Patients with Atrial Fibrillation," ClinicalTrials.gov, *U.S. National Library of Medicine* [online]. https://www.clinicaltrials.gov/ct2/show/NCT03398434?term=maa868&rank=1.
"Prevention of Thromboembolic Events in Total Knee Replacement Positions," ClinicalTrials.gov, *U.S. National Library of Medicine* [online]. https://www.clinicaltrials.gov/ct2/show/NCT03393481?term=maa868&rank=2.
Akiyama et al., "Mechanism of Activation of Coagulation factor XI by Factor XIIa Studied with monoclonal Antibodies," *J. Clin. Invest.*, 78:1631-1637. 1986.
(Continued)

*Primary Examiner* — Brad Duffy
*Assistant Examiner* — Elizabeth A Shupe
(74) *Attorney, Agent, or Firm* — Finnegan, Henderson, Farabow, Garrett & Dunner, LLP

(57) ABSTRACT

The present disclosure relates to reversal agents, which specifically bind to anti-Factor XI and/or anti-Factor XIa antibodies (e.g., NOV1401), and reverse one or more anticoagulant effects of the anti-Factor XI and/or anti-Factor XIa antibodies (e.g., NOV1401), as well as to methods of use thereof, such as methods for reversing anticoagulant effects of such anti-Factor XI and/or anti-Factor XIa antibodies (e.g., NOV1401), and to related methods for managing bleeding or bleeding risks.

19 Claims, 7 Drawing Sheets

Specification includes a Sequence Listing.

(56) References Cited

U.S. PATENT DOCUMENTS

| | | | |
|---|---|---|---|
| 7,842,708 | B2 | 11/2010 | Pinto et al. |
| 8,236,316 | B2 | 8/2012 | Gruber et al. |
| 8,268,783 | B2 | 9/2012 | Sinha et al. |
| 8,283,330 | B2 | 10/2012 | Sullenger et al. |
| 8,324,199 | B2 | 12/2012 | Corte et al. |
| 8,334,372 | B2 | 12/2012 | Freier et al. |
| 8,388,959 | B2 | 3/2013 | Gruber et al. |
| 8,399,648 | B2 | 3/2013 | Gruber et al. |
| 8,455,439 | B2 | 6/2013 | Lu et al. |
| 8,455,441 | B2 | 6/2013 | Lu et al. |
| 8,568,724 | B2 | 10/2013 | Hack |
| 8,586,524 | B2 | 11/2013 | Sullenger et al. |
| 8,735,370 | B2 | 5/2014 | Freier et al. |
| 8,889,129 | B2 | 11/2014 | Lu et al. |
| 8,940,833 | B2 | 1/2015 | Schmitt et al. |
| 9,023,795 | B2 | 5/2015 | Xu et al. |
| 9,056,106 | B2 | 6/2015 | Sinha et al. |
| 9,062,298 | B2 | 6/2015 | Lu et al. |
| 9,109,046 | B2 | 8/2015 | Sinha et al. |
| 9,125,895 | B2 | 9/2015 | Gruber et al. |
| 9,388,401 | B2 | 7/2016 | Lu et al. |
| 9,587,233 | B2 | 3/2017 | Sinha et al. |
| 9,636,399 | B2 | 5/2017 | Gruber et al. |
| 9,637,550 | B2 | 5/2017 | Gruber et al. |
| 9,783,614 | B2 | 10/2017 | Wilmen et al. |
| 10,053,515 | B2 | 8/2018 | Chen et al. |
| 10,221,247 | B2 | 3/2019 | Wilmen et al. |
| 10,465,011 | B2 | 11/2019 | Eder et al. |
| 10,647,780 | B2 | 5/2020 | Ewert et al. |
| 11,168,147 | B2 | 11/2021 | Aigner |
| 12,012,464 | B2 | 6/2024 | Aigner et al. |
| 2003/0083294 | A1 | 5/2003 | Sullenger et al. |
| 2004/0180855 | A1 | 9/2004 | Shumacher et al. |
| 2005/0037421 | A1 | 2/2005 | Honda et al. |
| 2005/0059705 | A1 | 3/2005 | Mjalli et al. |
| 2005/0143317 | A1 | 6/2005 | Abdel-Megui et al. |
| 2005/0196397 | A1 | 9/2005 | Scheiflinger et al. |
| 2006/0088523 | A1 | 4/2006 | Andya et al. |
| 2006/0154915 | A1 | 7/2006 | Corte et al. |
| 2007/0105832 | A1 | 5/2007 | Bannister et al. |
| 2008/0051339 | A1 | 2/2008 | Sullenger et al. |
| 2008/0146811 | A1 | 6/2008 | Deng et al. |
| 2008/0161373 | A1 | 7/2008 | Pinto et al. |
| 2009/0062287 | A1 | 3/2009 | Corte et al. |
| 2009/0098119 | A1 | 4/2009 | Lu et al. |
| 2010/0022506 | A1 | 1/2010 | Pinto et al. |
| 2010/0125052 | A1 | 5/2010 | Lu et al. |
| 2010/0129379 | A1 | 5/2010 | Carpenter et al. |
| 2010/0137414 | A1 | 6/2010 | Freier et al. |
| 2010/0249217 | A1 | 9/2010 | Sullenger et al. |
| 2010/0255000 | A1 | 10/2010 | Sinha et al. |
| 2010/0331392 | A1 | 12/2010 | Monia et al. |
| 2011/0015128 | A1 | 1/2011 | Sinha et al. |
| 2011/0020349 | A1 | 1/2011 | Gruber et al. |
| 2011/0021492 | A1 | 1/2011 | Corte et al. |
| 2011/0028446 | A1 | 2/2011 | Pinto et al. |
| 2011/0159006 | A1 | 6/2011 | Hack |
| 2011/0184057 | A1 | 7/2011 | Mundy et al. |
| 2012/0083522 | A1 | 4/2012 | Monia et al. |
| 2012/0214862 | A1 | 8/2012 | Freier et al. |
| 2012/0269788 | A1 | 10/2012 | Lu et al. |
| 2013/0129693 | A1 | 5/2013 | Sinha et al. |
| 2013/0190384 | A1 | 7/2013 | Freier et al. |
| 2013/0274308 | A1 | 10/2013 | Freier et al. |
| 2013/0296400 | A1 | 11/2013 | Monia et al. |
| 2014/0044773 | A1 | 2/2014 | Lu et al. |
| 2014/0079684 | A1 | 3/2014 | Lu et al. |
| 2014/0134151 | A1 | 5/2014 | Lu et al. |
| 2014/0194600 | A1 | 7/2014 | Hack |
| 2014/0275225 | A1 | 9/2014 | Sullenger et al. |
| 2014/0275226 | A1 | 9/2014 | Sullenger et al. |
| 2015/0025011 | A1 | 1/2015 | Sinha et al. |
| 2015/0057228 | A1 | 2/2015 | Lu et al. |
| 2015/0099298 | A1 | 4/2015 | Wilmen et al. |
| 2015/0175692 | A1 | 6/2015 | Di Padova et al. |
| 2015/0343034 | A1 | 12/2015 | Pittman et al. |
| 2016/0002617 | A1 | 1/2016 | Sinha et al. |
| 2016/0354449 | A1 | 12/2016 | Lu et al. |
| 2017/0014492 | A1 | 1/2017 | Sinha et al. |
| 2017/0022292 | A1 | 1/2017 | Eder et al. |
| 2017/0035798 | A1 | 2/2017 | Freier et al. |
| 2017/0355780 | A1 | 12/2017 | Chen et al. |
| 2018/0022825 | A1 | 1/2018 | Ewert et al. |
| 2018/0112009 | A1 | 4/2018 | Wilmen et al. |
| 2018/0118850 | A1 | 5/2018 | Hack |
| 2018/0216093 | A1 | 8/2018 | Goletz et al. |
| 2018/0243435 | A1 | 8/2018 | Dylla et al. |
| 2018/0355056 | A1 | 12/2018 | Eder et al. |
| 2018/0355057 | A1 | 12/2018 | Gruber et al. |
| 2018/0362661 | A1 | 12/2018 | Chen et al. |
| 2019/0330372 | A1 | 10/2019 | Aigner et al. |
| 2019/0367636 | A1 | 12/2019 | Olbrich et al. |
| 2020/0095334 | A1 | 3/2020 | Mikita et al. |
| 2020/0115468 | A1 | 4/2020 | Eder et al. |
| 2020/0231701 | A1 | 7/2020 | Friedman et al. |
| 2020/0300852 | A1 | 9/2020 | Dahl et al. |
| 2020/0308301 | A1 | 10/2020 | Ewert et al. |
| 2020/0317816 | A1 | 10/2020 | Ewert et al. |
| 2020/0363400 | A1 | 11/2020 | Partridge et al. |
| 2022/0025070 | A1 | 1/2022 | Ewert et al. |
| 2022/0162339 | A1 | 5/2022 | Aigner et al. |
| 2023/0002507 | A1 | 1/2023 | Friedman et al. |

FOREIGN PATENT DOCUMENTS

| | | | |
|---|---|---|---|
| CN | 108136015 | A | 6/2018 |
| EP | 0 125 023 | A1 | 11/1984 |
| EP | 0 171 496 | A2 | 2/1986 |
| EP | 0 173 494 | A2 | 3/1986 |
| EP | 0 184 187 | A2 | 6/1986 |
| EP | 0 338 841 | A1 | 10/1989 |
| EP | 0 517 024 | A2 | 12/1992 |
| EP | 2 070 939 | B1 | 6/2009 |
| EP | 2 297 207 | A1 | 3/2011 |
| EP | 2364990 | A1 | 9/2011 |
| EP | 2 915 564 | B1 | 9/2015 |
| EP | 2 453 910 | B1 | 8/2016 |
| EP | 2 414 517 | B1 | 9/2016 |
| EP | 3 078 743 | B1 | 10/2016 |
| EP | 3 121 271 | B1 | 1/2017 |
| EP | 3 404 045 | A1 | 11/2018 |
| JP | S6265693 | A | 3/1987 |
| JP | 2009524595 | A | 7/2009 |
| JP | 2010531898 | A | 9/2010 |
| WO | WO 1986/001533 | A1 | 3/1986 |
| WO | WO 1987/002671 | A1 | 5/1987 |
| WO | WO 1987/004462 | A1 | 7/1987 |
| WO | WO 1989/001036 | A1 | 2/1989 |
| WO | WO 1994/029351 | A2 | 12/1994 |
| WO | WO 1995/017420 | A1 | 6/1995 |
| WO | WO 1997/026010 | A1 | 7/1997 |
| WO | WO 2000/042072 | A2 | 7/2000 |
| WO | WO 2002/064634 | A2 | 8/2002 |
| WO | WO 2002/096926 | A1 | 12/2002 |
| WO | WO 2002/100348 | A2 | 12/2002 |
| WO | WO 2003/017935 | A2 | 3/2003 |
| WO | WO 2003/040169 | A2 | 5/2003 |
| WO | WO 2004/035607 | A2 | 4/2004 |
| WO | WO 2004/043989 | A2 | 5/2004 |
| WO | WO 2004/089297 | A2 | 10/2004 |
| WO | WO 2004/103270 | A1 | 12/2004 |
| WO | WO 2004/108749 | A2 | 12/2004 |
| WO | WO 2006/012504 | A1 | 2/2006 |
| WO | WO 2006/012504 | A2 | 2/2006 |
| WO | WO 2006/040153 | A2 | 4/2006 |
| WO | WO 2006/076575 | A1 | 7/2006 |
| WO | WO 2006/076575 | A2 | 7/2006 |
| WO | WO 2007/070826 | A1 | 6/2007 |
| WO | WO 2009/042962 | A2 | 4/2009 |
| WO | WO 2009/061841 | A2 | 5/2009 |
| WO | WO 2009/067660 | A2 | 5/2009 |
| WO | WO 2009/114677 | A1 | 9/2009 |
| WO | WO 2009/141458 | A1 | 11/2009 |
| WO | WO 2009/154461 | A1 | 12/2009 |

(56) References Cited

FOREIGN PATENT DOCUMENTS

| | | |
|---|---|---|
| WO | WO 2010/045509 A2 | 4/2010 |
| WO | WO 2010/056765 A2 | 5/2010 |
| WO | WO 2010/080623 A2 | 7/2010 |
| WO | WO 2010/117729 A1 | 10/2010 |
| WO | WO 2011/008885 A1 | 1/2011 |
| WO | WO 2011/008995 A1 | 1/2011 |
| WO | WO 2012/151575 A2 | 11/2012 |
| WO | WO 2013/167669 A1 | 11/2013 |
| WO | WO 2014/118677 A1 | 8/2014 |
| WO | WO 2015/176012 A1 | 11/2015 |
| WO | WO 2016/207858 A1 | 12/2016 |
| WO | WO 2017/015558 A1 | 1/2017 |
| WO | WO 2017/015619 A1 | 1/2017 |
| WO | WO 2017/021528 A1 | 2/2017 |
| WO | WO 2017/127468 A1 | 7/2017 |
| WO | WO 2017/162791 A1 | 9/2017 |
| WO | WO 2017/203450 A1 | 11/2017 |
| WO | WO 2017/218371 A1 | 12/2017 |
| WO | WO 2018/053597 A1 | 3/2018 |
| WO | WO 2018/054813 A1 | 3/2018 |
| WO | WO 2018/116255 A1 | 6/2018 |
| WO | WO 2018/116267 A2 | 6/2018 |
| WO | WO 2018/116267 A3 | 6/2018 |
| WO | WO 2018/134184 A1 | 7/2018 |
| WO | WO 2018/204368 A1 | 11/2018 |
| WO | WO 2019/102353 A1 | 5/2019 |
| WO | WO 2020/131935 A1 | 6/2020 |
| WO | WO 2021/127525 A1 | 6/2021 |
| WO | WO 2022/133263 A1 | 6/2022 |
| WO | WO 2023/092062 A1 | 5/2023 |
| WO | WO 2023/250463 A2 | 12/2023 |

OTHER PUBLICATIONS

Al-Horani et al., "Factor XIa inhibitors: A review of the patent literature," *Expert opinion on Therapeutic Patents,* 26(3):323-345. 2016.

Al-Horani et al., "Designing Allosteric Inhibitors of Factor XIa. Lessons from the Interactions of Sulfated Pentagalloylglucopyranosides," *Journal of Medicinal Chemistry, ACS Publications,* 2014, 57, pp. 4805-4818.

Argade, "Allosteric inhibition of Human Factor XIa: Discovery of Monosulfated Benzofurans as a Class of Promising Inhibitors", *Journal of Medicinal Chemistry, ACS Publications,* 2014, 57, pp. 3559-3569.

Baglia et al. "A Binding Site for Thrombin in the Apple 1 Domain of Factor XI," *The Journal of Biological Chemistry,* 1996 271(7):3652-3658.

Berge et al., "Pharmaceutical Salts," *Journal of Pharmaceutical Sciences,* 1977, 66(1):1-19.

Bern et al., "Treatment of Factor XI Inhibitor Using Recombinant Factor VIIa," *Haemophilia,* 11:20-25. 2005.

Buchmueller et al., "The Anti-Factor XIa Antibody BAY 1213790 is a Novel Anticoagulant that Shows Strong Antithrombotic Efficacy without an Increase Risk of Bleeding in Rabbit Model," *International Society on Thrombosis and Haemostasis,* Jul. 8-13, 2017, Berlin, Germany.

Chin et al., "Isolation of high-affinity, neutralizing anti-idiotype antibodies by phage and ribosome display for application in immunogenicity and pharmacokinetic analyses" Journal of Immunological Methods vol. 416, Jan. 2015, pp. 49-58; https://doi.org/10.1016/j.jim.2014.10.013.

David et al., "Factor XIa-specific IgG and a reversal agent to probe factor XI function in thrombosis and hemostasis," *Sci. Transl. Med.,* vol. 8 353ra112 (2016).

De La Cadena et al., "Naturally Occurring Human Antibodies Against Two Distinct Functional Domains in the Heavy Chain of FXI/FXIa," *Blood,* 72(5):1748-1754. 1988.

Duebel ed "Handbook of Therapeutic Antibodies Chapter 6". 2007 pp. 119-144.

Edwards et al., "The Remarkable Flexibility of the Human Antibody Repertoire; Isolation of Over One Thousand Different Antibodies to a Single Protein, BLyS," *J. Mol. Biol.* (2003) 334, 103-118, available online at www.sciencedirect.com; © 2003 Elsevier Ltd., 15 pages.

Eigenbrot et al., "Structural Insight into How an Anti-Idiotypic Antibody Against D3H44 (anti-tissue Factor Antibody) Restores Normal Coagulation," *Journal of Molecular Biology,* 331(2):433-446. (Aug. 2003).

Emsley et al., "Structure and function of factor XI," *Blood,* vol. 115, No. 13, Apr. 1, 2010, pp. 2569-2577.

Fanger et al., "Bispecific Antibodies," *Critical Reviews in Immunology,* 1992, 12(3,4):101-124.

Fradera et al., "High-Resolution crystal structures of factor XIa coagulation factor in complex with nonbasic high-affinity synthetic inhibitors," *Acta Cryst.* F68, 404-408 (2012).

Fujikawa et al., "Amino Acid Sequence of Human factor XI, a Blood Coagulation Factor with Four Tandem Repeats That Are Highly Homologous with Plasma Prekallikrein," *Biochemistry,* 25:2417-2424. 1986.

Gailani et al., "A murine model of factor XI deficiency," *Blood Coagulation and Fibrinolysis,* 1997, vol. 8, pp. 134-144.

Gailani et al., "Model for a factor IX activation complex on blood platelets: dimeric conformation of factor XIa is essential," *Blood,* 2001, 97(10):3117-3122.

Gailani et al., "The Intrinsic pathway of coagulation: a target for treating thromboembolic disease?," *Journal of Thrombosis and Haemostasis,* 2007, 5:1106-1112.

Goel et al., "Plasticity within the Antigen-Combining Site May Manifest as Molecular Mimicry in the Humoral Immune Response," 173(12):7358-67, 2004.

Goldsmith et al., "Inhibitors of plasma thromboplastin antecedent (factor XI): Studies on mechanism of inhibition," *J Lab. Clin Med.* 106(3):279-285. 1985.

Greinacher et al., "Reversal of Anticoagulants: An Overview of Current Developments," *Thrombosis and Haemostatis,* 113(5):931-942. (May 2015).

Gruber et al., "Factor XI-dependence of surface- and tissue factor-initiated thrombus propagation in primates," *Blood,* 102(3): 953-955, 2003.

Gruber et al., "Antithrombotic factor XI antibody inhibition of the intrinsic pathway," *Blood,* 2001 98(11):42a. (Abstract).

Hack et al., "Disruption of the internal thioester bond in the third component of complement (C3) results in the exposure of neodeterminants also present on activation products of C3. An analysis with monoclonal antibodies," *Journal of Immunology,* 1988, 141:1602-1609.

Holliger et al., "Diabodies: Small bivalent and bispecific antibody fragments," *Proc Natl. Acad. Sci.,* 1993, 90:6444-6448.

Holvoet et al., "Measurement of Free, one-Chain Tissue-Type Plasminogen Activator in Human Plasma With an Enzyme-Linked Immunosorbent Assay Based on an Active Site-Specific Murine Monoclonal Antibody," *Blood,* 69(1):284-289. 1987.

International Search Report and Written Opinion of the International Search Authority for International Application No. PCT/IB2017/053066 mailed on Sep. 1, 2017, 16 pgs.

International Search Report and Written Opinion of the International Search Authority for International Application No. PCT/IB2017/058312 mailed on Mar. 13, 2018, 17 pgs.

International Search Report and Written Opinion of the International Search Authority for International Application No. PCT/IB2017/058345 mailed on Jun. 19, 2018, 21 pgs.

International Search Report and Written Opinion of the International Search Authority for International Application No. PCT/IB2018/059143, mailed on Mar. 27, 2019, 14 pgs.

International Search Report and Written Opinion of the International Search Authority for International Application No. PCT/US2019/066949, mailed on Apr. 1, 2020, 16 pgs.

Janeway et al., "Immunobiology: The Immune System in Health and Disease," Third Edition, © 1997 by Current Biology Ltd./Garland Publishing Inc., 13 pages.

(56) References Cited

OTHER PUBLICATIONS

Jin et al., "Crystal Structures of the FXIa Catalytic Domain in Complex with Ecotin Mutants Reveal Substrate-like Interactions," *Journal of Biological Chemistry,* 280(6):4704-4712 (2005).
Jin et al., "Mutation of surface residues to promote crystallization of activated factor XI as a complex with benzamidine: an essential step for the iterative structure-based design of factor XI inhibitors," *Acta Cryst.* (2005) D61, pp. 1418-1425.
Kanyavuz et al., "Breaking the Law: Unconventional Strategies for Antibody Diversification," *Nature Reviews | Immunology,* vol. 19, Jun. 2019, 13 pages.
Kipriyanov et al., "Generation and Production of Engineered Antibodies," *Molecular Biotechnology,* 2004, 26:39-60.
Knappik et al., "Fully synthetic human combinatorial antibody libraries (HuCAL) based on modular consensus frameworks and CDRs randomized with trinucleotides" *J. Mol. Biol.* 296, 57-86, 2000.
Koch, "MAA868, a novel FXI antibody with a unique binding mode, shows durable effects on markers of anticoagulation in humans," *Blood,* 2019, 133(13): 1507-1516.
Kolyadko et al., "Molecular Mechanisms of Thrombosis, Fundamental and Applied Aspects of the Contact Activation," *Biological Membranes,* 2014, vol. 31, No. 4, pp. 231-243.
Konings et al., "Ongoing Contact Activation in Patients with Hereditary Angioedema," *PLOS ONE,* 8(8):1-9. 2013.
Kravtsov et al., "Factor XI contributes to thrombin generation in the absence of factor XII," *Blood,* 114(2): 452-458. 2009.
Leung et al., "Inhibition of Factor XII-Mediated Activation of Factor XI Provides Protection Against Experimental Acute Ischemic Stroke in Mice," *Translation Stroke Research,* Sep. 2012; 3(3):381-9, https://doi.org/10.1007/s12975-012-0186-5.
Lloyd et al., "Modelling the Human Immune Response: Performance of a 1011 Human Antibody Repertoire Against a Broad Panel of Therapeutically Relevant Antigens," *Protein Engineering, Design, & Selection,* vol. 22, No. 3, pp. 159-168, 2009; © The Arthur 2008, published by Oxford University Press, 9 pages.
Lou et al., "Affinity Maturation by Chain Shuffling and Site Directed Mutagenesis" 2010. pp. 377-379 Antibody Engineering vol. 1, Ch. 25; DOI 10.1007/978-3-642-01144-3_25, # Springer-Verlag Berlin Heidelberg 2010, R. Kontermann and S. Duebel (eds.).
Matafonov et al., "Evidence for factor IX-independent roles for factor XIa in blood coagulation", Journal of Thrombosis and Haemostasis, 2013, 11:2118-2127.
Mendez et al., "Functional transplant of megabase human immunoglobulin loci recapitulates human antibody response in mice," *Nature Genetics,* 1997, 15:146-156.
Minnema et al., "Activation of the contact System of Coagulation Does Not Contribute to the Hemostatic Imbalance in Hypertriglyceridemia," *Arterioscler Throm Vasc Biol.,* 1999, 19:2548-2553.
Minnema et al., "Enhancement of Rabbit Jugular Vein thrombolysis by neutralization of factor XI in Vivo Evidence for a Role of Factor XI as an Anti-fibrinolytic Factor," *J. Clin. Invest.,* 1998, 101(1):10-14.
Minnema et al., "Activation of Clotting Factor XI Without Detectable Contact Activation in Experimental Human Endotoxemia," *Blood,* 1998, 92(9):3294-3301.
Minnema et al., "Activation of Clotting Factors XI and IX in Patients With Acute Myocardial Infarction," *Arterioscler Thromb Vasc Biol.,* 2000, 20:2489-2493.
Mohammed et al., "An Update on Factor XI Structure and Function," *Thromb Res.,* Jan. 2018; 161:94-105, (32 pages).
Morgan et al., "Acquired Factor XI Inhibitors in Two Patients with Hereditary Factor XI Deficiency," *Thromb Haemostas,* 1984, 51(3):371-375.
Naito et al., "Activation of Human Blood Coagulation Factor XI Independent of Factor XII," *The Journal of Biological Chemistry,* 266(12):7353-7358. 1991.
Navaneetham et al., "Structural and Mutational Analyses of the Molecular Interactions between the Catalytic Domain of Factor XIa and the Kunitz Protease Inhibitor Domain of Protease Nexin 2," *Journal of Biological Chemistry,* 280(43):36165-36175 (2005).
Nishikado et al., "Murine Monoclonal Antibodies to Human Factor XI," *Thrombosis Research,* 42:225-234. 1986.
Ogawa et al., "Exosite-mediated Substrate Recognition of Factor XI by Factor XIa," *Journal of Biological Chemistry,* 2005, 280(25):23523-23530.
Ohkubo et al., "Characterization of a Panel of Monoclonal Antibodies to Human Coagulation Factor XI and Detection of Factor XI in Hep G2 Cell Conditioned Medium," *Thrombosis and Haemostasis,* 63(3):4170423, 1990.
Papagrigoriou et al., "Crystal Structure of the factor XI zymogen reveals a pathway for transactivation," *Nature Structural & Molecular Biology,* vol. 13, No. 6, Jun. 2006, pp. 557-558.
Peyvandi et al., "Factor XI deficiency in Iranians: its clinical manifestations in comparison with those of classic hemophilia," *Haemtologica,* 2002, 87(5):512-514.
Puy et al., "Activated factor XI increases the procoagulant activity of the extrinsic pathway by inactivating tissue factor pathway inhibitor," *Blood,* 2015, 125(9):1488-1496.
Reagents, "Supplemental Methods and Data," (Jan. 13, 2015), URL:http://www.bloodjournal.org/content/bloodjournal/suppl/2015/01/13/blood-2014-10-604587.DC1/blood-2014-10-604587-1.pdf.
Renne et al., "Factor XI deficiency in animal models," *Journal of Thrombosis and Haemostasis,* 7(Suppl. 1):79-83, 2009.
Renne et al., "Characterization of the H-kininogen-binding Site on Factor XI," *The Journal of Biological Chemistry,* 2002, 277(7):4892-4899.
Renne et al., "Defective thrombus formation in mice lacking coagulation factor XII," *The Journal of Experimental Medicine,* 2005, 202(2):271-281.
Rudikoff et al., "Single Amino Acid Substitution Altering Antigen-Binding Specificity," *Proc. Natl. Acad. Sci. USA,* vol. 79, Mar. 1982, pp. 1979-1983, Immunology.
Salomon et al., "Prevalence, causes, and characterization of factor XI inhibitors in patients with inherited factor XI deficiency," *Blood,* 101(12):4783-4788. 2003.
Samuel et al., "Solution structure of the A4 domain of factor XI sheds light on the mechanism of zymogen activation," *PNAS,* 104(40):15693-15698. 2007.
Schumacher et al., "Antithrombotic and hemostatic effects of a small molecule factor XIa inhibitor in rats," *European Journal of Pharmacology,* 570:167-174. 2007.
Scott et al., "Amidolytic Assay of Human Factor Xi in Plasma: Comparison With a coagulant Assay and a new Rapid Radioimmunoassay," *Blood,* 63(1):42-50. 1984.
Sela-Culang et al. "The structural Basis of Antibody-Antigen Recognition" *Frontiers In Immunology,* 2013, (13 pgs.) doi: 10.3389/fimmu.2013.00302.
Sie et al., "An Acquired Antithrombin Autoantibody Directed toward the Catalytic Center of the Enzyme," *J. Clin. Invest.,* 88:290-296. 1991.
Sinha et al., "Functional Characterization of Human Blood Coagulation factor XIa Using Hybridoma Antibodies," *The journal of Biological Chemistry,* 260(19):10714-10719. 1985.
Sinha et al., "Macromolecular Substrate-Binding Exosites on Both the Heavy and Light Chains of Factor XIa Mediate the Formation of the Michaelis Complex Required for Factor IX-Activation," *Biochemistry,* 2007, 46, 9830-9839.
Smeenk et al., "Is Anticardiolipin Activity a Cross-Reaction of Anti-DNA or a Separate Entity?," *Arthritis and Rheumatism,* 1987, 30(6): 607-617.
Spronk et al., "Monitoring thrombin generation: Is addition of corn trypsin inhibitor needed," *Throm Haemost,* 101:1156-1162. 2009.
St. Groth et al., "Production of Monoclonal Antibodies: Strategy and Tactics," *Journal of Immunological Methods,* 1980, 35:1-21.
Stern et al., "Acquired Antibody to Factor XI in a Patient with Congenital factor XI Deficiency," *J. Clin. Invest.,* 69:1270-1276. 1982.
Strejan et al., "Suppression of Chronic-Relapsing Experimental Allergic Encephalomyelitis in Strain-13 Guinea Pigs by Administration of Liposome-Associated Myelin Basic Protein," *Journal of Neuroimmunology,* 1984, 7:27-41.

(56) References Cited

OTHER PUBLICATIONS

Su et al., "The Role of Factor XIa (FXIa) Catalytic Domain Exosite Residues in Substrate Catalysis and Inhibition by the Kunitz Protease Inhibitor Domain of Protease Nexin 2," *The Journal of Biological Chemistry,* vol. 286, No. 36, Sep. 9, 2011, pp. 31904-31914.
Sun et al., "Identification of a Factor IX Binding Site on the Third Apple Domain of Activated Factor XI," *The Journal of Biological Chemistry,* 1996, 271(46):29023-29028.
Tait et al., "Primary Structure Requirements for the Binding of Human High Molecular Weight Kininogen to Plasma Prekallikrein and Factor XI," *Journal of Biological Chemistry,* 1987, 262(24): 11651-11656.
Takahashi et al., "Inhibition of factor XI reduced thrombus formation in rabbit jugular vein under endothelial denudation and/or blood stasis," *Thrombosis Research,* 2010, 125(5):464-470.
Tans et al., "Studies on the effect of serine protease inhibitors on activated contact factors Application in amidolytic assays for factor XIIa, plasma kallikrein and factor XIa," *Eur. J. Biochem,* 164, pp. 637-642 (1987).
Thomas et al., "First Evaluation of the Safety, Pharmacokinetics and Pharmacodynamics of BAY 1213790, a Full Human IgG1 Anitbody Targeting Coagulation Factor XIa, in Healthy Young Men," *International Society on Thrombosis and Haemostatis,* Jul. 8-13, Berlin, Germany.
Tornetta et al., "Isolation of Human Anti-Idiotypic Antibodies by Phage Display for Clinical Immune Response Assays," *Journal of Immunological Methods,* 328(2007), 33-44, published by Elsevier B.V., www.elsevier.com/location/jim, 11 pgs.
Tucker et al., "Prevention of vascular graft occlusion and thrombus-associated thrombin generation by inhibition of factor XI," *Blood,* 113(4):936-944. 2009.
Tucker et al., "Inhibition of Factor XI decreases thrombin production and prevents vascular occlusion in experimental thrombosis in primates," *Blood,* 2007 110(11):1-5.
Van Der Graaf et al., "Isolation and Functional Characterization of the Active Light Chain of Activated Human Blood Coagulation Factor XI," *The Journal of Biological Chemistry,* 1983, vol. 258, No. 16, pp. 9669-9675.
Van Montfoort et al., "Anticoagulation beyond direct thrombin and factor Xa inhibitors: indications for targeting the intrinsic pathway," *Thrombosis and Haemostasis,* 110(2):223-232, 2013.
Van Montfoort et al., "Two novel inhibitory anti-human factor XI antibodies prevent cessation of blood flow in a murine venous thrombosis model," *Thrombosis and Haemostasis,* 2013, 110:1065-1073.
Van Montfoort, "Factor XI as target for antithrombotic therapy," *Thesis,* 2014.
Wong et al., "A novel DFP tripeptide motif interacts with the coagulation factor XI apple 2 domain," *Blood,* vol. 127, No. 23, Jun. 9, 2016, pp. 2915-2923.
Wu et al., "Structural insight into distinct mechanisms of protease inhibition by antibodies," *PNAS,* Dec. 11, 2017, vol. 104, No. 50, pp. 19784-19789.
Wuillemin et al., "Activation of the Intrinsic Pathway of Coagulation in Children with Meningococcal Septic Shock," *Thrombosis and Haemostasis,* 74(6):1436-41, 1995.
Wuillemin et al., "Thrombin-mediated activation of endogenous factor XI in plasma in the presence of physiological glycosaminoglycans occurs only with high concentrations of thrombin," *British Journal of Haematology,* 92:466-472, 1996.
Yamashita et al., "Factor XI contributes to thrombus propagation on injured neointima of the rabbit iliac artery," *Journal of Thrombosis and Haemostasis,* 2006, 4:1496:1501.
Yang et al., "Crystalline monoclonal antibodies for subcutaneous delivery," *PNAS,* 2003 100(12):6934-6939.
Zhu et al., (2015) "FXIa and platelet polyphosphate as therapeutic targets during human blood clotting on collagen/ tissue factor surfaces under flow" *Blood* 126(12): 1494-1502.
Zucker et al., "Induction of an inhibitor antibody to factor XI in a patient with severe inherited factor XI deficiency by Rh immune globulin," *Blood,* 111(3):1306-1308, 2008.
Awad et al. "Activated prothrombin complex concentrates for the reversal of anticoagulant-associated coagulopathy,". P T. Nov. 2013;38(11):696-701.
Bagul et al., "Tunnelled catheters for the haemodialysis patient," Eur J Vasc Endovasc Surg. Jan. 2007;33(1):105-12.
Colman, "Effects of Amino Acid Sequence Changes on Antibody-antigen Interations", Research in Immunology 145.1 (1994): 33-36.
GUSKOVA "Drug toxicology and safety of drugs," 2014, Non-commercial partnership of healthcare assistance, Scientific Center of Quality control, 109074, Moscow, Russian Federation. 4 pgs.
Janeway, "The interaction of the antibody molecule with specifici antigen", Immunobiology: The Immune System in Health and Disease. 5th edition. New York: Garland Science; 2001 (5 pgs.).
Kaw et al., "Hematology: Issues in the Dialysis Patient: Platelet Dysfunction and End-Stage Renal Disease," Seminars in Dialysis. vol. 19. No. 4. Malden, USA: Blackwell Publishing Inc, 2006 (pp. 317-322).
Li Zhenyu, "Study on the Development and Function of a Monoclonal Antibody to FVIII-C2 Domain Inhibit FVIII", 2009, China Academic Journal Electronic Publishing House.
Lopez et al., "Discrimination of ischemic and hemorrhagic strokes using a multiplexed, mass spectrometry-based assay for serum apolipoproteins coupled to multi-marker ROC algorithm," Proteomics Clin Appl. Apr. 2012;6(3-4):190-200.
Mccullough et al. "Use of Oral Anticoagulation in the Management of Atrial Fibrillation in Patients with ESRD", Pro. Clin J Am Soc Nephrol. Nov. 7, 2016;11(11):2079-2084.
Merlin et al. "Escape or Fight: Inhibitors in Hemophilia A," Front Immunol. Mar. 24, 2020;11:476.
Power "Stroke in dialysis and chronic kidney disease," Blood Purif. 2013;36(3-4):179-83.
Schror "Aspirin and platelets: the antiplatelet action of aspirin and its role in thrombosis treatment and prophylaxis," Semin Thromb Hemost. 1997;23(4):349-56.
Schumacher et al., "Inhibition of Factor XIa as a New Approach to Anticoagulation," Arterioscler Thromb Vasc Biol. 2010; 30:338-392.
Stryer, Biochemistry 4th, WH Freeman, New York. 1995 pp. 18-23.
Clark et al., "Biomarkers for non-human primate type-I hypersensitivity: antigen-specific immunoglobulin E assays," J Immunol Methods. Jun. 28, 2013;392(1-2):29-37.
Gorovitz et al., "Recommendations for the characterization of immunogenicity response to multiple domain biotherapeutics," J Immunol Methods. Jun. 2014;408:1-12.
International Search Report and Written Opinion of the International Search Authority for International Application No. PCT/US2020/066151, mailed on Mar. 25, 2021, 10 pages.
International Search Report and Written Opinion of the International Search Authority for International Application No. PCT/US2021/064117, mailed on May 11, 2022, 13 pages.
International Search Report and Written Opinion of the International Search Authority for International Application No. PCT/US2022/080131, mailed on Mar. 28, 2023, 11 pages.
International Search Report and Written Opinion of the International Search Authority for International Application No. PCT/US2023/068956, mailed on Jan. 24, 2024, 11 pages.
Lorentz et al. "Contact Activation Inhibitor and Factor XI Antibody, AB023, Produces Safe, Dose-Dependent Anticoagulation in a Phase 1 First-In-Human Trial," Arterioscler Thromb Vasc Biol. Apr. 2019;39(4):799-809.
Nam et al., "Aspirin inhibits TGF#2-induced epithelial to mesenchymal transition of lens epithelial cells: selective acetylation of K56 and KI22 in histone H3," Biochem J, Jan. 17, 2020, vol. 477, pp. 75-97.
Patton et al., "An acid dissociation bridging ELISA for detection of antibodies directed against therapeutic proteins in the presence of antigen," J Immunol Methods. Sep. 2005;304(1-2):189-95.
Sadeghi et al., "Comparative Biochemical and Functional Studies on a Branded Human Recombinant Factor VIIa and a Biosimilar Equivalent Product," Clin Appl Thromb Hemost. 2014. vol. 20. pp. 565-72.

(56) References Cited

OTHER PUBLICATIONS

Wang et al., "Development of a Highly Specific Anti-drug Antibody Assay in Support of a Nanoparticle-based Therapeutic," AAPS J. Jun. 2, 2020;22(4):81.
Wu et al., "An electrochemiluminescence (ECL)-based assay for the specific detection of anti-drug antibodies of the IgE isotype," J Pharm Biomed Anal. Dec. 2013; 86:73-81.
Yi et al., "Pharmacokinetics and pharmacodynamics of Abelacimab (MAA868), a novel dual inhibitor of Factor XI and Factor Xia," Journal of Thrombosis and Haemostasis, Oct. 29, 2021.
Zoghbi et al., "A breakthrough novel method to resolve the drug and target interference problem in immunogenicity assays," J Immunol Methods. Nov. 2015;426:62-9.

* cited by examiner

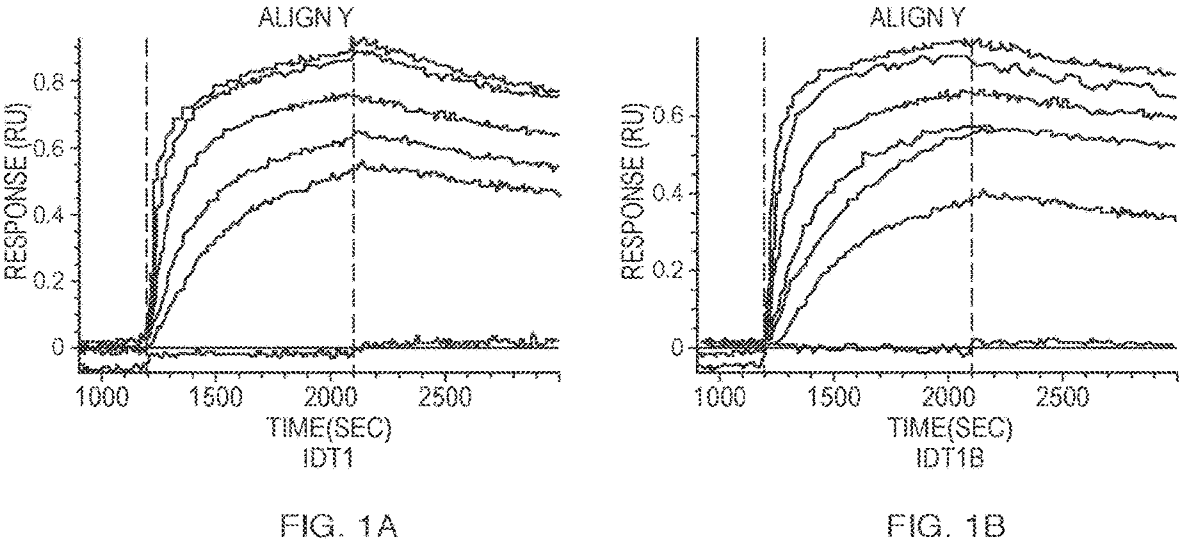
FIG. 1A
FIG. 1B
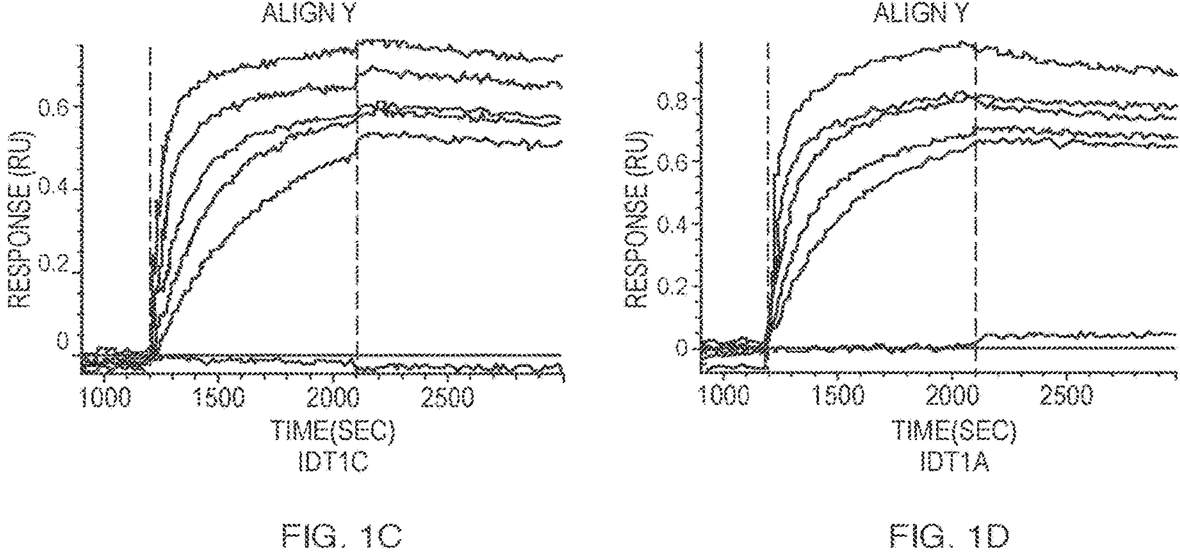
FIG. 1C
FIG. 1D

```
                                                     HCDR1                                   HCDR2
IDT1_HC      QVQLLESGGGLVQPGGSLRLSCAASGFTFSDYAMSWVRQAPGKGLEWVSVIDYSSSNTYY
IDT1B_HC     QVQLLESGGGLVQPGGSLRLSCAASGFTFSDYAMSWVRQAPGKGLEWVSTISYLGQEKHY
IDT1E_HC     QVQLLESGGGLVQPGGSLRLSCAASGFTFSDYAMSWVRQAPGKGLEWVSTISYLGQEKHY
IDT1C_HC     QVQLLESGGGLVQPGGSLRLSCAASGFTFSDYAMSWVRQAPGKGLEWVSTIAYLGAPTHY
IDT1D_HC     QVQLLESGGGLVQPGGSLRLSCAASGFTFSDYAMSWVRQAPGKGLEWVSTIAYVGAPTHY
IDT1A_HC     QVQLLESGGGLVQPGGSLRLSCAASGFTFSDYAMSWVRQAPGKGLEWVSVIDYSSSNTYY
             *************************************************.* *  . .:*

             HCDR2
                                                         HCDR3
IDT1_HC      ADSVKGRFTISRDNSKNTLYLQMNSLRAEDTAVYYCAREGYSYRSIRFDYWGQGTLVTVS
IDT1B_HC     ADSVKGRFTISRDNSKNTLYLQMNSLRAEDTAVYYCAREGYSYRSIRFDYWGQGTLVTVS
IDT1E_HC     ADSVKGRFTISRDNSKNTLYLQMNSLRAEDTAVYYCAREGYSYRSIRFDYWGQGTLVTVS
IDT1C_HC     ADSVKGRFTISRDNSKNTLYLQMNSLRAEDTAVYYCAREGYSYRSIRFDYWGQGTLVTVS
IDT1D_HC     ADSVKGRFTISRDNSKNTLYLQMNSLRAEDTAVYYCAREGYSYRSIRFDYWGQGTLVTVS
IDT1A_HC     ADSVKGRFTISRDNSKNTLYLQMNSLRAEDTAVYYCAREGYSYRSIRFDYWGQGTLVTVS
             ************************************************************

IDT1_HC      SASTKGPSVFPLAPSSKSTSGGTAALGCLVKDYFPEPVTVSWNSGALTSGVHTFPAVLQS
IDT1B_HC     SASTKGPSVFPLAPSSKSTSGGTAALGCLVKDYFPEPVTVSWNSGALTSGVHTFPAVLQS
IDT1E_HC     SASTKGPSVFPLAPSSKSTSGGTAALGCLVKDYFPEPVTVSWNSGALTSGVHTFPAVLQS
IDT1C_HC     SASTKGPSVFPLAPSSKSTSGGTAALGCLVKDYFPEPVTVSWNSGALTSGVHTFPAVLQS
IDT1D_HC     SASTKGPSVFPLAPSSKSTSGGTAALGCLVKDYFPEPVTVSWNSGALTSGVHTFPAVLQS
IDT1A_HC     SASTKGPSVFPLAPSSKSTSGGTAALGCLVKDYFPEPVTVSWNSGALTSGVHTFPAVLQS
             ************************************************************

IDT1_HC      SGLYSLSSVVTVPSSSLGTQTYICNVNHKPSNTKVDKRVEPKSC
IDT1B_HC     SGLYSLSSVVTVPSSSLGTQTYICNVNHKPSNTKVDKRVEPKSC
IDT1E_HC     SGLYSLSSVVTVPSSSLGTQTYICNVNHKPSNTKVDKRVEPKSC
IDT1C_HC     SGLYSLSSVVTVPSSSLGTQTYICNVNHKPSNTKVDKRVEPKSC
IDT1D_HC     SGLYSLSSVVTVPSSSLGTQTYICNVNHKPSNTKVDKRVEPKSC
IDT1A_HC     SGLYSLSSVVTVPSSSLGTQTYICNVNHKPSNTKVDKRVEPKSC
             ********************************************
```

FIG. 2

```
                                                LCDR1                      LCDR2
IDT1_LC      DIQMTQSPSSLSASVGDRVTITCRASQSISSNLNWYQQKPGKAPKLLIYAASNLQSGVPS
IDT1E_LC     DIQMTQSPSSLSASVGDRVTITCRASQSISSNLNWYQQKPGKAPKLLIYAASNLQSGVPS
IDT1D_LC     DIQMTQSPSSLSASVGDRVTITCRASQSISSNLNWYQQKPGKAPKLLIYAASNLQSGVPS
IDT1A_LC     DIQMTQSPSSLSASVGDRVTITCRASQSISSNLNWYQQKPGKAPKLLIYAASNLQSGVPS
IDT1B_LC     DIQMTQSPSSLSASVGDRVTITCRASQSISSNLNWYQQKPGKAPKLLIYAASNLQSGVPS
IDT1C_LC     DIQMTQSPSSLSASVGDRVTITCRASQSISSNLNWYQQKPGKAPKLLIYAASNLQSGVPS
             ************************************************************

                                                 LCDR3
IDT1_LC      RFSGSGSGTDFTLTISSLQPEDFATYYCLQFDHTPFTFGQGTKVEIKRTVAAPSVFIFPP
IDT1E_LC     RFSGSGSGTDFTLTISSLQPEDFATYYCLQYYHLPYTFGQGTKVEIKRTVAAPSVFIFPP
IDT1D_LC     RFSGSGSGTDFTLTISSLQPEDFATYYCLQYYHLPYTFGQGTKVEIKRTVAAPSVFIFPP
IDT1A_LC     RFSGSGSGTDFTLTISSLQPEDFATYYCLQYYHLPYTFGQGTKVEIKRTVAAPSVFIFPP
IDT1B_LC     RFSGSGSGTDFTLTISSLQPEDFATYYCLQFDHTPFTFGQGTKVEIKRTVAAPSVFIFPP
IDT1C_LC     RFSGSGSGTDFTLTISSLQPEDFATYYCLQFDHLPFTFGQGTKVEIKRTVAAPSVFIFPP
             ************************************************************

IDT1_LC      SDEQLKSGTASVVCLLNNFYPREAKVQWKVDNALQSGNSQESVTEQDSKDSTYSLSSTLT
IDT1E_LC     SDEQLKSGTASVVCLLNNFYPREAKVQWKVDNALQSGNSQESVTEQDSKDSTYSLSSTLT
IDT1D_LC     SDEQLKSGTASVVCLLNNFYPREAKVQWKVDNALQSGNSQESVTEQDSKDSTYSLSSTLT
IDT1A_LC     SDEQLKSGTASVVCLLNNFYPREAKVQWKVDNALQSGNSQESVTEQDSKDSTYSLSSTLT
IDT1B_LC     SDEQLKSGTASVVCLLNNFYPREAKVQWKVDNALQSGNSQESVTEQDSKDSTYSLSSTLT
IDT1C_LC     SDEQLKSGTASVVCLLNNFYPREAKVQWKVDNALQSGNSQESVTEQDSKDSTYSLSSTLT
             ************************************************************

IDT1_LC      LSKADYEKHKVYACEVTHQGLSSPVTKSFNRGEC
IDT1E_LC     LSKADYEKHKVYACEVTHQGLSSPVTKSFNRGEC
IDT1D_LC     LSKADYEKHKVYACEVTHQGLSSPVTKSFNRGEC
IDT1A_LC     LSKADYEKHKVYACEVTHQGLSSPVTKSFNRGEC
IDT1B_LC     LSKADYEKHKVYACEVTHQGLSSPVTKSFNRGEC
IDT1C_LC     LSKADYEKHKVYACEVTHQGLSSPVTKSFNRGEC
             **********************************
```

FIG. 3

REVERSAL BINDING AGENTS FOR ANTI-FACTOR XI/XIa ANTIBODIES AND USES THEREOF

CROSS REFERENCE TO RELATED APPLICATION

This application claims the benefit of and priority to U.S. Provisional Patent Application No. 62/781,236, filed Dec. 18, 2018, the disclosure of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Dec. 12, 2019, is named 14452_6015-00304_SL.txt and is 159,560 bytes in size.

TECHNICAL FIELD

The present disclosure relates to binding agents (e.g., antibodies or antigen-binding fragments, including Fabs), which specifically bind to anti-Factor XI and/or anti-Factor XIa ("anti-FXI/FXIa") antibodies (e.g., NOV1401), and reverse one or more anticoagulant effects of the anti-Factor XI and/or anti-Factor XIa antibodies (e.g., NOV1401), as well as to pharmaceutical compositions and to methods of use thereof, such as methods for reversing anticoagulant effects of such anti-Factor XI and/or anti-Factor XIa antibodies (e.g., NOV1401).

BACKGROUND

Thrombosis refers to thrombus formation inside blood vessels, subsequent to a combination of hereditary and acquired risk factors, known as thrombophilia or hypercoagulable states. Vessel wall damage, stasis, increased platelets reactivity, and activation of clotting factors are some of the fundamental features of thrombosis. Thrombosis can occur in both venous and arterial circulation and can result in the development of deep vein thrombosis (DVT), pulmonary embolism, and stroke. If a thrombus occurs in the arterial system, down-stream ischemia can occur, leading to acute coronary syndromes (ACS), ischemic stroke, and acute limb ischemia. Thrombus formation in the venous system typically leads to deep venous thrombosis, pulmonary embolism and chronic thromboembolic pulmonary hypertension. Clots may also form in the left atrial appendage in patients with atrial fibrillation (AF), and dislodged thrombi may result in potentially devastating complications, i.e. thromboembolic stroke and systemic embolism. The currently available antithrombotic medications, including low molecular weight heparin (LMWH), thrombin inhibitors, and Factor Xa (FXa) inhibitors, are all associated with a significant risk of bleeding (Weitz J. I. (2010) Thromb. Haemost. 103, 62). The development of an antithrombotic agent that does not affect hemostasis, and therefore does not result in bleeding complications, as well as specific reversal agents, would be highly desirable.

Current anticoagulants are either injected or taken orally. The injectable anticoagulant LMWH is widely used and offers an improved therapeutic profile over formerly applied unfractionated heparin. For the past few decades the most commonly used oral anticoagulant has been warfarin. Warfarin has a narrow therapeutic window that requires frequent monitoring of the coagulation status, and shows a variety of drug-drug interactions. More recently, orally available direct FXa and thrombin inhibitors have entered the anticoagulant market and are increasingly applied.

LMWHs, FXa inhibitors, and thrombin inhibitors are all efficacious in the prevention of post-operative venous thromboembolic disease, in the treatment of spontaneous DVT and pulmonary embolism, and in the stroke prevention in atrial fibrillation. However, these anticoagulants are also associated with bleeding complications that were generally comparable to those observed with the older drugs warfarin and unfractionated heparin. In the ADVANCE-2 clinical trial, the FXa inhibitor apixaban (ELIQUIS®) was compared to the LMWH enoxaparin in patients after total knee replacement. While acute apixaban therapy was more effective at preventing venous thromboembolic disease than enoxaparin, both agents were associated with a significant risk of bleeding. Clinically relevant bleeding occurred in 4% of patients receiving apixaban and in 5% of patients treated with enoxaparin (Lassen, M. R., et al. (2009) N. Engl. J. Med. 361, 594).

In the RE-LY trial, the direct thrombin inhibitor dabigatran (Pradaxa) was compared to warfarin in patients with atrial fibrillation and a risk of stroke (Connolly, S. J., et al. (2009) N. Engl. J. Med. 361, 1139). Chronic dabigatran therapy was associated with a significantly lower risk of stroke or systemic embolism. However, major bleeding complications occurred in 3.1% of patients receiving 150 mg per day of dabigatran and in 3.4% of patients receiving warfarin (p=0.31).

Atrial fibrillation (AF) remains the most common cardiac arrhythmia in clinical practice, accounting for approximately one third of hospitalizations for cardiac dysrhythmias. Currently, it is estimated to affect more than 6 million patients in Europe and approximately 2.3 million in the United States, and this number continues to grow rapidly because of the increasing proportion of the aging population. It is estimated that approximately 5% of the population over the age of 65 years, and 10% of people aged over 80 years, will develop AF, however, the prevalence of AF is increasing beyond that explained by age alone. AF risk factors such as hypertension, congestive heart failure, left ventricular hypertrophy, coronary artery disease and diabetes mellitus, and obstructive sleep apnea are also on the rise. As such, the number of affected individuals with AF is expected to increase two to three times over the next three decades in western populations. (Kannel and Benjamin (2008) Med Clin North Am. 2008; 92:17-40; Bunch, et al. (2012) J Innovations of Card Rhythm Manag 2012; 3: 855-63).

The principal risk of AF is a four- to five-fold increase in embolic stroke. The attributable risk for stroke associated with AF increases steeply with age to 23.5% at ages 80 to 89. AF is associated with a doubling of mortality in both genders (Kannel and Benjamin 2008). AF is also independently associated with cognitive decline and all forms of dementia (Marzona, et al. (2012) CMAJ 2012; 184: 329-36; Geita et al 2013; Bunch et al 2012).

Most patients with AF require life-long anticoagulation therapy to prevent cardioembolic stroke and systemic embolism. The $CHA_2DS_2$-VASc risk score is a validated and widely used stratification tool to predict thromboembolic risk in atrial fibrillation patients and to identify patients who should benefit from anticoagulation therapy (LIP 2011; Camm, et al. (2012) Eur Heart J 2012; 33: 2719-2747); the accumulated evidence shows that $CHA_2DS_2$-VASc is at least as accurate as or possibly better than, scores such as $CHADS_2$ in identifying patients who develop stroke and thromboembolism and definitively better at identifying 'truly low-risk' patients with AF. It is estimated that 85 to 90% of AF patients will require anticoagulation therapy.

In a meta-analysis comprising 6 trials which evaluated the effect of vitamin K antagonists (VKA) in reducing stroke and systemic embolism, a highly significant risk reduction in stroke incidence (relative risk reduction of 67% for stoke) was observed. All-cause mortality was significantly reduced (26%) by adjusted-dose VKA vs. control (Hart, Pearce, and Aguilar (2007) Ann Intern Med 2007; 146:857-867). An international normalized ratio (INR) target between 2 and 3 was associated with best benefit-risk ratio (Hylek et al (2003) N Engl J Med; 349:1019-1026) and universally adopted by international and national guidelines.

In recent years, new oral anticoagulants (NOAC) also referred to as direct oral anticoagulants (DOAC) have been approved and introduced to clinical practice. These drugs are at least as effective or even better than warfarin for reducing thrombo-embolic disease (Connolly, et al. (2009) N Engl J Med; 361:1139-51; Connolly, et al. (2011) N Engl J Med; 364:806-17; Patel, et al. (2011) N Engl J Med 2011; 365: 883-91). NOAC were also associated with large reductions in the most devastating complications of warfarin namely hemorrhagic stroke and intracranial hemorrhage. Major bleeding events were similar or slightly lower than well conducted warfarin therapy. In addition, NOAC are associated with a lower potential for drug-drug interaction than warfarin and could be used without routine monitoring; this is expected to ease their use in everyday medical practice.

Despite recent improvements, bleeding risk continues to be high with the use of anticoagulants. For instance, the annual incidence of major and clinically relevant non-major bleeding was 14.9%, and the annual incidence of major bleeding events was 3.6% in patients treated with rivaroxaban in the ROCKET study (Patel et al 2011). The annual incidence of major bleeding was >5% in patients at a high risk for bleeding defined as HAS Bled risk score ≥3 (Gallego, et al. (2012) Carc Arrhythm Electrophysiol.; 5:312-318). Major bleeding is a particularly relevant clinical outcome; for instance, in the ROCKET study, once major bleeding has occurred, all-cause mortality rate was 20.4% in the rivaroxaban group and 26.1% in the warfarin group. Once major bleeding events have occurred, stroke and systemic embolism occurred in 4.7% and 5.4% of patients in rivaroxaban and warfarin groups, respectively (Piccini, et al. (2014) Eur Heart J; 35:1873-80). Hospital stay, transfusion of blood products and resources utilization were also severely impacted by the occurrence of major bleeding. Bleeding risk is also a major reason for not receiving anticoagulants in eligible patients. In the Euro Heart Survey on Atrial Fibrillation comprising data from 182 hospitals in 35 countries and 5333 ambulant and hospitalized AF patients, only 67% of eligible patients received oral anticoagulant at discharge (Nieuwlaat, et al (2005) Eur Heart J; 26, 2422-2434). A high unmet medical need therefore exists for a safer therapy which can reduce AF thromboembolic complications such as stroke, systemic embolism, cognitive decline and mortality with comparable efficacy as existing therapies but with a lower bleeding liability.

Factor XI (FXI) holds important roles in both intrinsic and extrinsic coagulation pathways and in bridging the initiation and amplification phases of plasmatic hemostasis (Gailani and Renné (2007) Arterioscler Thromb Vasc Biol; 27(12): 2507-13). Both Factor XII and thrombin can activate FXI, resulting in a sustained thrombin generation and fibrinolysis inhibition. FXI plays a minor role in normal hemostasis in a high tissue factor environment "after vessel injury", whereas it appears to play a key role in thrombosis. Severe FXI deficiency is associated with a lower incidence of ischemic stroke and venous thromboembolic events (Salomon et al (2008) Blood; 111(8):4113-7; Salomon et al (2011) Thromb Haemost; 105(2):269-73). Furthermore, in a population-based study, a survival advantage of severe FXI deficiency was evoked as a result of a lower incidence of thromboembolic events (Duga and Salomon, (2013) Semin Thromb Hemost; 39(6):621-31). Bleeding manifestations in subjects with severe FXI deficiency are infrequent, usually mild, injury-related, and affect preferably tissues with increased fibrinolytic activity such as the oral mucosa, nasal mucosa, and the urinary tract (Bolton-Maggs, (2000) Haemophilia; 6 Suppl 1:100-9). Bleeding in vital organs is extremely rare or does not exist.

Lower bleeding risk is expected for anticoagulant therapies involving anti-FXI/FXIa antibodies compared to NOACs. For example, anti-Factor XI/FXIa antibody NOV1401 is a human antibody binding to the catalytic domain of FXI. NOV1401 inhibits both the zymogen (FXI) and the activated factor XI (FXIa) with high potency. Anti-FXI/FXIa antibody NOV1401 dose-dependently prolonged activated partial thromboplastin time (aPTT) in in vitro and in in vivo studies. After a single subcutaneous (s.c.) administration of NOV1401 at a 3 mg/kg dose, sustained anticoagulant activity lasting more than one month was observed in cynomolgus monkeys. Moreover, Anti-FXI/FXIa antibody NOV1401 prevented experimental carotid artery thrombosis induced by $FeCl_3$ and induced prolongation in aPTT in FXI−/− mice reconstituted with human FXI. NOV1401 was well tolerated in a 13-week Good Laboratory Practice (GLP)-compliant toxicity study conducted in cynomolgus monkeys.

Despite the expected lower bleeding risk associated with anti-FXI/FXIa antibodies, for example NOV1401, compared to NOACs, bleeding events may still occur in certain circumstances due to trauma, surgery, procedures, co-medication and high prevalence of comorbidities that increase bleeding risk such as hypertension, heart failure, renal impairment, hepatic impairment, older age, prior bleeding events, risk of falls, use of antiplatelet agents or non-steroidal anti-inflammatory drugs, etc.

Accordingly, there is an unmet medical need for specific reversal agents as part of efforts to address the remaining bleeding liability for anticoagulant therapies with anti-FXI/FXIa antibodies (e.g., anti-FXI/FXIa antibodies which specifically bind to the catalytic domain of FXI/FXIa, e.g., NOV1401), for example, in circumstances when reversal of the anticoagulant effects of a therapy is needed for emergency surgery/urgent procedures and in cases of life-threatening or uncontrolled bleeding.

SUMMARY

As part of efforts to lower bleeding liability, the present disclosure describes strategies to address the unmet medical need for specific reversal agents for anticoagulant therapies that are anti-Factor XI/XIa antibodies (e.g., anti-FXI/FXIa antibodies which specifically bind to the catalytic domain of FXI/FXIa) for example, anti-FXI/FXIa antibody NOV1401. In specific aspects, managing bleeding or bleeding risk is beneficial in circumstances when reversal of the anticoagulant effects of a therapy is needed, for example, for emergency surgery/urgent procedures and in cases of life-threatening or uncontrolled bleeding. In specific aspects, managing bleeding or bleeding risk is beneficial in patients identified as having high bleeding risk (e.g., previous history of bleeding).

Anti-idiotype antibody reversal agents (e.g., whole antibody, IgG, Fab fragment), which specifically bind to NOV1401 antibodies, have been recently described in WO 2017/203450 (e.g., referred to as IDT1 to IDT10 in WO 2017/203450). A maximum reversal of 38% to 64% of anticoagulant effects was observed at 10× molar excess of anti-NOV1401 Fabs IDT1 to IDT10 versus NOV1401, and a maximum reversal of 25% to 45% was observed at 3× molar excess, as shown by aPTT assay (Table 8 in WO 2017/203450). While the anti-NOV1401 antibodies described in WO 2017/203450 are capable of reversing NOV1401's anticoagulant effect, the present inventors continued to explore improved reversal agents, for example, reversal agents that can reverse the anticoagulant effects of anti-FXI/FXIa antibodies, such as NOV1401, at lower molar excess.

The present inventors have now generated new high-affinity variants of anti-idiotype antibody IDT1 disclosed in WO 2017/203450. The new high-affinity versions have higher affinity for NOV1401 than the first generation anti-NOV1401 antibody IDT1, and are capable of reversing anticoagulant effects of anti-FXI/FXIa antibodies NOV1401 (e.g., capable of reducing aPTT or bleeding time) to a higher degree and/or at lower excess molar ratios. For example, in in vitro aPTT assays described in Example 3 below, a 3× molar excess of Fab IDT1C versus NOV1401 was sufficient to achieve maximal reversal of 79%, while at least a 30× molar excess was required for the first generation anti-NOV1401 Fab IDT3 (disclosed in WO 2017/203450) to achieve a maximal reversal effect of approximately 73% (see Example 3, Table 5 below). A clear correlation was found between the level of affinities, in particular the off-rate level, and reversal capabilities of anti-NOV1401 antibodies. Without being bound by any particular theory, it is believed that higher affinity, for example, as a result of slower off-rate, can significantly reduce required molar excess of anti-NOV1401 antibodies versus NOV1401 necessary to achieve maximal anticoagulant reversal effects. These characteristics make the high-affinity reversal agents provided in the present disclosure desirable reversal agents to manage and/or reduce bleeding risks of anti-FXI/FXIa antibody therapies.

Accordingly, the present disclosure relates to further improved binding agents which specifically bind to antibodies that specifically bind coagulation Factor XI and XIa (activated Factor XI), e.g., NOV1401, and which are capable of reversing one or more anticoagulant effects of such anti-FXI/FXIa antibodies (e.g., capable of reducing aPTT or bleeding time). In particular, the present disclosure relates to high affinity antibodies (e.g., anti-idiotype antibodies, e.g., full length IgGs and fragments thereof such as Fabs), which specifically bind to antibodies that specifically bind coagulation Factor XI and XIa (activated Factor XI), e.g., NOV1401, and which are capable of reversing one or more anticoagulant effects of such anti-FXI/FXIa antibodies. In particular aspects, the reversal agents for NOV1401 described herein have a higher affinity, e.g., slower off-rate, than previously described reversal agents (e.g., IDT1 or IDT3) conferring for higher maximal anticoagulant reversal activities in comparison to the previously described reversal agents at the same molar excess.

In particular, the present disclosure also relates to pharmaceutical compositions comprising such binding agents, and methods of reversing one or more anticoagulant effects of an anti-FXI/FXIa antibody in a patient (e.g., human patient) being treated with the anti-FXI/FXIa antibody (e.g., NOV1401), comprising administering the binding agent. Such binding agents capable of reversing one or more anticoagulant effects of anti-FXI/FXIa antibodies (e.g., NOV1401) achieve an unmet need in circumstances when reversal of the anticoagulant effects of a therapy, such as anti-FXI/XIa antibodies, is needed for emergency surgery/urgent procedures and in cases of life-threatening or uncontrolled bleeding. In specific embodiments, such patients (e.g., human patients) are being treated with an anti-FXI/FXIa antibody for the prevention and/or treatment of thrombosis or thromboembolic disease/disorder (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, systemic embolism).

In specific embodiments, binding agents provided herein that reverse (e.g., partially reverse, for example, by at least 40%, at least 50%, at least 60%, at least 70%, at least 75%, at least 80%, or at least 85%) one or more anticoagulant effects of anti-FXI/FXIa antibodies are anti-idiotype antibodies, and in further specific embodiments, such anti-idiotype antibodies are full length IgGs of Fabs. In further specific embodiments, such anti-idiotype antibodies are monoclonal antibodies, such as human monoclonal antibodies, e.g., recombinant human monoclonal antibodies.

In particular aspects, the present disclosure also relates to isolated polynucleotides and nucleic acids comprising a sequence encoding a binding agent provided herein, to vectors comprising one or more of the polynucleotides or nucleic acids provided herein, to host cells comprising such vectors or polynucleotides or nucleic acids. In specific aspects, the host cells are non-human mammalian cells, such as Chinese hamster ovary (CHO) cells.

In particular aspects, the present disclosure also relates to kits comprising the binding agent or the antibody provided herein and, optionally, instructions for use.

Non-limiting embodiments of the present disclosure are described in the following embodiments:

1. A binding agent which binds a target human anti-Factor XI ("FXI") and/or Factor XIa ("FXIa") antibody or antigen-binding fragment thereof, wherein the binding agent inhibits an anticoagulant activity of the target antibody, and wherein the binding agent binds to the target antibody with a dissociation constant ($K_D$) of 20 pM or less, 15 pM or less, preferably 10 pM or less.
2. A binding agent, which binds a human anti-Factor XI ("FXI") and/or Factor XIa ("FXIa") antibody or antigen-binding fragment thereof, wherein the binding agent is an antibody or antigen-binding fragment thereof comprising a heavy chain variable region (VH) comprising complementarity determining region HCDR2 selected from the group consisting of SEQ ID NO: 121, 122, 123, 105, 106, 107, 75, 76, 77, 52, 56, 58, 75, 76, 77, 105, 106, and 107, and a light chain variable region (VL) comprising complementarity determining region LCDR3 selected from the group consisting of SEQ ID NO: 125, 126, 66, 69, 94, and 95, wherein the human anti-FXI and/or FXIa antibody or antigen-binding fragment thereof comprises (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9.

3. A binding agent which specifically binds a target antibody that binds human Factor XI ("FXI") and/or Factor XIa ("FXIa") within the catalytic domain, wherein the binding agent inhibits an anticoagulant activity of the target antibody, and wherein the binding agent binds to the target antibody with a dissociation constant ($K_D$) of at least 5 times lower, preferably at least 10 times lower, than a $K_D$ of a reference antibody, wherein the reference antibody comprises a heavy chain variable region (VH) comprising the amino acid sequence of SEQ ID NO: 60 and a light chain variable region (VL) comprising the amino acid sequence of SEQ ID NO: 71.
4. The binding agent of embodiment 1 or embodiment 3, wherein the $K_D$ is measured by solution equilibrium titration, in particular wherein the $K_D$ is measured by solution equilibrium titration at 25° C., in more particular wherein the $K_D$ is measured by solution equilibrium titration at 25° C. for the binding agent in a Fab format.
5. The binding agent of any one of embodiments 1 or 3 to 4, wherein the binding agent binds to the target antibody with an association rate ($k_{on}$) of at least 1E+05 $M^{-1}s^{-1}$, preferably with an association rate ($k_{on}$) of 1E+05 $M^{-1}s^{-1}$ to 1E+06 $M^{-1}s^{-1}$ as measured by surface plasmon resonance at 25° C.
6. The binding agent of any one of embodiments 1 or 3 to 5, wherein the binding agent is capable of reversing the anticoagulant activity of the target antibody.
7. The binding agent of embodiment 6, wherein the binding agent, when present in a three times molar excess in comparison to the target antibody, is at least 1.5 times more efficient in reversing the anticoagulant activity of the target antibody in comparison to a reference antibody present in a three times molar excess in comparison to the target antibody, and wherein the reference antibody comprises a heavy chain variable region (VH) comprising the amino acid sequence of SEQ ID NO: 60 and a light chain variable region (VL) comprising the amino acid sequence of SEQ ID NO: 71, in particular wherein the anticoagulation activity is measured in an aPTT assay at 37° C.
8. The binding agent of embodiment 6 or 7, wherein the binding agent:
   (i) when present in a three times molar excess in comparison to the target antibody, is capable of a maximal reversal of 60% or more, in particular 63% or more, of the anticoagulant activity of the target antibody, as measured in an activated partial thromboplastin time (aPTT) assay, in particular as measured in an aPTT assay at 37° C.; and/or
   (ii) when present in a nine times molar excess in comparison to the target antibody, is capable of a maximal reversal of 70% or more, in particular 72% or more, of the anticoagulant activity of the target antibody, as measured in an activated partial thromboplastin time (aPTT) assay, in particular as measured in an aPTT assay at 37° C.; and/or
   (iii) when present in a thirty times molar excess in comparison to the target antibody, is capable of a maximal reversal of 75% or more, in particular 78% or more, of the anticoagulant activity of the target antibody, as measured in an activated partial thromboplastin time (aPTT) assay, in particular as measured in an aPTT assay at 37° C.
9. The binding agent of any one of embodiments 1 or 3 to 7, wherein the target antibody comprises (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9.
10. The binding agent of any one of embodiments 1 to 9, wherein the binding agent is an antibody or antigen-binding fragment thereof comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein:
    a) the HCDR1 comprises the amino acid sequence selected from the group consisting of SEQ ID NO: 51, 54, 55 and 57, the HCDR2 comprises the amino acid sequence selected from the group consisting of SEQ ID NO: 52, 56, 58, 75, 76, 77, 105, 106, 107, 121, 122, and 123, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94, 95, 125, and 126; or
    b) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76, 77, 105, 106, 107, 121, 122, and 123, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66, 69, 125, and 126.
11. The binding agent of embodiment 10, wherein:
    a) the HCDR1 comprises the amino acid sequence selected from the group consisting of SEQ ID NO: 51, 54, 55 and 57, the HCDR2 comprises the amino acid sequence selected from the group consisting of SEQ ID NO: 121, 122, and 123, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 125 and 126;
    b) the HCDR1 comprises the amino acid sequence selected from the group consisting of SEQ ID NO: 51, 54, 55 and 57, the HCDR2 comprises the amino acid sequence selected from the group consisting of SEQ ID NO: 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69;

c) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76 and 77, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;

d) the HCDR1 comprises the amino acid sequence selected from the group consisting of SEQ ID NO: 51, 54, 55 and 57, the HCDR2 comprises the amino acid sequence selected from the group consisting of SEQ ID NO: 52, 56 and 58, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;

e) the HCDR1 comprises the amino acid sequence selected from the group consisting of SEQ ID NO: 51, 54, 55 and 57, the HCDR2 comprises the amino acid sequence selected from the group consisting of SEQ ID NO: 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95; or f) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76 and 77, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69.

12. The binding agent of embodiment 9, wherein:

a. the HCDR1 comprises the amino acid sequence of SEQ ID NO: 51, the HCDR2 comprises the amino acid sequence of SEQ ID NO: 52 or 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94; or b. the HCDR1 comprises the amino acid sequence of SEQ ID NO: 51, the HCDR2 comprises the amino acid sequence of SEQ ID NO: 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

13. The binding agent of embodiment 12, wherein a) the HCDR1 comprises the amino acid sequence of SEQ ID NO: 51, the HCDR2 comprises the amino acid sequence of SEQ ID NO: 52, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

b) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

c) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO:53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

d) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66: or e) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

14. The binding agent of embodiment 13, wherein:

a. the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

b. the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;
c. the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;
d. the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively;
e. the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 94, respectively.

15. The binding agent of any one of embodiments 1 to 14, wherein the binding agent is an antibody or antigen-binding fragment thereof comprising a heavy chain variable region (VH) and a light chain variable region (VL), wherein:
a) the VH comprises the amino acid sequence that is at least 90%, or at least 95% identical, to the amino acid sequence of SEQ ID NO: 124, and the VL comprises the amino acid sequence that is at least 90%, or at least 95% identical, to the amino acid sequence of SEQ ID NO: 127;
b) the VH comprises the amino acid sequence that is at least 90%, or at least 95% identical, to the amino acid sequence of SEQ ID NO: 78 or 85, preferably SEQ ID NO: 85, and the VL comprises the amino acid sequence that is at least 90%, or at least 95% identical, to the amino acid sequence of SEQ ID NO: 71;
c) the VH comprises the amino acid sequence that is at least 90%, or at least 95% identical, to the amino acid sequence of SEQ ID NO: 90 or 60, preferably SEQ ID NO: 60, and the VL comprises the amino acid sequence that is at least 90%, or at least 95% identical, to the amino acid sequence of SEQ ID NO: 96;
d) the VH comprises the amino acid sequence that is at least 90%, or at least 95% identical, to the amino acid sequence of SEQ ID NO: 108 or 112, preferably SEQ ID NO: 112, and the VL comprises the amino acid sequence that is at least 90%, or at least 95% identical, to the amino acid sequence of SEQ ID NO: 71;
e) the VH comprises the amino acid sequence that is at least 90%, or at least 95% identical, to the amino acid sequence of SEQ ID NO: 112 and the VL comprises the amino acid sequence that is at least 90%, or at least 95% identical, to the amino acid sequence of SEQ ID NO: 96; or
f) the VH comprises the amino acid sequence that is at least 90%, or at least 95% identical, to the amino acid sequence of SEQ ID NO: 85 and the VL comprises the amino acid sequence that is at least 90%, or at least 95% identical, to the amino acid sequence of SEQ ID NO: 96.

16. The binding agent of embodiment 15, wherein the differences in amino acid sequence are not within the complementarity determining regions.

17. The binding agent of any one of embodiments 1 to 16, wherein the binding agent is an antibody or antigen-binding fragment thereof comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein:
(i) the VH comprises the amino acid sequence that is 90% to 99% identical, e.g, 90% to 98% identical, 95% to 97% identical, 96% or 97% identical, to the amino acid sequence of SEQ ID NO: 60, and wherein HCDR1 and HCDR3 of the binding agent are the same as HCDR1 and HCDR3 of SEQ ID NO: 60, respectively, and wherein HCDR2 of the binding agent is not the same as HCDR2 of SEQ ID NO: 60; and/or
(ii) the VL comprises the amino acid sequence that is 90% to 99%, e.g, 95% to 98% identical, 98%, to the amino acid sequence of SEQ ID NO: 71, and wherein LCDR1 and LCDR2 of the binding agent are the same as LCDR1 and LCDR2, respectively, of SEQ ID NO: 71, and wherein LCDR3 of the binding agent is not the same as LCDR3 of SEQ ID NO: 71.

18. The binding agent of any one of embodiments 15 to 17, wherein the differences in amino acid sequence are conservative substitutions.

19. The binding agent of any one of embodiments 1 to 18, wherein the binding agent is an antibody or antigen-binding fragment thereof comprising a heavy chain variable region (VH) and a light chain variable region (VL), wherein:
a) the VH comprises the amino acid sequence of SEQ ID NO: 124, and the VL comprises the amino acid sequence of SEQ ID NO: 127;
b) the VH comprises the amino acid sequence of SEQ ID NO: 78 or 85, preferably SEQ ID NO: 85, and the VL comprises the amino acid sequence of SEQ ID NO: 71;
c) the VH comprises the amino acid sequence of SEQ ID NO: 90 or 60, preferably SEQ ID NO: 60, and the VL comprises the amino acid sequence of SEQ ID NO: 96;
d) the VH comprises the amino acid sequence of SEQ ID NO: 108 or 112, preferably SEQ ID NO: 112 and the VL comprises the amino acid sequence of SEQ ID NO: 71;
e) the VH comprises the amino acid sequence of SEQ ID NO: 112 and the VL comprises the amino acid sequence of SEQ ID NO: 96; or
f) the VH comprises the amino acid sequence of SEQ ID NO: 85 and the VL comprises the amino acid sequence of SEQ ID NO: 96.

20. The binding agent of any one of embodiments 1 to 19, wherein the binding agent is an antibody or antigen-binding fragment thereof in a format selected from the list consisting of Fab, Fab', F(ab')2, Fv, and scFv.

21. The binding agent of embodiment 20, wherein the binding agent is a Fab fragment.

22. The binding agent of any one of embodiments 1 to 21, wherein the binding agent is an antibody comprising an Fc region.

23. The binding agent of embodiment 22, wherein the Fc region is selected from the group consisting of an Fc region from an IgG1, IgG2, IgG3, IgG4, IgA, IgM, IgE, and IgD.

24. The binding agent of embodiment 22 or 23, wherein the binding agent is an IgG1, IgG2, IgG3 or IgG4 isotype antibody.

25. The binding agent of any one of embodiments 1 to 24, wherein the binding agent is an isolated antibody.

26. The binding agent of any one of embodiments 1 to 25, wherein the binding agent is a monoclonal human antibody.
27. An antibody that specifically binds to an anti-FXI/FXIa antibody, in particular NOV1401, wherein the antibody comprises a heavy chain variable region (VH) comprising complementarity determining regions HCDR1, HCDR2, and HCDR3, and a light chain variable region (VL) comprising complementarity determining regions LCDR1, LCDR2, and LCDR3, wherein:
    a. the HCDR1 comprises the amino acid sequence selected from the group consisting of SEQ ID NO: 51, 54, 55 and 57, the HCDR2 comprises the amino acid sequence selected from the group consisting of SEQ ID NO: 52, 56, 58, 75, 76, 77, 105, 106, 107, 121, 122, and 123, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94, 95; 125, and 126, or
    b. the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76, 77, 105, 106, 107, 121, 122, and 123, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66, 69, 125, and 126.
28. The antibody of embodiment 27, wherein
    a) the HCDR1 comprises the amino acid sequence selected from the group consisting of SEQ ID NO: 51, 54, 55 and 57, the HCDR2 comprises the amino acid sequence selected from the group consisting of SEQ ID NO: 121, 122, and 123, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 125 and 126;
    b) the HCDR1 comprises the amino acid sequence selected from the group consisting of SEQ ID NO: 51, 54, 55 and 57, the HCDR2 comprises the amino acid sequence selected from the group consisting of SEQ ID NO: 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69;
    c) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76 and 77, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;
    d) the HCDR1 comprises the amino acid sequence selected from the group consisting of SEQ ID NO: 51, 54, 55 and 57, the HCDR2 comprises the amino acid sequence selected from the group consisting of SEQ ID NO: 52, 56 and 58, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;
    e) the HCDR1 comprises the amino acid sequence selected from the group consisting of SEQ ID NO: 51, 54, 55 and 57, the HCDR2 comprises the amino acid sequence selected from the group consisting of SEQ ID NO: 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95; or
    f) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76 and 77, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69.
29. The antibody of embodiment 27, wherein:
    a. the HCDR1 comprises the amino acid sequence of SEQ ID NO: 51, the HCDR2 comprises the amino acid sequence of SEQ ID NO: 52 or 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94; or b. the HCDR1 comprises the amino acid sequence of SEQ ID NO: 51, the HCDR2 comprises the amino acid sequence of SEQ ID NO: 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

30. The antibody of embodiment 29, wherein a) the HCDR1 comprises the amino acid sequence of SEQ ID NO: 51, the HCDR2 comprises the amino acid sequence of SEQ ID NO: 52, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

b) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

c) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

d) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66: or e) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

31. The antibody of embodiment 30, wherein:

a. the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

b. the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

c. the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

d. the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively;

e. the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 94, respectively 32. The antibody of any one of embodiments 27 to 31, wherein the antibody comprises a heavy chain variable region (VH) and a light chain variable region (VL), wherein:

a) the VH comprises the amino acid sequence that is at least 90%, or at least 95% identical, to the amino acid sequence of SEQ ID NO: 124, and the VL comprises the amino acid sequence that is at least 90%, or at least 95% identical, to the amino acid sequence of SEQ ID NO: 127;

b) the VH comprises the amino acid sequence that is at least 90% or at least 95% identical, to the amino acid sequence of SEQ ID NO: 78 or 85, preferably SEQ ID NO: 85, and the VL comprises the amino acid sequence that is at least 90% or at least 95% identical, to the amino acid sequence of SEQ ID NO: 71;

c) the VH comprises the amino acid sequence that is at least 90% or at least 95% identical, to the amino acid sequence of SEQ ID NO: 90 or 60, preferably SEQ ID NO: 60, and the VL comprises the amino acid sequence that is at least 90% or at least 95% identical, to the amino acid sequence of SEQ ID NO: 96;

d) the VH comprises the amino acid sequence that is at least 90% or at least 95% identical, to the amino acid sequence of SEQ ID NO: 108 or 112, preferably SEQ ID NO: 112, and the VL comprises the amino acid sequence that is at least 90% or at least 95% identical, to the amino acid sequence of SEQ ID NO: 71;

e) the VH comprises the amino acid sequence that is at least 90% or at least 95% identical, to the amino acid sequence of SEQ ID NO: 112 and the VL comprises the amino acid sequence that is at least 90% or at least 95% identical, to the amino acid sequence of SEQ ID NO: 96; or f) the VH comprises the amino acid sequence that is at least 90% or at least 95% identical, to the amino acid sequence of SEQ ID NO: 85 and the VL comprises the amino acid sequence that is at least 90% or at least 95% identical, to the amino acid sequence of SEQ ID NO: 96.

33. The antibody of embodiment 32 wherein the differences in amino acid sequence are not within the complementarity determining regions.

34. The antibody of embodiment 32 or embodiment 33, wherein the differences in amino acid sequence are conservative substitutions.

35. The antibody of any one of embodiments 27 to 34, wherein the antibody comprises a heavy chain variable region (VH) and a light chain variable region (VL), wherein:

a) the VH comprises the amino acid sequence of SEQ ID NO: 124, and the VL comprises the amino acid sequence of SEQ ID NO: 127;

b) the VH comprises the amino acid sequence of SEQ ID NO: 78 or 85, preferably SEQ ID NO: 85, and the VL comprises the amino acid sequence of SEQ ID NO: 71;

c) the VH comprises the amino acid sequence of SEQ ID NO: 90 or 60, preferably SEQ ID NO: 60, and the VL comprises the amino acid sequence of SEQ ID NO: 96;

d) the VH comprises the amino acid sequence of SEQ ID NO: 108 or 112, preferably SEQ ID NO: 112 and the VL comprises the amino acid sequence of SEQ ID NO: 71;

e) the VH comprises the amino acid sequence of SEQ ID NO: 112 and the VL comprises the amino acid sequence of SEQ ID NO: 96; or f) the VH comprises the amino acid sequence of SEQ ID NO: 85 and the VL comprises the amino acid sequence of SEQ ID NO: 96.

36. The antibody of any one of embodiments 27 to 35, wherein the antibody is in a format selected from the list consisting of Fab, Fab', F(ab')2, Fv, and scFv.

37. The antibody of embodiment 36, wherein the antibody is a Fab fragment.

38. The antibody of any one of embodiments 27 to 35, wherein the antibody comprises an Fc region.

39. The antibody of embodiment 38, wherein the Fc region is selected from the group consisting of an Fc region from an IgG1, IgG2, IgG3, IgG4, IgA, IgM, IgE, and IgD.

40. The antibody of embodiment 38 or 39, wherein the binding agent is an IgG1, IgG2, IgG3 or IgG4 isotype antibody.

41. The antibody of any one of embodiments 27 to 40, wherein the antibody is an isolated antibody.

42. The antibody of any one of embodiments 27 to 41, wherein the antibody is a monoclonal human antibody.

43. A polynucleotide comprising nucleotide sequences encoding the binding agent of any one of embodiments 1 to 26 or the antibody of any one of embodiments 27 to 42.

44. A vector comprising the polynucleotide of embodiment 43.

45. A host cell comprising the polynucleotide of embodiment 43 or the vector of embodiment 44.

46. A method of producing a binding agent or an antibody, said method comprises culturing the host cell of embodiment 45 under suitable conditions for expression of the binding agent or a portion thereof or the antibody, wherein the method optionally comprises purifying the binding agent or the antibody.

47. A pharmaceutical composition comprising the binding agent of any one of embodiments 1 to 26 or the antibody of any one of embodiments 27 to 42.

48. A pharmaceutical composition for use as a medicament for reversing the anticoagulant effect of an anti-FXI/FXIa antibody in a patient being treated with an anti-Factor XI/Factor XIa antibody, wherein the pharmaceutical composition comprises an effective amount of the binding agent of any one of embodiments 1 to 26 or the antibody of any one of embodiments 27 to 42.

49. The pharmaceutical composition of embodiment 48, wherein the anti-FXI/FXIa antibody comprises: (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9.

50. The binding agent of any one of embodiments 1 to 26 or the antibody of any one of embodiments 27 to 42 or the pharmaceutical composition of any one of embodiments 47 to 49 for use as a medicament.

51. The binding agent of any one of embodiments 1 to 26 or the antibody of any one of embodiments 26 to 41 or the pharmaceutical composition of any one of embodiments 47 to 49 for use in a manufacture of a medicament for reversing the anticoagulant effect of an anti-FXI/FXIa antibody.

52. The binding agent of any one of embodiments 1 to 26 or the antibody of any one of embodiments 26 to 41 or the pharmaceutical composition of any one of embodiments 47 to 49 for use in treatment of a patient, wherein said patient is being treated with an anti-FXI/FXIa antibody, and wherein said patient is in need of reversing the anticoagulant effect of said anti-FXI/FXIa antibody.

53. A method for reversing the anticoagulant effect of an anti-FXI/FXIa antibody in a patient being treated with the anti-FXI/FXIa antibody comprising administering an effective amount of the binding agent of any one of embodiments 1 to 25 or the antibody of any one of embodiments 27 to 42 or the pharmaceutical composition of any one of embodiments 47 to 49 to a patient in need thereof.

54. The method of embodiment 53, wherein the method further comprises applying one of the following to the patient: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant, activated factor VII.

55. The binding agent or the antibody or the composition of embodiment 51 or 52, or the method of embodiment 53 or embodiment 54, wherein the anti-FXI/FXIa antibody comprises (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9.

56. The binding agent or the antibody or the composition of any one of embodiments 51 or 52 or 55, or the method of any one of embodiments 53 to 55, wherein the patient has or is at risk of developing thrombosis.

57. The binding agent or the antibody or the composition of any one of embodiments 51, 52, 55 to 56, or the method of any one of embodiments 53 to 56, wherein the patient has a. atrial fibrillation;

b. suspected or confirmed cardiac arrhythmia such as paroxysmal, persistent or permanent atrial fibrillation or atrial flutter;

c. Chronic Thromboembolic Pulmonary Hypertension (CTEPH);

d. valvular heart disease with or without atrial fibrillation;

e. pulmonary hypertension;

f. congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia; or g. chronic kidney disease.

58. The binding agent or the antibody or the composition of any one of embodiments 51, 52, 53 to 57, or the method of any one of embodiments 53 to 57, wherein the patient has non-valvular atrial fibrillation.

59. The binding agent or the antibody or the composition of any one of embodiments 51, 52, 55 to 58, or the method of any one of embodiments 53 to 58, wherein the patient has a demonstrated high risk of bleeding.

60. The binding agent or the antibody or the composition of any one of embodiments 51, 52, 55 to 59, or the method of any one of embodiments 53 to 59, wherein the patient has chronic kidney disease.

61. The binding agent or the antibody or the composition or the method of embodiment 60, wherein patient has end stage renal disease (ESRD).

62. The binding agent or the antibody or the composition or the method of embodiment 61, wherein the patient has ESRD and is undergoing dialysis.

63. The binding agent or the antibody or the composition or the method of embodiment 62, wherein the patient has non-valvular atrial fibrillation.

64. The binding agent or the antibody or the composition of any one of embodiments 51, 52, 55 to 63, or the method of any one of embodiments 53 to 63, wherein the patient is being administered the anti-FXI/FXIa antibody to reduce the risk of stroke and/or systemic embolism.

65. The binding agent or the antibody or the composition of any one of embodiments 51, 52, 55 to 64, or the method of any one of embodiments 53 to 64, wherein reversal of the anticoagulant effect of the anti-FXI/FXIa antibody is needed for emergency surgery/urgent procedures and in life-threatening or uncontrolled bleeding.

66. A kit comprising the binding agent of any one of embodiments 1 to 26 or the antibody of any one of embodiments 27 to 42 and, optionally, instructions for use.

BRIEF DESCRIPTION OF THE DRAWINGS

FIG. 1A-FIG. 1D show Octet measurements for IDT1 (parental Fab, FIG. 1A) and affinity matured Fabs IDT1B (FIG. 1B), IDT1C (FIG. 1C), and IDT1A (FIG. 1D).

FIG. 2 shows CLUSTAL 2.1 multiple sequence alignments of heavy chains of Fabs IDT1 (SEQ ID NO: 62), IDT1A (SEQ ID NO: 62), IDT1B (SEQ ID NO: 119), IDT1C (SEQ ID NO: 116), IDT1D (SEQ ID NO: 116) and IDT1E (SEQ ID NO: 119). The HCDR1, HCDR2 and HCDR3 are underlined. The HCDR2 sequences differing from the HCDR2 sequence of IDT1 are highlighted.

FIG. 3 shows CLUSTAL 2.1 multiple sequence alignments of light chains of Fabs IDT1 (SEQ ID NO: 73), IDT1A (SEQ ID NO: 103), IDT1B (SEQ ID NO: 73), IDT1C (SEQ ID NO: 73), IDT1D (SEQ ID NO: 103) and IDT1E (SEQ ID NO: 103). The LCDR1, LCDR2 and LCDR3 are underlined. The LCDR3 sequences differing from the LCDR3 sequence of IDT1 are highlighted.

DETAILED DESCRIPTION

Terminology

Figure 4:
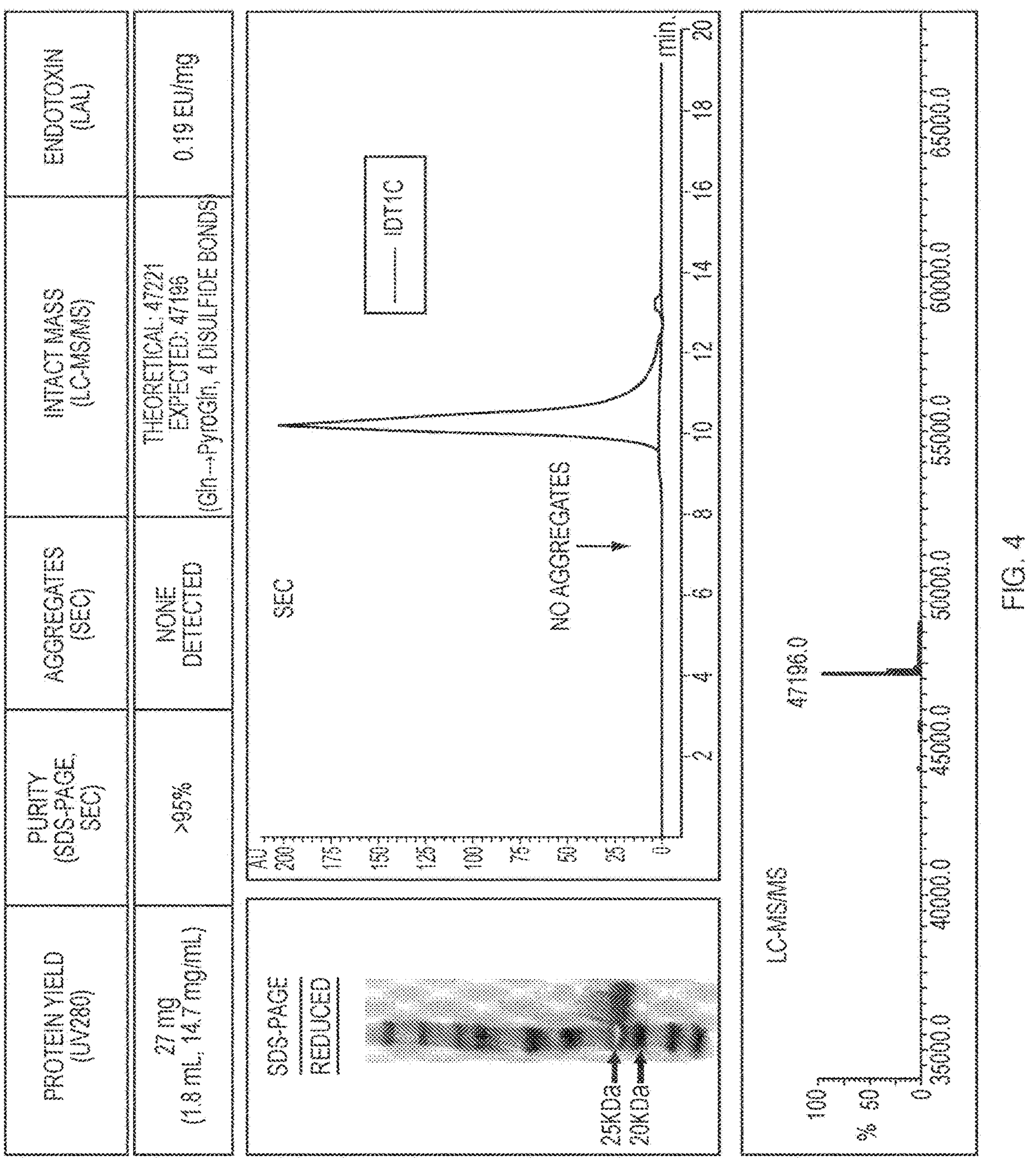
FIG. 4 shows the purification results for IDT1C: SDS-PAGE, SEC, LC-MS/MS, and LAL analyses of IDT1C.

Unless defined otherwise, all technical and scientific terms used herein have the same meaning as commonly understood by those of ordinary skill in the art to which this present disclosure pertains.

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely examples and that equivalents of such are known in the art.

The terms "binding agent", "reversal agent", and "antidote" are used interchangeably, and, in the context of an antibody which specifically binds to Factor XI and/or Factor XIa ("anti-FXI/FXIa antibody"), refer to a protein, polypeptide, or a complex thereof, such as an anti-idiotype antibody (e.g., whole antibody, IgG, Fab fragment), or an inactive FXI/FXIa-derived polypeptide or protein fragment that specifically binds to an anti-FXI/FXIa antibody, such as, the antigen-binding region(s) or variable region(s) of the anti-FXI/FXIa antibody. In specific embodiments provided herein, the binding agent is capable of reversing (e.g., partially reversing by at least 10%, at least 20%, at least 30%, at least 40%, at least 50%, at least 60%, at least 70%) one or more anticoagulant effects of the anti-FXI/FXIa antibody (e.g., antibody NOV1401). In further specific embodiments provided herein, the binding agent is capable of blocking binding of an anti-FXI/FXIa antibody to its antigen, e.g., FXI/FXIa. In a specific embodiment, as used herein, the terms "anti-NOV1401", "anti-NOV1401 antibody", "anti-NOV1401 Fab", "anti-NOV1401 IgG", "NOV1401 binding agent", "NOV1401 antidote", and the likes, are used interchangeably and refer to a binding agent or reversal agent, such as an anti-idiotype antibody (e.g., whole antibody, IgG, Fab fragment), which specifically binds to anti-Factor XI antibody NOV1401 (see Table 1). Non-limiting examples of NOV1401 binding/reversal agents are described herein, for example, Table 2.

The terms "FXI protein", "FXI antigen", and "FXI" are used interchangeably, and refer to the Factor XI protein in different species. Factor XI is the mammalian plasma coagulation factor XI, a glycoprotein present in human plasma at a concentration of 25-30 nM as a zymogen that when converted by limited proteolysis to an active serine protease, participates in the intrinsic pathway of blood coagulation.

The terms "FXIa protein", "FXIa antigen", and "FXIa" are used interchangeably, and refers to the activated FXI protein in different species. The zymogen Factor XI is converted into its active form, the coagulation factor XIa (FXIa), either via the contact phase of blood coagulation or through thrombin-mediated activation on the platelet surface. During this activation of factor XI, an internal peptide bond is cleaved in each of the two chains, resulting in the activated factor XIa, a serine protease composed of two heavy and two light chains held together by disulfide bonds. This serine protease FXIa converts the coagulation Factor IX into IXa, which subsequently activates coagulation Factor X (Xa). Xa then can mediate coagulation Factor II/Thrombin activation. For example, human FXI has the sequence as set out in Table 1 (SEQ ID NO: 1), and has been described in previous reports and literature (Mandle R J Jr, et al. (1979) Blood; 54(4):850; NCBI Reference Sequence: AAA51985).

In the context of this disclosure, the terms "FXI" and "FXIa" (and the like) include mutants and variants of the natural FXI and FXIa protein, respectively, which have substantially the same amino acid sequence as that of the native primary structure (amino acid sequence) described in the above-mentioned reports.

The term "antibody" as used herein means a whole antibody and any antigen binding fragment (i.e., "antigen-binding portion") or single chain thereof and is derived from an immunoglobulin ("Ig") molecule that specifically binds to an antigen. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. Antibodies can be of any isotype (e.g., immunoglobulin G (IgG), immunoglobulin E (IgE), immunoglobulin M (IgM), immunoglobulin D (IgD), immunoglobulin A (IgA) and immunoglobulin Y (IgY)), class (e.g., IgG1, IgG2, IgG3, IgG4, IgA1 and IgA2) or subclass. The term "IgG" or "IgG antibody" as used herein, and unless specified otherwise, means a type G whole antibody or Ig.

The terms "complementarity determining region" and "CDR", as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest", 5th Ed. Public Health Service, National Institutes of Health, Bethesda, MD ("Kabat" numbering scheme), Al-Lazikani et al., (1997) JMB 273, 927-948 ("Chothia" numbering scheme), or Lefranc et al., (2003) Dev. Comp. Immunol., 27, 55-77 ("IMGT" numbering scheme). Other methods for delineating the CDR regions may alternatively be used. For example, the CDR definitions of both Kabat and Chothia may be combined ("Combined" system).

For example, under Kabat, the CDR amino acid residues of an antibody in the heavy chain variable domain (VH) are numbered 31-35 (HCDR1), 50-66 (HCDR2), and 99-111 (HCDR3); and the CDR amino acid residues in the light chain variable domain (VL) are numbered 22-35 (LCDR1), 51-57 (LCDR2), and 90-100 (LCDR3). Under Chothia the CDR amino acids in the VH are numbered 26-32 (HCDR1), 52-57 (HCDR2), and 99-111 (HCDR3); and the amino acid residues in VL are numbered 25-33 (LCDR1), 51-53 (LCDR2), and 92-99 (LCDR3). By combining the CDR definitions of both Kabat and Chothia, the "Combined" CDRs consist of amino acid residues 26-35 (HCDR1), 50-66 (HCDR2), and 99-108 (HCDR3) in human VH and amino acid residues 24-38 (LCDR1), 54-60 (LCDR2), and 93-101 (LCDR3) in human VL. As another example, under IMGT, the CDR amino acid residues in the heavy chain variable domain (VH) are numbered 26-33 (HCDR1), 51-58 (HCDR2), and 97-108 (HCDR3); and the CDR amino acid residues in the light chain variable domain (VL) are numbered 27-36 (LCDR1), 54-56 (LCDR2), and 93-101 (LCDR3).

The term "antigen binding portion" or "antigen binding fragment" of an antibody, as used herein, refers to one or more fragments of an intact antibody that retain the ability to specifically bind to a given antigen (e.g., anti-FXI/FXIa antibody, such as NOV1401). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab')2 fragment, a bivalent fragment comprising two Fab fragments linked by a disulfide bridge at the hinge region; a Fab' fragment, a monovalent fragment derived by splitting F(ab')2 fragment into two Fab' fragments; an Fv fragment consisting of the VL and VH domains of a single arm of an antibody; a scFv fragment consisting of the VL and VH domains in a single protein chain.

Although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

In some specific embodiments, an antibody can be a monoclonal antibody, human antibody, humanized antibody, or chimeric antibody.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the present disclosure may include amino acid residues not encoded by human sequences (e.g., mutations introduced by random or site-specific mutagenesis in vitro or by somatic mutation in vivo).

The terms "monoclonal antibody" or "monoclonal antibody composition", as used herein, refer to a preparation of antibody molecules of single molecular composition. A monoclonal antibody composition displays a single binding specificity and affinity for a particular epitope.

The term "human monoclonal antibody" refers to antibodies displaying a single binding specificity which have variable regions in which both the framework and CDR regions are derived from human sequences. In one embodiment, the human monoclonal antibodies are prepared using phage display methods for screening libraries of human immunoglobulin genes.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isolated antibody" refers to an antibody that is substantially free of other antibodies having different antigenic specificities (e.g., an isolated antibody that specifically binds FXI and/or FXIa is substantially free of antibodies that specifically bind antigens other than FXI and/or FXIa, or an isolated anti-idiotype antibody that specifically binds an anti-FXI/FXIa antibody is substantially free of antibodies that specifically bind antigens other than the anti-FXI/FXIa antibody). An isolated antibody that specifically binds FXI and/or FXIa may, however, have cross-reactivity to other antigens. Moreover, an isolated antibody may be substantially free of other cellular material and/or chemicals.

The antibodies of the present disclosure are anti-idiotype antibodies. The terms "anti-idiotype antibody", "anti-Id antibody", and "anti-idiotypic antibody" are used interchangeably, and refer to an antibody (e.g., whole antibody, IgG, Fab fragment) that specifically binds to the antigen-binding region(s) of another antibody. Anti-idiotype antibodies are typically raised against the antigen-binding region(s) or complementarity determining regions (CDRs) (idiotype) of a target antibody. Anti-idiotype antibodies can be produced by various methods described previously, see, e.g., Pan et al., 1995, FASEB J. 9:43-49.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody (e.g., IgG, a Fab fragment) generally refers to an antibody having a $K_D$ of $5\times10^{-11}$ M or less (e.g., a $K_D$ of $4\times10^{-11}$ M or less, a $K_D$ of $3\times10^{-11}$ M or less, a $K_D$ of $2\times10^{-11}$ M or less, a $K_D$ of $10^{-11}$ M or less, etc.).

The term "kassoc" or "ka" or "$k_{on}$", as used herein, is intended to refer to the association rate of a particular antibody-antigen interaction, whereas the term "kdis" or "k" or "$k_{off}$" as used herein, is intended to refer to the dissociation rate of a particular antibody-antigen interaction. The term "KD", as used herein, is intended to refer to the dissociation constant, which is obtained from the ratio of kd to ka (i.e. kd/ka) and is expressed as a molar concentration (M). KD values for antibodies can be determined using methods well established in the art. Methods for determining the KD of an antibody include measuring surface plasmon resonance using a biosensor system such as a Biacorem system, or measuring affinity in solution by solution equilibrium titration (SET).

The term "binding specificity" as used herein refers to the ability of an individual antibody combining site to react with only one antigenic determinant.

As used herein, the terms "immunospecifically binds", "immunospecifically recognizes", "specifically binds", and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, Biacore™, KinExA 3000 instrument (Sapidyne Instruments, Boise, ID), or other assays known in the art. In a specific embodiment, molecules that immunospecifically bind to an antigen bind to the antigen with a Ka that is at least 2 logs, 2.5 logs, 3 logs, 4 logs or greater than the Ka when the molecules bind to another antigen. In another specific embodiment, molecules that immunospecifically bind to an antigen do not cross react with other proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the present disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The terms "identical" or percent "identity", in the context of two or more nucleic acids or polypeptide sequences, refer to two or more sequences or subsequences that are the same. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "FXI and/or FXIa mediated" refers to the fact that FXI and/or FXIa mediates the intrinsic and/or common coagulation pathways by directly or indirectly activating Factor IX (also known as FIX), Factor X (FX), and/or thrombin, and/or by binding to platelet receptors.

The term "hemostasis" represents the principal mechanisms for arresting the flow of blood at sites of injury and restoring vascular patency during wound healing, respectively. During normal hemostasis and pathological thrombosis, three mechanisms become activated simultaneously: primary hemostasis meaning the interactions of activated platelets with the vessel wall, the formation of fibrin, and a process termed as fibrinolysis.

The terms "coagulation and coagulation cascade", "cascade model of coagulation", and the like, refer to the protein-based system which serves to stabilize a clot that has formed to seal up a wound. The coagulation pathway is a proteolytic cascade. Each enzyme of the pathway is present in the plasma as a Zymogen (in an inactive form), which on activation undergoes proteolytic cleavage to release the active factor from the precursor molecule. The coagulation cascade functions as a series of positive and negative feedback loops which control the activation process. The ultimate goal of the pathway is to produce thrombin, which can then convert soluble fibrinogen into fibrin that forms a clot.

The process of generation of thrombin can be divided into three phases: the intrinsic and extrinsic pathways, which provide alternative routes for the generation of an active clotting factor: FXa (Activated Factor-X), and the final common pathway, which results in thrombin formation (Hoffman M. M. and Monroe D. M. (2005) Curr Hematol Rep. 4:391-396; Johne J, et al. (2006) Biol Chem. 387:173-178).

"Platelet aggregation" refers to the process whereby when a break in a blood vessel occurs, substances are exposed that normally are not in direct contact with the blood flow. These substances (primarily collagen and von Willebrand factor) allow the platelets to adhere to the broken surface. Once a platelet adheres to the surface, it releases chemicals that attract additional platelets to the damaged area, referred to as platelet aggregation. These two processes are the first responses to stop bleeding.

A "thromboembolic disorder", or similar terms as used herein, refer to any number of conditions or diseases in which the intrinsic and/or common coagulation pathways are aberrantly activated or are not naturally deactivated (e.g., without therapeutic means). These conditions include but are not limited to thrombic stroke, atrial fibrillation, stroke prevention in atrial fibrillation (SPAF), deep vein thrombosis, venous thromboembolism, and pulmonary embolism. These can also include catheter-related conditions (e.g., Hickman catheter in oncology patients) in which catheters become thrombosed, and extracorporeal membrane oxygenation (ECMO), in which the tubing develops clots.

A "thromboembolic" or similar terms as used herein, can also refer to any number of the following, which the anti-FXI and/or FXIa Abs, e.g., NOV1401, can be used to prevent or treat or to reduce the risk of:

thromboembolism in subjects with suspected or confirmed cardiac arrhythmia such as paroxysmal, persistent or permanent atrial fibrillation or atrial flutter;

stroke prevention in atrial fibrillation (SPAF), a subpopulation of which is AF patients undergoing percutaneous coronary interventions (PCI);

acute venous thromboembolic events (VTE) treatment and extended secondary VTE prevention in patients at high risk for bleeding;

cerebral and cardiovascular events in secondary prevention after transient ischemic attack (TIA) or non-disabling stroke and prevention of thromboembolic events in heart failure with sinus rhythm;

clot formation in left atrium and thromboembolism in subjects undergoing cardioversion for cardiac arrhythmia;

thrombosis before, during and after ablation procedure for cardiac arrhythmia;

venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;

thrombosis on any artificial surface in the veins like catheter or pacemaker wires;

pulmonary embolism in patients with or without venous thrombosis;

Chronic Thromboembolic Pulmonary Hypertension (CTEPH);

arterial thrombosis on ruptured atherosclerotic plaque, thrombosis on intra-arterial prosthesis or catheter and thrombosis in apparently normal arteries, this includes but not limited to acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;

thrombosis and thromboembolism in patients undergoing percutaneous coronary interventions (PCI);

cardioembolic and cryptogenic strokes;

thrombosis in patients with invasive and non-invasive cancer malignancies;

thrombosis over an indwelling catheter;

thrombosis and thromboembolism in severely ill patients;

cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;

thromboembolism in patients with valvular heart disease with or without atrial fibrillation;

thromboembolism over valvular mechanic or biologic prostheses;

thromboembolism in patients who had native or artificial cardiac patches, arterial or venous conduit tubes after heart repair of simple or complex cardiac malformations;

venous thrombosis and thromboembolism after knee replacement surgery, hip replacement surgery, and orthopedic surgery, thoracic or abdominal surgery;

arterial or venous thrombosis after neurosurgery including intracranial and spinal cord interventions;

congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;

thrombosis and thromboembolism in chronic kidney disease; and thrombosis and thromboembolism in patients undergoing hemodialysis and in patients undergoing extra-corporal membrane oxygenation.

The term "subject" includes human and non-human animals. Non-human animals include all vertebrates (e.g., mammals and non-mammals) such as, non-human primates (e.g., cynomolgus monkey), sheep, rabbit, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*). In some specific embodiments provided herein, a patient or a subject is a human.

As used herein, the terms "manage", "managing", and "management" refer to the beneficial effects that a subject derives from a therapy (e.g., a prophylactic or therapeutic agent), which does not result in a cure of a disease, disorder, or condition (e.g., thrombosis or thromboembolic disorder). In certain embodiments, a subject is administered one or more therapies (e.g., NOV1401) to "manage" thrombosis or thromboembolic disorder, one or more symptoms thereof, so as to prevent the progression or worsening of the condition or disorder.

As used herein, the term "treating" or "treatment" of any disease or disorder or condition (e.g., a thromboembolic disorder, a high risk of bleeding in a patient treated with an anti-FXI/FXIa antibody) refers in one embodiment, to ameliorating the disease or disorder (i.e., slowing or arresting or reducing the development of the disease or at least one of the clinical symptoms thereof). In another embodiment, the term "treating" or "treatment" refers to reversing an effect of another treatment, e.g., reversing the anticoagulant effect of a anti-FXI/FXIa antibody, e.g., NOV1401, in a patient in need of such reversal.

In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., a thromboembolic disorder, means any action that prevents or slows a worsening in e.g., a thromboembolic disease parameters, as described below, in a patient at risk for being afflicted with a thromboembolic disorder or at risk for said worsening.

Factor XI/XIa and Anti-Factor XI/FXIa Antibodies

This section describes exemplary anti-FXI/FXIa antibodies (e.g., antibodies described in Table 1) to which reversal binding agents provided herein (e.g., anti-idiotype antibodies) specifically bind, wherein reversal binding agents are capable of reversing (e.g., partially reversing, for example, by at least 40%, at least 50%, at least 60%, at least 70%, at least 75%, at least 80%, or at least 85%) one or more anticoagulant effects of such anti-FXI/FXIa antibodies and/or inhibits binding of such anti-FXI/FXIa antibodies to FXI and/or FXIa.

FXI holds important roles in both intrinsic and extrinsic coagulation pathways and in bridging the initiation and amplification phases of plasmatic hemostasis. Both Factor XIIa and thrombin can activate FXI, resulting in a sustained thrombin generation and fibrinolysis inhibition. FXI plays a minor role in normal hemostasis in a high tissue factor environment "after vessel injury" whereas it appears to play a key role in thrombosis. Severe Factor XI deficiency is associated with a lower incidence of ischemic stroke and venous thromboembolic events (Salomon et al 2008; Salomon, et al. (2011) Thromb Haemost.; 105:269-73). Bleeding manifestations in subjects with severe factor XI deficiency are infrequent, often mild, injury-induced and affect preferably tissues with increased fibrinolytic activity such as the oral mucosa, nasal mucosa and urinary tract (Salomon et al 2011). Bleeding in critical organs is extremely rare or not existing.

Table 1 provides exemplary amino acid sequences and corresponding encoding nucleotide sequences for human FXI and anti-FXI/FXIa antibodies, for example, antibodies NOV1401. In particular, Table 1 provides the following amino acid sequences for antibodies NOV1401, NOV1090, AM1, AM2, AM3, and AM4, as well as corresponding encoding nucleotide sequences: heavy chain variable region (VH), light chain variable region (VL), heavy chain, light chain. In specific embodiments, reversal binding agents provided herein specifically bind to an anti-FXI/FXIa antibody described in Table 1 and is capable of inhibiting (e.g., in a dose dependent manner) binding of the anti-FXI/FXIa antibody to human FXI/FXIa, and/or of reversing one or more anticoagulant activities of the anti-FXI/FXIa antibody. In specific embodiments, reversal binding agents provided herein (e.g., anti-idiotype antibody) specifically bind to anti-FXI/FXIa antibody NOV1401, NOV1090, AM1, AM2, AM3, and/or AM4, and are capable of inhibiting binding of the anti-FXI/FXIa antibody to human FXI/FXIa and/or are capable of reversing an anticoagulant effect of the anti-FXI/FXIa antibody.

Other anti-FXI/FXIa antibodies described in Table 1 herein include NOV1090, AM1, AM2, AM3, and AM4. Antibodies NOV1401 and NOV1090 share the same CDRs. Antibodies AM1, AM2, AM3, and AM4 are exemplary affinity matured variants of antibody NOV1090.

In particular embodiments, an anti-FXI/FXIa antibody has one or more of the following anticoagulant activities, which can be reversed (e.g., partially reversed, for example, by at least 40%, at least 50%, at least 60%, at least 70%, at least 75%, at least 80%, or at least 85%) by a reversal binding agent (e.g., anti-idiotype antibody) provided herein: (i) aPTT prolongation as determined by aPTT assay, and (ii) inhibition of Factor XI activity. These activities can be readily measured with assays described in the art and provided herein. For example, aPTT assay is described in the art and herein (e.g., Examples Section). In further embodiments, other biomarkers of the extrinsic coagulation pathway can be measured to determine anticoagulant activity, for example, prothrombin time (PT) assay and thrombin time (TT) assay. Other, non-limiting examples of assays for anticoagulation/coagulation activity include TGA assay, chromogenic assays such as ecarin chromogenic assay (ECA), ecarin clotting time (ECT) assay, and anti-Factor Xa activity assay. In specific embodiments, reversal binding agents provided herein (e.g., anti-idiotype antibodies) are capable of reversing (e.g., partially reversing, for example, by at least 40%, at least 50%, at least 60%, at least 70%, at least 75%, at least 80%, or at least 85%) one or more of these anticoagulant activities. In particular embodiments, reversal binding agents provided herein are capable of reducing the bleeding time in patients administered an anti-FXI/FXIa antibody.

TABLE 1

Examples of FXI/FXIa Antibodies and FXI/FXIa Proteins

| Sequence Description | Sequence Identifier (SEQ ID NO:) | Amino acid or polynucleotide sequence |
|---|---|---|
| Human FXI full-length protein sequence (NCBI Reference Sequence: AAA51985) | 1 | MIFLYQVVHFILFTSVSGEC VTQLLKDTCFEGGDITTVFT PSAKYCQVVCTYHPRCLLFT FTAESPSEDPTRWFTCVLKD SVTETLPRVNRTAAISGYSF KQCSHQISACNKDIYVDLDM KGINYNSSVAKSAQECQERC TDDVHCHFFTYATRQFPSLE HRNICLLKHTQTGTPTRITK LDKVVSGFSLKSCALSNLAC IRDIFPNTVFADSNIDSVMA PDAFVSGRICTHHPGCLFFT FFSQEWPKESQRNLCLLKTS ESGLPSTRIKKSKALSGFSL QSCRHSIPVFCHSSFYHDTD FLGEELDIVAAKSHEACQKL CTNAVRCQFFTYTPAQASCN EGKGKCYLKLSSNGSPTKIL HGRGGISGYTLRLCKMDNEC TTKIKPRIVGGTASVRGEWP WQVTLHTTSPTQRHLCGGSI IGNQWILTAAHCFYGVESPK ILRVYSGILNQSEIKEDTSF FGVQEIIIHDQYKMAESGYD IALLKLETTVNYTDSQRPIC LPSKGDRNVIYTDCWVTGWG YRKLRDKIQNTLQKAKIPLV TNEECQKRYRGHKITHKMIC AGYREGGKDACKGDSGGPLS CKHNEVWHLVGITSWGEGCA QRERPGVYTNVVEYVDWILE KTQAV |
| Human FXI full-length nucleotide sequence (NCBI Reference Sequence: NM_000128.3) | 2 | AGGCACACAGGCAAAATCAA GTTCTACATCTGTCCCTGTG TATGTCACTTGTTTGAATAC GAAATAAAATTAAAAAAATA AATTCAGTGTATTGAGAAAG CAAGCAATTCTCTCAAGGTA TATTTCTGACATACTAAGAT TTTAACGACTTTCACAAATA TGCTGTACTGAGAGAGAATG TTACATAACATTGAGAACTA GTACAAGTAAATATTAAAGT GAAGTGACCATTTCCTACAC AAGCTCATTCAGAGGAGGAT GAAGACCATTTTGGAGGAAG AAAAGCACCCTTATTAAGAA TTGCAGCAAGTAAGCCAACA AGGTCTTTTCAGGATGATTT TCTTATATCAAGTGGTACAT TTCATTTTATTTACTTCAGT TTCTGGTGAATGTGTGACTC AGTTGTTGAAGGACACCTGC TTTGAAGGAGGGGACATTAC TACGGTCTTCACACCAAGCG |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | CCAAGTACTGCCAGGTAGTC TGCACTTACCACCCAAGATG TTTACTCTTCACTTTCACGG CGGAATCACCATCTGAGGAT CCCACCCGATGGTTTACTTG TGTCCTGAAAGACAGTGTTA CAGAAACACTGCCAAGAGTG AATAGGACAGCAGCGATTTC TGGGTATTCTTTCAAGCAAT GCTCACACCAAATAAGCGCT TGCAACAAAGACATTTATGT GGACCTAGACATGAAGGGCA TAAACTATAACAGCTCAGTT GCCAAGAGTGCTCAAGAATG CCAAGAAAGATGCACGGATG ACGTCCACTGCCACTTTTTC ACGTACGCCACAAGGCAGTT TCCCAGCCTGGAGCATCGTA ACATTTGTCTACTGAAGCAC ACCCAAACAGGGACACCAAC CAGAATAACGAAGCTCGATA AAGTGGTGTCTGGATTTTCA CTGAAATCCTGTGCACTTTC TAATCTGGCTTGTATTAGGG ACATTTTCCCTAATACGGTG TTTGCAGACAGCAACATCGA CAGTGTCATGGCTCCCGATG CTTTTGTCTGTGGCCGAATC TGCACTCATCATCCCGGTTG CTTGTTTTTTACCTTCTTTT CCCAGGAATGGCCCAAAGAA TCTCAAAGAAATCTTTGTCT CCTTAAAACATCTGAGAGTG GATTGCCCAGTACACGCATT AAAAAGAGCAAAGCTCTTTC TGGTTTCAGTCTACAAAGCT GCAGGCACAGCATCCCAGTG TTCTGCCATTCTTCATTTTA CCATGACACTGATTTCTTGG GAGAAGAACTGGATATTGTT GCTGCAAAAAGTCACGAGGC CTGCCAGAAACTGTGCACCA ATGCCGTCCGCTGCCAGTTT TTTACCTATACCCCAGCCCA AGCATCCTGCAACGAAGGGA AGGGCAAGTGTTACTTAAAG CTTTCTTCAAACGGATCTCC AACTAAAATACTTCACGGGA GAGGAGGCATCTCTGGATAC ACATTAAGGTTGTGTAAAAT GGATAATGAGTGTACCACCA AAATCAAGCCCAGGATCGTT GGAGGAACTGCGTCTGTTCG TGGTGAGTGGCCGTGGCAGG TGACCCTGCACACAACCTCA CCCACTCAGAGACACCTGTG TGGAGGCTCCATCATTGGAA ACCAGTGGATATTAACAGCC GCTCACTGTTTCTATGGGGT AGAGTCACCTAAGATTTTGC GTGTCTACAGTGGCATTTTA AATCAATCTGAAATAAAAGA GGACACATCTTTCTTTGGGG TTCAAGAAATAATAATCCAT GATCAGTATAAAATGGCAGA AAGCGGGTATGATATTGCCT TGTTGAAACTGGAAACCACA GTGAATTACACAGATTCTCA ACGACCCATATGCCTGCCTT CCAAAGGAGATAGAAATGTA |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | ATATACACTGATTGCTGGGTGACTGGATGGGGGTACAGAAAACTAAGAGACAAAATACAAAATACTCTCCAGAAAGCCAAGATACCCTTAGTGACCAACGAAGAGTGCCAGAAGAGATACAGAGGACATAAAATAACCCATAAGATGATCTGTGCCGGCTACAGGGAAGGAGGGAAGGACGCTTGCAAGGGAGATTCGGGAGGCCCTCTGTCCTGCAAACACAATGAGGTCTGGCATCTGGTAGGCATCACGAGCTGGGGCGAAGGCTGTGCTCAAAGGGAGCGGCCAGGTGTTTACACCAACGTGGTCGAGTACGTGGACTGGATTCTGGAGAAAACTCAAGCAGTGTGAATGGGTTCCCAGGGGCCATTGGAGTCCCTGAAGGACCCAGGATTTGCTGGGAGAGGGTGTTGAGTTCACTGTGCCAGCATGCTTCCTCCACAGTAACACGCTGAAGGGGCTTGGTGTTTGTAAGAAAATGCTAGAAGAAAACAAACTGTCACAAGTTGTTATGTCCAAAACTCCCGTTCTATGATCGTTGTAGTTTGTTTGAGCATTCAGTCTCTTTGTTTTTGATCACGCTTCTATGGAGTCCAAGAATTACCATAAGGCAATATTTCTGAAGATTACTATATAGGCAGATATAGCAGAAAATAACCAAGTAGTGGCAGTGGGGATCAGGCAGAAGAACTGGTAAAAGAAGCCACCATAAATAGATTTGTTCGATGAAAGATGAAAACTGGAAGAAAGGAGAACAAAGACAGTCTTCACCATTTTGCAGGAATCTACACTCTGCCTATGTGAACACATTTCTTTTGTAAAGAAAGAAATTGATTGCATTTAATGGCAGATTTTCAGAATAGTCAGGAATTCTTGTCATTTCCATTTTAAAATATATATTAAAAAAAATCAGTTCGAGTAGACACGAGCTAAGAGTGAATGTGAAGATAACAGAATTTCTGTGTGGAAGAGGATTACAAGCAGCAATTTACCTGGAAGTGATACCTTAGGGGCAATCTTGAAGATACACTTTCCTGAAAAATGATTTGTGATGGATTGTATATTTATTTAAAATATCTTGGGAGGGGAGGCTGATGGAGATAGGGAGCATGCTCAAACCTCCCTAAGACAAGCTGCTGCTGTGACTATGGGCTCCCAAAGAGCTAGATCGTATATTTATTTGACAAAAATCACCATAGACTGCATCCATACTACAGAGAAAAAACAATTAGGGCGCAAATGGATAGTTACAGTAAAGTCTTCAGCAAGCAGCTGCCTGTATTCTAAGCACTGGGATTTTCTGTTTCGTGCAAATATTTATCTCATTATTGTTGTGATCTAGTTCAATAACCTAGAATTTGAATTGTCACCACATAGCTTTCAATCTGTGCCAACAACTATACAATTCATCAAGTGTG |
| NOV1401 | | |
| VH | 3 | QVQLLESGGGLVQPGGSLRLSCAASGFTFSTAAMSWVRQAPGKGLEWVSGISGSGSSTYYADSVKGRFTISRDNSKNTLYLQMNSLRAEDTAVYYCARELSYLYSGYYFDYWGQGTLVTVSS |
| DNA encoding VH | 4 | CAGGTGCAGCTGCTGGAATCAGGCGGCGGACTGGTGCAGCCTGGCGGTAGCCTGAGACTGAGCTGCGCTGCTAGTGGCTTCACCTTTAGCACCGCCGCTATGAGCTGGGTTCGACAGGCCCCAGGGAAAGGCCTCGAGTGGGTCTCAGGGATTAGCGGTAGCGGCTCTAGCACCTACTACGCCGATAGCGTGAAGGGCCGGTTCACTATCTCTAGGGATAACTCTAAGAACACCCTGTACCTGCAGATGAATAGCCTGAGAGCCGAGGACACCGCCGTCTACTACTGCGCTAGAGAGCTGAGCTACCTGTATAGCGGCTACTACTTCGACTACTGGGGTCAAGGCACCCTGGTCACCGTGTCTAGC |
| Heavy Chain | 5 | QVQLLESGGGLVQPGGSLRLSCAASGFTFSTAAMSWVRQAPGKGLEWVSGISGSGSSTYYADSVKGRFTISRDNSKNTLYLQMNSLRAEDTAVYYCARELSYLYSGYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALAAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DNA encoding Heavy Chain | 6 | CAGGTGCAGCTGCTGGAATCAGGCGGCGGACTGGTGCAGCCTGGCGGTAGCCTGAGACTGAGCTGCGCTGCTAGTGGCTTCACCTTTAGCACCGCCGCTATGAGCTGGGTTCGACAGGCCCCAGGGAAAGGCCTCGAGTGGGTCTCAGGGATTAGCGGTAGCGGCTCTAGCACCTACTACGCCGATAGCGTGAAGGGCCGGTTCACTATCTCTAGGGATAACTCTAAGAACACCCTGTAC |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | CTGCAGATGAATAGCCTGAGAGCCGAGGACACCGCCGTCTACTACTGCGCTAGAGAGCTGAGCTACCTGTATAGCGGCTACTACTTCGACTACTGGGGTCAAGGCACCCTGGTCACCGTGTCTAGCGCTAGCACTAAGGGCCCCTCCGTGTTCCCTCTGGCCCCTTCCAGCAAGTCTACCTCCGGCGGCACAGCTGCTCTGGGCTGCCTGGTCAAGGACTACTTCCCTGAGCCTGTGACAGTGTCCTGGAACTCTGGCGCCCTGACCTCTGGCGTGCACACCTTCCCTGCCGTGCTGCAGTCCTCCGGCCTGTACTCCCTGTCCTCCGTGGTCACAGTGCCTTCAAGCAGCCTGGGCACCCAGACCTATATCTGCAACGTGAACCACAAGCCTTCCAACACCAAGGTGGACAAGCGGGTGGAGCCTAAGTCCTGCGACAAGACCCACACCTGTCCTCCCTGCCCTGCTCCTGAACTGCTGGGCGGCCCTTCTGTGTTCCTGTTCCCTCCAAAGCCCAAGGACACCCTGATGATCTCCCGGACCCCTGAAGTGACCTGCGTGGTGGTGGCCGTGTCCCACGAGGATCCTGAAGTGAAGTTCAATTGGTACGTGGACGGCGTGGAGGTGCACAACGCCAAGACCAAGCCTCGGGAGGAACAGTACAACTCCACCTACCGGGTGGTGTCCGTGCTGACCGTGCTGCACCAGGACTGGCTGAACGGCAAAGAGTACAAGTGCAAAGTCTCCAACAAGGCCCTGGCCGCCCCTATCGAAAAGACAATCTCCAAGGCCAAGGGCCAGCCTAGGGAACCCCAGGTGTACACCCTGCCACCCAGCCGGGAGGAAATGACCAAGAACCAGGTGTCCCTGACCTGTCTGGTCAAGGGCTTCTACCCTTCCGATATCGCCGTGGAGTGGGAGTCTAACGGCCAGCCTGAGAACAACTACAAGACCACCCCTCCTGTGCTGGACTCCGACGGCTCCTTCTTCCTGTACTCCAAACTGACCGTGGACAAGTCCCGGTGGCAGCAGGGCAACGTGTTCTCCTGCTCCGTGATGCACGAGGCCCTGCACAACCACTACACCCAGAAGTCCCTGTCCCTGTCTCCCGGCAAG |
| VL | 7 | QSVLTQPPSASGTPGQRVTISCSGSSSNIGSNDVSWYQQLPGTAPKLLIYKNYNRPSGVPDRFSGSKSGTSASLAISGLQSEDEADYYCSAWDQRQFDVVFGGGTKLTVL |
| DNA encoding VL | 8 | CAGTCAGTCCTGACTCAGCCCCCTAGCGCTAGTGGCACCCCTGGTCAAAGAGTGACTATTAGCTGTAGCGGCTCTAGCTCTAATATCGGCTCTAACGACGTCAGCTGGTATCAGCAGCTGCCCGGCACCGCCCCTAAGCTGCTGATCTATAAGAACTATAATAGGCCTAGCGGCGTGCCCGATAGGTTTAGCGGATCTAAATCAGGGACTTCTGCTAGTCTGGCTATTAGCGGCCTGCAGTCAGAGGACGAGGCCGACTACTACTGTAGCGCCTGGGATCAGCGTCAGTTCGACGTGGTGTTCGGCGGAGGCACTAAGCTGACCGTGCTG |
| Light Chain | 9 | QSVLTQPPSASGTPGQRVTISCSGSSSNIGSNDVSWYQQLPGTAPKLLIYKNYNRPSGVPDRFSGSKSGTSASLAISGLQSEDEADYYCSAWDQRQFDVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| DNA encoding Light Chain | 10 | CAGTCAGTCCTGACTCAGCCCCCTAGCGCTAGTGGCACCCCTGGTCAAAGAGTGACTATTAGCTGTAGCGGCTCTAGCTCTAATATCGGCTCTAACGACGTCAGCTGGTATCAGCAGCTGCCCGGCACCGCCCCTAAGCTGCTGATCTATAAGAACTATAATAGGCCTAGCGGCGTGCCCGATAGGTTTAGCGGATCTAAATCAGGGACTTCTGCTAGTCTGGCTATTAGCGGCCTGCAGTCAGAGGACGAGGCCGACTACTACTGTAGCGCCTGGGATCAGCGTCAGTTCGACGTGGTGTTCGGCGGAGGCACTAAGCTGACCGTGCTGGGTCAACCTAAGGCTGCCCCCAGCGTGACCCTGTTCCCCCCCAGCAGCGAGGAGCTGCAGGCCAACAAGGCCACCCTGGTGTGCCTGATCAGCGACTTCTACCCAGGCGCCGTGACCGTGGCCTGGAAGGCCGACAGCAGCCCCGTGAAGGCCGGCGTGGAGACCACCACCCCCAGCAAGCAGAGCAACAACAAGTACGCCGCCAGCAGCTACCTGAGCCTGACCCCCGAGCAGTGGAAGAGCCACAGGTCCTACAGCTGCCAGGTGACCCACGAGGGCAGCACCGTGGAAAAGACCGTGGCCCCAACCGAGTGCAGC |
| NOV1090 | | |
| VH | 11 | QVQLLESGGGLVQPGGSLRLSCAASGFTFSTAAMSWVRQAPGKGLEWVSGISGSGSSTYYADSVKGRFTISRDNSKNTLYLQMNSLRAEDTAVYYCARELSYLYSGYYFDYWGQGTLVTVSS |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| DNA encoding VH | 12 | CAGGTGCAATTGCTGGAAAGCGGCGGTGGCCTGGTGCAGCCGGGTGGCAGCCTGCGTCTGAGCTGCGCGGCGTCCGGATTCACCTTTTCTACTGCTGCTATGTCTTGGGTGCGCCAGGCCCCGGGCAAAGGTCTCGAGTGGGTTTCCGGTATCTCTGGTTCTGGTTCTTCTACCTACTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTGAACTGTCTTACCTGTACTCTGGTTACTACTTCGATTACTGGGGCCAAGGCACCCTGGTGACTGTTAGCTCA |
| Heavy Chain | 13 | QVQLLESGGGLVQPGGSLRLSCAASGFTFSTAAMSWVRQAPGKGLEWVSGISGSGSSTYYADSVKGRFTISRDNSKNTLYLQMNSLRAEDTAVYYCARELSYLYSGYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DNA encoding Heavy Chain | 14 | CAGGTGCAATTGCTGGAAAGCGGCGGTGGCCTGGTGCAGCCGGGTGGCAGCCTGCGTCTGAGCTGCGCGGCGTCCGGATTCACCTTTTCTACTGCTGCTATGTCTTGGGTGCGCCAGGCCCCGGGCAAAGGTCTCGAGTGGGTTTCCGGTATCTCTGGTTCTGGTTCTTCTACCTACTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTGAACTGTCTTACCTGTACTCTGGTTACTACTTCGATTACTGGGGCCAAGGCACCCTGGTGACTGTTAGCTCAGCCTCCACCAAGGGTCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAAGCAGCGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGGGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA |
| VL | 15 | DIVLTQPPSVSGAPGQRVTISCSGSSSNIGSNDVSWYQQLPGTAPKLLIYKNYNRPSGVPDRFSGSKSGTSASLAITGLQAEDEADYYCSAWDQRQFDVVFGGGTKLTVL |
| DNA encoding VL | 16 | GATATCGTGCTGACCCAGCCGCCGAGCGTGAGCGGTGCACCGGGCCAGCGCGTGACCATTAGCTGTAGCGGCAGCAGCAGCAACATTGGTTCTAACGACGTGTCTTGGTACCAGCAGCTGCCGGGCACGGCGCCGAAACTGCTGATCTACAAAAACTACAACCGCCCGAGCGGCGTGCCGGATCGCTTTAGCGGATCCAAAAGCGGCACCAGCGCCAGCCTGGCGATTACCGGCCTGCAAGCAGAAGACGAAGCGGATTATTACTGCTCTGCTTGGGACCAGCGTCAGTTCGACGTTGTGTTTGGCGGCGGCACGAAGTTAACCGTCCTA |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| Light Chain | 17 | DIVLTQPPSVSGAPGQRVTISCSGSSSNIGSNDVSWYQQLPGTAPKLLIYKNYNRPSGVPDRFSGSKSGTSASLAITGLQAEDEADYYCSAWDQRQFDVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| DNA encoding Light Chain | 18 | GATATCGTGCTGACCCAGCCGCCGAGCGTGAGCGGTGCACCGGGCCAGCGCGTGACCATTAGCTGTAGCGGCAGCAGCAGCAACATTGGTTCTAACGACGTGTCTTGGTACCAGCAGCTGCCGGGCACGGCGCCGAAACTGCTGATCTACAAAAACTACAACCGCCCGAGCGGCGTGCCGGATCGCTTTAGCGGATCCAAAAGCGGCACCAGCGCCAGCCTGGCGATTACCGGCCTGCAAGCAGAAGACGAAGCGGATTATTACTGCTCTGCTTGGGACCAGCGTCAGTTCGACGTTGTGTTTGGCGGCGGCACGAAGTTAACCGTCCTAGGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTATCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCA |
| AM1 | | |
| VH | 19 | QVQLLESGGGLVQPGGSLRLSCAASGFTFSTAAMSWVRQAPGKGLEWVSTIDSWGDDTDYADSVKGRFTISRDNSKNTLYLQMNSLRAEDTAVYYCARELSYLYSGYYFDYWGQGTLVTVSS |
| DNA VH | 20 | CAGGTGCAATTGCTGGAAAGCGGCGGTGGCCTGGTGCAGCCGGGTGGCAGCCTGCGTCTGAGCTGCGCGGCGTCCGGATTCACCTTTTCTACTGCTGCTATGTCTTGGGTGCGCCAGGCCCCGGGCAAAGGTCTCGAGTGGGTTTCCACTATCGACTCTTGGGGCGACGACACTGACTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTGAACTGTCTTACCTGTACTCTGGTTACTACTTCGATTACTGGGGCCAAGGCACCCTGGTGACTGTTAGCTCA |
| Heavy Chain | 21 | QVQLLESGGGLVQPGGSLRLSCAASGFTFSTAAMSWVRQAPGKGLEWVSTIDSWGDDTDYADSVKGRFTISRDNSKNTLYLQMNSLRAEDTAVYYCARELSYLYSGYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DNA Heavy Chain | 22 | CAGGTGCAATTGCTGGAAAGCGGCGGTGGCCTGGTGCAGCCGGGTGGCAGCCTGCGTCTGAGCTGCGCGGCGTCCGGATTCACCTTTTCTACTGCTGCTATGTCTTGGGTGCGCCAGGCCCCGGGCAAAGGTCTCGAGTGGGTTTCCACTATCGACTCTTGGGGCGACGACACTGACTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTGAACTGTCTTACCTGTACTCTGGTTACTACTTCGATTACTGGGGCCAAGGCACCCTGGTGACTGTTAGCTCAGCCTCCACCAAGGGTCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAAGCAGCGGGGGGACCGTCAGTCTTCCTCTTCCCCCCAAAACCCAAGGACACCCTCATGATCTCCCGG |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | ACCCCTGAGGTCACATGCGT GGTGGTGGACGTGAGCCACG AAGACCCTGAGGTCAAGTTC AACTGGTACGTGGACGGCGT GGAGGTGCATAATGCCAAGA CAAAGCCGCGGGAGGAGCAG TACAACAGCACGTACCGGGT GGTCAGCGTCCTCACCGTCC TGCACCAGGACTGGCTGAAT GGCAAGGAGTACAAGTGCAA GGTCTCCAACAAAGCCCTCC CAGCCCCCATCGAGAAAACC ATCTCCAAAGCCAAAGGGCA GCCCCGAGAACCACAGGTGT ACACCCTGCCCCCATCCCGG GAGGAGATGACCAAGAACCA GGTCAGCCTGACCTGCCTGG TCAAAGGCTTCTATCCCAGC GACATCGCCGTGGAGTGGGA GAGCAATGGGCAGCCGGAGA ACAACTACAAGACCACGCCT CCCGTGCTGGACTCCGACGG CTCCTTCTTCCTCTACAGCA AGCTCACCGTGGACAAGAGC AGGTGGCAGCAGGGGAACGT CTTCTCATGCTCCGTGATGC ATGAGGCTCTGCACAACCAC TACACGCAGAAGAGCCTCTC CCTGTCTCCGGGTAAA |
| VL | 23 | DIVLTQPPSVSGAPGQRVTI SCSGSSSNIGSNDVSWYQQL PGTAPKLLIYKNYNRPSGVP DRFSGSKSGTSASLAITGLQ AEDEADYYCSAWDQRQFDVV FGGGTKLTVL |
| DNA VL | 24 | GATATCGTGCTGACCCAGCC GCCGAGCGTGAGCGGTGCAC CGGGCCAGCGCGTGACCATT AGCTGTAGCGGCAGCAGCAG CAACATTGGTTCTAACGACG TGTCTTGGTACCAGCAGCTG CCGGGCACGGCGCCGAAACT GCTGATCTACAAAAACTACA ACCGCCCGAGCGGCGTGCCG GATCGCTTTAGCGGATCCAA AAGCGGCACCAGCGCCAGCC TGGCGATTACCGGCCTGCAA GCAGAAGACGAAGCGGATTA TTACTGCTCTGCTTGGGACC AGCGTCAGTTCGACGTTGTG TTTGGCGGCGGCACGAAGTT AACCGTCCTA |
| Light Chain | 25 | DIVLTQPPSVSGAPGQRVTI SCSGSSSNIGSNDVSWYQQL PGTAPKLLIYKNYNRPSGVP DRFSGSKSGTSASLAITGLQ AEDEADYYCSAWDQRQFDVV FGGGTKLTVLGQPKAAPSVT LFPPSSEELQANKATLVCLI SDFYPGAVTVAWKADSSPVK AGVETTTPSKQSNNKYAASS YLSLTPEQWKSHRSYSCQVT HEGSTVEKTVAPTECS |
| DNA Light Chain | 26 | GATATCGTGCTGACCCAGCC GCCGAGCGTGAGCGGTGCAC CGGGCCAGCGCGTGACCATT |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | AGCTGTAGCGGCAGCAGCAG CAACATTGGTTCTAACGACG TGTCTTGGTACCAGCAGCTG CCGGGCACGGCGCCGAAACT GCTGATCTACAAAAACTACA ACCGCCCGAGCGGCGTGCCG GATCGCTTTAGCGGATCCAA AAGCGGCACCAGCGCCAGCC TGGCGATTACCGGCCTGCAA GCAGAAGACGAAGCGGATTA TTACTGCTCTGCTTGGGACC AGCGTCAGTTCGACGTTGTG TTTGGCGGCGGCACGAAGTT AACCGTCCTAGGTCAGCCCA AGGCTGCCCCCTCGGTCACT CTGTTCCCGCCCTCCTCTGA GGAGCTTCAAGCCAACAAGG CCACACTGGTGTGTCTCATA AGTGACTTCTACCCGGGAGC CGTGACAGTGGCCTGGAAGG CAGATAGCAGCCCCGTCAAG GCGGGAGTGGAGACCACCAC ACCCTCCAAACAAAGCAACA ACAAGTACGCGGCCAGCAGC TATCTGAGCCTGACGCCTGA GCAGTGGAAGTCCCACAGAA GCTACAGCTGCCAGGTCACG CATGAAGGGAGCACCGTGGA GAAGACAGTGGCCCCTACAG AATGTTCA |
| AM2 | | |
| VH | 27 | QVQLLESGGGLVQPGGSLRL SCAASGFTFSTAAMSWVRQA PGKGLEWVSSIEYYDTDTHY ADSVKGRFTISRDNSKNTLY LQMNSLRAEDTAVYYCAREL SYLYSGYYFDYWGQGTLVTV SS |
| DNA VH | 28 | CAGGTGCAATTGCTGGAAAG CGGCGGTGGCCTGGTGCAGC CGGGTGGCAGCCTGCGTCTG AGCTGCGCGGCGTCCGGATT CACCTTTTCTACTGCTGCTA TGTCTTGGGTGCGCCAGGCC CCGGGCAAAGGTCTCGAGTG GGTTTCCTCTATCGAATACT ACGACACTGACACTCATTAT GCGGATAGCGTGAAAGGCCG CTTTACCATCAGCCGCGATA ATTCGAAAAACACCCTGTAT CTGCAAATGAACAGCCTGCG TGCGGAAGATACGGCCGTGT ATTATTGCGCGCGTGAACTG TCTTACCTGTACTCTGGTTA CTACTTCGATTACTGGGGCC AAGGCACCCTGGTGACTGTT AGCTCA |
| Heavy Chain | 29 | QVQLLESGGGLVQPGGSLRL SCAASGFTFSTAAMSWVRQA PGKGLEWVSSIEYYDTDTHY ADSVKGRFTISRDNSKNTLY LQMNSLRAEDTAVYYCAREL SYLYSGYYFDYWGQGTLVTV SSASTKGPSVFPLAPSSKST SGGTALGCLVKDYFPEPVT VSWNSGALTSGVHTFPAVLQ |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | SSGLYSLSSVVTVPSSSLGT QTYICNVNHKPSNTKVDKRV EPKSCDKTHTCPPCPAPEAA GGPSVFLFPPKPKDTLMISR TPEVTCVVVDVSHEDPEVKF NWYVDGVEVHNAKTKPREEQ YNSTYRVVSVLTVLHQDWLN GKEYKCKVSNKALPAPIEKT ISKAKGQPREPQVYTLPPSR EEMTKNQVSLTCLVKGFYPS DIAVEWESNGQPENNYKTTP PVLDSDGSFFLYSKLTVDKS RWQQGNVFSCSVMHEALHNH YTQKSLSLSPGK |
| DNA Heavy Chain | 30 | CAGGTGCAATTGCTGGAAAG CGGCGGTGGCCTGGTGCAGC CGGGTGGCAGCCTGCGTCTG AGCTGCGCGGCGTCCGGATT CACCTTTTCTACTGCTGCTA TGTCTTGGGTGCGCCAGGCC CCGGGCAAAGGTCTCGAGTG GGTTTCCTCTATCGAATACT ACGACACTGACACTCATTAT GCGGATAGCGTGAAAGGCCG CTTTACCATCAGCCGCGATA ATTCGAAAAACACCCTGTAT CTGCAAATGAACAGCCTGCG TGCGGAAGATACGGCCGTGT ATTATTGCGCGCGTGAACTG TCTTACCTGTACTCTGGTTA CTACTTCGATTACTGGGGCC AAGGCACCCTGGTGACTGTT AGCTCAGCCTCCACCAAGGG TCCATCGGTCTTCCCCCTGG CACCCTCCTCCAAGAGCACC TCTGGGGGCACAGCGGCCCT GGGCTGCCTGGTCAAGGACT ACTTCCCCGAACCGGTGACG GTGTCGTGGAACTCAGGCGC CCTGACCAGCGGCGTGCACA CCTTCCCGGCTGTCCTACAG TCCTCAGGACTCTACTCCCT CAGCAGCGTGGTGACCGTGC CCTCCAGCAGCTTGGGCACC CAGACCTACATCTGCAACGT GAATCACAAGCCCAGCAACA CCAAGGTGGACAAGAGAGTT GAGCCCAAATCTTGTGACAA AACTCACACATGCCCACCGT GCCCAGCACCTGAAGCAGCG GGGGGACCGTCAGTCTTCCT CTTCCCCCCAAAACCCAAGG ACACCCTCATGATCTCCCGG ACCCCTGAGGTCACATGCGT GGTGGTGGACGTGAGCCACG AAGACCCTGAGGTCAAGTTC AACTGGTACGTGGACGGCGT GGAGGTGCATAATGCCAAGA CAAAGCCGCGGGAGGAGCAG TACAACAGCACGTACCGGGT GGTCAGCGTCCTCACCGTCC TGCACCAGGACTGGCTGAAT GGCAAGGAGTACAAGTGCAA GGTCTCCAACAAAGCCCTCC CAGCCCCCATCGAGAAAACC ATCTCCAAAGCCAAAGGGCA GCCCCGAGAACCACAGGTGT ACACCCTGCCCCCATCCCGG GAGGAGATGACCAAGAACCA |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | GGTCAGCCTGACCTGCCTGG TCAAAGGCTTCTATCCCAGC GACATCGCCGTGGAGTGGGA GAGCAATGGGCAGCCGGAGA ACAACTACAAGACCACGCCT CCCGTGCTGGACTCCGACGG CTCCTTCTTCCTCTACAGCA AGCTCACCGTGGACAAGAGC AGGTGGCAGCAGGGGAACGT CTTCTCATGCTCCGTGATGC ATGAGGCTCTGCACAACCAC TACACGCAGAAGAGCCTCTC CCTGTCTCCGGGTAAA |
| VL | 31 | DIVLTQPPSVSGAPGQRVTI SCSGSSSNIGSNDVSWYQQL PGTAPKLLIYKNYNRPSGVP DRFSGSKSGTSASLAITGLQ AEDEADYYCSAWDQRQFDVV FGGGTKLTVL |
| DNA VL | 32 | GATATCGTGCTGACCCAGCC GCCGAGCGTGAGCGGTGCAC CGGGCCAGCGCGTGACCATT AGCTGTAGCGGCAGCAGCAG CAACATTGGTTCTAACGACG TGTCTTGGTACCAGCAGCTG CCGGGCACGGCGCCGAAACT GCTGATCTACAAAAACTACA ACCGCCCGAGCGGCGTGCCG GATCGCTTTAGCGGATCCAA AAGCGGCACCAGCGCCAGCC TGGCGATTACCGGCCTGCAA GCAGAAGACGAAGCGGATTA TTACTGCTCTGCTTGGGACC AGCGTCAGTTCGACGTTGTG TTTGGCGGCGGCACGAAGTT AACCGTCCTA |
| Light Chain | 33 | DIVLTQPPSVSGAPGQRVTI SCSGSSSNIGSNDVSWYQQL PGTAPKLLIYKNYNRPSGVP DRFSGSKSGTSASLAITGLQ AEDEADYYCSAWDQRQFDVV FGGGTKLTVLGQPKAAPSVT LFPPSSEELQANKATLVCLI SDFYPGAVTVAWKADSSPVK AGVETTTPSKQSNNKYAASS YLSLTPEQWKSHRSYSCQVT HEGSTVEKTVAPTECS |
| DNA Light Chain | 34 | GATATCGTGCTGACCCAGCC GCCGAGCGTGAGCGGTGCAC CGGGCCAGCGCGTGACCATT AGCTGTAGCGGCAGCAGCAG CAACATTGGTTCTAACGACG TGTCTTGGTACCAGCAGCTG CCGGGCACGGCGCCGAAACT GCTGATCTACAAAAACTACA ACCGCCCGAGCGGCGTGCCG GATCGCTTTAGCGGATCCAA AAGCGGCACCAGCGCCAGCC TGGCGATTACCGGCCTGCAA GCAGAAGACGAAGCGGATTA TTACTGCTCTGCTTGGGACC AGCGTCAGTTCGACGTTGTG TTTGGCGGCGGCACGAAGTT AACCGTCCTAGGTCAGCCCA AGGCTGCCCCCTCGGTCACT CTGTTCCCGCCCTCCTCTGA |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | GGAGCTTCAAGCCAACAAGG CCACACTGGTGTGTCTCATA AGTGACTTCTACCCGGGAGC CGTGACAGTGGCCTGGAAGG CAGATAGCAGCCCCGTCAAG GCGGGAGTGGAGACCACCAC ACCCTCCAAACAAAGCAACA ACAAGTACGCGGCCAGCAGC TATCTGAGCCTGACGCCTGA GCAGTGGAAGTCCCACAGAA GCTACAGCTGCCAGGTCACG CATGAAGGGAGCACCGTGGA GAAGACAGTGGCCCCTACAG AATGTTCA |
| AM3 | | |
| VH | 35 | QVQLLESGGGLVQPGGSLRL SCAASGFTFSSTAAMSWVRQA PGKGLEWVSTIEYSSQETYY ADSVKGRFTISRDNSKNTLY LQMNSLRAEDTAVYYCAREL SYLYSGYYFDYWGQGTLVTV SS |
| DNA VH | 36 | CAGGTGCAATTGCTGGAAAG CGGCGGTGGCCTGGTGCAGC CGGGTGGCAGCCTGCGTCTG AGCTGCGCGGCGTCCGGATT CACCTTTTCTACTGCTGCTA TGTCTTGGGTGCGCCAGGCC CCGGGCAAAGGTCTCGAGTG GGTTTCCACTATCGAATACT CTAGCCAGGAAACTTACTAT GCGGATAGCGTGAAAGGCCG CTTTACCATCAGCCGCGATA ATTCGAAAAACACCCTGTAT CTGCAAATGAACAGCCTGCG TGCGGAAGATACGGCCGTGT ATTATTGCGCGCGTGAACTG TCTTACCTGTACTCTGGTTA CTACTTCGATTACTGGGGCC AAGGCACCCTGGTGACTGTT AGCTCA |
| Heavy Chain | 37 | QVQLLESGGGLVQPGGSLRL SCAASGFTFSSTAAMSWVRQA PGKGLEWVSTIEYSSQETYY ADSVKGRFTISRDNSKNTLY LQMNSLRAEDTAVYYCAREL SYLYSGYYFDYWGQGTLVTV SSASTKGPSVFPLAPSSKST SGGTAALGCLVKDYFPEPVT VSWNSGALTSGVHTFPAVLQ SSGLYSLSSVVTVPSSSLGT QTYICNVNHKPSNTKVDKRV EPKSCDKTHTCPPCPAPEAA GGPSVFLFPPKPKDTLMISR TPEVTCVVVDVSHEDPEVKF NWYVDGVEVHNAKTKPREEQ YNSTYRVVSVLTVLHQDWLN GKEYKCKVSNKALPAPIEKT ISKAKGQPREPQVYTLPPSR EEMTKNQVSLTCLVKGFYPS DIAVEWESNGQPENNYKTTP PVLDSDGSFFLYSKLTVDKS RWQQGNVFSCSVMHEALHNH YTQKSLSLSPGK |
| DNA Heavy Chain | 38 | CAGGTGCAATTGCTGGAAAG CGGCGGTGGCCTGGTGCAGC CGGGTGGCAGCCTGCGTCTG AGCTGCGCGGCGTCCGGATT CACCTTTTCTACTGCTGCTA TGTCTTGGGTGCGCCAGGCC CCGGGCAAAGGTCTCGAGTG GGTTTCCACTATCGAATACT CTAGCCAGGAAACTTACTAT GCGGATAGCGTGAAAGGCCG CTTTACCATCAGCCGCGATA ATTCGAAAAACACCCTGTAT CTGCAAATGAACAGCCTGCG TGCGGAAGATACGGCCGTGT ATTATTGCGCGCGTGAACTG TCTTACCTGTACTCTGGTTA CTACTTCGATTACTGGGGCC AAGGCACCCTGGTGACTGTT AGCTCAGCCTCCACCAAGGG TCCATCGGTCTTCCCCCTGG CACCCTCCTCCAAGAGCACC TCTGGGGGCACAGCGGCCCT GGGCTGCCTGGTCAAGGACT ACTTCCCCGAACCGGTGACG GTGTCGTGGAACTCAGGCGC CCTGACCAGCGGCGTGCACA CCTTCCCGGCTGTCCTACAG TCCTCAGGACTCTACTCCCT CAGCAGCGTGGTGACCGTGC CCTCCAGCAGCTTGGGCACC CAGACCTACATCTGCAACGT GAATCACAAGCCCAGCAACA CCAAGGTGGACAAGAGAGTT GAGCCCAAATCTTGTGACAA AACTCACACATGCCCACCGT GCCCAGCACCTGAAGCAGCG GGGGGACCGTCAGTCTTCCT CTTCCCCCCAAAACCCAAGG ACACCCTCATGATCTCCCGG ACCCCTGAGGTCACATGCGT GGTGGTGGACGTGAGCCACG AAGACCCTGAGGTCAAGTTC AACTGGTACGTGGACGGCGT GGAGGTGCATAATGCCAAGA CAAAGCCGCGGGAGGAGCAG TACAACAGCACGTACCGGGT GGTCAGCGTCCTCACCGTCC TGCACCAGGACTGGCTGAAT GGCAAGGAGTACAAGTGCAA GGTCTCCAACAAAGCCCTCC CAGCCCCCATCGAGAAAACC ATCTCCAAAGCCAAAGGGCA GCCCCGAGAACCACAGGTGT ACACCCTGCCCCCATCCCGG GAGGAGATGACCAAGAACCA GGTCAGCCTGACCTGCCTGG TCAAAGGCTTCTATCCCAGC GACATCGCCGTGGAGTGGGA GAGCAATGGGCAGCCGGAGA ACAACTACAAGACCACGCCT CCCGTGCTGGACTCCGACGG CTCCTTCTTCCTCTACAGCA AGCTCACCGTGGACAAGAGC AGGTGGCAGCAGGGGAACGT CTTCTCATGCTCCGTGATGC ATGAGGCTCTGCACAACCAC TACACGCAGAAGAGCCTCTC CCTGTCTCCGGGTAAA |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| VL | 39 | DIVLTQPPSVSGAPGQRVTISCSGSSSNIGSNDVSWYQQLPGTAPKLLIYKNYNRPSGVPDRFSGSKSGTSASLAITGLQAEDEADYYCSAWDQRQFDVVFGGGTKLTVL |
| DNA VL | 40 | GATATCGTGCTGACCCAGCCGCCGAGCGTGAGCGGTGCACCGGGCCAGCGCGTGACCATTAGCTGTAGCGGCAGCAGCAGCAACATTGGTTCTAACGACGTGTCTTGGTACCAGCAGCTGCCGGGCACGGCGCCGAAACTGCTGATCTACAAAAACTACAACCGCCCGAGCGGCGTGCCGGATCGCTTTAGCGGATCCAAAAGCGGCACCAGCGCCAGCCTGGCGATTACCGGCCTGCAAGCAGAAGACGAAGCGGATTATTACTGCTCTGCTTGGGACCAGCGTCAGTTCGACGTTGTGTTTGGCGGCGGCACGAAGTTAACCGTCCTA |
| Light Chain | 41 | DIVLTQPPSVSGAPGQRVTISCSGSSSNIGSNDVSWYQQLPGTAPKLLIYKNYNRPSGVPDRFSGSKSGTSASLAITGLQAEDEADYYCSAWDQRQFDVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| DNA Light Chain | 42 | GATATCGTGCTGACCCAGCCGCCGAGCGTGAGCGGTGCACCGGGCCAGCGCGTGACCATTAGCTGTAGCGGCAGCAGCAGCAACATTGGTTCTAACGACGTGTCTTGGTACCAGCAGCTGCCGGGCACGGCGCCGAAACTGCTGATCTACAAAAACTACAACCGCCCGAGCGGCGTGCCGGATCGCTTTAGCGGATCCAAAAGCGGCACCAGCGCCAGCCTGGCGATTACCGGCCTGCAAGCAGAAGACGAAGCGGATTATTACTGCTCTGCTTGGGACCAGCGTCAGTTCGACGTTGTGTTTGGCGGCGGCACGAAGTTAACCGTCCTAGGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTATCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCA |
| AM4 | | |
| VH | 43 | QVQLLESGGGLVQPGGSLRLSCAASGFTFSTAAMSWVRQAPGKGLEWVSTIEYSSQETYYADSVKGRFTISRDNSKNTLYLQMNSLRAEDTAVYYCARELSYLYSGYYFDYWGQGTLVTVSS |
| DNA VH | 44 | CAAGTGCAGCTGCTTGAATCTGGCGGCGGACTGGTGCAGCCTGGCGGCTCCCTGAGACTGTCTTGCGCCGCCTCCGGCTTCACCTTCTCCACCGCCGCTATGTCCTGGGTCCGACAGGCTCCCGGCAAGGGCCTGGAATGGGTGTCCACCATTGAGTACTCCAGCCAGGAAACCTACTACGCCGACTCCGTGAAGGGCCGGTTCACCATCTCCCGGGACAACTCCAAGAACACCCTGTACCTGCAGATGAACTCCCTGCGGGCCGAGGACACCGCCGTGTACTACTGCGCCAGAGAGCTGTCCTACCTGTACTCCGGCTACTACTTCGACTACTGGGGCCAGGGCACCCTGGTCACCGTGTCCTCT |
| Heavy Chain | 45 | QVQLLESGGGLVQPGGSLRLSCAASGFTFSTAAMSWVRQAPGKGLEWVSTIEYSSQETYYADSVKGRFTISRDNSKNTLYLQMNSLRAEDTAVYYCARELSYLYSGYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DNA Heavy Chain | 46 | CAAGTGCAGCTGCTTGAATCTGGCGGCGGACTGGTGCAGCCTGGCGGCTCCCTGAGACTGTCTTGCGCCGCCTCCGGCTTCACCTTCTCCACCGCCGCTATGTCCTGGGTCCGACAGGCTCCCGGCAAGGGCCTGGAATGGGTGTCCACCATTGAGTACTCCAGCCAGGAAACCTACTACGCCGACTCCGTGAAGGGCCGGTTCACCATCTCCCGGGACAACTCCAAGAACACCCTGTACCTGCAGATGAACTCCCTGCGGGCCGAGGACACCGCCGTGTACTACTGCGCCAGAGAGCTG |

TABLE 1-continued

Examples of FXI/FXIa Antibodies and FXI/FXIa Proteins

| Sequence Description | Sequence Identifier (SEQ ID NO:) | Amino acid or polynucleotide sequence |
|---|---|---|
| | | TCCTACCTGTACTCCGGCTACTACTTCGACTACTGGGGCCAGGGCACCCTGGTCACCGTGTCCTCTGCTAGCACCAAGGGCCCCTCCGTGTTCCCTCTGGCCCCTTCCAGCAAGTCTACCTCCGGCGGCACAGCTGCTCTGGGCTGCCTGGTCAAGGACTACTTCCCTGAGCCTGTGACAGTGTCCTGGAACTCTGGCGCCCTGACCTCTGGCGTGCACACCTTCCCTGCCGTGCTGCAGTCCTCCGGCCTGTACTCCCTGTCCTCCGTGGTCACAGTGCCTTCAAGCAGCCTGGGCACCCAGACCTATATCTGCAACGTGAACCACAAGCCTTCCAACACCAAGGTGGACAAGCGGGTGGAGCCTAAGTCCTGCGACAAGACCCACACCTGTCCTCCCTGCCCTGCTCCTGAAGCTGCTGGCGGCCCTTCTGTGTTCCTGTTCCCTCCAAAGCCCAAGGACACCCTGATGATCTCCCGGACCCCTGAAGTGACCTGCGTGGTGGTGGACGTGTCCCACGAGGATCCTGAAGTGAAGTTCAATTGGTACGTGGACGGCGTGGAGGTGCACAACGCCAAGACCAAGCCTCGGGAGGAACAGTACAACTCCACCTACCGGGTGGTGTCCGTGCTGACCGTGCTGCACCAGGACTGGCTGAACGGCAAAGAGTACAAGTGCAAAGTCTCCAACAAGGCCCTGCCTGCCCCTATCGAAAAGACAATCTCCAAGGCCAAGGGCCAGCCTAGGGAACCCCAGGTGTACACCCTGCCACCCAGCCGGGAGGAAATGACCAAGAACCAGGTGTCCCTGACCTGTCTGGTCAAGGGCTTCTACCCTTCCGATATCGCCGTGGAGTGGGAGTCTAACGGCCAGCCTGAGAACAACTACAAGACCACCCCTCCTGTGCTGGACTCCGACGGCTCCTTCTTCCTGTACTCCAAACTGACCGTGGACAAGTCCCGGTGGCAGCAGGGCAACGTGTTCTCCTGCTCCGTGATGCACGAGGCCCTGCACAACCACTACACCCAGAAGTCCCTGTCCCTGTCTCCCGGCAAG |
| VL | 47 | QSVLTQPPSVSGAPGQRVTISCSGSSSNIGSNDVSWYQQLPGTAPKLLIYKNYNRPSGVPDRFSGSKSGTSASLAITGLQAEDEADYYCSAWDQRQFDVVFGGGTKLTVL |
| DNA VL | 48 | CAGAGCGTGCTGACACAGCCTCCCTCCGTGTCTGGCGCCCCTGGCCAGAGAGTGACCATCTCCTGCTCCGGCTCCTCCTCCAACATCGGCTCCAACGACGTGTCCTGGTATCAGCAGCTGCCCGGCACCGCCCCTAAGCTGCTGATCTACAAGAACTACAACCGGCCCTCCGGCGTGCCCGACCGGTTCTCTGGCTCCAAGTCTGGCACCTCCGCCTCCCTGGCTATCACCGGCCTGCAGGCTGAGGACGAGGCCGACTACTACTGCTCCGCCTGGGACCAGCGGCAGTTCGACGTGGTGTTCGGCGGAGGCACCAAGCTGACCGTGCTG |
| Light Chain | 49 | QSVLTQPPSVSGAPGQRVTISCSGSSSNIGSNDVSWYQQLPGTAPKLLIYKNYNRPSGVPDRFSGSKSGTSASLAITGLQAEDEADYYCSAWDQRQFDVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| DNA Light Chain | 50 | CAGAGCGTGCTGACACAGCCTCCCTCCGTGTCTGGCGCCCCTGGCCAGAGAGTGACCATCTCCTGCTCCGGCTCCTCCTCCAACATCGGCTCCAACGACGTGTCCTGGTATCAGCAGCTGCCCGGCACCGCCCCTAAGCTGCTGATCTACAAGAACTACAACCGGCCCTCCGGCGTGCCCGACCGGTTCTCTGGCTCCAAGTCTGGCACCTCCGCCTCCCTGGCTATCACCGGCCTGCAGGCTGAGGACGAGGCCGACTACTACTGCTCCGCCTGGGACCAGCGGCAGTTCGACGTGGTGTTCGGCGGAGGCACCAAGCTGACCGTGCTGGGCCAGCCTAAGGCTGCCCCCAGCGTGACCCTGTTCCCCCCCAGCAGCGAGGAGCTGCAGGCCAACAAGGCCACCCTGGTGTGCCTGATCAGCGACTTCTACCCAGGCGCCGTGACCGTGGCCTGGAAGGCCGACAGCAGCCCCGTGAAGGCCGGCGTGGAGACCACCACCCCCAGCAAGCAGAGCAACAACAAGTACGCCGCCAGCAGCTACCTGAGCCTGACCCCCGAGCAGTGGAAGAGCCACAGGTCCTACAGCTGCCAGGTGACCCACGAGGGCAGCACCGTGGAAAAGACCGTGGCCCCAACCGAGTGCAGC |

Binding/Reversal Agents

In one aspect, the present disclosure relates to a binding agent, as well as a pharmaceutical composition comprising the binding agent, wherein the binding agent specifically binds a target antibody that binds human Factor XI ("FXI") and/or Factor XIa ("FXIa") ("anti-FXI/FXIa antibody") within the catalytic domain, for example, an anti-FXI/FXIa antibody described in Table 1, such as antibody NOV1401, or affinity matured variants thereof, such as antibody AM1, AM2, AM3, or AM4, and wherein the binding agent inhibits an anticoagulant activity of the target antibody. Suitably, a binding agent of the present disclosure is an antibody or antigen-binding fragment (e.g., whole antibody, IgG, Fab fragment), in particular a binding agent of the present disclosure is an anti-idiotype antibody.

In one embodiment, the present invention relates to a binding agent, as well as a pharmaceutical composition comprising the binding agent, wherein the binding agent specifically binds a target antibody that binds human Factor XI ("FXI") and/or Factor XIa ("FXIa") within the catalytic domain, and wherein the binding agent inhibits an anticoagulant activity of the target antibody, and wherein the binding agent binds to the target antibody with a dissociation constant ($K_D$) of 50 pM or less, 40 pM or less, 30 pM or less, 20 pM or less, 15 pM or less, preferably 10 pM or less. In a specific embodiment, the present invention relates to a binding agent, as well as a pharmaceutical composition comprising the binding agent, wherein the binding agent specifically binds a target antibody that binds human Factor XI ("FXI") and/or Factor XIa ("FXIa") with a dissociation constant ($K_D$) of 50 pM to 0.01 pM, 40 pM to 0.01 pM, 30 pM to 0.01 pM, 20 pM to 0.01 pM, 15 pM to 0.01 pM, preferably 10 pM to 0.1 pM. In a specific embodiment, the $K_D$ is measured by solution equilibrium titration, in particular the $K_D$ is measured by solution equilibrium titration at 25° C., in more particular the $K_D$ is measured by solution equilibrium titration at 25° C. for the binding agent in a Fab format. In a further embodiment, the binding agent of the disclosure binds to the target antibody with an association rate ($k_{on}$) of at least 1E+05 $M^{-1}s^{-1}$, preferably with an association rate ($k_{on}$) of 1E+05 $M^{-1}s^{-1}$ to 1E+06 $M^{-1}s^{-1}$ as measured by surface plasmon resonance at 25° C.

In another embodiment, the present disclosure relates to binding agent, as well as a pharmaceutical composition comprising the binding agent, wherein the binding agent specifically binds a target antibody that binds human Factor XI ("FXI") and/or Factor XIa ("FXIa") within the catalytic domain, and wherein the binding agent inhibits an anticoagulant activity of the target antibody, and wherein the binding agent binds to the target antibody with a dissociation constant ($K_D$) of at least 5 times lower, preferably at least 10 times lower, than a $K_D$ of a reference antibody, wherein the reference antibody comprises a heavy chain variable region (VH) comprising the amino acid sequence of SEQ ID NO: 60 and a light chain variable region (VL) comprising the amino acid sequence of SEQ ID NO: 71. In a specific embodiment, the $K_D$ is measured by solution equilibrium titration, in particular the $K_D$ is measured by solution equilibrium titration at 25° C., in more particular the $K_D$ is measured by solution equilibrium titration at 25° C. for the binding agent in a Fab format. In a further embodiment, the binding agent of the disclosure binds to the target antibody with an association rate ($k_{on}$) of at least 1E+05 $M^{-1}s^{-1}$, preferably with an association rate ($k_{on}$) of 1E+05 $M^{-1}s^{-1}$ to 1E+06 $M^{-1}s^{-1}$ as measured by surface plasmon resonance at 25° C.

Suitably, the present disclosure relates to a reversal binding agent, as well as a pharmaceutical composition comprising the binding agent, wherein the binding agent is an anti-idiotype antibody or antigen-binding fragment (e.g., whole antibody, IgG, Fab fragment), which specifically binds a target antibody that binds human Factor XI ("FXI") and/or Factor XIa ("FXIa") ("anti-FXI/FXIa antibody"), for example an anti-FXI/FXIa antibody described in Table 1, such as antibody NOV1401, or affinity matured variants thereof, such as antibody AM1, AM2, AM3, or AM4. In a particular embodiment, provided herein is a binding agent, as well as a pharmaceutical composition comprising such binding agent, wherein the binding agent specifically binds a target antibody that binds human Factor XI ("FXI") and/or Factor XIa ("FXIa") ("anti-FXI/FXIa antibody", such as antibody NOV1401) within the catalytic domain, wherein the binding agent reduces, inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody (e.g., NOV1401). Protocols and assays to measure these anticoagulant activities have been described, and exemplary assays are described herein, e.g., in the Examples Section.

Suitably, the present disclosure relates to a binding agent, as well as a pharmaceutical composition comprising the binding agent, wherein the binding agent specifically binds a target antibody that binds human Factor XI ("FXI") and/or Factor XIa ("FXIa") within the catalytic domain, and wherein the binding agent, when present in a three times molar excess in comparison to the target antibody, is at least 1.5 times more efficient in reversing the anticoagulant activity of the target antibody in comparison to a reference antibody, which is present in a three times molar excess in comparison to the target antibody, and wherein the reference antibody comprises a heavy chain variable region (VH) comprising the amino acid sequence of SEQ ID NO: 60 and a light chain variable region (VL) comprising the amino acid sequence of SEQ ID NO: 71, and in particular wherein the anticoagulation activity is measured in an activated partial thromboplastin time (aPTT) assay, in particular wherein the anticoagulation activity is measured in an aPTT assay at 37° C.

Suitably, the present disclosure relates to a binding agent, as well as a pharmaceutical composition comprising the binding agent, wherein the binding agent specifically binds a target antibody that binds human Factor XI ("FXI") and/or Factor XIa ("FXIa") within the catalytic domain, and wherein the binding agent (i) when present in a three times molar excess in comparison to the target antibody, is capable of a maximal reversal of 60% or more, in particular 63% or more, of the anticoagulant activity of the target antibody, as measured in an activated partial thromboplastin time (aPTT) assay, in particular as measured in an aPTT assay at 37° C.; and/or (ii) when present in a nine times molar excess in comparison to the target antibody, is capable of a maximal reversal of 70% or more, in particular 72% or more, of the anticoagulant activity of the target antibody, as measured in an activated partial thromboplastin time (aPTT) assay, in particular as measured in an aPTT assay at 37° C.; and/or (iii) when present in a thirty times molar excess in comparison to the target antibody, is capable of a maximal reversal of 75% or more, in particular 78% or more, of the anticoagulant activity of the target antibody, as measured in an activated partial thromboplastin time (aPTT) assay, in particular as measured in an aPTT assay at 37° C.

Methods for determining aPTT and delay to aPTT have been described in the art, and are also described herein, e.g., Examples Section.

In further specific embodiments, provided herein is a binding agent (e.g., anti-idiotype antibody), as well as a pharmaceutical composition comprising such binding agent, which specifically binds a target anti-FXI/FXIa antibody (e.g., NOV1401), wherein the binding agent inhibits an anticoagulant activity of the target anti-FXI/FXIa antibody, and wherein the target anti-FXI/FXIa antibody comprises (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9.

Suitably, the binding agent of the disclosure, which inhibits or reverses an anticoagulant activity of a target anti-FXI/FXIa antibody (e.g., NOV1401), is an antibody, in particular, is an isolated antibody. Suitably, the binding agent is a monoclonal human antibody.

In specific embodiments, the binding agent of the disclosure is an antibody or antigen-binding fragment in a format selected from the list consisting of Fab, Fab', F(ab')2, Fv, and scFv. In specific embodiments, the binding agent of the disclosure is a Fab fragment. In specific embodiments, provided herein are binding agents, as well as pharmaceutical compositions comprising such binding agents, which inhibit or reverse an anticoagulant activity of a target anti-FXI/FXIa antibody (e.g., NOV1401), wherein the binding agents are antigen-binding human antibody such as human Fabs. In particular embodiments, provided herein are binding agents, as well as pharmaceutical compositions comprising such binding agents, which inhibit or reverse an anticoagulant activity of a target anti-FXI/FXIa antibody (e.g., NOV1401), wherein the binding agents are human anti-idiotype Fabs.

In another embodiment, the binding agent of the disclosure is an antibody comprising an Fc region. Specifically, the binding agent of the disclosure is an antibody comprising an Fc region selected from the group consisting of an Fc region from an IgG1, IgG2, IgG3, IgG4, IgA, IgM, IgE, and IgD. In a specific embodiment, the binding agent of the disclosure is an IgG1, IgG2, IgG3 or IgG4 isotype antibody, in particular IgG1. In specific embodiments, provided herein are binding agents, as well as pharmaceutical compositions comprising such binding agents, which inhibit or reverse an anticoagulant activity of a target anti-FXI/FXIa antibody (e.g., NOV1401), wherein the binding agents are human IgG1, IgG2, or IgG4 antibodies, or variants thereof.

In specific embodiments, provided herein is a binding agent (e.g., anti-idiotype antibody), as well as a pharmaceutical composition comprising such binding agent, which specifically binds a target anti-FXI/FXIa antibody, wherein the binding agent reduces or inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, wherein the binding agent is an antibody comprising (1) a VH comprising complementarity determining regions HCDR1, HCDR2, and HCDR3 selected from those set forth in Table 2, and (2) a VL comprising complementarity determining regions LCDR1, LCDR2, and LCDR3 selected from those set forth in Table 2. In further specific embodiments, provided herein is a binding agent (e.g., anti-idiotype antibody), as well as a pharmaceutical composition comprising such a binding agent, which specifically binds a target anti-FXI/FXIa antibody, wherein the binding agent reduces or inhibits or reverses an anticoagulant activity of the target anti-FXI/FXIa antibody, wherein the target anti-FXI/FXIa antibody comprises (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9, and wherein the binding agent is an antibody comprising (1) a VH comprising complementarity determining regions HCDR1, HCDR2, and HCDR3 selected from those set forth in Table 2, and (2) a VL comprising complementarity determining regions LCDR1, LCDR2, and LCDR3 selected from those set forth in Table 2. In a particular embodiment, the binding agent (e.g., anti-idiotype antibody) comprises Combined HCDR1, HCDR2, and HCDR3 selected from those set forth in Table 2 and Combined LCDR1, LCDR2, and LCDR3 selected from those set forth in Table 2. In a particular embodiment, the binding agent (e.g., anti-idiotype antibody) comprises Kabat HCDR1, HCDR2, and HCDR3 selected from those set forth in Table 2 and Kabat LCDR1, LCDR2, and LCDR3 selected from those set forth in Table 2. In a particular embodiment, the binding agent (e.g., anti-idiotype antibody) comprises Chothia HCDR1, HCDR2, and HCDR3 selected from those set forth in Table 2 and Chothia LCDR1, LCDR2, and LCDR3 selected from those set forth in Table 2. In a particular embodiment, the binding agent (e.g., anti-idiotype antibody) comprises IMGT HCDR1, HCDR2, and HCDR3 selected from those set forth in Table 2 and IMGT LCDR1, LCDR2, and LCDR3 selected from those set forth in Table 2. Table 2 provides exemplary Kabat, Chothia, Combined, and IMGT HCDR1, HCDR2, HCDR3, LCDR1, LCDR2, and LCDR3 for anti-FXI/FXIa antibody (e.g., NOV1401) binding agents (e.g., antibodies), e.g., IDT1, IDT1A, IDT1B, IDT1C, IDT1D, IDT1E.

TABLE 2

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| IDT1 | | |
| HCDR1 (Combined) | 51 | GFTFSDYAMS |
| HCDR2 (Combined) | 52 | VIDYSSSNTYYADSVKG |
| HCDR3 (Combined) | 53 | EGYSYRSIRFDY |
| HCDR1 (Kabat) | 54 | DYAMS |
| HCDR2 (Kabat) | 52 | VIDYSSSNTYYADSVKG |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR3 (Kabat) | 53 | EGYSYRSIRFDY |
| HCDR1 (Chothia) | 55 | GFTFSDY |
| HCDR2 (Chothia) | 56 | DYSSSN |
| HCDR3 (Chothia) | 53 | EGYSYRSIRFDY |
| HCDR1 (IMGT) | 57 | GFTFSDYA |
| HCDR2 (IMGT) | 58 | IDYSSSNT |
| HCDR3 (IMGT) | 59 | AREGYSYRSIRFDY |
| VH | 60 | QVQLLESGGGLVQPGGSLRLSCAASGFTFSDYAMS WVRQAPGKGLEWVSVIDYSSSNTYYADSVKGRFTIS RDNSKNTLYLQMNSLRAEDTAVYYCAREGYSYRSI RFDYWGQGTLVTVSS |
| DNA VH | 61 | CAAGTGCAGCTGCTGGAATCTGGCGGCGGACTGG TGCAGCCTGGCGGTAGTCTGAGACTGTCTTGCGCC GCCTCCGGCTTCACCTTCTCCGACTACGCCATGTC CTGGGTCCGACAGGCCCCTGGCAAGGGCCTGGAG TGGGTGTCCGTGATCGACTACTCCTCCTCCAACAC CTACTACGCCGACTCCGTGAAGGGCCGGTTCACC ATCTCCCGGGACAACTCCAAGAACACCCTGTACCT GCAGATGAACTCCCTGCGGGCCGAGGACACCGCC GTGTACTACTGCGCCAGAGAGGGCTACTCCTACC GGTCCATCAGATTCGACTACTGGGGCCAGGGCAC CCTGGTCACCGTGTCCTCT |
| Heavy Chain | 62 | QVQLLESGGGLVQPGGSLRLSCAASGFTFSDYAMS WVRQAPGKGLEWVSVIDYSSSNTYYADSVKGRFTIS RDNSKNTLYLQMNSLRAEDTAVYYCAREGYSYRSI RFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKRVEPKSC |
| DNA Heavy Chain | 63 | CAAGTGCAGCTGCTGGAATCTGGCGGCGGACTGG TGCAGCCTGGCGGTAGTCTGAGACTGTCTTGCGCC GCCTCCGGCTTCACCTTCTCCGACTACGCCATGTC CTGGGTCCGACAGGCCCCTGGCAAGGGCCTGGAG TGGGTGTCCGTGATCGACTACTCCTCCTCCAACAC CTACTACGCCGACTCCGTGAAGGGCCGGTTCACC ATCTCCCGGGACAACTCCAAGAACACCCTGTACCT GCAGATGAACTCCCTGCGGGCCGAGGACACCGCC GTGTACTACTGCGCCAGAGAGGGCTACTCCTACC GGTCCATCAGATTCGACTACTGGGGCCAGGGCAC CCTGGTCACCGTGTCCTCTGCTAGCACCAAGGGCC CCTCCGTGTTCCCTCTGGCCCCTTCCAGCAAGTCT ACCTCTGGCGGCACCGCTGCTCTGGGCTGCCTGGT GAAGGACTACTTCCCTGAGCCTGTGACAGTGTCCT GGAACTCTGGCGCCCTGACCTCCGGCGTGCACAC CTTCCCTGCCGTGCTGCAGTCCTCCGGCCTGTACT CCCTGTCCTCCGTGGTGACAGTGCCTTCCTCCAGC CTGGGCACCCAGACCTATATCTGCAACGTGAACC ACAAGCCTTCCAACACCAAGGTGGACAAGCGGGT GGAGCCTAAGTCATGC |
| LCDR1 (Combined) | 64 | RASQSISSNLN |
| LCDR2 (Combined) | 65 | AASNLQS |
| LCDR3 (Combined) | 66 | LQFDHTPFT |
| LCDR1 (Kabat) | 64 | RASQSISSNLN |
| LCDR2 (Kabat) | 65 | AASNLQS |
| LCDR3 (Kabat) | 66 | LQFDHTPFT |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| LCDR1 (Chothia) | 67 | SQSISSN |
| LCDR2 (Chothia) | 68 | AAS |
| LCDR3 (Chothia) | 69 | FDHTPF |
| LCDR1 (IMGT) | 70 | QSISSN |
| LCDR2 (IMGT) | 68 | AAS |
| LCDR3 (IMGT) | 66 | LQFDHTPFT |
| VL | 71 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIK |
| DNA VL | 72 | GACATCCAGATGACCCAGAGCCCCTCCAGCCTGT CCGCCTCCGTGGGCGACAGAGTGACCATCACCTG TCGGGCCTCCCAGTCCATCTCCTCCAACCTGAACT GGTATCAGCAGAAGCCCGGCAAGGCCCCTAAGCT GCTGATCTACGCCGCCAGCAACCTGCAGTCCGGC GTGCCCTCCAGATTCTCCGGCTCTGGCTCCGGCAC CGACTTCACCCTGACCATCTCCAGCCTGCAGCCCG AGGACTTCGCCACCTACTACTGCCTGCAGTTCGAC CACACCCCTTTCACCTTCGGCCAGGGCACCAAAGT GGAAATCAAG |
| Light Chain | 73 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 74 | GACATCCAGATGACCCAGAGCCCCTCCAGCCTGT CCGCCTCCGTGGGCGACAGAGTGACCATCACCTG TCGGGCCTCCCAGTCCATCTCCTCCAACCTGAACT GGTATCAGCAGAAGCCCGGCAAGGCCCCTAAGCT GCTGATCTACGCCGCCAGCAACCTGCAGTCCGGC GTGCCCTCCAGATTCTCCGGCTCTGGCTCCGGCAC CGACTTCACCCTGACCATCTCCAGCCTGCAGCCCG AGGACTTCGCCACCTACTACTGCCTGCAGTTCGAC CACACCCCTTTCACCTTCGGCCAGGGCACCAAAGT GGAAATCAAGCGTACGGTGGCCGCTCCCAGCGTG TTCATCTTCCCCCCCAGCGACGAGCAGCTGAAGA GCGGCACCGCCAGCGTGGTGTGCCTGCTGAACAA CTTCTACCCCCGGGAGGCCAAGGTGCAGTGGAAG GTGGACAACGCCCTGCAGAGCGGCAACAGCCAGG AGAGCGTCACCGAGCAGGACAGCAAGGACTCCAC CTACAGCCTGAGCAGCACCCTGACCCTGAGCAAG GCCGACTACGAGAAGCATAAGGTGTACGCCTGCG AGGTGACCCACCAGGGCCTGTCCAGCCCCGTGAC CAAGAGCTTCAACAGGGGCGAGTGC |
| IDT1B *E. coli* format | | |
| HCDR1 (Combined) | 51 | GFTFSDYAMS |
| HCDR2 (Combined) | 75 | TISYLGQEKHYADSVKG |
| HCDR3 (Combined) | 53 | EGYSYRSIRFDY |
| HCDR1 (Kabat) | 54 | DYAMS |
| HCDR2 (Kabat) | 75 | TISYLGQEKHYADSVKG |
| HCDR3 (Kabat) | 53 | EGYSYRSIRFDY |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR1 (Chothia) | 55 | GFTFSDY |
| HCDR2 (Chothia) | 76 | SYLGQE |
| HCDR3 (Chothia) | 53 | EGYSYRSIRFDY |
| HCDR1 (IMGT) | 57 | GFTFSDYA |
| HCDR2 (IMGT) | 77 | ISYLGQEK |
| HCDR3 (IMGT) | 59 | AREGYSYRSIRFDY |
| VH | 78 | EVQLLESGGGLVQPGGSLRLSCAASGFTFSDYAMS WVRQAPGKGLEWVSTISYLGQEKHYADSVKGRFTI SRDNSKNTLYLQMNSLRAEDTAVYYCAREGYSYRS IRFDYWGQGTLVTVSS |
| DNA VH | 79 | GAAGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCTCTTACCTGGGCCAGGAAA AACATTATGCGGATAGCGTGAAAGGCCGCTTTAC CATCAGCCGCGATAATTCGAAAAACACCCTGTAT CTGCAAATGAACAGCCTGCGTGCGGAAGATACGG CCGTGTATTATTGCGCGCGTGAAGGTTACTCTTAC CGTTCTATCCGTTTCGATTACTGGGGCCAAGGCAC CCTGGTGACTGTTAGCTCA |
| Heavy Chain | 80 | EVQLLESGGGLVQPGGSLRLSCAASGFTFSDYAMS WVRQAPGKGLEWVSTISYLGQEKHYADSVKGRFTI SRDNSKNTLYLQMNSLRAEDTAVYYCAREGYSYRS IRFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSEFDYKDDDDKGAPHHHHHH |
| DNA Heavy Chain | 81 | GAAGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCTCTTACCTGGGCCAGGAAA AACATTATGCGGATAGCGTGAAAGGCCGCTTTAC CATCAGCCGCGATAATTCGAAAAACACCCTGTAT CTGCAAATGAACAGCCTGCGTGCGGAAGATACGG CCGTGTATTATTGCGCGCGTGAAGGTTACTCTTAC CGTTCTATCCGTTTCGATTACTGGGGCCAAGGCAC CCTGGTGACTGTTAGCTCAGCGTCGACCAAAGGC CCGAGCGTGTTTCCGCTGGCCCCGAGCAGCAAAA GCACCAGCGGCGGCACCGCCGCACTGGGCTGCCT GGTGAAAGATTATTTCCCGGAACCAGTGACCGTG AGCTGGAACAGCGGTGCCCTGACCAGCGGCGTGC ATACCTTTCCGGCGGTGCTGCAAAGCAGCGGCCT GTATAGCCTGAGCAGCGTTGTGACCGTGCCGAGC AGCAGCCTGGGCACCCAGACCTATATTTGCAACG TCAACCATAAACCGAGCAACACCAAAGTCGATAA AAAAGTCGAACCGAAAAGCGAATTCGACTATAAA GATGACGATGACAAAGGCGCGCCGCACCATCATC ACCATCAC |
| LCDR1 (Combined) | 64 | RASQSISSNLN |
| LCDR2 (Combined) | 65 | AASNLQS |
| LCDR3 (Combined) | 66 | LQFDHTPFT |
| LCDR1 (Kabat) | 64 | RASQSISSNLN |
| LCDR2 (Kabat) | 65 | AASNLQS |
| LCDR3 (Kabat) | 66 | LQFDHTPFT |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| LCDR1 (Chothia) | 67 | SQSISSN |
| LCDR2 (Chothia) | 68 | AAS |
| LCDR3 (Chothia) | 69 | FDHTPF |
| LCDR1 (IMGT) | 70 | QSISSN |
| LCDR2 (IMGT) | 68 | AAS |
| LCDR3 (IMGT) | 66 | LQFDHTPFT |
| VL | 71 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIK |
| DNA VL | 82 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAA |
| Light Chain | 83 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEA |
| DNA Light Chain | 84 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAACGTACGGTGGCCGCACCGAGCGTG TTTATCTTTCCGCCGAGCGATGAACAGCTGAAAAG CGGCACCGCCAGCGTGGTGTGCCTGCTGAACAAC TTTTATCCGCGCGAAGCCAAAGTGCAGTGGAAAG TGGATAACGCCCTGCAAAGCGGCAACAGCCAGGA AAGCGTTACCGAACAGGATAGCAAAGATAGCACC TACAGCCTGAGCAGCACCCTGACCCTGAGCAAAG CCGATTATGAAAAACATAAAGTGTATGCCTGCGA AGTGACCCATCAGGGCCTGAGCAGCCCAGTGACC AAAAGTTTTAACCGCGGCGAGGCC |
| IDT1B variant | | |
| HCDR1 (Combined) | 51 | GFTFSDYAMS |
| HCDR2 (Combined) | 75 | TISYLGQEKHYADSVKG |
| HCDR3 (Combined) | 53 | EGYSYRSIRFDY |
| HCDR1 (Kabat) | 54 | DYAMS |
| HCDR2 (Kabat) | 75 | TISYLGQEKHYADSVKG |
| HCDR3 (Kabat) | 53 | EGYSYRSIRFDY |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| HCDR1 (Chothia) | 55 | GFTFSDY |
| HCDR2 (Chothia) | 76 | SYLGQE |
| HCDR3 (Chothia) | 53 | EGYSYRSIRFDY |
| HCDR1 (IMGT) | 57 | GFTFSDYA |
| HCDR2 (IMGT) | 77 | ISYLGQEK |
| HCDR3 (IMGT) | 59 | AREGYSYRSIRFDY |
| VH | 85 | QVQLLESGGGLVQPGGSLRLSCAASGFTFSDYAMS WVRQAPGKGLEWVSTISYLGQEKHYADSVKGRFTI SRDNSKNTLYLQMNSLRAEDTAVYYCAREGYSYRS IRFDYWGQGTLVTVSS |
| DNA VH | 86 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCTCTTACCTGGGCCAGGAAA AACATTATGCGGATAGCGTGAAAGGCCGCTTTAC CATCAGCCGCGATAATTCGAAAAACACCCTGTAT CTGCAAATGAACAGCCTGCGTGCGGAAGATACGG CCGTGTATTATTGCGCGCGTGAAGGTTACTCTTAC CGTTCTATCCGTTTCGATTACTGGGGCCAAGGCAC CCTGGTGACTGTTAGCTCA |
| Heavy Chain | 87 | QVQLLESGGGLVQPGGSLRLSCAASGFTFSDYAMS WVRQAPGKGLEWVSTISYLGQEKHYADSVKGRFTI SRDNSKNTLYLQMNSLRAEDTAVYYCAREGYSYRS IRFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSC |
| DNA Heavy Chain | 88 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCTCTTACCTGGGCCAGGAAA AACATTATGCGGATAGCGTGAAAGGCCGCTTTAC CATCAGCCGCGATAATTCGAAAAACACCCTGTAT CTGCAAATGAACAGCCTGCGTGCGGAAGATACGG CCGTGTATTATTGCGCGCGTGAAGGTTACTCTTAC CGTTCTATCCGTTTCGATTACTGGGGCCAAGGCAC CCTGGTGACTGTTAGCTCAGCGTCGACCAAAGGC CCGAGCGTGTTTCCGCTGGCCCCGAGCAGCAAAA GCACCAGCGGCGGCACCGCCGCACTGGGCTGCCT GGTGAAAGATTATTTCCCGGAACCAGTGACCGTG AGCTGGAACAGCGGTGCCCTGACCAGCGGCGTGC ATACCTTTCCGGCGGTGCTGCAAAGCAGCGGCCT GTATAGCCTGAGCAGCGTTGTGACCGTGCCGAGC AGCAGCCTGGGCACCCAGACCTATATTTGCAACG TCAACCATAAACCGAGCAACACCAAAGTCGATAA AAAAGTCGAACCGAAAAGCTGC |
| LCDR1 (Combined) | 64 | RASQSISSNLN |
| LCDR2 (Combined) | 65 | AASNLQS |
| LCDR3 (Combined) | 66 | LQFDHTPFT |
| LCDR1 (Kabat) | 64 | RASQSISSNLN |
| LCDR2 (Kabat) | 65 | AASNLQS |
| LCDR3 (Kabat) | 66 | LQFDHTPFT |
| LCDR1 (Chothia) | 67 | SQSISSN |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| LCDR2 (Chothia) | 68 | AAS |
| LCDR3 (Chothia) | 69 | FDHTPF |
| LCDR1 (IMGT) | 70 | QSISSN |
| LCDR2 (IMGT) | 68 | AAS |
| LCDR3 (IMGT) | 66 | LQFDHTPFT |
| VL | 71 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIK |
| DNA VL | 82 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAA |
| Light Chain | 73 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 89 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAACGTACGGTGGCCGCACCGAGCGTG TTTATCTTTCCGCCGAGCGATGAACAGCTGAAAAG CGGCACCGCCAGCGTGGTGTGCCTGCTGAACAAC TTTTATCCGCGCGAAGCCAAAGTGCAGTGGAAAG TGGATAACGCCCTGCAAAGCGGCAACAGCCAGGA AAGCGTTACCGAACAGGATAGCAAAGATAGCACC TACAGCCTGAGCAGCACCCTGACCCTGAGCAAAG CCGATTATGAAAAACATAAAGTGTATGCCTGCGA AGTGACCCATCAGGGCCTGAGCAGCCCAGTGACC AAAAGTTTTAACCGCGGCGAGTGC |
| IDT1A *E. coli* format | | |
| HCDR1 (Combined) | 51 | GFTFSDYAMS |
| HCDR2 (Combined) | 52 | VIDYSSSNTYYADSVKG |
| HCDR3 (Combined) | 53 | EGYSYRSIRFDY |
| HCDR1 (Kabat) | 54 | DYAMS |
| HCDR2 (Kabat) | 52 | VIDYSSSNTYYADSVKG |
| HCDR3 (Kabat) | 53 | EGYSYRSIRFDY |
| HCDR1 (Chothia) | 55 | GFTFSDY |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| HCDR2 (Chothia) | 56 | DYSSSN |
| HCDR3 (Chothia) | 53 | EGYSYRSIRFDY |
| HCDR1 (IMGT) | 57 | GFTFSDYA |
| HCDR2 (IMGT) | 58 | IDYSSSNT |
| HCDR3 (IMGT) | 59 | AREGYSYRSIRFDY |
| VH | 90 | EVQLLESGGGLVQPGGSLRLSCAASGFTFSDYAMS WVRQAPGKGLEWVSVIDYSSSNTYYADSVKGRFTIS RDNSKNTLYLQMNSLRAEDTAVYYCAREGYSYRSI RFDYWGQGTLVTVSS |
| DNA VH | 91 | GAAGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCGTTATCGACTACTCTTCTTCTAACA CCTACTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCA |
| Heavy Chain | 92 | EVQLLESGGGLVQPGGSLRLSCAASGFTFSDYAMS WVRQAPGKGLEWVSVIDYSSSNTYYADSVKGRFTIS RDNSKNTLYLQMNSLRAEDTAVYYCAREGYSYRSI RFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSEFDYKDDDDKGAPHHHHHH |
| DNA Heavy Chain | 93 | GAAGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCGTTATCGACTACTCTTCTTCTAACA CCTACTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCAGCGTCGACCAAAGGCCC GAGCGTGTTTCCGCTGGCCCCGAGCAGCAAAAGC ACCAGCGGCGGCACCGCCGCACTGGGCTGCCTGG TGAAAGATTATTTCCCGGAACCAGTGACCGTGAG CTGGAACAGCGGTGCCCTGACCAGCGGCGTGCAT ACCTTTCCGGCGGTGCTGCAAAGCAGCGGCCTGT ATAGCCTGAGCAGCGTTGTGACCGTGCCGAGCAG CAGCCTGGGCACCCAGACCTATATTTGCAACGTCA ACCATAAACCGAGCAACACCAAAGTCGATAAAAA AGTCGAACCGAAAAGCGAATTCGACTATAAAGAT GACGATGACAAAGGCGCGCCGCACCATCATCACC ATCAC |
| LCDR1 (Combined) | 64 | RASQSISSNLN |
| LCDR2 (Combined) | 65 | AASNLQS |
| LCDR3 (Combined) | 94 | LQYYHLPYT |
| LCDR1 (Kabat) | 64 | RASQSISSNLN |
| LCDR2 (Kabat) | 65 | AASNLQS |
| LCDR3 (Kabat) | 94 | LQYYHLPYT |
| LCDR1 (Chothia) | 67 | SQSISSN |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| LCDR2 (Chothia) | 68 | AAS |
| LCDR3 (Chothia) | 95 | YYHLPY |
| LCDR1 (IMGT) | 70 | QSISSN |
| LCDR2 (IMGT) | 68 | AAS |
| LCDR3 (IMGT) | 94 | LQYYHLPYT |
| VL | 96 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIK |
| DNA VL | 97 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAA |
| Light Chain | 98 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEA |
| DNA Light Chain | 99 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAACGTACGGTGGCCGCACCGAGCGT GTTTATCTTTCCGCCGAGCGATGAACAGCTGAAAA GCGGCACCGCCAGCGTGGTGTGCCTGCTGAACAA CTTTTATCCGCGCGAAGCCAAAGTGCAGTGGAAA GTGGATAACGCCCTGCAAAGCGGCAACAGCCAGG AAAGCGTTACCGAACAGGATAGCAAAGATAGCAC CTACAGCCTGAGCAGCACCCTGACCCTGAGCAAA GCCGATTATGAAAAACATAAAGTGTATGCCTGCG AAGTGACCCATCAGGGCCTGAGCAGCCCAGTGAC CAAAAGTTTTAACCGCGGCGAGGCC |
| IDT1A variant | | |
| HCDR1 (Combined) | 51 | GFTFSDYAMS |
| HCDR2 (Combined) | 52 | VIDYSSSNTYYADSVKG |
| HCDR3 (Combined) | 53 | EGYSYRSIRFDY |
| HCDR1 (Kabat) | 54 | DYAMS |
| HCDR2 (Kabat) | 52 | VIDYSSSNTYYADSVKG |
| HCDR3 (Kabat) | 53 | EGYSYRSIRFDY |
| HCDR1 (Chothia) | 55 | GFTFSDY |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR2 (Chothia) | 56 | DYSSSN |
| HCDR3 (Chothia) | 53 | EGYSYRSIRFDY |
| HCDR1 (IMGT) | 57 | GFTFSDYA |
| HCDR2 (IMGT) | 58 | IDYSSSNT |
| HCDR3 (IMGT) | 59 | AREGYSYRSIRFDY |
| VH | 60 | QVQLLESGGGLVQPGGSLRLSCAASGFTFSDYAMS WVRQAPGKGLEWVSVIDYSSSNTYYADSVKGRFTIS RDNSKNTLYLQMNSLRAEDTAVYYCAREGYSYRSI RFDYWGQGTLVTVSS |
| DNA VH | 100 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCGTTATCGACTACTCTTCTTCTAACA CCTACTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCA |
| Heavy Chain | 101 | QVQLLESGGGLVQPGGSLRLSCAASGFTFSDYAMS WVRQAPGKGLEWVSVIDYSSSNTYYADSVKGRFTIS RDNSKNTLYLQMNSLRAEDTAVYYCAREGYSYRSI RFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSC |
| DNA Heavy Chain | 102 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCGTTATCGACTACTCTTCTTCTAACA CCTACTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCAGCGTCGACCAAAGGCCC GAGCGTGTTTCCGCTGGCCCCGAGCAGCAAAAGC ACCAGCGGCGGCACCGCCGCACTGGGCTGCCTGG TGAAAGATTATTTCCCGGAACCAGTGACCGTGAG CTGGAACAGCGGTGCCCTGACCAGCGGCGTGCAT ACCTTTCCGGCGGTGCTGCAAAGCAGCGGCCTGT ATAGCCTGAGCAGCGTTGTGACCGTGCCGAGCAG CAGCCTGGGCACCCAGACCTATATTTGCAACGTCA ACCATAAACCGAGCAACACCAAAGTCGATAAAAA AGTCGAACCGAAAAGCTGC |
| LCDR1 (Combined) | 64 | RASQSISSNLN |
| LCDR2 (Combined) | 65 | AASNLQS |
| LCDR3 (Combined) | 94 | LQYYHLPYT |
| LCDR1 (Kabat) | 64 | RASQSISSNLN |
| LCDR2 (Kabat) | 65 | AASNLQS |
| LCDR3 (Kabat) | 94 | LQYYHLPYT |
| LCDR1 (Chothia) | 67 | SQSISSN |
| LCDR2 (Chothia) | 68 | AAS |

TABLE 2-continued

| Sequence Description | Sequence Identifier (SEQ ID NO:) | Amino acid or polynucleotide sequence |
|---|---|---|
| Examples of anti-FXI/FXIa Antibody Binding Agents (e.g., anti-idiotype antibody) | | |
| LCDR3 (Chothia) | 95 | YYHLPY |
| LCDR1 (IMGT) | 70 | QSISSN |
| LCDR2 (IMGT) | 68 | AAS |
| LCDR3 (IMGT) | 94 | LQYYHLPYT |
| VL | 96 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIK |
| DNA VL | 97 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAA |
| Light Chain | 103 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 104 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAACGTACGGTGGCCGCACCGAGCGT GTTTATCTTTCCGCCGAGCGATGAACAGCTGAAAA GCGGCACCGCCAGCGTGGTGTGCCTGCTGAACAA CTTTTATCCGCGCGAAGCCAAAGTGCAGTGGAAA GTGGATAACGCCCTGCAAAGCGGCAACAGCCAGG AAAGCGTTACCGAACAGGATAGCAAAGATAGCAC CTACAGCCTGAGCAGCACCCTGACCCTGAGCAAA GCCGATTATGAAAAACATAAAGTGTATGCCTGCG AAGTGACCCATCAGGGCCTGAGCAGCCCAGTGAC CAAAAGTTTTAACCGCGGCGAGTGC |
| IDT1C *E. coli* format | | |
| HCDR1 (Combined) | 51 | GFTFSDYAMS |
| HCDR2 (Combined) | 105 | TIAYVGAPTHYADSVKG |
| HCDR3 (Combined) | 53 | EGYSYRSIRFDY |
| HCDR1 (Kabat) | 54 | DYAMS |
| HCDR2 (Kabat) | 105 | TIAYVGAPTHYADSVKG |
| HCDR3 (Kabat) | 53 | EGYSYRSIRFDY |
| HCDR1 (Chothia) | 55 | GFTFSDY |
| HCDR2 (Chothia) | 106 | AYVGAP |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR3 (Chothia) | 53 | EGYSYRSIRFDY |
| HCDR1 (IMGT) | 57 | GFTFSDYA |
| HCDR2 (IMGT) | 107 | IAYVGAPT |
| HCDR3 (IMGT) | 59 | AREGYSYRSIRFDY |
| VH | 108 | EVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRS IRFDYWGQGTLVTVSS |
| DNA VH | 109 | GAAGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCA |
| Heavy Chain | 110 | EVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRS IRFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSEFDYKDDDDKGAPHHHHHH |
| DNA Heavy Chain | 111 | GAAGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCAGCGTCGACCAAAGGCCC GAGCGTGTTTCCGCTGGCCCCGAGCAGCAAAAGC ACCAGCGGCGGCACCGCCGCACTGGGCTGCCTGG TGAAAGATTATTTCCCGGAACCAGTGACCGTGAG CTGGAACAGCGGTGCCCTGACCAGCGGCGTGCAT ACCTTTCCGGCGGTGCTGCAAAGCAGCGGCCTGT ATAGCCTGAGCAGCGTTGTGACCGTGCCGAGCAG CAGCCTGGGCACCCAGACCTATATTTGCAACGTCA ACCATAAACCGAGCAACACCAAAGTCGATAAAAA AGTCGAACCGAAAAGCGAATTCGACTATAAAGAT GACGATGACAAAGGCGCGCCGCACCATCATCACC ATCAC |
| LCDR1 (Combined) | 64 | RASQSISSNLN |
| LCDR2 (Combined) | 65 | AASNLQS |
| LCDR3 (Combined) | 66 | LQFDHTPFT |
| LCDR1 (Kabat) | 64 | RASQSISSNLN |
| LCDR2 (Kabat) | 65 | AASNLQS |
| LCDR3 (Kabat) | 66 | LQFDHTPFT |
| LCDR1 (Chothia) | 67 | SQSISSN |
| LCDR2 (Chothia) | 68 | AAS |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| LCDR3 (Chothia) | 69 | FDHTPF |
| LCDR1 (IMGT) | 70 | QSISSN |
| LCDR2 (IMGT) | 68 | AAS |
| LCDR3 (IMGT) | 66 | LQFDHTPFT |
| VL | 71 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIK |
| DNA VL | 82 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAA |
| Light Chain | 83 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEA |
| DNA Light Chain | 84 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAACGTACGGTGGCCGCACCGAGCGTG TTTATCTTTCCGCCGAGCGATGAACAGCTGAAAAG CGGCACCGCCAGCGTGGTGTGCCTGCTGAACAAC TTTTATCCGCGCGAAGCCAAAGTGCAGTGGAAAG TGGATAACGCCCTGCAAAGCGGCAACAGCCAGGA AAGCGTTACCGAACAGGATAGCAAAGATAGCACC TACAGCCTGAGCAGCACCCTGACCCTGAGCAAAG CCGATTATGAAAAACATAAAGTGTATGCCTGCGA AGTGACCCATCAGGGCCTGAGCAGCCCAGTGACC AAAAGTTTTAACCGCGGCGAGGCC |
| IDT1C *E. coli* format, variant | | |
| HCDR1 (Combined) | 51 | GFTFSDYAMS |
| HCDR2 (Combined) | 105 | TIAYVGAPTHYADSVKG |
| HCDR3 (Combined) | 53 | EGYSYRSIRFDY |
| HCDR1 (Kabat) | 54 | DYAMS |
| HCDR2 (Kabat) | 105 | TIAYVGAPTHYADSVKG |
| HCDR3 (Kabat) | 53 | EGYSYRSIRFDY |
| HCDR1 (Chothia) | 55 | GFTFSDY |
| HCDR2 (Chothia) | 106 | AYVGAP |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR3 (Chothia) | 53 | EGYSYRSIRFDY |
| HCDR1 (IMGT) | 57 | GFTFSDYA |
| HCDR2 (IMGT) | 107 | IAYVGAPT |
| HCDR3 (IMGT) | 59 | AREGYSYRSIRFDY |
| VH | 112 | QVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRS IRFDYWGQGTLVTVSS |
| DNA VH | 113 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCA |
| Heavy Chain | 114 | QVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRS IRFDYWGQGTLVTVSSASTKGPSVFFLAPSSKSTSGG TAALGCLVKDYFPEPVTVSWNSGALTSGVHTFPAVL QSSGLYSLSSVVTVPSSSLGTQTYICNVNHKPSNTKV DKKVEPKSC |
| DNA Heavy Chain | 115 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCAGCGTCGACCAAAGGCCC GAGCGTGTTTCCGCTGGCCCCGAGCAGCAAAAGC ACCAGCGGCGGCACCGCCGCACTGGGCTGCCTGG TGAAAGATTATTTCCCGGAACCAGTGACCGTGAG CTGGAACAGCGGTGCCCTGACCAGCGGCGTGCAT ACCTTTCCGGCGGTGCTGCAAAGCAGCGGCCTGT ATAGCCTGAGCAGCGTTGTGACCGTGCCGAGCAG CAGCCTGGGCACCCAGACCTATATTTGCAACGTCA ACCATAAACCGAGCAACACCAAAGTCGATAAAAA AGTCGAACCGAAAAGCTGC |
| LCDR1 (Combined) | 64 | RASQSISSNLN |
| LCDR2 (Combined) | 65 | AASNLQS |
| LCDR3 (Combined) | 66 | LQFDHTPFT |
| LCDR1 (Kabat) | 64 | RASQSISSNLN |
| LCDR2 (Kabat) | 65 | AASNLQS |
| LCDR3 (Kabat) | 66 | LQFDHTPFT |
| LCDR1 (Chothia) | 67 | SQSISSN |
| LCDR2 (Chothia) | 68 | AAS |
| LCDR3 (Chothia) | 69 | FDHTPF |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| LCDR1 (IMGT) | 70 | QSISSN |
| LCDR2 (IMGT) | 68 | AAS |
| LCDR3 (IMGT) | 66 | LQFDHTPFT |
| VL | 71 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIK |
| DNA VL | 82 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAA |
| Light Chain | 73 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 89 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAACGTACGGTGGCCGCACCGAGCGTG TTTATCTTTCCGCCGAGCGATGAACAGCTGAAAAG CGGCACCGCCAGCGTGGTGTGCCTGCTGAACAAC TTTTATCCGCGCGAAGCCAAAGTGCAGTGGAAAG TGGATAACGCCCTGCAAAGCGGCAACAGCCAGGA AAGCGTTACCGAACAGGATAGCAAAGATAGCACC TACAGCCTGAGCAGCACCCTGACCCTGAGCAAAG CCGATTATGAAAAACATAAAGTGTATGCCTGCGA AGTGACCCATCAGGGCCTGAGCAGCCCAGTGACC AAAAGTTTTAACCGCGGCGAGTGC |
| IDT1C mammalian format (HC1 + LC1) | | |
| HCDR1 (Combined) | 51 | GFTFSDYAMS |
| HCDR2 (Combined) | 105 | TIAYVGAPTHYADSVKG |
| HCDR3 (Combined) | 53 | EGYSYRSIRFDY |
| HCDR1 (Kabat) | 54 | DYAMS |
| HCDR2 (Kabat) | 105 | TIAYVGAPTHYADSVKG |
| HCDR3 (Kabat) | 53 | EGYSYRSIRFDY |
| HCDR1 (Chothia) | 55 | GFTFSDY |
| HCDR2 (Chothia) | 106 | AYVGAP |
| HCDR3 (Chothia) | 53 | EGYSYRSIRFDY |
| HCDR1 (IMGT) | 57 | GFTFSDYA |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| HCDR2 (IMGT) | 107 | IAYVGAPT |
| HCDR3 (IMGT) | 59 | AREGYSYRSIRFDY |
| VH | 112 | QVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRSI RFDYWGQGTLVTVSS |
| DNA VH | 113 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCA |
| Heavy Chain | 116 | QVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRSI RFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKRVEPKSC |
| DNA Heavy Chain | 117 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCAGCGTCGACCAAAGGCCC GAGCGTGTTTCCGCTGGCCCCGAGCAGCAAAAGC ACCAGCGGCGGCACCGCCGCACTGGGCTGCCTGG TGAAAGATTATTTCCCGGAACCAGTGACCGTGAG CTGGAACAGCGGTGCCCTGACCAGCGGCGTGCAT ACCTTTCCGGCGGTGCTGCAAAGCAGCGGCCTGTA TAGCCTGAGCAGCGTTGTGACCGTGCCGAGCAGC AGCCTGGGCACCCAGACCTATATTTGCAACGTCAA CCATAAACCGAGCAACACCAAAGTCGATAAACGA GTCGAACCGAAAAGCTGC |
| LCDR1 (Combined) | 64 | RASQSISSNLN |
| LCDR2 (Combined) | 65 | AASNLQS |
| LCDR3 (Combined) | 66 | LQFDHTPFT |
| LCDR1 (Kabat) | 64 | RASQSISSNLN |
| LCDR2 (Kabat) | 65 | AASNLQS |
| LCDR3 (Kabat) | 66 | LQFDHTPFT |
| LCDR1 (Chothia) | 67 | SQSISSN |
| LCDR2 (Chothia) | 68 | AAS |
| LCDR3 (Chothia) | 69 | FDHTPF |
| LCDR1 (IMGT) | 70 | QSISSN |
| LCDR2 (IMGT) | 68 | AAS |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| LCDR3 (IMGT) | 66 | LQFDHTPFT |
| VL | 71 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIK |
| DNA VL | 82 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAA |
| Light Chain | 73 | DIQMTQSPSSLSASVGDRVTITCRASQSISSNLNWYQ QKPGKAPKLLIYAASNLQSGVPSRFSGSGSGTDFTLT ISSLQPEDFATYYCLQFDHTPFTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 118 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTTCGAC CATACTCCGTTCACCTTTGGCCAGGGCACGAAAGT TGAAATTAAACGTACGGTGGCCGCACCGAGCGTG TTTATCTTTCCGCCGAGCGATGAACAGCTGAAAAG CGGCACCGCCAGCGTGGTGTGCCTGCTGAACAAC TTTTATCCGCGCGAAGCCAAAGTGCAGTGGAAAG TGGATAACGCCCTGCAAAGCGGCAACAGCCAGGA AAGCGTTACCGAACAGGATAGCAAAGATAGCACC TACAGCCTGAGCAGCACCCTGACCCTGAGCAAAG CCGATTATGAAAAACATAAAGTGTATGCCTGCGA AGTGACCCATCAGGGCCTGAGCAGCCCAGTGACC AAAAGTTTTAACCGCGGCGAGTGT |
| IDT1D (HC1 + LC2) | | |
| HCDR1 (Combined) | 51 | GFTFSDYAMS |
| HCDR2 (Combined) | 105 | TIAYVGAPTHYADSVKG |
| HCDR3 (Combined) | 53 | EGYSYRSIRFDY |
| HCDR1 (Kabat) | 54 | DYAMS |
| HCDR2 (Kabat) | 105 | TIAYVGAPTHYADSVKG |
| HCDR3 (Kabat) | 53 | EGYSYRSIRFDY |
| HCDR1 (Chothia) | 55 | GFTFSDY |
| HCDR2 (Chothia) | 106 | AYVGAP |
| HCDR3 (Chothia) | 53 | EGYSYRSIRFDY |
| HCDR1 (IMGT) | 57 | GFTFSDYA |
| HCDR2 (IMGT) | 107 | IAYVGAPT |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR3 (IMGT) | 59 | AREGYSYRSIRFDY |
| VH | 112 | QVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRS IRFDYWGQGTLVTVSS |
| DNA VH | 113 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCA |
| Heavy Chain | 116 | QVQLLESGGGLVQPGGSLRLSCAASGFTFSDYAMS WVRQAPGKGLEWVSTIAYVGAPTHYADSVKGRFTI SRDNSKNTLYLQMNSLRAEDTAVYYCAREGYSYRS IRFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKRVEPKSC |
| DNA Heavy Chain | 117 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCGCTTACGTTGGCGCTCCGA CTCATTATGCGGATAGCGTGAAAGGCCGCTTTACC ATCAGCCGCGATAATTCGAAAAACACCCTGTATCT GCAAATGAACAGCCTGCGTGCGGAAGATACGGCC GTGTATTATTGCGCGCGTGAAGGTTACTCTTACCG TTCTATCCGTTTCGATTACTGGGGCCAAGGCACCC TGGTGACTGTTAGCTCAGCGTCGACCAAAGGCCC GAGCGTGTTTCCGCTGGCCCCGAGCAGCAAAAGC ACCAGCGGCGGCACCGCCGCACTGGGCTGCCTGG TGAAAGATTATTTCCCGGAACCAGTGACCGTGAG CTGGAACAGCGGTGCCCTGACCAGCGGCGTGCAT ACCTTTCCGGCGGTGCTGCAAAGCAGCGGCCTGT ATAGCCTGAGCAGCGTTGTGACCGTGCCGAGCAG CAGCCTGGGCACCCAGACCTATATTTGCAACGTCA ACCATAAACCGAGCAACACCAAAGTCGATAAACG AGTCGAACCGAAAAGCTGC |
| LCDR1 (Combined) | 64 | RASQSISSNLN |
| LCDR2 (Combined) | 65 | AASNLQS |
| LCDR3 (Combined) | 94 | LQYYHLPYT |
| LCDR1 (Kabat) | 64 | RASQSISSNLN |
| LCDR2 (Kabat) | 65 | AASNLQS |
| LCDR3 (Kabat) | 94 | LQYYHLPYT |
| LCDR1 (Chothia) | 67 | SQSISSN |
| LCDR2 (Chothia) | 68 | AAS |
| LCDR3 (Chothia) | 95 | YYHLPY |
| LCDR1 (IMGT) | 70 | QSISSN |
| LCDR2 (IMGT) | 68 | AAS |
| LCDR3 (IMGT) | 94 | LQYYHLPYT |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| VL | 96 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIK |
| DNA VL | 97 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAA |
| Light Chain | 103 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 104 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAACGTACGGTGGCCGCACCGAGCGT GTTTATCTTTCCGCCGAGCGATGAACAGCTGAAAA GCGGCACCGCCAGCGTGGTGTGCCTGCTGAACAA CTTTTATCCGCGCGAAGCCAAAGTGCAGTGGAAA GTGGATAACGCCCTGCAAAGCGGCAACAGCCAGG AAAGCGTTACCGAACAGGATAGCAAAGATAGCAC CTACAGCCTGAGCAGCACCCTGACCCTGAGCAAA GCCGATTATGAAAAACATAAAGTGTATGCCTGCG AAGTGACCCATCAGGGCCTGAGCAGCCCAGTGAC CAAAAGTTTTAACCGCGGCGAGTGC |
| IDT1E (HC2 + LC2) | | |
| HCDR1 (Combined) | 51 | GFTFSDYAMS |
| HCDR2 (Combined) | 75 | TISYLGQEKHYADSVKG |
| HCDR3 (Combined) | 53 | EGYSYRSIRFDY |
| HCDR1 (Kabat) | 54 | DYAMS |
| HCDR2 (Kabat) | 75 | TISYLGQEKHYADSVKG |
| HCDR3 (Kabat) | 53 | EGYSYRSIRFDY |
| HCDR1 (Chothia) | 55 | GFTFSDY |
| HCDR2 (Chothia) | 76 | SYLGQE |
| HCDR3 (Chothia) | 53 | EGYSYRSIRFDY |
| HCDR1 (IMGT) | 57 | GFTFSDYA |
| HCDR2 (IMGT) | 77 | ISYLGQEK |
| HCDR3 (IMGT) | 59 | AREGYSYRSIRFDY |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| VH | 85 | QVQLLESGGGLVQPGGSLRLSCAASGFTFSDYAMS WVRQAPGKGLEWVSTISYLGQEKHYADSVKGRFTI SRDNSKNTLYLQMNSLRAEDTAVYYCAREGYSYRS IRFDYWGQGTLVTVSS |
| DNA VH | 86 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCTCTTACCTGGGCCAGGAAA AACATTATGCGGATAGCGTGAAAGGCCGCTTTAC CATCAGCCGCGATAATTCGAAAAACACCCTGTAT CTGCAAATGAACAGCCTGCGTGCGGAAGATACGG CCGTGTATTATTGCGCGCGTGAAGGTTACTCTTAC CGTTCTATCCGTTTCGATTACTGGGGCCAAGGCAC CCTGGTGACTGTTAGCTCA |
| Heavy Chain | 119 | QVQLLESGGGLVQPGGSLRLSCAASGFTFSDYAMS WVRQAPGKGLEWVSTISYLGQEKHYADSVKGRFTI SRDNSKNTLYLQMNSLRAEDTAVYYCAREGYSYRS IRFDYWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKRVEPKSC |
| DNA Heavy Chain | 120 | CAGGTGCAATTGCTGGAAAGCGGCGGTGGCCTGG TGCAGCCGGGTGGCAGCCTGCGTCTGAGCTGCGC GGCGTCCGGATTCACCTTTTCTGACTACGCTATGT CTTGGGTGCGCCAGGCCCCGGGCAAAGGTCTCGA GTGGGTTTCCACTATCTCTTACCTGGGCCAGGAAA AACATTATGCGGATAGCGTGAAAGGCCGCTTTAC CATCAGCCGCGATAATTCGAAAAACACCCTGTAT CTGCAAATGAACAGCCTGCGTGCGGAAGATACGG CCGTGTATTATTGCGCGCGTGAAGGTTACTCTTAC CGTTCTATCCGTTTCGATTACTGGGGCCAAGGCAC CCTGGTGACTGTTAGCTCAGCGTCGACCAAAGGC CCGAGCGTGTTTCCGCTGGCCCCGAGCAGCAAAA GCACCAGCGGCGGCACCGCCGCACTGGGCTGCCT GGTGAAAGATTATTTCCCGGAACCAGTGACCGTG AGCTGGAACAGCGGTGCCCTGACCAGCGGCGTGC ATACCTTTCCGGCGGTGCTGCAAAGCAGCGGCCT GTATAGCCTGAGCAGCGTTGTGACCGTGCCGAGC AGCAGCCTGGGCACCCAGACCTATATTTGCAACG TCAACCATAAACCGAGCAACACCAAAGTCGATAA ACGAGTCGAACCGAAAAGCTGC |
| LCDR1 (Combined) | 64 | RASQSISSNLN |
| LCDR2 (Combined) | 65 | AASNLQS |
| LCDR3 (Combined) | 94 | LQYYHLPYT |
| LCDR1 (Kabat) | 64 | RASQSISSNLN |
| LCDR2 (Kabat) | 65 | AASNLQS |
| LCDR3 (Kabat) | 94 | LQYYHLPYT |
| LCDR1 (Chothia) | 67 | SQSISSN |
| LCDR2 (Chothia) | 68 | AAS |
| LCDR3 (Chothia) | 95 | YYHLPY |
| LCDR1 (IMGT) | 70 | QSISSN |
| LCDR2 (IMGT) | 68 | AAS |
| LCDR3 (IMGT) | 94 | LQYYHLPYT |

TABLE 2-continued

| Examples of anti-FXI/FXIa Antibody Binding Agents (e.g., anti-idiotype antibody) | | |
|---|---|---|
| Sequence Description | Sequence Identifier (SEQ ID NO:) | Amino acid or polynucleotide sequence |
| VL | 96 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIK |
| DNA VL | 97 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAA |
| Light Chain | 103 | DIQMTQSPSSLSASVGDRVTITCRASQSISSNLNWYQ QKPGKAPKLLIYAASNLQSGVPSRFSGSGSGTDFTLT ISSLQPEDFATYYCLQYYHLPYTFGQGTKVEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |
| DNA Light Chain | 104 | GATATCCAGATGACCCAGAGCCCGAGCAGCCTGA GCGCCAGCGTGGGCGATCGCGTGACCATTACCTG CAGAGCCAGCCAGTCTATTTCTTCTAACCTGAACT GGTACCAGCAGAAACCGGGCAAAGCGCCGAAACT ATTAATCTACGCTGCTTCTAACCTGCAAAGCGGCG TGCCGAGCCGCTTTAGCGGCAGCGGATCCGGCAC CGATTTCACCCTGACCATTAGCTCTCTGCAACCGG AAGACTTTGCGACCTATTATTGCCTGCAGTACTAC CATCTGCCGTACACCTTTGGCCAGGGCACGAAAG TTGAAATTAAACGTACGGTGGCCGCACCGAGCGT GTTTATCTTTCCGCCGAGCGATGAACAGCTGAAAA GCGGCACCGCCAGCGTGGTGTGCCTGCTGAACAA CTTTTATCCGCGCGAAGCCAAAGTGCAGTGGAAA GTGGATAACGCCCTGCAAAGCGGCAACAGCCAGG AAAGCGTTACCGAACAGGATAGCAAAGATAGCAC CTACAGCCTGAGCAGCACCCTGACCCTGAGCAAA GCCGATTATGAAAAACATAAAGTGTATGCCTGCG AAGTGACCCATCAGGGCCTGAGCAGCCCAGTGAC CAAAAGTTTTAACCGCGGCGAGTGC |
| IDT1C-IDT1E consensus | | |
| HCDR1 (Combined) | 51 | GFTFSDYAMS |
| HCDR2 (Combined) | 121 | TI$X_1$Y$X_2$G$X_3X_4X_5$HYADSVKG, where $X_1$ is A or S, $X_2$ is V or L, $X_3$ is A or Q, $X_4$ is P or E, and $X_5$ is T or K |
| HCDR3 (Combined) | 53 | EGYSYRSIRFDY |
| HCDR1 (Kabat) | 54 | DYAMS |
| HCDR2 (Kabat) | 121 | TI$X_1$YX2G$X_3X_4X_5$HYADSVKG, where $X_1$ is A or S, $X_2$ is V or L, $X_3$ is A or Q, $X_4$ is P or E, and $X_5$ is T or K |
| HCDR3 (Kabat) | 53 | EGYSYRSIRFDY |
| HCDR1 (Chothia) | 55 | GFTFSDY |
| HCDR2 (Chothia) | 122 | $X_1$Y$X_2$G$X_3X_4$where $X_1$ is A or S, $X_2$ is V or L, $X_3$ is A or Q, and $X_4$ is P or E |
| HCDR3 (Chothia) | 53 | EGYSYRSIRFDY |
| HCDR1 (IMGT) | 57 | GFTFSDYA |

TABLE 2-continued

Examples of anti-FXI/FXIa Antibody Binding Agents (e.g., anti-idiotype antibody)

| Sequence Description | Sequence Identifier (SEQ ID NO:) | Amino acid or polynucleotide sequence |
|---|---|---|
| HCDR2 (IMGT) | 123 | $IX_1YX_2GX_3X_4$where $X_1$ is A or S, $X_2$ iS V or L, $X_3$ is A or Q, and $X_4$ is P or E |
| HCDR3 (IMGT) | 59 | AREGYSYRSIRFDY |
| VH | 124 | QVQLLESGGGLVQPGGSLRLSCAASGFTFSDYAMS $WVRQAPGKGLEWVSTIX_1YX_2GX_3X_4X_5HYADSVKG$ RFTISRDNSKNTLYLQMNSLRAEDTAVYYCAREGYS YRSIRFDYWGQGTLVTVSS, where $X_1$ is A or S, $X_2$ is V or L, $X_3$ is A or Q, $X_4$ is P or E, and $X_5$ is T or K |
| LCDR1 (Combined) | 64 | RASQSISSNLN |
| LCDR2 (Combined) | 65 | AASNLQS |
| LCDR3 (Combined) | 125 | $LQX_1X_2HX_3PX_4T$, where X1 is F or Y, $X_2$ is D or Y, $X_3$ is T or L, $X_4$ is F or Y |
| LCDR1 (Kabat) | 64 | RASQSISSNLN |
| LCDR2 (Kabat) | 65 | AASNLQS |
| LCDR3 (Kabat) | 125 | $LQX_1X_2HX_3PX_4T$, where $X_1$ is F or Y, $X_2$ is D or Y, $X_3$ is T or L, $X_4$ is F or Y |
| LCDR1 (Chothia) | 67 | SQSISSN |
| LCDR2 (Chothia) | 68 | AAS |
| LCDR3 (Chothia) | 126 | $X_1X_2HX_3PX_4$, where $X_1$ is F or Y, $X_2$ is D or Y, $X_3$ is T or L, $X_4$ is F or Y |
| LCDR1 (IMGT) | 70 | QSISSN |
| LCDR2 (IMGT) | 68 | AAS |
| LCDR3 (IMGT) | 125 | $LQX_1X_2HX_3PX_4T$, where $X_1$ is F or Y, $X_2$ is D or Y, $X_3$ is T or L, $X_4$ is F or Y |
| VL | 127 | DIQMTQSPSSLSASVGDRVTITCRASQSISSNLNWYQ QKPGKAPKLLIYAASNLQSGVPSRFSGSGSGTDFTLT $ISSLQPEDFATYYCLQX_1X_2HX_3PX_4TFGQGTKVEIK$, where $X_1$ is F or Y, $X_2$ is D or Y, $X_3$ is T or L, $X_4$ is F or Y |

Since each of the antibodies disclosed in Table 2 can bind to anti-FXI/FXIa antibody NOV1401, and antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched), although each antibody preferably contains a VH CDR1, 2 and 3 and a VL CDR1, 2 and 3 to create other FXI and/or FXIa binding molecules provided herein. Such "mixed and matched" anti-FXI/FXIa antibody binding agents can be tested using the binding assays known in the art and those described in the Examples (e.g., ELISAs, SET, BIACORE™ assays). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for antibodies provided herein. In addition to the foregoing, in one embodiment, binding agents provided herein may be antigen-binding fragments and can comprise a VH CDR1, 2, and 3, or a VL CDR 1, 2, and 3, wherein the fragment binds to an anti-FXI/FXIa antibody, such as NOV1401, as a single variable domain.

In particular embodiments, provided herein is a binding agent (e.g., anti-idiotype antibody, for example a Fab) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (e.g., comprising a VH comprising the amino acid sequence of SEQ ID NO: 3 and a VL comprising the amino acid sequence of SEQ ID NO: 7), and wherein the binding agent is an antibody (e.g., full length IgG, Fab fragment) comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence selected from the group consisting of SEQ ID NO: 51, 54, 55 and 57, the HCDR2 comprises the amino acid sequence selected from the group consisting of SEQ ID NO: 52, 56, 58, 75, 76, 77, 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95; or
b) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76, 77, 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69.

In particular embodiments, provided herein is a binding agent (e.g., anti-idiotype antibody, for example a Fab) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (e.g., comprising a VH comprising the amino acid sequence of SEQ ID NO: 3 and a VL comprising the amino acid sequence of SEQ ID NO: 7), and wherein the binding agent is an antibody (e.g., full length IgG, Fab fragment) comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence selected from the group consisting of SEQ ID NO: 51, 54, 55 and 57, the HCDR2 comprises the amino acid sequence selected from the group consisting of SEQ ID NO: 52, 56 and 58, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;
b) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76 and 77, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;
c) the HCDR1 comprises the amino acid sequence selected from the group consisting of SEQ ID NO: 51, 54, 55 and 57, the HCDR2 comprises the amino acid sequence selected from the group consisting of SEQ ID NO: 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 94 and 95;
d) the HCDR1 comprises the amino acid sequence selected from the group consisting of SEQ ID NO: 51, 54, 55 and 57, the HCDR2 comprises the amino acid sequence selected from the group consisting of SEQ ID NO: 75, 76 and 77, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69; or
e) the HCDR1 comprises the amino acid sequence selected from the group consisting of SEQ ID NO: 51, 54, 55 and 57, the HCDR2 comprises the amino acid sequence selected from the group consisting of SEQ ID NO: 105, 106 and 107, the HCDR3 comprises the amino acid sequence selected from the group consisting of SEQ ID NO: 53 and 59, the LCDR1 comprises the amino acid sequence selected from the group consisting of SEQ ID NO: 64, 67 and 70, the LCDR2 comprises the amino acid sequence selected from the group consisting of SEQ ID NO: 65 and 68, and the LCDR3 comprises the amino acid sequence selected from the group consisting of SEQ ID NO: 66 and 69.

In particular embodiments, provided herein is a binding agent (e.g., anti-idiotype antibody, for example a Fab) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence of SEQ ID NO: 51, the HCDR2 comprises the amino acid sequence of SEQ ID NO: 52 or 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94; or b) the HCDR1 comprises the amino acid sequence of SEQ ID NO: 51, the HCDR2 comprises the amino acid sequence of SEQ ID NO: 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

In a more specific embodiment, provided herein is a binding agent (e.g., anti-idiotype antibody, for example a Fab) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence of SEQ ID NO: 51, the HCDR2 comprises the amino acid sequence of SEQ ID NO: 52, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

b) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

c) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO:53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

d) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66: or e) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

Suitably, the binding agent of the disclosure is an antibody or antigen-binding fragment (e.g., Fab) comprising (1) a VH comprising complementarity determining regions HCDR1, HCDR2, and HCDR3, and (2) a VL comprising complementarity determining regions LCDR1, LCDR2, and LCDR3; wherein:

a) the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

b) the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

c) the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

d) the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively;

e) the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 94, respectively.

Since each of the binding agents (e.g., antibodies) disclosed in Table 2 can bind to anti-FXI/FXIa antibody NOV1401, the VH, VL, full length light chain, and full length heavy chain sequences (amino acid sequences and the nucleotide sequences encoding the amino acid sequences) can be "mixed and matched" to create other anti-FXI/FXIa antibody binding agents. Such "mixed and matched" anti-FXI/FXIa antibody binding agents can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

In particular embodiments, provided herein is a binding agent (e.g., anti-idiotype antibody, for example a Fab) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/

FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain variable region (VH) and a light chain variable region (VL), wherein:

(i) the VH comprises the amino acid sequence that is at least 90% or at least 95% identical, to the amino acid sequence of SEQ ID NO: 78, 85, 108, or 112, and the VL comprises the amino acid sequence that is at least 90% or at least 95% identical, to the amino acid sequence of SEQ ID NO: 71; or (ii) the VH comprises the amino acid sequence that is at least 90% or at least 95% identical, to the amino acid sequence of SEQ ID NO: 60, 78, 85, 90, 108, or 112, and the VL comprises the amino acid sequence that is at least 90% or at least 95% identical, to the amino acid sequence of SEQ ID NO: 96.

In particular embodiments, provided herein is a binding agent (e.g., anti-idiotype antibody, for example a Fab) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain variable region (VH) and a light chain variable region (VL), wherein:

a) the VH comprises the amino acid sequence that is at least 90% or at least 95% identical, to the amino acid sequence of SEQ ID NO: 78 or 85, preferably SEQ ID NO: 85, and the VL comprises the amino acid sequence that is at least 90% or at least 95% identical, to the amino acid sequence of SEQ ID NO: 71;

b) the VH comprises the amino acid sequence that is at least 90% or at least 95% identical, to the amino acid sequence of SEQ ID NO: 90 or 60, preferably SEQ ID NO: 60, and the VL comprises the amino acid sequence that is at least 90% or at least 95% identical, to the amino acid sequence of SEQ ID NO: 96;

c) the VH comprises the amino acid sequence that is at least 90% or at least 95% identical, to the amino acid sequence of SEQ ID NO: 108 or 112, preferably SEQ ID NO: 112, and the VL comprises the amino acid sequence that is at least 90% or at least 95% identical, to the amino acid sequence of SEQ ID NO: 71;

d) the VH comprises the amino acid sequence that is at least 90% or at least 95% identical, to the amino acid sequence of SEQ ID NO: 112 and the VL comprises the amino acid sequence that is at least 90% or at least 95% identical, to the amino acid sequence of SEQ ID NO: 96; or e) the VH comprises the amino acid sequence that is at least 90% or at least 95% identical, to the amino acid sequence of SEQ ID NO: 85 and the VL comprises the amino acid sequence that is at least 90% or at least 95% identical, to the amino acid sequence of SEQ ID NO: 96.

In a preferred embodiment, the differences in amino acid sequence are not within the complementarity determining regions. Thus, in specific embodiments, provided herein is a binding agent (e.g., anti-idiotype antibody, for example a Fab) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the VH comprises the amino acid sequence that is at least 90% or at least 95% identical, to the amino acid sequence of SEQ ID NO: 78 or 85, preferably SEQ ID NO: 85, and the VL comprises the amino acid sequence that is at least 90% or at least 95% identical, to the amino acid sequence of SEQ ID NO: 71, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

b) the VH comprises the amino acid sequence that is at least 90% or at least 95% identical, to the amino acid sequence of SEQ ID NO: 90 or 60, preferably SEQ ID NO: 60, and the VL comprises the amino acid sequence that is at least 90% or at least 95% identical, to the amino acid sequence of SEQ ID NO: 96, and wherein the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

c) the VH comprises the amino acid sequence that is at least 90% or at least 95% identical, to the amino acid sequence of SEQ ID NO: 108 or 112, preferably SEQ ID NO: 112, and the VL comprises the amino acid sequence that is at least 90% or at least 95% identical, to the amino acid sequence of SEQ ID NO: 71, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

d) the VH comprises the amino acid sequence that is at least 90% or at least 95% identical, to the amino acid sequence of SEQ ID NO: 112 and the VL comprises the amino acid sequence that is at least 90% or at least 95% identical, to the amino acid sequence of SEQ ID NO: 96, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 94, respectively;

e) the VH comprises the amino acid sequence that is at least 90% or at least 95% identical, to the amino acid sequence of SEQ ID NO: 85 and the VL comprises the amino acid sequence that is at least 90% or at least 95% identical, to the amino acid sequence of SEQ ID NO: 96, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively; or f) the VH comprises the amino acid sequence that is at least 90% or at least 95% identical, to the amino acid sequence of SEQ ID NO: 124 and the VL comprises the amino acid sequence that is at least 90% or at least 95% identical, to the amino acid sequence of SEQ ID NO: 127, and wherein the HCDR1, HCDR2 and HCDR3 are as set forth in SEQ ID NOs: 51, 121, and 53, respectively, and the LCDR1, LCDR2, and LCDR3 are as set forth in SEQ ID NOs: 64, 65 and 125, respectively.

In more particular embodiments, the differences in amino acid sequence are conservative substitutions.

In particular embodiments, provided herein is a binding agent (e.g., anti-idiotype antibody, for example a Fab) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein:

f) the VH comprises the amino acid sequence that is 90% to 99% identical, e.g, 90% to 98% identical, 95% to 97% identical, 96% or 97% identical, to the amino acid sequence of SEQ ID NO: 60, and wherein HCDR1 and HCDR3 of the binding agent are the same as HCDR1 and HCDR3 of SEQ ID NO: 60, respectively, and wherein HCDR2 of the binding agent is not the same as HCDR2 of SEQ ID NO: 60; and/or g) the VL comprises the amino acid sequence that is 90% to 99%, e.g, 95% to 98% identical, 98%, to the amino acid sequence of SEQ ID NO: 71, and wherein LCDR1 and LCDR2 of the binding agent are the same as LCDR1 and LCDR2, respectively, of SEQ ID NO: 71, and wherein LCDR3 of the binding agent is not the same as LCDR3 of SEQ ID NO: 71.

In more particular embodiments, the differences in amino acid sequence are conservative substitutions.

In specific embodiments, provided herein is a binding agent (e.g., anti-idiotype antibody, e.g., IgG, Fab) which specifically binds a target anti-FXI/FXIa antibody, as well as a pharmaceutical composition comprising such a binding agent, wherein the binding agent inhibits or reverses (e.g., partially reverses) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain variable region (VH) and a light chain variable region (VL), wherein:

a) the VH comprises the amino acid sequence of SEQ ID NO: 78 or 85, preferably SEQ ID NO: 85, and the VL comprises the amino acid sequence of SEQ ID NO: 71;

b) the VH comprises the amino acid sequence of SEQ ID NO: 90 or 60, preferably SEQ ID NO: 60, and the VL comprises the amino acid sequence of SEQ ID NO: 96;

c) the VH comprises the amino acid sequence of SEQ ID NO: 108 or 112, preferably SEQ ID NO: 112 and the VL comprises the amino acid sequence of SEQ ID NO: 71;

d) the VH comprises the amino acid sequence of SEQ ID NO: 112 and the VL comprises the amino acid sequence of SEQ ID NO: 96;

e) the VH comprises the amino acid sequence of SEQ ID NO: 85 and the VL comprises the amino acid sequence of SEQ ID NO: 96; or f) the VH comprises the amino acid sequence of SEQ ID NO: 124 and the VL comprises the amino acid sequence of SEQ ID NO: 127.

In one embodiment, provided herein is a binding agent, wherein the binding agent is an antibody comprising a heavy chain variable region (VH) and a light chain variable region (VL), wherein the VH comprises the amino acid sequence of SEQ ID NO: 78 and the VL comprises the amino acid sequence of SEQ ID NO: 71. In one embodiment, provided herein is a binding agent, wherein the binding agent is an antibody comprising a heavy chain variable region (VH) and a light chain variable region (VL), wherein the VH comprises the amino acid sequence of SEQ ID NO: 85 and the VL comprises the amino acid sequence of SEQ ID NO: 71. In another embodiment, provided herein is a binding agent, wherein the binding agent is an antibody comprising a heavy chain variable region (VH) and a light chain variable region (VL), wherein the VH comprises the amino acid sequence of SEQ ID NO: 90 and the VL comprises the amino acid sequence of SEQ ID NO: 96. In a further embodiment, provided herein is a binding agent, wherein the binding agent is an antibody comprising a heavy chain variable region (VH) and a light chain variable region (VL), wherein the VH comprises the amino acid sequence of SEQ ID NO: 60 and the VL comprises the amino acid sequence of SEQ ID NO: 96. In one embodiment, provided herein is a binding agent, wherein the binding agent is an antibody comprising a heavy chain variable region (VH) and a light chain variable region (VL), wherein the VH comprises the amino acid sequence of SEQ ID NO: 108 and the VL comprises the amino acid sequence of SEQ ID NO: 71. In one embodiment, provided herein is a binding agent, wherein the binding agent is an antibody comprising a heavy chain variable region (VH) and a light chain variable region (VL), wherein the VH comprises the amino acid sequence of SEQ ID NO: 112 and the VL comprises the amino acid sequence of SEQ ID NO: 71. In one embodiment, provided herein is a binding agent, wherein the binding agent is an antibody comprising a heavy chain variable region (VH) and a light chain variable region (VL), wherein the VH comprises the amino acid sequence of SEQ ID NO: 112 and the VL comprises the amino acid sequence of SEQ ID NO: 96. In one embodiment, provided herein is a binding agent, wherein the binding agent is an antibody comprising a heavy chain variable region (VH) and a light chain variable region (VL), wherein the VH comprises the amino acid sequence of SEQ ID NO: 85 and the VL comprises the amino acid sequence of SEQ ID NO: 96. In one embodiment, provided herein is a binding agent, wherein the binding agent is an antibody comprising a heavy chain variable region (VH) and a light chain variable region (VL), wherein the VH comprises the amino acid sequence of SEQ ID NO: 124 and the VL comprises the amino acid sequence of SEQ ID NO: 127.

In particular aspects, provided herein is a binding agent (e.g., anti-idiotype antibody, e.g., IgG, Fab) which specifically binds a target anti-FXI/FXIa antibody (e.g., NOV1401 comprising a VH comprising the amino acid sequence of SEQ ID NO: 3 and a VL comprising the amino acid sequence of SEQ ID NO: 7), as well as a pharmaceutical composition comprising the binding agent which specifically binds a target anti-FXI/FXIa antibody, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), wherein the binding agent is an antibody comprising a VH and a VL, wherein:

a) the VH comprises 3 VH CDRs of the VH amino acid sequence of SEQ ID NO: 78, 85, 108, or 112, and the VL comprises the 3 VL CDRs of the VL amino acid sequence of SEQ ID NO: 71; or
b) the VH comprises 3 VH CDRs of the VH amino acid sequence of SEQ ID NO: 60, 78, 85, 90, 108, or 112, and the VL comprises the 3 VL CDRs of the VL amino acid sequence of SEQ ID NO: 96.

In particular aspects, provided herein is a binding agent (e.g., anti-idiotype antibody, e.g., IgG, Fab) which specifically binds a target anti-FXI/FXIa antibody (e.g., NOV1401 comprising a VH comprising the amino acid sequence of SEQ ID NO: 3 and a VL comprising the amino acid sequence of SEQ ID NO: 7), as well as a pharmaceutical composition comprising the binding agent which specifically binds a target anti-FXI/FXIa antibody, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), wherein the binding agent is an antibody comprising a VH and a VL, wherein:

a) the VH comprises 3 VH CDRs of the VH amino acid sequence of SEQ ID NO: 78, and the VL comprises the 3 VL CDRs of the VL amino acid sequence of SEQ ID NO: 71; or
b) the VH comprises 3 VH CDRs of the VH amino acid sequence of SEQ ID NO: 85, and the VL comprises the 3 VL CDRs of the VL amino acid sequence of SEQ ID NO: 71; or
c) the VH comprises 3 VH CDRs of the VH amino acid sequence of SEQ ID NO: 108, and the VL comprises the 3 VL CDRs of the VL amino acid sequence of SEQ ID NO: 71; or
d) the VH comprises 3 VH CDRs of the VH amino acid sequence of SEQ ID NO: 112, and the VL comprises the 3 VL CDRs of the VL amino acid sequence of SEQ ID NO: 71; or
e) the VH comprises 3 VH CDRs of the VH amino acid sequence of SEQ ID NO: 60, and the VL comprises the 3 VL CDRs of the VL amino acid sequence of SEQ ID NO: 96; or
f) the VH comprises 3 VH CDRs of the VH amino acid sequence of SEQ ID NO: 78, and the VL comprises the 3 VL CDRs of the VL amino acid sequence of SEQ ID NO: 96; or
g) the VH comprises 3 VH CDRs of the VH amino acid sequence of SEQ ID NO: 85, and the VL comprises the 3 VL CDRs of the VL amino acid sequence of SEQ ID NO: 96; or
h) the VH comprises 3 VH CDRs of the VH amino acid sequence of SEQ ID NO: 90, and the VL comprises the 3 VL CDRs of the VL amino acid sequence of SEQ ID NO: 96; or
i) the VH comprises 3 VH CDRs of the VH amino acid sequence of SEQ ID NO: 108, and the VL comprises the 3 VL CDRs of the VL amino acid sequence of SEQ ID NO: 96; or
j) the VH comprises 3 VH CDRs of the VH amino acid sequence of SEQ ID NO: 112, and the VL comprises the 3 VL CDRs of the VL amino acid sequence of SEQ ID NO: 96; or
k) the VH comprises 3 VH CDRs of the VH amino acid sequence of SEQ ID NO: 124, and the VL comprises the 3 VL CDRs of the VL amino acid sequence of SEQ ID NO: 127.

In specific embodiments, provided herein is a binding agent (e.g., anti-idiotype antibody) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain and a light chain, wherein:

a) the heavy chain comprises the amino acid sequence that is at least 90% or at least 95% identical, to the amino acid sequence of SEQ ID NO: 80, 87, 110, 114, 116 or 119, and the light chain comprises the amino acid sequence that is at least 90% or at least 95% identical, to the amino acid sequence of SEQ ID NO: 73 or 83; or
b) the heavy chain comprises the amino acid sequence that is at least 90% or at least 95% identical, to the amino acid sequence of SEQ ID NO: 62, 80, 87, 92, 101, 110, 114, 116, or 119, and the light chain comprises the amino acid sequence that is at least 90% or at least 95% identical, to the amino acid sequence of SEQ ID NO: 98 or 103.

In particular embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain and a light chain, wherein:

a) the heavy chain comprises the amino acid sequence that is at least 90% or at least 95% identical, to the amino acid sequence of SEQ ID NO: 92 or 101, preferably SEQ ID NO: 101, and the light chain comprises the amino acid sequence that is at least 90% or at least 95% identical, to the amino acid sequence of SEQ ID NO: 98 or 103, preferably SEQ ID NO: 103;
b) the heavy chain comprises the amino acid sequence that is at least 90% or at least 95% identical, to the amino acid sequence of SEQ ID NO: 80 or 87, preferably SEQ ID NO: 87, and the light chain comprises the amino acid sequence that is at least 90% or at least 95% identical, to the amino acid sequence of SEQ ID NO: 83 or 73, preferably SEQ ID NO: 73;

c) the heavy chain comprises the amino acid sequence that is at least 90% or at least 95% identical, to the amino acid sequence of SEQ ID NO: 110 or 114 or 116, preferably SEQ ID NO: 116, and the light chain comprises the amino acid sequence that is at least 90% or at least 95% identical, to the amino acid sequence of SEQ ID NO: 83 or 73, preferably SEQ ID NO: 73;

d) the heavy chain comprises the amino acid sequence that is at least 90% or at least 95% identical, to the amino acid sequence of SEQ ID NO: 116 and the light chain comprises the amino acid sequence that is at least 90% or at least 95% identical, to the amino acid sequence of SEQ ID NO: 103; or e) the heavy chain comprises the amino acid sequence that is at least 90% or at least 95% identical, to the amino acid sequence of SEQ ID NO: 119 and the light chain comprises the amino acid sequence that is at least 90% or at least 95% identical, to the amino acid sequence of SEQ ID NO: 103.

In particular embodiments, provided herein is a binding agent (e.g., anti-idiotype antibody) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain and a light chain, wherein:

a) the heavy chain comprises the amino acid sequence that is at least 90% or at least 95% identical, to the amino acid sequence of SEQ ID NO: 92, and the light chain comprises the amino acid sequence that is at least 90% or at least 95% identical, to the amino acid sequence of SEQ ID NO: 98;

b) the heavy chain comprises the amino acid sequence that is at least 90% or at least 95% identical, to the amino acid sequence of SEQ ID NO: 101, and the light chain comprises the amino acid sequence that is at least 90% or at least 95% identical, to the amino acid sequence of SEQ ID NO: 103;

c) the heavy chain comprises the amino acid sequence that is at least 90% or at least 95% identical, to the amino acid sequence of SEQ ID NO: 80, and the light chain comprises the amino acid sequence that is at least 90% or at least 95% identical, to the amino acid sequence of SEQ ID NO: 83;

d) the heavy chain comprises the amino acid sequence that is at least 90% or at least 95% identical, to the amino acid sequence of SEQ ID NO: 87, and the light chain comprises the amino acid sequence that is at least 90% or at least 95% identical, to the amino acid sequence of SEQ ID NO: 73;

e) the heavy chain comprises the amino acid sequence that is at least 90% or at least 95% identical, to the amino acid sequence of SEQ ID NO: 110, and the light chain comprises the amino acid sequence that is at least 90% or at least 95% identical, to the amino acid sequence of SEQ ID NO: 83;

f) the heavy chain comprises the amino acid sequence that is at least 90% or at least 95% identical, to the amino acid sequence of SEQ ID NO: 114, and the light chain comprises the amino acid sequence that is at least 90% or at least 95% identical, to the amino acid sequence of SEQ ID NO: 73;

g) the heavy chain comprises the amino acid sequence that is at least 90% or at least 95% identical, to the amino acid sequence of SEQ ID NO: 116, and the light chain comprises the amino acid sequence that is at least 90% or at least 95% identical, to the amino acid sequence of SEQ ID NO: 73;

h) the heavy chain comprises the amino acid sequence that is at least 90% or at least 95% identical, to the amino acid sequence of SEQ ID NO: 116 and the light chain comprises the amino acid sequence that is at least 90% or at least 95% identical, to the amino acid sequence of SEQ ID NO: 103; or i) the heavy chain comprises the amino acid sequence that is at least 90% or at least 95% identical, to the amino acid sequence of SEQ ID NO: 119 and the light chain comprises the amino acid sequence that is at least 90% or at least 95% identical, to the amino acid sequence of SEQ ID NO: 103.

In a preferred embodiment, the differences in amino acid sequence are not within the complementarity determining regions. Thus, in specific embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses for example by at least 50%, at least 60%, at least 70%, at least 75%, or at least 80%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a heavy chain comprising complementarity determining regions HCDR1, HCDR2, and HCDR3, and (2) a light chain comprising complementarity determining regions LCDR1, LCDR2, and LCDR3; wherein:

a) the heavy chain comprises the amino acid sequence that is at least 90% or at least 95% identical, to the amino acid sequence of SEQ ID NO: 80 or 87, preferably SEQ ID NO: 87, and the light chain comprises the amino acid sequence that is at least 90% or at least 95% identical, to the amino acid sequence of SEQ ID NO: 83 or 73, preferably SEQ ID NO: 73, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

b) the heavy chain comprises the amino acid sequence that is at least 90% or at least 95% identical, to the amino acid sequence of SEQ ID NO: 92 or 101, preferably SEQ ID NO: 101, and the light chain comprises the amino acid sequence that is at least 90% or at least 95% identical, to the amino acid sequence of SEQ ID NO: 98 or 103, preferably SEQ ID NO: 103, and wherein the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

c) the heavy chain comprises the amino acid sequence that is at least 90% or at least 95% identical, to the amino acid sequence of SEQ ID NO: 110 or 114 or 116, preferably SEQ ID NO: 116, and the light chain comprises the amino acid sequence that is at least 90% or at least 95% identical, to the amino acid sequence of SEQ ID NO: 83 or 73, preferably SEQ ID NO: 73, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

d) the heavy chain comprises the amino acid sequence that is at least 90% or at least 95% identical, to the amino acid sequence of SEQ ID NO: 116 and the light chain comprises the amino acid sequence that is at least 90% or at least 95% identical, to the amino acid sequence of SEQ ID NO: 103, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 94, respectively; or e) the heavy chain comprises the amino acid sequence that is at least 90% or at least 95% identical, to the amino acid sequence of SEQ ID NO: 119 and the light chain comprises the amino acid sequence that is at least 90% or at least 95% identical, to the amino acid sequence of SEQ ID NO: 103, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively.

In a specific embodiment, the differences in amino acid sequence are not within the complementarity determining regions. Thus, in specific embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses for example by at least 50%, at least 60%, at least 70%, at least 75%, or at least 80%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a heavy chain comprising complementarity determining regions HCDR1, HCDR2, and HCDR3, and (2) a light chain comprising complementarity determining regions LCDR1, LCDR2, and LCDR3; wherein:

a) the heavy chain comprises the amino acid sequence that is at least 90% or at least 95% identical, to the amino acid sequence of SEQ ID NO: 80, and the light chain comprises the amino acid sequence that is at least 90% or at least 95% identical, to the amino acid sequence of SEQ ID NO: 83, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

b) the heavy chain comprises the amino acid sequence that is at least 90% or at least 95% identical, to the amino acid sequence of SEQ ID NO: 87, and the light chain comprises the amino acid sequence that is at least 90% or at least 95% identical, to the amino acid sequence of SEQ ID NO: 73, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

c) the heavy chain comprises the amino acid sequence that is at least 90% or at least 95% identical, to the amino acid sequence of SEQ ID NO: 92, and the light chain comprises the amino acid sequence that is at least 90% or at least 95% identical, to the amino acid sequence of SEQ ID NO: 98, and wherein the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

d) the heavy chain comprises the amino acid sequence that is at least 90% or at least 95% identical, to the amino acid sequence of SEQ ID NO: 101, and the light chain comprises the amino acid sequence that is at least 90% or at least 95% identical, to the amino acid sequence of SEQ ID NO: 103, and wherein the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

e) the heavy chain comprises the amino acid sequence that is at least 90% or at least 95% identical, to the amino acid sequence of SEQ ID NO: 110, and the light chain comprises the amino acid sequence that is at least 90% or at least 95% identical, to the amino acid sequence of SEQ ID NO: 83, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

f) the heavy chain comprises the amino acid sequence that is at least 90% or at least 95% identical, to the amino acid sequence of SEQ ID NO: 114, and the light chain comprises the amino acid sequence that is at least 90% or at least 95% identical, to the amino acid sequence of SEQ ID NO: 73, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

g) the heavy chain comprises the amino acid sequence that is at least 90% or at least 95% identical, to the amino acid sequence of SEQ ID NO: 116, and the light chain comprises the amino acid sequence that is at least 90% or at least 95% identical, to the amino acid sequence of SEQ ID NO: 73, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 66, respectively;

h) the heavy chain comprises the amino acid sequence that is at least 90% or at least 95% identical, to the amino acid sequence of SEQ ID NO: 116 and the light chain comprises the amino acid sequence that is at least 90% or at least 95% identical, to the amino acid sequence of SEQ ID NO: 103, and wherein the HCDR1, HCDR2 and HCDR3 are as set forth in SEQ ID NOs: 51, 105 and 53, respectively, and the LCDR1, LCDR2, and LCDR3 are as set forth in SEQ ID NOs: 64, 65 and 94, respectively; or i) the heavy chain comprises the amino acid sequence that is at least 90% or at least 95% identical, to the amino acid sequence of SEQ ID NO: 119 and the light chain comprises the amino acid sequence that is at least 90% or at least 95% identical, to the amino acid sequence of SEQ ID NO: 103, and wherein the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively.

In more particular embodiments, the differences in amino acid sequence are conservative substitutions.

In specific embodiments, provided herein is a binding agent (e.g., anti-idiotype antibody, e.g., IgG, Fab) which specifically binds a target anti-FXI/FXIa antibody, as well as a pharmaceutical composition comprising such a binding agent, wherein the binding agent inhibits or reverses (e.g., partially reverses) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain and a light chain, wherein:

a) the heavy chain comprises the amino acid sequence of SEQ ID NO: 92 or 101, preferably SEQ ID NO: 101, and the light chain comprises the amino acid sequence of SEQ ID NO: 98 or 103, preferably SEQ ID NO: 103;
b) the heavy chain comprises the amino acid sequence of SEQ ID NO: 80 or 87, preferably SEQ ID NO: 87, and the light chain comprises the amino acid sequence of SEQ ID NO: 83 or 73, preferably SEQ ID NO: 73;
c) the heavy chain comprises the amino acid sequence of SEQ ID NO: 110 or 114 or 116, preferably SEQ ID NO: 116, and the light chain comprises the amino acid sequence of SEQ ID NO: 83 or 73, preferably SEQ ID NO: 73;
d) the heavy chain comprises the amino acid sequence of SEQ ID NO: 116 and the light chain comprises the amino acid of SEQ ID NO: 103; or
e) the heavy chain comprises the amino acid sequence of SEQ ID NO: 119 and the light chain comprises the amino acid sequence of SEQ ID NO: 103.

In more specific embodiments, provided herein is a binding agent (e.g., anti-idiotype antibody, e.g., IgG, Fab) which specifically binds a target anti-FXI/FXIa antibody, as well as a pharmaceutical composition comprising such a binding agent, wherein the binding agent inhibits or reverses (e.g., partially reverses) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain and a light chain, wherein:

a) the heavy chain comprises the amino acid sequence of SEQ ID NO: 92, and the light chain comprises the amino acid sequence of SEQ ID NO: 98;
b) the heavy chain comprises the amino acid sequence of SEQ ID NO: 101, and the light chain comprises the amino acid sequence of SEQ ID NO: 103;
c) the heavy chain comprises the amino acid sequence of SEQ ID NO: 80, and the light chain comprises the amino acid sequence of SEQ ID NO: 83;
d) the heavy chain comprises the amino acid sequence of SEQ ID NO: 87, and the light chain comprises the amino acid sequence of SEQ ID NO: 73;
e) the heavy chain comprises the amino acid sequence of SEQ ID NO: 110, and the light chain comprises the amino acid sequence of SEQ ID NO: 83;
f) the heavy chain comprises the amino acid sequence of SEQ ID NO: 114, and the light chain comprises the amino acid sequence of SEQ ID NO: 73;
g) the heavy chain comprises the amino acid sequence of SEQ ID NO: 116, and the light chain comprises the amino acid sequence of SEQ ID NO: 73;
h) the heavy chain comprises the amino acid sequence of SEQ ID NO: 116 and the light chain comprises the amino acid of SEQ ID NO: 103; or
i) the heavy chain comprises the amino acid sequence of SEQ ID NO: 119 and the light chain comprises the amino acid sequence of SEQ ID NO: 103.

In specific embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is antibody IDT1A, IDT1B, IDT1C, IDT1D, or IDT1E, for example, as set forth in Table 2, wherein said antibody comprises a Fab fragment or is an IgG antibody.

In specific embodiments, provided herein is a binding agent (e.g., anti-idiotype antibody) which specifically binds a target anti-FXI/FXIa antibody, as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is antibody IDT1A, IDT1B, IDT1C, IDT1D, or IDT1E, for example, as set forth in Table 2, and is a recombinant, monoclonal human antibody, and wherein said antibody comprises a Fab fragment or is an IgG antibody.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in specific embodiments, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

In specific embodiments, typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described here, as well as DP47 and DPK9.

Homologous Antibodies

In another embodiment, the present disclosure provides a binding agent comprising amino acid sequences that are homologous to sequences described in Table 2, as well as a pharmaceutical composition comprising such a binding agent, wherein the binding agent binds to an anti-FXI/FXIa antibody, and (i) retains the desired functional properties (e.g., reversal or partial reversal of one or more anticoagulant effects) of those antibodies described in Table 2, e.g., any one of antibodies IDT1A-IDT1E; and/or (ii) is functionally similar to those antibodies described in Table 2, e.g., any one of antibodies IDT1A-IDT1E. In a particular embodiment, the homologous antibodies provided herein are not any one of antibodies IDT1-IDT10 as described in PCT International Publication No. WO2017/203450.

By the term "functionally similar", it is meant that the effects observed are comparable to the effects observed by the binding agents mentioned in the context of the present invention, e.g., antibodies described in Table 2, e.g., any one of antibodies IDT1A-IDT1E. For example, a functionally similar binding agent (i) when present in a three times molar excess in comparison to the target antibody NOV1401, is capable of a maximal reversal of 60% or more of the anticoagulant activity of the target antibody NOV1401, as measured in an activated partial thromboplastin time (aPTT) assay at 37° C.; and/or (ii) when present in a nine times molar excess in comparison to the target antibody, is capable of a maximal reversal of 70% or more of the anticoagulant activity of the target antibody, as measured in an activated partial thromboplastin time (aPTT) assay, in particular as measured in an aPTT assay at 37° C.; and/or (iii) when present in a thirty times molar excess in comparison to the target antibody NOV1401, is capable of a maximal reversal of 75% or more of the anticoagulant activity of the target antibody, as measured in an activated partial thromboplastin time (aPTT) assay at 37° C. These functionally similar binding agents may substitute the specifically mentioned binding agents.

In specific embodiments, such homologous antibodies retain the CDR amino acid sequences described in Table 2 (e.g., Kabat CDRs, Chothia CDRs, IMGT CDRs, or Combined CDRs). In a specific embodiment, such homologous antibodies are human full length IgGs.

In particular embodiments, provided herein is a binding agent (e.g., anti-idiotype antibody, e.g., IgG, fragment) which specifically binds a target anti-FXI/FXIa antibody (e.g., NOV1401 comprising a VH comprising the amino acid sequence of SEQ ID NO: 3 and a VL comprising the amino acid sequence of SEQ ID NO: 7) as well as a pharmaceutical composition comprising the binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, wherein the binding agent is an antibody comprising a VH and a VL, and wherein the VH and VL comprise amino acid sequences that are at least 80%, at least 85%, at least 90%, at least 91%, at least 92%, at least 93%, at least 94%, at least 95%, at least 96%, at least 97%, at least 98% or at least 99% identical to the VH and VL sequences selected from Table 2. In a further specific embodiment, the differences in amino acid sequence in the VL and/or VH of the binding agent are not within the complementarity determining regions.

The present disclosure also provides a binding agent (e.g., anti-idiotype antibody, e.g., IgG, Fab fragment) which specifically binds a target anti-FXI/FXIa antibody (e.g., NOV1401), wherein the binding agent is an antibody comprising a VH amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have been mutated (wherein a mutation is, as various non-limiting examples, an addition, substitution or deletion).

The present disclosure also provides a binding agent (e.g., anti-idiotype antibody, e.g., IgG, Fab fragment) which specifically binds a target anti-FXI/FXIa antibody (e.g., NOV1401), wherein the binding agent is an antibody comprising a VL amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have been mutated (wherein a mutation is, as various non-limiting examples, an addition, substitution or deletion).

Antibodies with Conservative Modifications

In certain embodiments, the present disclosure relates to a binding agent, which is an antibody (e.g., IgG, Fab fragment) that specifically binds to an anti-FXI/FXIa antibody such as NOV1401, as well as a pharmaceutical composition comprising such binding agent, wherein the binding agent comprises VH comprising CDR1, CDR2, and CDR3 sequences and a VL comprising CDR1, CDR2, and CDR3 sequences, wherein one or more of these CDR sequences have specified amino acid sequences based on the antibodies described herein, such as those described in Table 2, or conservative modifications thereof, and wherein the binding agents (i) retain the desired functional properties (e.g., reversing one or more anticoagulant effects of an anti-FXI/FXIa antibody) of the binding agents described herein, e.g., binding agents IDT1A, IDT1B, IDT1C, IDT1D, or IDT1E; and/or (ii) are functionally similar to those antibodies described in Table 2, e.g., any one of antibodies IDT1A-IDT1E.

By the term "functionally similar", it is meant that the effects observed are comparable to the effects observed by the binding agents mentioned in the context of the present invention, e.g., antibodies described in Table 2, e.g., any one of antibodies IDT1A-IDT1E. For example, a functionally similar binding agent (i) when present in a three times molar excess in comparison to the target antibody NOV1401, is capable of a maximal reversal of 60% or more of the anticoagulant activity of the target antibody NOV1401, as measured in an activated partial thromboplastin time (aPTT) assay at 37° C.; and/or (ii) when present in a nine times molar excess in comparison to the target antibody, is capable of a maximal reversal of 70% or more of the anticoagulant activity of the target antibody, as measured in an activated partial thromboplastin time (aPTT) assay, in particular as measured in an aPTT assay at 37° C.; and/or (iii) when present in a thirty times molar excess in comparison to the target antibody NOV1401, is capable of a maximal reversal of 75% or more of the anticoagulant activity of the target antibody, as measured in an activated partial thromboplastin time (aPTT) assay at 37° C. These functionally similar binding agents may substitute the specifically mentioned binding agents.

In specific embodiments, a binding agent described herein, which is an antibody (e.g., full length IgG, Fab fragment) that specifically binds to an anti-FXI/FXIa antibody such as NOV1401, comprises VH comprising CDR1, CDR2, and CDR3 sequences and a VL comprising CDR1, CDR2, and CDR3 sequences set forth in Table 2 with one, two, three, or more conservative modifications in one or more CDRs, and wherein the binding agents (i) retain the desired functional properties (e.g., binding to anti-FXI/FXIa antibody and/or reversing (e.g., partially reversing, for example, by at least 40%, at least 50%, at least 60%, at least 70%, at least 75%, at least 80%, or at least 85%) one or more anticoagulant effects of an anti-FXI/FXIa antibody) of the binding agents described herein, e.g., binding agents IDT1A, IDT1B, IDT1C, IDT1D, or IDT1E; and/or (ii) are functionally similar to those antibodies described in Table 2, e.g., any one of antibodies IDT1A, IDT1B, IDT1C, IDT1D, or IDT1E.

In further specific embodiments, provided herein is a binding agent (e.g., anti-idiotype antibody, e.g., IgG, Fab fragment) which specifically binds a target anti-FXI/FXIa antibody such as NOV1401, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, wherein the binding agent is an antibody comprising (1) a VH comprising complementarity determining regions HCDR1, HCDR2, and HCDR3 selected from those set forth in Table 2 and conservative modifications thereof, and (2) a VL comprising complementarity determining regions LCDR1, LCDR2, and LCDR3 selected from those set forth in Table 2 and conservative modifications thereof. In a particular embodiment, the binding agent (e.g., anti-idiotype antibody) comprises Combined HCDR1, HCDR2, and HCDR3 selected from those set forth in Table 2 and conservative modifications thereof, and Combined LCDR1, LCDR2, and LCDR3 selected from those set forth in Table 2 and conservative modifications thereof. In a particular embodiment, the binding agent (e.g., anti-idiotype antibody) comprises Kabat HCDR1, HCDR2, and HCDR3 selected from those set forth in Table 2 and conservative modifications thereof, and Kabat LCDR1, LCDR2, and LCDR3 selected from those set forth in Table 2 and conservative modifications thereof. In a particular embodiment, the binding agent (e.g., anti-idiotype antibody) comprises Chothia HCDR1, HCDR2, and HCDR3 selected from those set forth in Table 2 and conservative modifications thereof, and Chothia LCDR1, LCDR2, and LCDR3 selected from those set forth in Table 2 and conservative modifications thereof. In a particular embodiment, the binding agent (e.g., anti-idiotype antibody) comprises IMGT HCDR1, HCDR2, and HCDR3 selected from those set forth in Table 2 and conservative modifications thereof, and IMGT LCDR1, LCDR2, and LCDR3 selected from those set forth in Table 2 and conservative modifications thereof. In a specific embodiment, the binding agent is a Fab fragment. In another specific embodiment, the binding agent is a full length IgG.

In particular embodiments, provided herein is a binding agent (e.g., anti-idiotype antibody, e.g., IgG, Fab fragment) which specifically binds a target anti-FXI/FXIa antibody such as NOV1401, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence selected from the group consisting of SEQ ID NO: 51, 54, 55, 57 and conservative modifications thereof, the HCDR2 comprises the amino acid sequence selected from the group consisting of SEQ ID NO: 52, 56, 58 and conservative modifications thereof, the HCDR3 comprises the amino acid sequence selected from the group consisting of SEQ ID NO: 53, 59 and conservative modifications thereof, the LCDR1 comprises the amino acid sequence selected from the group consisting of SEQ ID NO: 64, 67, 70 and conservative modifications thereof, the LCDR2 comprises the amino acid sequence selected from the group consisting of SEQ ID NO: 65, 68 and conservative modifications thereof, and the LCDR3 comprises the amino acid sequence selected from the group consisting of SEQ ID NO: 94, 95 and conservative modifications thereof, b) the HCDR1 comprises the amino acid sequence selected from the group consisting of SEQ ID NO: 51, 54, 55, 57 and conservative modifications thereof, the HCDR2 comprises the amino acid sequence selected from the group consisting of SEQ ID NO: 75, 76, 77 and conservative modifications thereof, the HCDR3 comprises the amino acid sequence selected from the group consisting of SEQ ID NO: 53, 59 and conservative modifications thereof, the LCDR1 comprises the amino acid sequence selected from the group consisting of SEQ ID NO: 64, 67, 70 and conservative modifications thereof, the LCDR2 comprises the amino acid sequence selected from the group consisting of SEQ ID NO: 65, 68 and conservative modifications thereof, and the LCDR3 comprises the amino acid sequence selected from the group consisting of SEQ ID NO: 94, 95 and conservative modifications thereof;

c) the HCDR1 comprises the amino acid sequence selected from the group consisting of SEQ ID NO: 51, 54, 55, 57 and conservative modifications thereof, the HCDR2 comprises the amino acid sequence selected from the group consisting of SEQ ID NO: 105, 106, 107 and conservative modifications thereof, the HCDR3 comprises the amino acid sequence selected from the group consisting of SEQ ID NO: 53, 59 and conservative modifications thereof, the LCDR1 comprises the amino acid sequence selected from the group consisting of SEQ ID NO: 64, 67, 70 and conservative modifications thereof, the LCDR2 comprises the amino acid sequence selected from the group consisting of SEQ ID NO: 65, 68 and conservative modifications thereof, and the LCDR3 comprises the amino acid sequence selected from the group consisting of SEQ ID NO: 94, 95 and conservative modifications thereof;

d) the HCDR1 comprises the amino acid sequence selected from the group consisting of SEQ ID NO: 51, 54, 55, 57 and conservative modifications thereof, the HCDR2 comprises the amino acid sequence selected from the group consisting of SEQ ID NO: 75, 76, 77 and conservative modifications thereof, the HCDR3 comprises the amino acid sequence selected from the group consisting of SEQ ID NO: 53, 59 and conservative modifications thereof, the LCDR1 comprises the amino acid sequence selected from the group consisting of SEQ ID NO: 64, 67, 70 and conservative modifications thereof, the LCDR2 comprises the amino acid sequence selected from the group consisting of SEQ ID NO: 65, 68 and conservative modifications thereof, and the LCDR3 comprises the amino acid sequence selected from the group consisting of SEQ ID NO: 66, 69 and conservative modifications thereof; or e) the HCDR1 comprises the amino acid sequence selected from the group consisting of SEQ ID NO: 51, 54, 55, 57 and conservative modifications thereof, the HCDR2 comprises the amino acid sequence selected from the group consisting of SEQ ID NO: 105, 106, 107 and conservative modifications thereof, the HCDR3 comprises the amino acid sequence selected from the group consisting of SEQ ID NO: 53, 59 and conservative modifications thereof, the LCDR1 comprises the amino acid sequence selected from the group consisting of SEQ ID NO: 64, 67, 70 and conservative modifications thereof, the LCDR2 comprises the amino acid sequence selected from the group consisting of SEQ ID NO: 65, 68 and conservative modifications thereof, and the LCDR3 comprises the amino acid sequence selected from the group consisting of SEQ ID NO: 66, 69 and conservative modifications thereof.

In particular embodiments, provided herein is a binding agent (e.g., anti-idiotype antibody, e.g., IgG, Fab fragment) which specifically binds a target anti-FXI/FXIa antibody such as NOV1401, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence of SEQ ID NO: 51 or conservative modifications thereof, the HCDR2 comprises the amino acid sequence of SEQ ID NO: 52 or conservative modifications thereof, the HCDR3 comprises the amino acid sequence of SEQ ID NO: 53 or conservative modifications thereof, the LCDR1 comprises the amino acid sequence of SEQ ID NO: 64 or conservative modifications thereof, the LCDR2 comprises the amino acid sequence of SEQ ID NO: 65 or conservative modifications thereof, and the LCDR3 comprises the amino acid sequence of SEQ ID NO: 94 or conservative modifications thereof, b) the HCDR1 comprises the amino acid sequence of SEQ ID NO: 51 or conservative modifications thereof, the HCDR2 comprises the amino acid sequence of SEQ ID NO: 75 or conservative modifications thereof, the HCDR3 comprises the amino acid sequence of SEQ ID NO: 53 or conservative modifications thereof, the LCDR1 comprises the amino acid sequence of SEQ ID NO: 64 or conservative modifications thereof, the LCDR2 comprises the amino acid sequence of SEQ ID NO: 65 or conservative modifications thereof, and the LCDR3 comprises the amino acid sequence of SEQ ID NO: 94 or conservative modifications thereof, c) the HCDR1 comprises the amino acid sequence of SEQ ID NO: 51 or conservative modifications thereof, the HCDR2 comprises the amino acid sequence of SEQ ID NO: 105 or conservative modifications thereof, the HCDR3 comprises the amino acid sequence of SEQ ID NO:53 or conservative modifications thereof, the LCDR1 comprises the amino acid sequence of SEQ ID NO: 64 or conservative modifications thereof, the LCDR2 comprises the amino acid sequence of SEQ ID NO: 65 or conservative modifications thereof, and the LCDR3 comprises the amino acid sequence of SEQ ID NO: 94 or conservative modifications thereof, d) the HCDR1 comprises the amino acid sequence of SEQ ID NO: 51 or conservative modifications thereof, the HCDR2 comprises the amino acid sequence of SEQ ID NO: 75 or conservative modifications thereof, the HCDR3 comprises the amino acid sequence of SEQ ID NO: 53 or conservative modifications thereof, the LCDR1 comprises the amino acid sequence of SEQ ID NO: 64 or conservative modifications thereof, the LCDR2 comprises the amino acid sequence of SEQ ID NO: 65 or conservative modifications thereof, and the LCDR3 comprises the amino acid sequence of SEQ ID NO: 66 or conservative modifications thereof, or e) the HCDR1 comprises the amino acid sequence of SEQ ID NO: 51 or conservative modifications thereof, the HCDR2 comprises the amino acid sequence of SEQ ID NO: 105 or conservative modifications thereof, the HCDR3 comprises the amino acid sequence of SEQ ID NO: 53 or conservative modifications thereof, the LCDR1 comprises the amino acid sequence of SEQ ID NO: 64 or conservative modifications thereof, the LCDR2 comprises the amino acid sequence of SEQ ID NO: 65 or conservative modifications thereof, and the LCDR3 comprises the amino acid sequence of SEQ ID NO: 66 or conservative modifications thereof.

The present disclosure also provides a binding agent (e.g., anti-idiotype antibody, e.g., IgG, Fab fragment) which specifically binds a target anti-FXI/FXIa antibody (e.g., NOV1401), as well as a pharmaceutical composition comprising such a binding agent, wherein the binding agent is an antibody comprising a VH amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have conservative modifications.

The present disclosure also provides a binding agent (e.g., anti-idiotype antibody, e.g., IgG, Fab fragment) which specifically binds a target anti-FXI/FXIa antibody (e.g., NOV1401), wherein the binding agent is an antibody comprising a VL amino acid sequence listed in Table 2, wherein no more than about 1, 2, 3, 4, 5, 6, 7, 8, 9, 10, 11, 12, 13, 14, 15, 16, 17, 18, 19, or 20 amino acids in a framework sequence (for example, a sequence which is not a CDR) have conservative modifications.

In particular embodiments, provided herein is a binding agent (e.g., anti-idiotype antibody, e.g., IgG, Fab fragment) which specifically binds a target anti-FXI/FXIa antibody such as NOV1401, as well as a pharmaceutical composition comprising such a binding agent, wherein the binding agent inhibits or reverses (e.g., partially reverses) an anticoagulant activity of the target anti-FXI/FXIa antibody, wherein the binding agent is an antibody comprising a VH, and a VL; wherein:

a) the VH comprises the amino acid sequence of SEQ ID NO: 78 or 85, preferably SEQ ID NO: 85, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the VL comprises the amino acid sequence of SEQ ID NO: 71 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

b) the VH comprises the amino acid sequence of SEQ ID NO: 90 or 60, preferably SEQ ID NO: 60, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the VL comprises the amino acid sequence of SEQ ID NO: 96 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

c) the VH comprises the amino acid sequence of SEQ ID NO: 108 or 112, preferably SEQ ID NO: 112, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity and the VL comprises the amino acid sequence of SEQ ID NO: 71 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

d) the VH comprises the amino acid sequence of SEQ ID NO: 112 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity and the VL comprises the amino acid sequence of SEQ ID NO: 96 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity; or e) the VH comprises the amino acid sequence of SEQ ID NO: 85 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity and the VL comprises the amino acid sequence of SEQ ID NO: 96 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity.

In a further specific embodiment, the mutation is not within the complementarity determining regions.

In particular embodiments, provided herein is a binding agent (e.g., anti-idiotype antibody, e.g., IgG, Fab fragment) which specifically binds a target anti-FXI/FXIa antibody such as NOV1401, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, and wherein the binding agent is an antibody comprising a heavy chain and a light chain, wherein:

a) the heavy chain comprises the amino acid sequence of SEQ ID NO: 92 or 101, preferably SEQ ID NO: 101, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 98 or 103, preferably SEQ ID NO: 103, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

b) the heavy chain comprises the amino acid sequence of SEQ ID NO: 80 or 87, preferably SEQ ID NO: 87, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 83 or 73, preferably SEQ ID NO: 73, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

c) the heavy chain comprises the amino acid sequence of SEQ ID NO: 110 or 114 or 116, preferably SEQ ID NO: 116, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 83 or 73, preferably SEQ ID NO: 73, with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

d) the heavy chain comprises the amino acid sequence of SEQ ID NO: 116 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid of SEQ ID NO: 103 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity; or e) the heavy chain comprises the amino acid sequence of SEQ ID NO: 119 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 103 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity.

In a further specific embodiment, the mutation is not within the complementarity determining regions.

In particular embodiments, provided herein is a binding agent (e.g., anti-idiotype antibody, e.g., IgG, Fab fragment) which specifically binds a target anti-FXI/FXIa antibody such as NOV1401, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, and wherein the binding agent is an antibody comprising a heavy chain and a light chain, wherein:

a) the heavy chain comprises the amino acid sequence of SEQ ID NO: 92 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 98 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

b) the heavy chain comprises the amino acid sequence of SEQ ID NO: 101 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 103 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

c) the heavy chain comprises the amino acid sequence of SEQ ID NO: 80 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 83 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

d) the heavy chain comprises the amino acid sequence of SEQ ID NO: 87 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 73 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

e) the heavy chain comprises the amino acid sequence of SEQ ID NO: 110 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 83 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

f) the heavy chain comprises the amino acid sequence of SEQ ID NO: 114 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 73 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

g) the heavy chain comprises the amino acid sequence of SEQ ID NO: 116 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 73 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity;

h) the heavy chain comprises the amino acid sequence of SEQ ID NO: 116 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid of SEQ ID NO: 103 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity; or i) the heavy chain comprises the amino acid sequence of SEQ ID NO: 119 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity, and the light chain comprises the amino acid sequence of SEQ ID NO: 103 with 1, 2, 3, 4, 5, 6, 7, 8, 9, 10, 11, 12, 13, 14, 15, 16, 17, 18, 19, or 20 mutations, such as conservative amino acid mutations, that do not substantially affect activity.

In a further specific embodiment, the mutation is not within the complementarity determining regions.

Engineered and Modified Antibodies

Binding agents (e.g., anti-FXI/FXIa antibody binding agent) provided herein which are antibodies, such as a full length IgG or a Fab fragment, can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i. e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in antibodies of the present disclosure are those that are structurally similar to the framework sequences used by selected antibodies described herein, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies described herein include, but are not limited to VH1A, VH1B, VH3, Vk1, Vl2, and Vk2. Additional frameworks are known in the art and may be found, for example, in the vBase data base on the world wide web at vbase.mrc-cpe.cam.ac.uk/index.php?&MMN_position=1:1.

Accordingly, in specific embodiments, the present disclosure relates to binding agents, such as isolated antibodies which bind an anti-FXI/FXIa antibody such as NOV1401, as well as a pharmaceutical composition comprising such binding agents, comprising:

(ii) a VH comprising the amino acid sequence selected from the group consisting of SEQ ID NO: 78, 85, 108, and 112 and an amino acid sequence having one, two, three, four or five amino acid substitutions, deletions or additions in the framework region of such sequences, and a VL comprising the amino acid sequence SEQ ID NO: 71 and an amino acid sequence having one, two, three, four or five amino acid substitutions, deletions or additions in the framework region of such sequences; or (iii) a VH comprising the amino acid sequence selected from the group consisting of SEQ ID NO: 60, 78, 85, 90, 108, and 112 and an amino acid sequence having one, two, three, four or five amino acid substitutions, deletions or additions in the framework region of such sequences, and a VL comprising the amino acid sequence of SEQ ID NO: 96 and an amino acid sequence having one, two, three, four or five amino acid substitutions, deletions or additions in the framework region of such sequences.

In specific embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising a heavy chain and a light chain, wherein:

a) the heavy chain comprises the amino acid sequence selected from the group consisting of SEQ ID NO: 80, 87, 110, 114, 116, 119 and an amino acid sequence having one, two, three, four or five amino acid substitutions, deletions or additions in the framework region of such sequences, and the light chain comprises the amino acid sequence selected from the group consisting of SEQ ID NO: 73, 83 and an amino acid sequence having one, two, three, four or five amino acid substitutions, deletions or additions in the framework region of such sequences; or b) the heavy chain comprises the amino acid sequence selected from the group consisting of SEQ ID NO: 62, 80, 87, 92, 101, 110, 114, 116, 119, and an amino acid sequence having one, two, three, four or five amino acid substitutions, deletions or additions in the framework region of such sequences, and the light chain comprises the amino acid sequence selected from the group consisting of SEQ ID NO: 98, 103 and an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation". Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples Section. Conservative modifications (as discussed above) can be introduced. The mutations may be amino acid substitutions, additions or deletions. Moreover, typically no more than one, two, three, four, or five residues within a CDR region are altered.

Accordingly, in specific embodiments, provided herein are binding agents that are further affinity matured variants of antibody IDT1A, IDT1B, IDT1C, IDT1D, or IDT1E, as well as a pharmaceutical composition comprising such binding agents, wherein the further affinity matured variant has higher affinity for the anti-FXI/FXIa antibody NOV1401 than the parental IDT1A, IDT1B, IDT1C, IDT1D, or IDT1E, and is capable of reversing one or more anticoagulant effects of NOV1401. In particular embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence selected from the group consisting of SEQ ID NO: 51, 54, 55, 57 and an amino acid sequence thereof having one, two, three, four or five amino acid substitutions, deletions or additions, the HCDR2 comprises the amino acid sequence selected from the group consisting of SEQ ID NO: 52, 56, 58 and an amino acid sequence thereof having one, two, three, four or five amino acid substitutions, deletions or additions, the HCDR3 comprises the amino acid sequence selected from the group consisting of SEQ ID NO: 53, 59 and an amino acid sequence thereof having one, two, three, four or five amino acid substitutions, deletions or additions, the LCDR1 comprises the amino acid sequence selected from the group consisting of SEQ ID NO: 64, 67, 70 and an amino acid sequence thereof having one, two, three, four or five amino acid substitutions, deletions or additions, the LCDR2 comprises the amino acid sequence selected from the group consisting of SEQ ID NO: 65, 68 and an amino acid sequence thereof having one, two, three, four or five amino acid substitutions, deletions or additions, and the LCDR3 comprises the amino acid sequence selected from the group consisting of SEQ ID NO: 94, 95 and an amino acid sequence thereof having one, two, three, four or five amino acid substitutions, deletions or additions;

b) the HCDR1 comprises the amino acid sequence selected from the group consisting of SEQ ID NO: 51, 54, 55, 57 and an amino acid sequence thereof having one, two, three, four or five amino acid substitutions, deletions or additions, the HCDR2 comprises the amino acid sequence selected from the group consisting of SEQ ID NO: 75, 76, 77 and an amino acid sequence thereof having one, two, three, four or five amino acid substitutions, deletions or additions, the HCDR3 comprises the amino acid sequence selected from the group consisting of SEQ ID NO: 53, 59 and an amino acid sequence thereof having one, two, three, four or five amino acid substitutions, deletions or additions, the LCDR1 comprises the amino acid sequence selected from the group consisting of SEQ ID NO: 64, 67, 70 and an amino acid sequence thereof having one, two, three, four or five amino acid substitutions, deletions or additions, the LCDR2 comprises the amino acid sequence selected from the group consisting of SEQ ID NO: 65, 68 and an amino acid sequence thereof having one, two, three, four or five amino acid substitutions, deletions or additions, and the LCDR3 comprises the amino acid sequence selected from the group consisting of SEQ ID NO: 94, 95 and an amino acid sequence thereof having one, two, three, four or five amino acid substitutions, deletions or additions;

c) the HCDR1 comprises the amino acid sequence selected from the group consisting of SEQ ID NO: 51, 54, 55, 57 and an amino acid sequence thereof having one, two, three, four or five amino acid substitutions, deletions or additions, the HCDR2 comprises the amino acid sequence selected from the group consisting of SEQ ID NO: 105, 106, 107 and an amino acid sequence thereof having one, two, three, four or five amino acid substitutions, deletions or additions, the HCDR3 comprises the amino acid sequence selected from the group consisting of SEQ ID NO: 53, 59 and an amino acid sequence thereof having one, two, three, four or five amino acid substitutions, deletions or additions, the LCDR1 comprises the amino acid sequence selected from the group consisting of SEQ ID NO: 64, 67, 70 and an amino acid sequence thereof having one, two, three, four or five amino acid substitutions, deletions or additions, the LCDR2 comprises the amino acid sequence selected from the group consisting of SEQ ID NO: 65, 68 and an amino acid sequence thereof having one, two, three, four or five amino acid substitutions, deletions or additions, and the LCDR3 comprises the amino acid sequence selected from the group consisting of SEQ ID NO: 94, 95 and an amino acid sequence thereof having one, two, three, four or five amino acid substitutions, deletions or additions;

d) the HCDR1 comprises the amino acid sequence selected from the group consisting of SEQ ID NO: 51, 54, 55, 57 and an amino acid sequence thereof having one, two, three, four or five amino acid substitutions, deletions or additions, the HCDR2 comprises the amino acid sequence selected from the group consisting of SEQ ID NO: 75, 76, 77 and an amino acid sequence thereof having one, two, three, four or five amino acid substitutions, deletions or additions, the HCDR3 comprises the amino acid sequence selected from the group consisting of SEQ ID NO: 53, 59 and an amino acid sequence thereof having one, two, three, four or five amino acid substitutions, deletions or additions, the LCDR1 comprises the amino acid sequence selected from the group consisting of SEQ ID NO: 64, 67, 70 and an amino acid sequence thereof having one, two, three, four or five amino acid substitutions, deletions or additions, the LCDR2 comprises the amino acid sequence selected from the group consisting of SEQ ID NO: 65, 68 and an amino acid sequence thereof having one, two, three, four or five amino acid substitutions, deletions or additions, and the LCDR3 comprises the amino acid sequence selected from the group consisting of SEQ ID NO: 66, 69 and an amino acid sequence thereof having one, two, three, four or five amino acid substitutions, deletions or additions; or e) the HCDR1 comprises the amino acid sequence selected from the group consisting of SEQ ID NO: 51, 54, 55, 57 and an amino acid sequence thereof having one, two, three, four or five amino acid substitutions, deletions or additions, the HCDR2 comprises the amino acid sequence selected from the group consisting of SEQ ID NO: 105, 106, 107 and an amino acid sequence thereof having one, two, three, four or five amino acid substitutions, deletions or additions, the HCDR3 comprises the amino acid sequence selected from the group consisting of SEQ ID NO: 53, 59 and an amino acid sequence thereof having one, two, three, four or five amino acid substitutions, deletions or additions, the LCDR1 comprises the amino acid sequence selected from the group consisting of SEQ ID NO: 64, 67, 70 and an amino acid sequence thereof having one, two, three, four or five amino acid substitutions, deletions or additions, the LCDR2 comprises the amino acid sequence selected from the group consisting of SEQ ID NO: 65, 68 and an amino acid sequence thereof having one, two, three, four or five amino acid substitutions, deletions or additions, and the LCDR3 comprises the amino acid sequence selected from the group consisting of SEQ ID NO: 66, 69 and an amino acid sequence thereof having one, two, three, four or five amino acid substitutions, deletions or additions.

In particular embodiments, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 52 or 75 or 105 or an amino acid sequence thereof having one, two, three, four or five amino acid substitutions, deletions or additions, the HCDR3 comprises the amino acid sequence of SEQ ID NO: 53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 94 or an amino acid sequence thereof having one, two, three, four or five amino acid substitutions, deletions or additions; or b) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 75 or 105 or an amino acid sequence thereof having one, two, three, four or five amino acid substitutions, deletions or additions, the HCDR3 comprises the amino acid sequence of SEQ ID NO: 53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 66 or an amino acid sequence thereof having one, two, three, four or five amino acid substitutions, deletions or additions.

In a more specific embodiment, provided herein is a binding agent (e.g., anti-idiotype antibody) which specifically binds a target anti-FXI/FXIa antibody, as well as a pharmaceutical composition comprising such a binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody, in particular wherein the target anti-FXI/FXIa antibody is antibody NOV1401 (comprising a VH comprising the amino acid sequence of SEQ ID NO: 3 and a VL comprising the amino acid sequence of SEQ ID NO: 7), and wherein the binding agent is an antibody comprising (1) a VH comprising complementarity determining regions HCDR1, HCDR2, and HCDR3, and (2) a VL comprising complementarity determining regions LCDR1, LCDR2, and LCDR3; wherein:

a) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 52 or an amino acid sequence thereof having one, two, three, four or five amino acid substitutions, deletions or additions, the HCDR3 comprises the amino acid sequence of SEQ ID NO: 53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 94 or an amino acid sequence thereof having one, two, three, four or five amino acid substitutions, deletions or additions;

b) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 75 or an amino acid sequence thereof having one, two, three, four or five amino acid substitutions, deletions or additions, the HCDR3 comprises the amino acid sequence of SEQ ID NO: 53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 94 or an amino acid sequence thereof having one, two, three, four or five amino acid substitutions, deletions or additions;

c) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 105 or an amino acid sequence thereof having one, two, three, four or five amino acid substitutions, deletions or additions, the HCDR3 comprises the amino acid sequence of SEQ ID NO:53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 94 or an amino acid sequence thereof having one, two, three, four or five amino acid substitutions, deletions or additions;

d) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 75 or an amino acid sequence thereof having one, two, three, four or five amino acid substitutions, deletions or additions, the HCDR3 comprises the amino acid sequence of SEQ ID NO: 53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 66 or an amino acid sequence thereof having one, two, three, four or five amino acid substitutions, deletions or additions; or e) the HCDR1 comprises the amino acid sequence of SEQ ID NO: 51 or an amino acid sequence thereof having one, two, three, four or five amino acid substitutions, deletions or additions, the HCDR2 comprises the amino acid sequence of SEQ ID NO: 105 or an amino acid sequence thereof having one, two, three, four or five amino acid substitutions, deletions or additions, the HCDR3 comprises the amino acid sequence of SEQ ID NO: 53 or an amino acid sequence thereof having one, two, three, four or five amino acid substitutions, deletions or additions, the LCDR1 comprises the amino acid sequence of SEQ ID NO: 64 or an amino acid sequence thereof having one, two, three, four or five amino acid substitutions, deletions or additions, the LCDR2 comprises the amino acid sequence of SEQ ID NO: 65 or an amino acid sequence thereof having one, two, three, four or five amino acid substitutions, deletions or additions, and the LCDR3 comprises the amino acid sequence of SEQ ID NO: 66 or an amino acid sequence thereof having one, two, three, four or five amino acid substitutions, deletions or additions.

Grafting Antigen-Binding Domains into Alternative Frameworks or Scaffolds

With respect to anti-FXI/FXIa antibody binding agents provided herein which are antibodies, a wide variety of antibody/immunoglobulin frameworks or scaffolds can be employed so long as the resulting polypeptide includes at least one binding region which specifically binds to a target anti-FXI/FXIa antibody. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard.

In one embodiment, the present disclosure pertains to generating non-immunoglobulin-based antibodies using non-immunoglobulin scaffolds onto which CDRs such as those described in Table 2 can be grafted. Known or future non-immunoglobulin frameworks and scaffolds may be employed, as long as they comprise a binding region specific for the target anti-FXI/FXIa antibody such as NOV1401. Known non-immunoglobulin frameworks or scaffolds include, but are not limited to, fibronectin (Compound Therapeutics, Inc., Waltham, MA), ankyrin (Molecular Partners AG, Zurich, Switzerland), domain antibodies (Domantis, Ltd., Cambridge, MA, and Ablynx nv, Zwijnaarde, Belgium), lipocalin (Pieris Proteolab AG, Freising, Germany), small modular immuno-pharmaceuticals (Trubion Pharmaceuticals Inc., Seattle, WA), maxybodies (Avidia, Inc., Mountain View, CA), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is PCT Publication No. WO 199916873.

Affilin molecules are small non-immunoglobulin proteins which are designed for specific affinities towards proteins and small molecules. New affilin molecules can be efficiently selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO 2001/04144 and examples of "ubiquitin-like" proteins are described in WO 2004/106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

In specific embodiments, the present disclosure provides fully human antibodies that specifically bind to a target anti-FXI/FXIa antibody such as NOV1401. Compared to the chimeric or humanized antibodies, human antibodies have further reduced antigenicity when administered to human subjects.

Methods of Producing Antibodies

Provided herein are nucleic acid molecules (e.g., substantially purified nucleic acid molecules) which encode polypeptides of binding agents described herein such as IDT1A, IDT1B, IDT1C, IDT1D, or IDT1E as set forth in Table 2, vectors (e.g., expression vectors) comprising the same, host cells comprising such vectors or nucleic acid molecules, and methods of producing binding agents described herein, e.g., antibodies, which specifically binds an anti-FXI/FXIa antibody, e.g., NOV1401.

In specific aspects, provided herein is a vector (e.g., expression vector) comprising a polynucleotide described herein (e.g., Table 2), e.g., a polynucleotide encoding a heavy chain of IDT1A, IDT1B, IDT1C, IDT1D, or IDT1E and/or a light chain of IDT1A, IDT1B, IDT1C, IDT1D, or IDT1E.

In certain aspects, provided herein is a host cell comprising a vector described herein or a polynucleotide described herein e.g., polynucleotide encoding a heavy chain of IDT1A, IDT1B, IDT1C, IDT1D, or IDT1E and/or a light chain of IDT1A, IDT1B, IDT1C, IDT1D, or IDT1E. In specific embodiments, the host cell is a eukaryotic cell. In certain embodiments, the host cell is a mammalian cell (e.g., a non-human mammalian cell, such as CHO cells). In particular embodiments, a host cell comprises (i) a vector or polynucleotide comprising nucleotide sequences encoding a VH or a heavy chain of IDT1A, IDT1B, IDT1C, IDT1D, or IDT1E, and (ii) a vector or polynucleotide comprising nucleotide sequences encoding a VL or a light chain of IDT1A, IDT1B, IDT1C, IDT1D, or IDT1E. In specific embodiments, a first host cell comprises a vector or polynucleotide comprising nucleotide sequences encoding a VH or a heavy chain of IDT1A, IDT1B, IDT1C, IDT1D, or IDT1E, and a second host cell comprises a vector or polynucleotide comprising nucleotide sequences encoding a VL or a light chain of IDT1A, IDT1B, IDT1C, IDT1D, or IDT1E.

In particular aspects, provided herein is a method of producing a binding agent, e.g., an antibody, that binds an anti-FXI/FXIa antibody, such as NOV1401, comprising the step of culturing a host cell described herein under conditions suitable for expression of the binding agent. In certain embodiments, the method of producing a binding agent provided herein (e.g., IDT1A, IDT1B, IDT1C, IDT1D, or IDT1E) further comprises purifying the binding agent or fragment thereof.

Nucleic Acids Encoding Binding Agents

The present disclosure provides polynucleotides comprising nucleotide sequences encoding binding agents described herein. In specific embodiments, the present disclosure provides polynucleotides comprising nucleic acid sequences that encode the VH, VL, full length heavy chain, and/or full length light chain of antibodies described herein that specifically bind to a target anti-FXI/FXIa antibody, for example, antibodies IDT1A, IDT1B, IDT1C, IDT1D, or IDT1E. Such nucleic acid sequences can be optimized for expression in mammalian cells (for example, see Table 2).

In specific embodiments where a binding agent is an antibody, provided herein is a polynucleotide comprising nucleotide sequences encoding a heavy chain, a light chain, or a heavy chain and a light chain of an anti-FXI/FXIa antibody binding agent described herein, e.g., antibody IDT1A, IDT1B, IDT1C, IDT1D, or IDT1E. In one embodiment, a polynucleotide provided herein comprises a nucleotide sequence encoding a heavy chain of an anti-FXI/FXIa antibody binding agent described herein, e.g., antibody IDT1A, IDT1B, IDT1C, IDT1D, or IDT1E. In one embodiment, a polynucleotide provided herein comprises a nucleotide sequence encoding a light chain of an anti-FXI/FXIa antibody binding agent described herein, e.g., antibody IDT1A, IDT1B, IDT1C, IDT1D, or IDT1E. In one embodiment, a polynucleotide provided herein comprises a nucleotide sequence encoding a heavy chain and a light chain of an anti-FXI/FXIa antibody binding agent described herein, e.g., antibody IDT1A, IDT1B, IDT1C, IDT1D, or IDT1E.

In particular embodiments, provided herein is a polynucleotide comprising one or more nucleotide sequences set forth in Table 2, for example:

l) a polynucleotide comprising the nucleotide sequence of SEQ ID NO: 81, 88, 93, 102, 111, 115, 117 or 120 encoding a heavy chain; and/or a polynucleotide comprising the nucleotide sequence of SEQ ID NO: 84, 89, 99, 104, or 118 encoding a light chain; or m) a polynucleotide comprising the nucleotide sequence of SEQ ID NO: 79, 86, 91, 100, 109, or 113 encoding a VH; and/or a polynucleotide comprising the nucleotide sequence of SEQ ID NO: 82 or 97 encoding a VL.

In certain embodiments, polynucleotides provided herein comprise nucleotide sequences that are substantially identical (e.g., at least 65%, 80%, 80%, 90%, 95%, 98%, or 99%) to the nucleotide sequences of those identified in Table 2, for example, SEQ ID NO: 117 or 120 encoding a heavy chain of IDT1C or IDT1D or IDT1E; and SEQ ID NO: 118 or 104 encoding a light chain of IDT1C or IDT1D or IDT1E. When expressed from appropriate expression vectors, polypeptides encoded by these polynucleotides are capable of binding to an anti-FXI/FXIa antibody, such as antibody NOV1401.

Because of the degeneracy of the code, a variety of nucleic acid sequences will encode each of the immunoglobulin amino acid sequences.

Polynucleotide sequences can be produced by de novo solid-phase DNA synthesis or by PCR mutagenesis of an existing sequence (e.g., sequences as described herein) encoding a binding agent, e.g., a binding agent which is an antibody (e.g., IgG, Fab fragment) that binds an anti-FXI/FXIa-antibody. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the present disclosure are expression vectors and host cells for producing a binding agent described herein, e.g., a binding agent which is an antibody that binds an anti-FXI/FXIa-antibody. Various expression vectors can be employed to express the polynucleotides encoding the FXIa-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of polynucleotides and polypeptides in mammalian (e.g., human) cells include pThioHis A, B & C, pcDNA3.1/His, pEBVHis A, B & C, (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a binding agent described herein, e.g., a binding agent which is an antibody that binds an anti-FXI/FXIa-antibody, such as NOV1401. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a binding agent, e.g., a binding agent which is an antibody that binds an anti-FXI/FXIa-antibody, such as NOV1401. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-FXI/FXIa-antibody binding agent sequences. In specific embodiments, inserted anti-FXI/FXIa-antibody binding agent sequences are linked to a signal sequences before inclusion in the vector. Vectors to be used to receive sequences encoding anti-FXI/FXIa-antibody binding agent (e.g., antibody NOV1401 binding agent) light and heavy chain variable domains, and in certain embodiments, also encode constant regions or parts thereof. Such vectors allow expression of the variable regions as fusion proteins with the constant regions thereby leading to production of intact antibodies or fragments thereof. Typically, such constant regions are human.

Host cells for harboring and expressing an anti-FXI/FXIa-antibody binding agent (e.g., antibody NOV1401 binding agent) can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express FXIa-binding polypeptides of the present disclosure. Insect cells in combination with baculovirus vectors can also be used.

In some specific embodiments, mammalian host cells are used to express and produce anti-FXI/FXIa-antibody binding agent (e.g., antibody NOV1401 binding agent) polypeptides of the present disclosure. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, and transformed B-cells. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences.

These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation-nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express FXIa-binding antibody chains can be prepared using expression vectors of the present disclosure which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Accordingly, in another aspect, the present disclosure provides a method for preparing an anti-FXI/FXIa antibody binding agent (e.g., anti-NOV1401 binding agent) optimized for expression in a mammalian cell consisting of a full length heavy chain antibody sequence having a sequence selected from those provided in Table 2; and a full length light chain antibody sequence having a sequence selected from those provided in Table 2; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity within CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of anti-FXI/FXIa-antibody binding agents (e.g., anti-NOV1401 binding agents) described herein, which functional properties include, but are not limited to, specifically binding an anti-FXI/FXIa antibody (e.g., NOV1401), for example, and contacting the one or more CDR amino acid residues of the anti-FXI/FXIa; inhibiting binding of a target anti-FXI/FXIa antibody (e.g., NOV1401) to human FXI and/or FXIa; inhibiting the ability of a target anti-FXI/FXIa antibody (e.g., NOV1401) to block the activity of FXIa; and inhibiting or reversing (e.g., partially reversing, for example, by at least 40%, at least 50%, at least 60%, at least 70%, at least 75%, at least 80%, or at least 85%) one or more anticoagulant effects of a target anti-FXI/FXIa antibody (e.g., NOV1401).

In certain embodiments of the methods of engineering antibodies of the present disclosure, mutations can be introduced randomly or selectively along all or part of an anti-FXI/FXIa antibody binding agent coding sequence and the resulting modified anti-FXI/FXIa antibody binding agents can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the present disclosure anti-FXI/FXIa antibody binding agents (e.g., antibody NOV1401 binding agent) have been engineered to remove sites of deamidation. Deamidation is known to cause structural and functional changes in a peptide or protein. Deamidation can result in decreased bioactivity, as well as alterations in pharmacokinetics and antigenicity of the protein pharmaceutical. (Anal Chem. 2005 Mar. 1; 77(5):1432-9).

The functional properties of the altered antibodies can be assessed using standard assays available in the art and/or described herein, such as those set forth in the Examples (e.g., SET, SPR, aPTT assay).

Prophylactic and Therapeutic Uses

In one aspect, the present disclosure provides a binding agent (e.g., anti-idiotype antibody, for example a Fab) which specifically binds a target anti-FXI/FXIa antibody (e.g., NOV1401), as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody (e.g., NOV1401), for use as a medicament.

In one aspect, the present disclosure provides a binding agent (e.g., anti-idiotype antibody) which specifically binds a target anti-FXI/FXIa antibody (e.g., NOV1401), as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody (e.g., NOV1401), for use in a manufacture of a medicament for reversing the anticoagulant effect of the anti-FXI/FXIa antibody.

The present disclosure provides a binding agent (e.g., anti-idiotype antibody, for example a Fab) which specifically binds a target anti-FXI/FXIa antibody (e.g., NOV1401), as well as a pharmaceutical composition comprising such binding agent, wherein the binding agent inhibits or reverses (e.g., partially reverses, for example, by at least 40%, at least 50%, at least 60%, at least 70%, at least 75%, at least 80%, or at least 85%) an anticoagulant activity of the target anti-FXI/FXIa antibody (e.g., NOV1401), for use in treatment of a patient, wherein said patient being treated with an anti-FXI/FXIa antibody (e.g., NOV1401), and wherein said patient is in need of reversing the anticoagulant effect of said anti-FXI/FXIa antibody.

The present disclosure further relates to methods for reversing (e.g., partially reversing, for example, by at least about 50%, at least about 60%, at least about 70%, at least about 75%, at least about 80%) or decreasing the anticoagulant effect of an anti-FXI/FXIa antibody (e.g., NOV1401) in a patient being treated with the anti-FXI/FXIa antibody, comprising administering an effective amount of a binding agent provided herein, e.g., antibody IDT1A, IDT1B, IDT1C, IDT1D, or IDT1E, which binds an anti-FXI/FXIa antibody and is capable of reversing one or more anticoagulant effects. In certain aspects, the present disclosure relates to methods for reversing (e.g., partially reversing, for example, by at least 40%, at least 50%, at least 60%, at least 70%, at least 75%, at least 80%, or at least 85%) or decreasing the anticoagulant effect of an anti-FXI/FXIa antibody (e.g., antibody NOV1401) in a patient being treated with the anti-FXI/FXIa antibody, comprising administering an effective amount of a pharmaceutical composition comprising a binding agent provided herein, e.g., antibody IDT1A, IDT1B, IDT1C, IDT1D, or IDT1E, which binds an anti-FXI/FXIa antibody and is capable of reversing one or more anticoagulant effects.

In specific embodiments, reversal of the anticoagulant effects of an anti-FXI/FXIa antibody may be needed by a patient for emergency surgery/urgent procedures and in life-threatening or uncontrolled bleeding. In certain embodiments, reversal (e.g., partial reversal) of the anticoagulant effects of an anti-FXI/FXIa antibody may be needed by a patient in the case of uncontrolled bleeding such as gastrointestinal (GI) bleeding, intracranial (IC) bleeding, or hemorrhagic stroke. In particular embodiments, a patient is being treated with an anti-FXI/FXIa antibody to manage, treat, prevent, or reduce the risk of a thromboembolic disease or disorder, for example reducing the risk of stroke or thrombosis (e.g., systemic embolism) in patients with atrial fibrillation (e.g., non-valvular atrial fibrillation), chronic kidney disease, such as end stage renal failure (ESRD) undergoing hemodialysis. In further specific embodiments, the patient has a demonstrated high risk of bleeding. In specific embodiments, non-limiting examples of anti-FXI/FXIa antibody binding agents for use in these methods include antibodies (e.g., anti-idiotype antibodies) described herein, e.g., in Table 2, for example, antibodies IDT1A, IDT1B, IDT1C, IDT1D, and IDT1E.

In certain embodiments, the present disclosure relates to methods for reducing clotting time in a subject administered an anti-FXI/FXIa antibody (e.g., antibody described in Table 1 such as antibody NOV1401), comprising administering an effective amount of a binding agent provided herein, e.g., an anti-idiotype antibody as set forth in Table 2, which binds the anti-FXI/FXIa antibody and is capable of inhibiting binding of the anti-FXI/FXIa antibody to human FXI/FXIa. In certain embodiments, the present disclosure relates to methods for reducing clotting time in a subject administered an anti-FXI/FXIa antibody (e.g., antibody described in Table 1 such as antibody NOV1401), comprising administering an effective amount of a pharmaceutical compositions comprising a binding agent provided herein, e.g., anti-idiotype antibody as set forth in Table 2 (in particular, IDT1A, IDT1B, IDT1C, IDT1D, or IDT1E), which binds the anti-FXI/FXIa antibody and is capable of inhibiting binding of the anti-FXI/FXIa antibody to human FXI/FXIa.

In specific embodiments, the present disclosure relates to methods for managing bleeding or bleeding risk or for reducing bleeding or bleeding risk in a patient being treated with an anti-FXI/FXIa antibody (e.g., antibody described in Table 1 such as antibody NOV1401), comprising administering an effective amount of a binding agent provided herein, e.g., a binding agent (e.g., antibody as described in Table 2, in particular IDT1A, IDT1B, IDT1C, IDT1D, or IDT1E) which binds an anti-FXI/FXIa antibody and is capable of reversing one or more anticoagulant effects, or administering an effective amount of a pharmaceutical composition comprising such binding agent provided herein. In specific embodiments, reversal of the anticoagulant effects of an anti-FXI/FXIa antibody may be needed by a patient for emergency surgery/urgent procedures and in life-threatening or uncontrolled bleeding (e.g., GI bleeding, IC bleeding, or hemorrhagic stroke). In particular embodiments, a patient is being treated with an anti-FXI/FXIa antibody to manage, treat, prevent, or reduce the risk of a thromboembolic disease or disorder, for example reducing the risk of stroke or thrombosis (e.g., systemic embolism) in patients with atrial fibrillation (e.g., non-valvular atrial fibrillation), chronic kidney disease, such as end stage renal failure (ESRD) undergoing hemodialysis. In further specific embodiments, the patient has a demonstrated high risk of bleeding. In specific embodiments, non-limiting examples of anti-FXI/FXIa antibody binding agents for use in these methods include antibodies (e.g., anti-idiotype antibodies) described herein, e.g., in Table 2, for example, antibodies IDT1A, IDT1B, IDT1C, IDT1D, and IDT1E; antibodies comprising VH CDRs and VL CDRs of such antibodies; antibodies that bind the same epitope(s) within target antibody NOV1401 as such antibodies.

In particular embodiments, provided herein are methods of managing bleeding or bleeding risk in a patient treated or administered an anti-FXI antibody described herein (e.g., antibody described in Table 1 such as NOV1401 or an anti-FXI antibody comprising HCDRs and LCDRs of NOV1401), comprising the step of administering to the patient in need thereof an anti-idiotype antibody of the anti-FXI antibody, wherein the anti-idiotype antibody specifically binds to the anti-FXI antibody and blocks the anti-FXI antibody from binding to FXI. In specific embodiments, an anti-idiotype antibody (e.g., IDT1A, IDT1B, IDT1C, IDT1D, or IDT1E) reverses the effects of an anti-FXI antibody described herein to mitigate bleeding risks, for example during urgent major surgery or trauma.

In specific embodiments, an anti-idiotype antibody reverses (e.g., partially reverses, for example, by at least 40%, at least 50%, at least 60%, at least 70%, at least 75%, at least 80%, or at least 85%) or inhibits an anti-FXI antibody's anti-coagulant effects. In particular embodiments, the anti-idiotype antibody is administered to a patient in need thereof to temporarily reverse the anti-coagulant effect of an anti-FXI antibody described herein (e.g., antibody described in Table 1 such as NOV1401 or an anti-FXI antibody comprising HCDRs and LCDRs of NOV1401).

In particular embodiments, provided herein are methods of managing bleeding or bleeding risk in a patient treated or administered an anti-FXI antibody such as NOV1401 (e.g., SEQ ID NOs: 3 and 7, SEQ NOs: 5 and 9), comprising the step of administering to the patient in need thereof, an anti-idiotype antibody (e.g., IDT1A, IDT1B, IDT1C, IDT1D, or IDT1E) of the anti-FXI antibody such as NOV1401 (e.g., SEQ ID NOs: 3 and 7, SEQ ID NOs: 5 and 9), wherein the anti-idiotype antibody specifically binds to the antigen-binding region of an anti-FXI antibody such as NOV1401 (e.g., SEQ ID NOs: 3 and 7, SEQ ID NOs: 5 and 9) and blocks the anti-FXI antibody from binding to FXI and/or FXIa. In a specific embodiment, the anti-idiotype antibody (e.g., IDT1A, IDT1B, IDT1C, IDT1D, or IDT1E) of an anti-FXI antibody such as NOV1401 (e.g., SEQ ID NOs: 3 and 7, SEQ ID NOs: 5 and 9) reverses or inhibits one or more of the anti-coagulant effects of the anti-FXI antibody (e.g., NOV1401). In certain embodiments, a temporary reversal or inhibition of one or more of the anti-coagulant effects of the anti-FXI antibody (e.g., NOV1401) is achieved. In specific embodiments, following the temporary reversal or inhibition of the anti-FXI antibody (e.g., NOV1401), the anti-FXI antibody (e.g., NOV1401) is again administered to the patient.

As used herein, the terms "effective amount" or "therapeutically effective amount" refer to an amount of a therapy (e.g., a binding agent provided herein such as an anti-idiotype antibody that binds an anti-FXI/FXIa antibody (e.g., NOV1401) or a pharmaceutical composition provided herein) which is sufficient to reduce and/or ameliorate the severity and/or duration of a given condition, disorder, or disease and/or a symptom related thereto. These terms also encompass an amount necessary for the reduction, slowing, or amelioration of the advancement or progression of a given condition, disorder, or disease, reduction, slowing, or amelioration of the recurrence, development or onset of a given condition, disorder or disease, and/or to improve or enhance the prophylactic or therapeutic effect(s) of another therapy (e.g., a therapy other than an anti-FXI/FXIa antibody binding agent provided herein). In some embodiments, "effective amount" as used herein also refers to an amount of an antibody described herein to achieve a specified result, for example, reduction or reversal in one or more anticoagulant effects (e.g., aPTT prolongation) of a target anti-FXI/FXIa antibody; and reduction in, or blocking, binding of a target anti-FXI/FXIa antibody to FXI/FXIa. In some embodiments, "effective amount" as used herein refers to an amount of reversal agent described herein to achieve at least 40%, at least 50% or at least 60% reduction or reversal in one or more anticoagulant effects (e.g., aPTT prolongation for example as described herein in the Examples Section) of a target anti-FXI/FXIa antibody; and/or reduction in, or blocking, binding of a target anti-FXI/FXIa antibody to FXI/FXIa. In some embodiments, "effective amount" as used herein refers to an amount of reversal agent described herein to achieve at least 60%, at least 70% or at least 75% reduction or reversal in one or more anticoagulant effects (e.g., aPTT prolongation for example as described herein in the Examples Section) of a target anti-FXI/FXIa antibody; and/or reduction in, or blocking, binding of a target anti-FXI/FXIa antibody to FXI/FXIa. In some embodiments, "effective amount" as used herein refers to an amount of reversal agent described herein to achieve at least 75%, 80%, or at least 85% reduction or reversal in one or more anticoagulant effects (e.g., aPTT prolongation for example as described herein in the Examples Section) of a target anti-FXI/FXIa antibody; and/or reduction in, or blocking, binding of a target anti-FXI/FXIa antibody to FXI/FXIa.

In specific embodiments, a patient, who may be in need of, or may benefit from, the methods described herein (e.g., methods for reversing anticoagulant effects with anti-FXI/FXIa antibody binding agents), has been treated with an anti-FXI/FXIa antibody (e.g., antibody described in Table 1 such as antibody NOV1401) to manage, treat, prevent, or reduce the risk of a thromboembolic disease or disorder, e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, or systemic embolism. In further specific embodiments, the patient has a demonstrated high risk of bleeding.

In other embodiments, a patient, who may be in need of, or may benefit from, the methods described herein (e.g., methods for reversing anticoagulant effects with anti-FXI/FXIa antibody binding agents), has been treated with an anti-FXI/FXIa antibody (e.g., antibody described in Table 1 such as antibody NOV1401) for treatment of acute VTE, primary and extended secondary prevention of VTE, prevention of major adverse thromboembolic events in patient undergoing dialysis (with or without AF), prevention of major cardiovascular and cerebral events (MACCE) in patients with CAD undergoing PCI and receiving single or dual antiplatelet therapy, post-acute coronary syndromes (ACS) patients, heparin induced thrombocytopenia (HIT), prevention of thromboembolic events in heart failure patients and secondary stroke prevention.

In specific embodiments, one of the following groups of subjects is being treated with an anti-FXI/FXIa antibody (e.g., antibody described in Table 1 such as antibody NOV1401) and may be in need of, or benefit from, the methods described herein (e.g., methods for reversing anticoagulant effects with anti-FXI/FXIa antibody binding agents):

- Subjects with indications for chronic anticoagulation therapy (e.g., AF, left ventricular thrombus, prior cardioembolic stroke)
- subjects at intermediate-to-high risk for major bleeding;
- subjects undergoing elective or primary percutaneous coronary intervention (PCI) with stenting which may be require to receive dual antiplatelet therapy (aspirin and P2Y12 receptor antagonists) to prevent stent thrombosis.

In specific embodiments, a subject, who may be in need of, or benefit from, the methods described herein (e.g., methods for reversing anticoagulant effects with anti-FXI/FXIa antibody binding agents), has been treated with an anti-FXI/FXIa antibody (e.g., antibody described in Table 1 such as antibody NOVT401) to manage, treat, prevent, or reduce the risk of one of the following conditions:

- thromboembolism in subjects with suspected or confirmed cardiac arrhythmia such as paroxysmal, persistent or permanent atrial fibrillation or atrial flutter;
- stroke prevention in atrial fibrillation (SPAF), a subpopulation of which is AF patients undergoing percutaneous coronary interventions (PCI);
- acute venous thromboembolic events (VTE) treatment and extended secondary VTE prevention in patients at high risk for bleeding;
- cerebral and cardiovascular events in secondary prevention after transient ischemic attack (TIA) or non-disabling stroke and prevention of thromboembolic events in heart failure with sinus rhythm;
- clot formation in left atrium and thromboembolism in subjects undergoing cardioversion for cardiac arrhythmia;
- thrombosis before, during and after ablation procedure for cardiac arrhythmia;
- venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;
- thrombosis on any artificial surface in the veins like catheter or pacemaker wires;
- pulmonary embolism in patients with or without venous thrombosis;
- Chronic Thromboembolic Pulmonary Hypertension (CTEPH);
- arterial thrombosis on ruptured atherosclerotic plaque, thrombosis on intra-arterial prosthesis or catheter and thrombosis in apparently normal arteries, this includes but not exclusively acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;
- thrombosis and thromboembolism in patients undergoing percutaneous coronary interventions (PCI);
- cardioembolic and cryptogenic strokes;
- thrombosis in patients with invasive and non-invasive cancer malignancies;

thrombosis over an indwelling catheter;

thrombosis and thromboembolism in severely ill patients;

cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;

thromboembolism in patients with valvular heart disease with or without atrial fibrillation;

thromboembolism over valvular mechanic or biologic prostheses;

injuries or trauma in patients who had native or artificial cardiac patches, arterial or venous conduit tubes after heart repair of simple or complex cardiac malformations;

venous thrombosis and thromboembolism after knee replacement surgery, hip replacement surgery, and orthopedic surgery, thoracic or abdominal surgery;

arterial or venous thrombosis after neurosurgery including intracranial and spinal cord interventions;

congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;

thrombosis and thromboembolism in chronic kidney disease;

thrombosis and thromboembolism in end stage renal disease (ESRD);

thrombosis and thromboembolism in patients with chronic kidney disease or ESRD undergoing hemodialysis; and thrombosis and thromboembolism in patients undergoing hemodialysis and/or extra-corporal membrane oxygenation.

In specific embodiments, an anti-FXI/FXIa antibody binding agent (e.g., IDT1A, IDT1B, IDT1C, IDT1D, or IDT1E) or a pharmaceutical composition comprising such a binding agent is for use in methods of reducing bleeding or bleeding risk, or managing bleeding or bleeding risk, in a patient being treated or administered an anti-FXI/FXIa antibody (e.g., antibody described in Table 1 such as antibody NOV1401) to reduce the risk of stroke and/or systemic embolism, wherein the patient has non-valvular atrial fibrillation.

In a specific embodiment, an anti-FXI/FXIa antibody binding agent (e.g., IDT1A, IDT1B, IDT1C, IDT1D, or IDT1E) or a pharmaceutical composition comprising such a binding agent is for use in methods of reducing bleeding or bleeding risk, or managing bleeding or bleeding risk, in a patient being treated or administered an anti-FXI/FXIa antibody (e.g., antibody described in Table 1 such as antibody NOV1401) to reduce the risk of stroke and/or systemic embolism, wherein the patient has non-valvular atrial fibrillation with a demonstrated high risk of bleeding.

In a specific embodiment, an anti-FXI/FXIa antibody binding agent (e.g., IDT1A, IDT1B, IDT1C, IDT1D, or IDT1E) or a pharmaceutical composition comprising such binding agent is for use in methods of reducing bleeding or bleeding risk, or managing bleeding or bleeding risk, in a patient being treated or administered an anti-FXI/FXIa antibody (e.g., antibody described in Table 1 such as antibody NOV1401) to reduce the risk of stroke and/or systemic embolism, wherein the patient has ESRD and is undergoing dialysis.

In a specific embodiment, an anti-FXI/FXIa antibody binding agent (e.g., IDT1A, IDT1B, IDT1C, IDT1D, or IDT1E) or a pharmaceutical composition comprising such a binding agent is for use in methods of reducing bleeding or bleeding risk, or managing bleeding or bleeding risk, in a patient being treated or administered an anti-FXI/FXIa antibody (e.g., antibody described in Table 1 such as antibody NOV1401) to reduce the risk of stroke and/or systemic embolism, wherein the patient has non-valvular atrial fibrillation and ESRD and is undergoing dialysis.

In specific embodiments, a subject, who may be in need of, or benefit from, the methods described herein (e.g., methods for reversing anticoagulant effects with anti-FXI/FXIa antibody binding agents), has been treated with an anti-FXI/FXIa antibody (e.g., antibody described in Table 1 such as antibody NOV1401) in combination with other agents for the prevention, treatment, or improvement of thromboembolic disorders. For example, statin therapies may be used in combination with the FXIa antibodies of the present disclosure for the treatment of patients with thrombotic and/or thromboembolic disorders. Such subjects undergoing combination therapy may be in need of, or benefit from, the methods described herein (e.g., methods for reversing anticoagulant effects with anti-FXI/FXIa antibody binding agents).

In a specific embodiment, provided herein are methods of reducing bleeding or bleeding risk, or managing bleeding or bleeding risk, in a patient being treated or administered an anti-FXI/FXIa antibody (e.g., antibody described in Table 1 such as antibody NOV1401), said method comprises administering a binding agent which specifically binds to the anti-FXI/FXIa antibody (e.g., antibody NOV1401), and reverses an anticoagulant effect of the anti-FXI/FXIa antibody. In particular embodiments, the bleeding or bleeding risk is associated with trauma, surgery, or post-delivery. In another particular embodiment, the bleeding or bleeding risk is associated with emergency surgery or urgent procedures. In other particular embodiments, the bleeding is life-threatening or uncontrolled, such as GI bleed or IC bleed. In specific embodiments, the binding agent is an antibody, such as an anti-idiotype antibody (e.g., IDT1A, IDT1B, IDT1C, IDT1D, or IDT1E) which specifically binds an anti-FXI/FXIa antibody (e.g., NOV1401). In additional specific embodiments, the binding agent is an anti-idiotype antibody which specifically binds to one or more epitopes within the variable regions of an anti-FXI/FXIa antibody (e.g., NOV1401). In more specific embodiments, the binding agent is a full length IgG anti-idiotype antibody which specifically binds to an anti-FXI/FXIa antibody (e.g., NOV1401). In particular embodiments, the binding agent is an anti-idiotype comprising amino acid sequences selected from Table 2. In particular embodiments, the binding agent is an anti-idiotype antibody, such as antibody IDT1A, IDT1B, IDT1C, IDT1D, or IDT1E, as set forth in Table 2. In particular embodiments, the binding agent is an anti-idiotype antibody, such as IDT1C, as set forth in Table 2. In particular embodiments, the binding agent is an anti-idiotype antibody, such as IDT1D, as set forth in Table 2. In particular embodiments, the binding agent is an anti-idiotype antibody, such as IDT1E, as set forth in Table 2.

In specific embodiments, bleeding is typically associated with, but not limited to, trauma, surgery, menstruation or post-delivery. Therefore, under these circumstances, a subject, who has been treated with an anti-FXI/FXIa antibody (e.g., antibody described in Table 1 such as NOV1401), may be in need of quick and effective therapy, such as an anti-FXI/FXIa antibody binding agent described herein, to reduce bleeding or to reduce bleeding risk. In specific embodiments, prolonged bleeding may occur after a major trauma or after surgery, such as surgery involving organs with high fibrinolytic area such as buccal, nasal, genital or urinary mucosa. Tooth extraction, tonsillectomy and ablation of the uterus or prostate are more non-limiting examples of surgeries that entail a high risk of bleeding. In specific embodiments, concomitant use of antiplatelets, other anticoagulants and fibrinolytic agents can increase the risk of bleeding.

In certain embodiments, a temporary reversal or inhibition of one or more of the anticoagulant effects of an anti-FXI antibody (e.g., antibody described in Table 1 such as antibody NOV1401) is desired. In a particular embodiment, provided herein are methods of reducing or managing bleeding or bleeding risk in a patient treated or administered an anti-FXI/FXIa antibody such as antibody NOV1401, comprising the step of administering to the patient in need thereof, a pharmaceutical composition comprising a binding agent described herein, such as antibody IDT1A, IDT1B, IDT1C, IDT1D, or IDT1E, once or twice, over a period of time (e.g., 1 hour to 24 hours or to 48 hours), followed by administering the anti-FXI/FXIa antibody, wherein a temporary reversal or inhibition of one or more of the anticoagulant effects of the anti-FXI antibody is achieved. In a particular embodiment, provided herein are methods of reducing or managing bleeding or bleeding risk in a patient treated or administered an anti-FXI/FXIa antibody such as antibody NOV1401, comprising the step of administering to the patient in need thereof, IDT1A, IDT1B, IDT1C, IDT1D, or IDT1E or a pharmaceutical composition comprising IDT1A, IDT1B, IDT1C, IDT1D, or IDT1E, once or twice or more, over a period of time (e.g., 1 hour to 24 hours or to 48 hours), followed by administering the anti-FXI/FXIa antibody, wherein a temporary reversal or inhibition of one or more of the anticoagulant effects of the anti-FXI antibody is achieved.

In certain embodiments, an anti-FXI/FXIa antibody binding agent described herein (e.g., IDT1A, IDT1B, IDT1C, IDT1D, or IDT1E) can be administered in combination with another anticoagulant reversal therapy. Non-limiting examples of conventional strategies for reversing anticoagulant effects include (i) fluid replacement using colloids, crystalloids, human plasma or plasma proteins such as albumin; or (ii) transfusion with packed red blood or whole blood, or (iii) administration of fresh frozen plasma (FFP), prothrombin complex concentrates (PCC), activated PCC (APCC), such as, factor VIII inhibitor, and/or recombinant, activated factor VII.

In specific embodiments, the present disclosure relates to methods for reversing the anticoagulant effect of an anti-FXI/FXIa antibody (e.g., antibody described in Table 1 such as antibody NOV1401) in a patient being treated with the anti-FXI/FXIa antibody, comprising (i) administering to the patient an effective amount of a binding agent provided herein, e.g., a binding agent (e.g., IDT1A, IDT1B, IDT1C, IDT1D, or IDT1E) which binds an anti-FXI/FXIa antibody and is capable of reversing one or more anticoagulant effects; and (ii) administering to the patient another anticoagulant reversal therapy, such as fresh frozen plasma (FFP), prothrombin complex concentrates (PCC), activated PCC or recombinant activated factor VII (rFVIIa). In specific embodiments, the present disclosure relates to methods for reversing the anticoagulant effect of an anti-FXI/FXIa antibody (e.g., antibody NOV1401) in a patient being treated with the anti-FXI/FXIa antibody, comprising (i) administering to the patient an effective amount of a binding agent provided herein, e.g., IDT1A, IDT1B, IDT1C, IDT1D, or IDT1E, which binds an anti-FXI/FXIa antibody and is capable of reversing one or more anticoagulant effects; and (ii) administering to the patient fresh frozen plasma (FFP). In specific embodiments, such method achieves homeostasis.

In certain embodiments, provided herein is a method of managing bleeding in a patient being treated with an anti-FXI antibody provided herein (e.g., an antibody described in Table 1, such as, an anti-FXI antibody comprising VL CDRs and VH CDRs of NOV1401), said method comprises temporarily reversing of the anticoagulant effect for a sufficient time to manage the bleeding.

In certain embodiments, provided herein is a method of managing bleeding or bleeding risk in a patient being treated with an anti-FXI/FXIa antibody provided herein (e.g., an antibody described in Table 1, such as, NOV1401 or an anti-FXI/FXIa antibody comprising VL CDRs and VH CDRs of NOV1401), said method comprising administering to the patient an anticoagulant reversal therapy capable of reversing (e.g., partially reversing, for example, by at least 40%, at least 50%, at least 60%, at least 70%, at least 75%, at least 80%, or at least 85%) the anticoagulant effects of the anti-FXI/FXIa antibody. In specific embodiments, the anticoagulant reversal therapy capable of reversing the anticoagulant effect of the anti-FXI/FXIa antibody is rFVIIa (recombinant Factor VIIa), emicizumab (ACE910), tranexamic acid, Fresh Frozen Plasma (FFP), Hemoeleven, Prothrombin Complex Concentrate (PCC), Activated PCC, or FEIBA (a FVIII inhibitor complex). In specific embodiments, the anticoagulant reversal therapy is administered alone, or in combination with a binding agent provided herein (e.g., binding agent described in Table 2, such as IDT1A, IDT1B, IDT1C, IDT1D, or IDT1E) or a pharmaceutical composition comprising such binding agent.

In specific embodiments, the present disclosure relates to methods for reversing the anticoagulant effect of an anti-FXI/FXIa antibody (e.g., an anti-FXI/FXIa antibody described in Table 1 such as antibody NOV1401 or an anti-FXI/FXIa antibody comprising VH CDRs and VL CDRs of NOV1401) in a patient being treated with the anti-FXI/FXIa antibody, comprising (i) administering to the patient an effective amount of a binding agent provided herein, e.g., a binding agent as set forth in Table 2 such as IDT1A, IDT1B, IDT1C, IDT1D, or IDT1E, which binds an anti-FXI/FXIa antibody and is capable of reversing one or more anticoagulant effects or a pharmaceutical composition comprising such binding agent; and (ii) administering to the patient another anticoagulant reversal therapy, such as rFVIIa (recombinant Factor VIIa), emicizumab (ACE910), tranexamic acid, Fresh Frozen Plasma (FFP), Hemoeleven, Prothrombin Complex Concentrate (PCC), Activated PCC, or FEIBA (a FVIII inhibitor complex).

In specific embodiments, the risk of thromboembolic events including stroke, systemic embolism, coronary or peripheral artery thrombosis, venous thrombosis and pulmonary embolism increases with presence of predisposing factors such as thrombophilia, vessel wall damage and stasis. Evaluation of medical history, familiar antecedents and associated co-morbidities can help to stratify patients according to their thromboembolic risks. In patients with atrial fibrillation, several scoring systems e.g., $CHADS_2$ and $CHA_2DS_2$-VASc have been developed to assess stroke risk. Each was developed based on data from randomized trials, and clinical and epidemiologic cohort studies, and translated a weighted, multivariate formula of stroke risk factors to a simplified, easy-to-use mnemonic device, algorithm, calculator, or online tool. The $CHADS_2$ risk score was used stratification tool to predict thromboembolic risk in atrial fibrillation patients (Lip (2011) Am J Med; 124(2):111-4; Camm et al (2012) Eur Heart J; 33: 2719-2747); however, accumulated evidence shows that $CHA_2DS_2$-VASc is at least as good as or possibly better than, scores such as $CHADS_2$ in identifying patients who develop stroke and thromboembolism and definitively better at identifying 'truly low-risk' patients with atrial fibrillation. The $CHA_2DS_2$-VASc score is presently recommended by Guidelines (Camm et al (2012) Eur Heart J 33, 2719-2747; January et al, AHA/ACC/HRS Atrial Fibrillation Guideline; J Am Coll Cardiol 2014; 64:2246-80) to guide the decision with regard to patients who should benefit of anticoagulant therapy and also to identify low risk patients in whom anticoagulation therapy is not warranted.

Bleeding risk assessment tools specific to the atrial fibrillation patients e.g., HAS-BLED, ATRIA, HEMORR2HAGES; ORBIT and ABC risk score were developed to predict the bleeding risk in patients with atrial fibrillation. Unfortunately, as the bleeding risk is tightly correlated with the stroke risk, those risk score were of rather limited value to guide therapeutic decisions to use vitamin K antagonists such as warfarin or NOACS. However, bleeding risk scores may become of considerable help to identify patients who can benefit of a new therapy with a reduced bleeding risk e.g. anti-FXI/FXIa antibody (e.g., antibody NOV1401).

In certain embodiments, subjects with a bleeding risk, for example a demonstrated high risk of bleeding, may be identified by previous medical history of bleeding, for example, bleeding during or after surgery or bleeding when treated with an anticoagulant (e.g. Warfarin). In addition, subjects with a bleeding risk, for example a demonstrated high risk of bleeding, may be identified by in vitro/ex vivo assays known in the art, for example, assays with a subject's plasma measuring aPTT and other biomarkers of the extrinsic coagulation pathways, such as prothrombin time (PT) and thrombin time (TT).

In particular embodiments, subjects with moderate to high risk for stroke and systemic embolism have a $CHA_2DS_2VASc$ risk score ≥2. In further particular embodiments, subjects with a HAS BLED risk score ≥3 is characterized as having a high risk of bleeding (see Gallego, et al., (2012) Carc Arrhythm Electrophysiol.; 5:312-318, and Friberg et al., (2012) Circulation.; 125:2298-2307). In particular embodiments, subjects being treated by the methods provided herein has a $CHA_2DS_2VASc$ risk score ≥2.

In specific embodiments, a subject being treated by the methods provided herein is a human subject at least 18 years old. In another embodiment, a subject being treated by the methods provided herein is a human subject at least 50 years old. In another embodiment, a subject being treated by the methods provided herein is a human subject at least 55 years old. In another embodiment, a subject being treated by the methods provided herein is a human subject at least 60 years old. In another embodiment, a subject being treated by the methods provided herein a human subject is at least 65 years old.

In particular embodiments, a subject being treated by the methods provided herein (e.g., methods for treating VTE or for secondary prevention of VTE) is between the ages of 2 and 18 years old. In particular embodiments, a subject being treated by the methods provided herein (e.g., methods for treating VTE or for secondary prevention of VTE) is between the ages of 12 and 18 years old. In particular embodiments, a subject being treated by the methods provided herein (e.g., methods for treating VTE or for secondary prevention of VTE) is a child at least 2 years old and under 18 years old. In particular embodiments, a subject being treated by the methods provided herein (e.g., methods for treating VTE or for secondary prevention of VTE) is a child at least 12 years old and under 18 years old.

In specific embodiments, a subject (e.g., human subject) being treated by the methods provided herein has a body mass index (BMI) that is greater than or equal to 18 $kg/m^2$. In another embodiment, a subject being treated by the methods provided herein has a BMI that is greater than or equal to 30 $kg/m^2$. In another embodiment, a subject being treated by the methods provided herein has a BMI that is greater than or equal to 35 $kg/m^2$. In another embodiment, a subject being treated by the methods provided herein has a BMI that is greater than or equal to 40 $kg/m^2$.

In certain embodiments, methods for reversing the anticoagulant effects of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in (i) reduction or reversal in aPTT prolongation as determined with aPTT assays with human plasma; (ii) reduction in the amount of thrombin in a thrombin generation assay (TGA) amount of thrombin in a thrombin generation assay (TGA) in human plasma; and/or (iii) reduction or reversal of bleeding or bleeding risk. In specific embodiments, reversal of the anticoagulant effects is less than 100%, but is sufficient to achieve a clinically beneficial outcome, e.g., a reduction or stop in bleeding.

In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in reduction or reversal in aPTT prolongation as determined with aPTT assays with human plasma, by at least 10%, at least 20%, at least 30%, at least 40%, at least 50%, at least 60%, at least 70%, at least 80%, or at least 90%. In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in reduction or reversal in aPTT prolongation as determined with aPTT assays with human plasma, by at least 40%, at least 50%, at least 60%, or at least 70%. In a preferred embodiment, methods for reversing the anticoagulant effect of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in reduction or reversal in aPTT prolongation as determined with aPTT assays with human plasma, by at least 60%.

In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in reduction or reversal in aPTT prolongation as determined with aPTT assays with human plasma, by at least 10%, at least 20%, at least 30%, at least 40%, at least 50%, at least 60%, at least 70%, at least 80%, or at least 90%, wherein the anti-FXI/FXIa antibody binding agent described herein is present in at least three times molar excess, e.g., at least five times molar excess, at least nine times molar excess, at least ten times molar excess, at least fifteen times molar excess, at least twenty times molar excess, at least thirty times molar excess, preferably in a three times molar excess, in comparison to the anti-FXI/FXIa antibody. In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in reduction or reversal in aPTT prolongation as determined with aPTT assays with human plasma, by at least 40%, at least 50%, at least 60%, or at least 70%, wherein the anti-FXI/FXIa antibody binding agent described herein is present in at least three times molar excess, e.g., at least five times molar excess, at least nine times molar excess, at least ten times molar excess, at least fifteen times molar excess, at least twenty times molar excess, at least thirty times molar excess, preferably in a three times molar excess, in comparison to the anti-FXI/FXIa antibody. In a preferred embodiment, methods for reversing the anticoagulant effect of an anti-FXI/FXIa antibody (e.g., antibody described in Table 1 such as antibody NOV1401) with an anti-FXI/FXIa antibody binding agent described herein (e.g., IDT1A, IDT1B, IDT1C, IDT1D, or IDT1E) or a pharmaceutical composition comprising such anti-FXI/FXIa antibody binding agent, results in reduction or reversal in aPTT prolongation as determined with aPTT assays with human plasma, by at least 60% wherein the anti-FXI/FXIa antibody binding agent described herein is present in at least three times molar excess, e.g., at least five times molar excess, at least nine times molar excess, at least ten times molar excess, at least fifteen times molar excess, at least twenty times molar excess, at least thirty times molar excess, preferably in a three times molar excess, in comparison to the anti-FXI/FXIa antibody.

In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., antibody as set forth in Table 2 such as IDT1A, IDT1B, IDT1C, IDT1D, or IDT1E) or a pharmaceutical composition comprising such anti-FXI/FXIa antibody binding agent, results in an increase in the serum level of free FXI/FXIa relative to levels prior to administration of the anti-FXI/FXIa antibody binding agent. In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., antibody as set forth in Table 2 such as IDT1A, IDT1B, IDT1C, IDT1D, or IDT1E) or a pharmaceutical composition comprising such anti-FXI/FXIa antibody binding agent, results in an increase in the serum level of free FXI/FXIa relative to levels prior to administration of the anti-FXI/FXIa antibody binding agent, by at least 10%, at least 20%, at least 30%, at least 40%, at least 50%, at least 60%, at least 70%, at least 80%, or at least 90%. In certain embodiments, methods for reversing the anticoagulant effect of an anti-FXI/FXIa antibody (e.g., antibody described in Table 1 such as antibody NOV1401) with an anti-FXI/FXIa antibody binding agent described herein (e.g., antibody as set forth in Table 2 such as IDT1A, IDT1B, IDT1C, IDT1D, or IDT1E) or a pharmaceutical composition comprising such anti-FXI/FXIa antibody binding agent, results in an increase in the serum level of free FXI/FXIa relative to levels prior to administration of the anti-FXI/FXIa antibody binding agent, by at least 40%, at least 50%, at least 60%, or at least 70%. The serum level of free FXI/FXIa can be determined by any methods previously described, e.g., by ELISA.

Pharmaceutical Compositions and Kits

The present disclosure provides pharmaceutical compositions comprising anti-FXI/FXIa antibody-binding agents described herein (e.g., antibody described in Table 2 such as IDT1A, IDT1B, IDT1C, IDT1D, or IDT1E) formulated together with a pharmaceutically acceptable carrier. The compositions can additionally contain one or more other therapeutic agents that are suitable for treating or preventing, for example, thromboembolic disorders (e.g., thrombotic disorders). Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, may be coated in a material to protect the compound from the action of acids and other natural conditions that may inactivate the compound.

In specific embodiments, a composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the present disclosure can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the FXIa-binding antibody is employed in the pharmaceutical compositions of the present disclosure. The FXIa-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present disclosure employed, thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the antibodies of the present disclosure employed in the pharmaceutical composition at levels lower than that required to achieve the desired therapeutic effect and gradually increase the dosage until the desired effect is achieved. In general, effective doses of the compositions of the present disclosure, for the treatment of a thrombotic and/or thromboembolic disorders described herein vary depending upon many different factors, including means of administration, target site, physiological state of the patient, other medications administered, and whether treatment is prophylactic or therapeutic. Treatment dosages need to be titrated to optimize safety and efficacy. For systemic administration with an antibody, in certain embodiments, the dosage may range from about 0.01 to 15 mg/kg of the host body weight. For administration with an antibody, the dosage may range from 0.1 mg to 500 mg.

In a certain embodiment, an anti-FXI/FXIa antibody described herein is administered, for example by i.v. or s.c. route, at a dose in the range of 5 mg to 600 mg.

In specific embodiments, an anti-FXI/FXIa antibody binding agent described herein (e.g., antibody as set forth in Table 2 such as IDT1A, IDT1B, IDT1C, IDT1D, or IDT1E) is administered for a temporary duration or period of time when reversal of anticoagulant effects of an anti-FXI/FXIa antibody (e.g., antibody described in Table 1 such as NOV1401) is desired. In specific embodiments, an anti-FXI/FXIa binding agent described herein (e.g., antibody as set forth in Table 2 such as IDT1A, IDT1B, IDT1C, IDT1D, or IDT1E) is administered once, or a few times, for a temporary duration or period of time when reversal of anticoagulant effects of an anti-FXI/FXIa antibody (e.g., antibody described in Table 1 such as NOV1401) is desired to achieve homeostasis.

In certain embodiments, a relatively high dosage at relatively short intervals is sometimes required until progression of the bleeding or bleeding risk is reduced or terminated, and in certain cases until the patient shows partial or complete amelioration of bleeding or risk of bleeding.

In one aspect, the present disclosure provides a kit comprising the binding agent or the antibody provided herein and, optionally, an instruction for use.

EXAMPLES

The following examples are provided to further illustrate the present disclosure but not to limit its scope. Other variants of the present disclosure will be readily apparent to one of ordinary skill in the art and are encompassed by the appended claims.

Example 1

Discovery of Affinity Matured Versions of Anti-NOV1401 Antibody IDT1

IDT1 Antibody

IDT1 antibody against anti-Factor XI (FXI) antibody NOV1401 was identified by selection of clones that specifically bound to NOV1401 using a commercially available phage display library, the Morphosys HuCAL PLATINUM® library (Knappik et al., 2000, J Mol Biol 296: 57-86) and described in WO 2017/203450. The sequence of IDT1 antibody is included in Table 2.

Affinity Maturation

To increase affinity and potentially biological activity of IDT1, LCDR3 and HCDR2 regions were optimized in parallel by cassette mutagenesis using trinucleotide-directed mutagenesis (Vimekas et al., 1994, Nucleic Acids Res. 22(25):5600-7), while the framework regions were kept constant. Prior to cloning for affinity maturation, parental Fab fragments were subcloned from the corresponding expression vector pMORPH11 into the CysDisplay™ vector pMORPH30 via XbaI/EcoRI.

For optimizing LCDR3 of Fab fragments, the parental LCDR3s—including flanking framework and the constant region of the light chain (405 bp)—were excised from the parental Fab-encoding CysDisplay™ vectors by BbsI/SphI and replaced by a diversified LCDR3 cassette (together with framework 4 and the light chain constant domain). In a second library set, the HCDR2s (XhoI/BssHII) were diversified, while the connecting framework regions were kept constant. In order to monitor the cloning efficiency, the parental LCDR3 and HCDR2 were replaced by a 587 bp dummy, before the diversified LCDR3 and HCDR2 maturation cassettes were cloned in.

All maturation libraries were prepared by ligation of 1 pg of the parental Fab-encoding CysDisplay™ vector fragment with a 5-fold molar excess of the insert fragment carrying the diversified CDRs. Ligation mixtures were electroporated into *E. coli* Top10F' yielding 7.5E+08 independent colonies for LCDR3 library and 7.49E+08 independent colonies for HCDR2 library. Amplification of the library was performed as described previously, for example see Rauchenberger et al., 2003 (J Biol Chem. 278(40):38194-205). For quality control, up to 36 single clones were randomly picked and sequenced.

For the selection of affinity-improved binders panning strategy was employed with direct coating of NOV1401 to a Maxisorp™ (Nunc) 96 well plate followed by three rounds of panning with increasing washing stringency. From this process, Fabs IDT1A, IDT1B and IDT1C were identified as high affinity binders to NOV1401. The sequences of IDT1A, IDT1B and IDT1C Fabs are included in Table 2.

Subcloning of Selected Fab Fragments

To facilitate rapid expression of soluble Fab fragments, the Fab encoding inserts of the selected HuCAL® PLATINUM phage particles were subcloned from the pMORPH®30 display vector into pMORPH®x11 pMORPH11_FH expression vector.

Overnight cultures of individual Fab-expressing *E. coli* clones were lysed using BEL lysate buffer (2.5 mg/mL lysozyme (Roche, Ref. 10837059001), 4 mM EDTA, 10 U/μl Benzonase (Merck, Ref. 1.01654.0001)). Resulting Fab lysates were blocked by adding 10 μL of 12.5% Milk in PBST per well. Fab containing *E. coli* lysates were used for ELISA screening.

ELISA Screening

Using ELISA screening, single Fab clones were identified from panning output for binding to NOV1401. Fab fragments were tested using Fab containing crude *E. coli* lysates.

The primary screening was performed using Maxisorp™ (Nunc) 384 well plates coated overnight at 4° C. with 5 μg/ml NOV1401 in PBS pH 7.4. After washing, plates were blocked for 2 h with 5% skimmed milk in PBS. Fab-containing *E. coli* lysates were added and binding allowed for 90 minutes at RT. To detect bound Fab fragments plates were washed 5× with TBST and AP-goat-anti-human IgG F(ab')2 Ab (Jackson-Immunoresearch, Ref. 109-055-097) was added in a 1:5000 dilution. After 30 minutes incubation at RT, plates were washed 5× with TBST and 40 μL per well of AttoPhosrm fluorescence substrate (Roche, Ref. 11681982001) was added according to the manufacturer's specifications. Plates were analyzed after 10 min incubation using an excitation wavelength of 430 nm and an emission wavelength of 535 nm with an ELISA plate reader.

Expression in *E. coli* and Purification of Antibody Clones

Expression of Fab fragments was performed in *E. coli* TG1F⁻ cells. Cultures with 2×YT medium supplemented with 34 pg/mL Cam and 0.1% glucose were incubated at 30° C. until the $OD_{600}$ reached a value of 0.6. Fab expression was induced by addition of IPTG to a final concentration of 0.75 mM and cultures were further incubated overnight at 30° C. and 180 rpm. Cells were harvested and disrupted in 20 mL lysis buffer (25 mM Tris/pH 8, 500 mM NaCl, 2 mM $MgCl_2$, 10 U/μl Benzonase (Merck, Ref. 1.01654.0001), 0.1% Lysozyme (Roche, Ref. 10837059001), Protease inhibitor Compete without EDTA 1 tablet/50 mL of buffer (Roche, Ref. 11873580001)) for 1 h at RT on a rocking table. Lysates were clarified by centrifugation for 30 min at 15000 g.

Clarified supernatants were used for Fab-$His_6$ ("$His_6$" disclosed as SEQ ID NO: 128) purification by affinity chromatography and subsequent gel filtration using an AKTA device. Fab concentration in the final eluates was determined by UV-spectrophotometry. The purity of the samples was analyzed in denaturing, reducing 15% SDS-PAGE. The identity of the samples was confirmed by Mass Spectrometry.

Affinity Measurements: Octet (ForteBio) Kinetics Measurement

Affinity assessments were performed via Bio-Layer Interferometry technology. Anti-Human IgG Fc Capture (AHC) biosensors (Fortebio, Ref. 18-5060) were used to capture NOV1401. The assessment was initiated by placing the sensors in the wells containing 2 μg/mL NOV1401, then moved to the wells containing purified Fab fragments of IDT1B or IDT1C (HCDR2 affinity matured) or IDT1A (LCDR3 affinity matured) at a concentration of 25, 50, 100, 200, 400 nM. Buffer (Fortebio, Ref. 18-5032) alone was used for background (0 nM) determination. Fab association and dissociation were each recorded by measuring the change in layer thickness (in nanometers, nm) with time for 800 s each, all under computer control.

Data were processed and analyzed using the Octet User Software version 3.0. Compared to the parental antibody IDT1, the Fab fragments of IDT1B (HCDR2 affinity matured), IDT1C (HCDR2 affinity matured) and IDT1A (LCDR3 affinity matured) were demonstrated to have an improved off-rate. Octet measurements for parental antibody IDT1 are shown in FIG. 1A; Octet measurements for affinity matured Fab fragments IDT1B, IDT1C, and IDT1D are shown in FIG. 1B, FIG. 1C, and FIG. 1D, respectively. Affinity maturation of IDT1 by cassette replacement phage display generated three clones (IDT1A, IDT1B and IDT1C) with increased affinity to target NOV1401.

Example 2

Generation of Further Affinity Matured Versions of Anti-NOV1401 Antibody IDT1 Based on IDT1A, IDT1B and IDT1C Generation of Further High Affinity Anti-NOV1401 Fabs The three highest affinity Fabs IDT1A, IDT1B and IDT1C generated by affinity maturation pannings with either randomized HCDR2 or LCDR3 libraries of IDT1 were selected for further characterization and for cross-cloning to combine two individually improved CDRs (HCDR2 and LCDR3). The Fab IDT1C had the highest affinity among all clones from maturing pannings with both HCDR2 and LCDR3 libraries, and was further characterized below. A new Fab IDT1D was generated by combining the affinity-matured heavy chain (HCDR2 library) of IDT1C with the affinity-matured light chain (LCDR3 library) of IDT1A, and therefore is a cross-clone between two candidates from two maturation libraries. An additional new Fab IDT1E was generated by combining the affinity-matured heavy chain (HCDR2 library) of IDT1B with the affinity-matured light chain (LCDR3 library) of IDT1A, and therefore is a cross-clone between two candidates from two maturation libraries. Amino acid sequences for all five Fabs (IDT1A, IDT1B, IDT1C, IDT1D and IDT1E) can be found in the Table 2 and in the FIG. 2 and FIG. 3. FIG. 2 and FIG. 3 represent multiple sequence alignments of newly generated high affinity Fabs IDT1A, IDT1B, IDT1C, IDT1D, IDT1E and the first generation Fab IDT1.

Fab Expression and Purification

The nucleotide sequences including signal sequences for light chains and heavy chains of IDT1C, IDT1D and IDT1E Fabs were codon optimized for human expression, and gene synthesized as gBlocks gene fragments (Integrated DNA Technologies). The nucleotide sequences were cloned into mammalian expression vector pPL1146 (pcDNA3.1-modified), downstream of the CMV promoter, using HiFi DNA Assembly Master Mix (NEB, Cat. #E2621L).

Heavy and light chain vectors were co-transfected in 293 HEK cells. Cells were grown at 37° C., and after 72 h post-transfection, the conditioned medium was used for purification of the Fabs. Fabs were purified from conditioned cell culture media using kappa select affinity chromatography.

Fab concentrations were determined by UV/VIS absorbance at 280 nm using theoretical extinction coefficients and a Nano drop UV280 instrument. Purified Fabs were characterized by injecting 5 μg (typically 25 μL of 0.2 mg/ml samples) onto an analytical size exclusion column (Superdex200 5/150 GL). Fab purity was also analyzed by SDS- PAGE, and the molecular weight was confirmed by LC-MS/MS. Endotoxin level were measured using Limulus Amebocyte Lysate Assay standardized with U.S. Std. Endotoxin (Endosafe-PTS, product code PTS20F).

All Fabs were >95% pure, homogeneous and had less than 1% aggregates, as judged by SDS-PAGE and analytical size exclusion chromatography. Typical yields were 15-20 mg/L cell culture media. All Fabs had low endotoxin amounts (<0.5 EU/mg). FIG. 4 shows purification results for IDT1C.

$K_D$ Determination by SET 14 serial 2-fold dilutions of NOV1401 (from 0.1 pM to 1 nM) were prepared in assay buffer (DPBS (Life Technologies) containing 0.5% BSA and 0.02% Tween-20), and a constant concentration of anti-NOV1401 Fab was added (10 pM, 20 pM or 40 pM). A volume of 60 μl/well of each NOV1401-anti-NOV1401 mix was dispensed in triplicates to a 384-well polypropylene microtiter plate (polypropylene MTP: Greiner, Cat. #781280). Assay buffer served as a negative control and a sample containing only anti-NOV1401 served as a positive control (Bmax). The plate was sealed and incubated overnight (o/n, at least 20 h) at room temperature (RT) on a shaker. A 384-well streptavidin (SA) plate from Life Technologies (Cat. #15505) was coated with 30 μl/well of Biotin-NOV1401 diluted in assay buffer for 2 h at RT on a shaker, then washed three times with wash buffer (PBS containing 0.05% Tween 20). After that 30 μl/well of the equilibrated NOV1401-anti-NOV1401 mix was transferred from the polypropylene MTP (Greiner) to the coated SA plate and incubated for 30 min at RT on a shaker. After an additional wash step, 30 μl/well anti-human Kappa LC-HRP detection antibody (BETHYL, Cat. #A80-115P; 0.05 μg/ml diluted in assay buffer) was added to each well and incubated for 60 min at RT on a shaker. The SA plate was washed, and 30 μl/well LumiGLO read buffer (KPL, Cat. #54-61-01; LumiGLO Peroxidase Chemiluminescent Substrate) was added and incubated for 1 min at RT. RLU signal was measured by the SPECTRAMAXM5 (Molecular Devices, Sunnyvale, California USA).

All measurements were performed as triplicates and average RLU signals were calculated. Data were baseline-adjusted by subtracting the value for the lowest concentration from all data points and plotted against the corresponding NOV1401 concentration. The KD was determined by non-linear curve fitting using a 1:1 fit model as shown in Equation (according to Haenel et al., 2005, Anal Biochem. 339(1):182-4):

$$y = B_{max} - \left(\frac{B_{max}}{2[Fab]}\left([Fab] + x + K_D - \sqrt{([Fab] + x + K_D)^2 - 4x[Fab]}\right)\right)$$

where y is the blank-subtracted RLU signal, [Fab] is the applied Fab concentration, x is the applied total antigen concentration, $B_{max}$ is maximal signal without antigen, and $K_D$ is the dissociation constant.

Figure 5A:
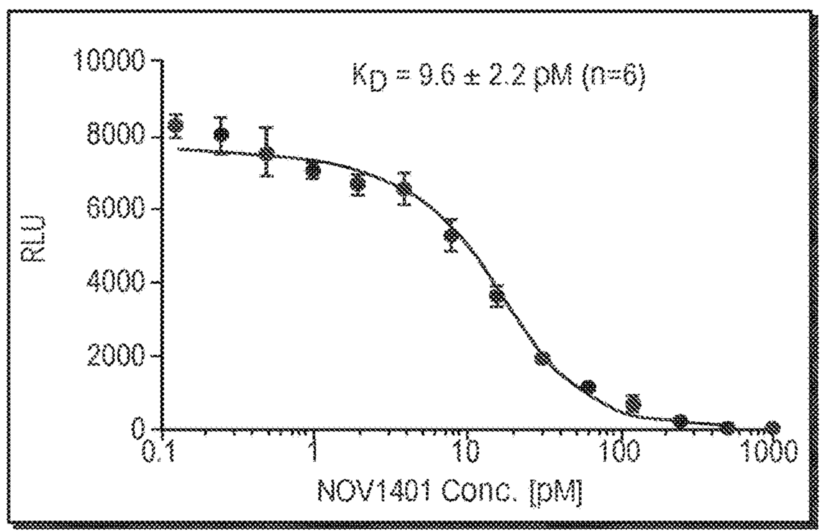
FIG. 5A-FIG. 5C show representative binding curves from SET experiments for each of the anti-NOV1401 antibodies IDT1C (FIG. 5A), IDT1E (FIG. 5B) and IDT1D (FIG. 5C) to NOV1401. $K_D$ values were determined from non-linear curve fitting the experimental data to a 1:1 fit model for Fabs as described in the Examples. Average $K_D$ values from three individual experiments are shown.
Figure 5B:
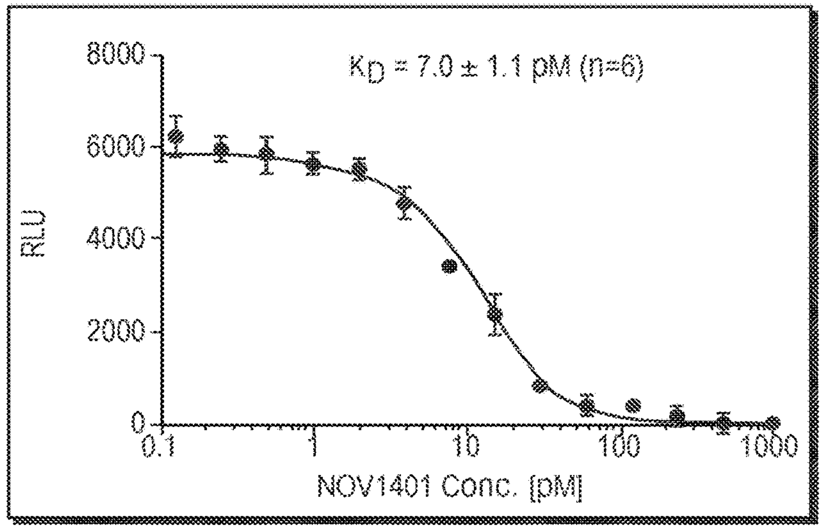
Figure 5C:
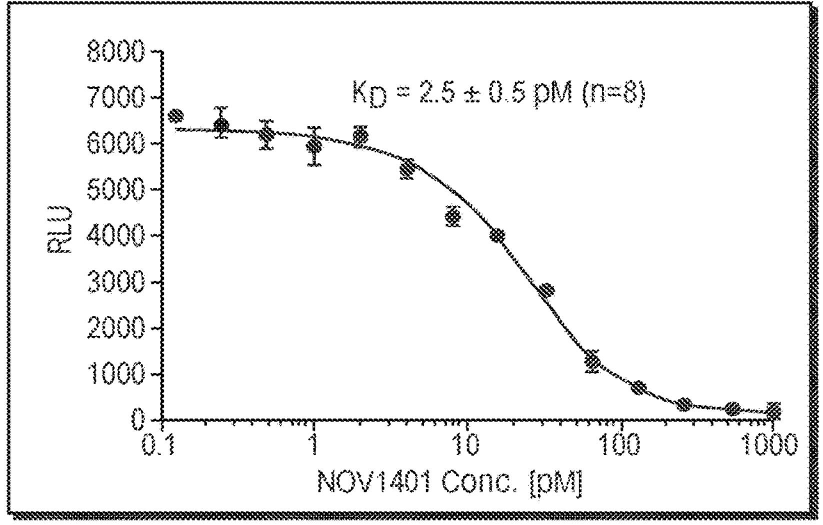

$K_D$ and $B_{max}$ were set as variables to be fitted by GraphPad Prism 7.03. $K_D$ values of 9.6, 7, and 2.5 pM were determined for IDT1C, IDT1E, and IDT1D, respectively (Table 3). Representative SET binding curves are shown in FIG. 5A-FIG. 5C: FIG. 5A shows SET binding for IDT1C, FIG. 5B shows SET binding for IDT1E, and FIG. 5C shows SET binding for IDT1D. In comparison, $K_D$ values of the first generation anti-NOV1401 Fabs IDT1 and IDT3 (described in WO 2017/203450) were determined to be 110 pM and 100 pM, respectively.

TABLE 3

Summary of SET results for anti-NOV1401 antibodies

| Antidote | Average $K_D$ (pM) | Stdev | n |
|---|---|---|---|
| IDT1 | 110 | 0.01 | 2 |
| IDT3 | 100 | 0.01 | 2 |
| IDT1C | 9.6 | 2.2 | 6 |
| IDT1D | 7 | 1.1 | 6 |
| IDT1E | 2.5 | 0.5 | 8 |

$K_D$ Determination by Surface Plasmon Resonance (SPR)

SPR binding experiments were performed on a ProteOn XPR36 instrument (Bio-Rad Laboratories, Inc.) in PBS/T buffer (50 mM phosphate, 150 mM NaCl, pH 7.4, 0.05% v/v Tween-20) at 25° C. NOV1401 ('Ligand') was immobilized onto an activated ProteOn GLC sensor chip (Bio-Rad Laboratories, Inc.) using standard amine coupling procedures as described by the manufacturer. Briefly, NOV1401 was injected at a concentration of 10 μg/ml in 20 mM sodium acetate, pH 5.0 and at a flow rate of 30 μl/min for 10 min. Unreacted groups were blocked by injecting 1 M ethanolamine.

For kinetic studies anti-NOV1401 Fabs ('Analytes') were diluted in PBS/T buffer to generate a dilution series with concentrations ranging from 0.125-4 nM. Fabs were injected onto surfaces with immobilized NOV1401 at a flow rate of 100 μL/min and sensorgrams were recorded for association and dissociation times of 220 s and 1800 s, respectively. Blank surfaces were used for background corrections. There was no need to regenerate surfaces since the ProteOn protein interaction array system allows to run up to six binding experiments on an identical surface in parallel.

Data processing and analysis including $k_{on}$, $k_{off}$, and $K_D$ determination were performed with the ProteOn Manager™ software version 3.1.0.6. Sensorgrams were fitted by applying a Langmuir 1:1 binding model (Rmax set at global) and dissociation constants were calculated from $k_{on}$ and $k_{off}$.

Figure 6A:
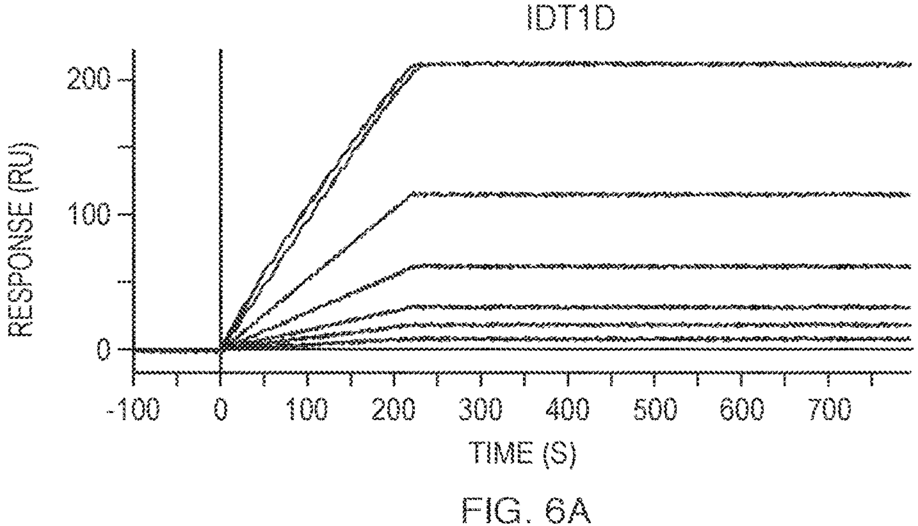
FIG. 6A-FIG. 6C show representative SPR response curves for binding of three anti-NOV1401 Fabs, IDT1D (FIG. 6A), IDT1E (FIG. 6B), and IDT1C (FIG. 6C), to immobilized NOV1401.
Figure 6B:
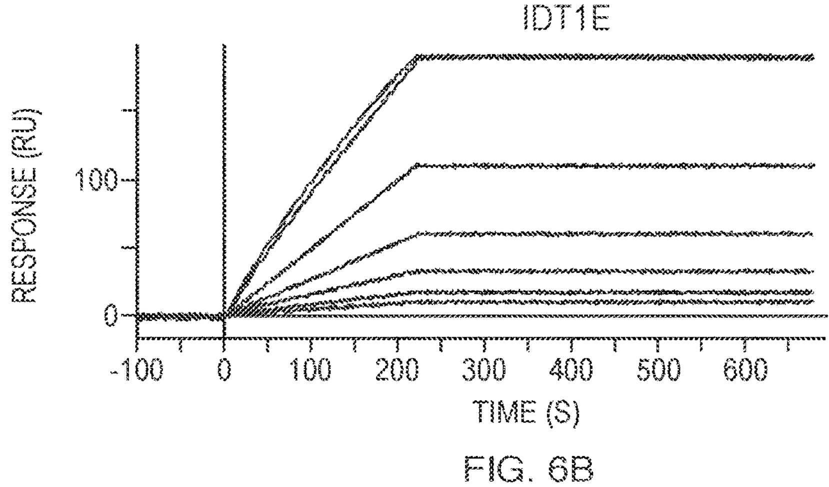
Figure 6C:
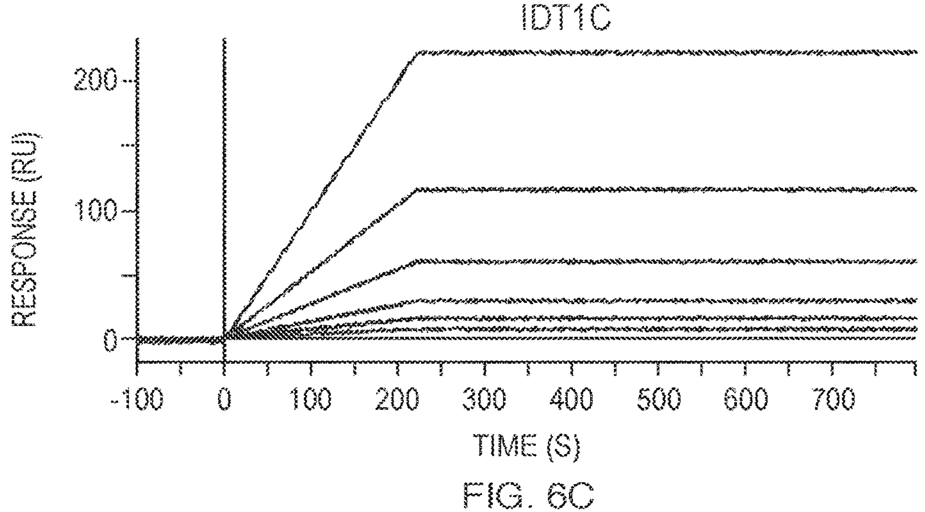

Affinity maturated anti-NOV1401 Fabs showed significantly higher affinity than parental Fab. Although $K_D$s for these high affinity Fabs could not be determined by SPR due to their too slow dissociation rates ($k_{off}$), the SPR data showed that the observed significant affinity improvements appear to be due to slower dissociation rates ($k_{off}$) since the association rates ($k_{on}$) did not change significantly. Table 4 shows the dissociation constants as determined by SPR. Representative SPR response curves are shown in FIG. 6A-FIG. 6C: FIG. 6A shows SPR response for IDT1D, FIG. 6B shows SPR response for IDT1E, and FIG. 6C shows SPR response for IDT1C.

TABLE 4

Summary of SPR results for anti-NOV1401 antibodies

| Antidote | $K_D$ (pM) | $k_{on}$ [1/Ms] | $k_{off}$ [1/s] |
|---|---|---|---|
| IDT1 | 440 | 5.5E+05 | 2.4E−04 |
| IDT3 | 240 | 3.8E+05 | 0.9E−04 |
| IDT1C | nd | 2.5E+05 | nd |
| IDT1D | nd | 4.4E+05 | nd |
| IDT1E | nd | 6.9E+05 | nd |

nd = not detectable due to technical limitation of SPR

Example 3

Reversal of the Anticoagulant Activity of NOV1401

Effects of anti-NOV1401 Fabs on the anticoagulant activity of NOV1401 were tested by using the activated partial thromboplastin time (aPTT) assay.

Competition Experiments with NOV1401 in an aPTT Assay

Lyophilized normal human plasma 'Coagulation Control N' (Cat #5020050), containing pooled citrated plasma samples from healthy donors was purchased from Technoclone GmbH (Vienna, Austria). Prior to its use, the plasma was re-suspended in 1 mL of distilled water. The measurements of the clotting time were performed in a ball coagulometer model MC10 (Merlin medical, Germany) utilizing a special cuvette with a stainless-steel ball (Merlin medical, Cat. #Z05100). The cuvette is placed into the measuring well of the ball coagulometer. After sample, plasma, and trigger are added to the cuvette, the measuring well rotates slowly causing the cuvette to rotate along its longitudinal axis. Because the cuvette is positioned at a slight angle, gravity and inertia always position the ball at the lowest point of the cuvette. Exactly opposite to the ball-position is a magnetic sensor. After an appropriate incubation period, the coagulation is initiated by adding calcium chloride solution, and the timer is started. As coagulation proceeds, fibrin forms strands that pull the ball away from its inertia position. This triggers an impulse in the magnetic sensor and electronically stops the timer.

All reagents were pre-warmed at 37° C. A 50 µl of human plasma was incubated in cuvette with 25 µl of PBS (Life Technologies, Cat #10010-023) or NOV1401 at 0.408 µM (8× the final concentration of 0.051 µM) at 37° C. for 5 minutes. After the FXI/NOV1401 complex was formed, 25 µl of PBS, control IgG, or anti-NOV1401 Fab at 3×, 9×, or 30× the concentration of NOV1401 was added and incubated at 37° C. for 10 minutes. Then, 50 µl of an aPTT trigger reagent (aPTT-s, SYCOmed, Germany, TE0350) was added and incubated for 3 minutes at 37° C. under rotation. Finally, 50 µl of 25 mM calcium chloride (Fluka, Cat #21115) was added with an automatic handystep pipette supplied with the Coagulometer, and this started the instrument timer. Coagulation time was recorded as the time when fibrin strands pulled the ball away, and the timer stopped.

In the aPTT reversal assay, NOV1401 was added to human plasma samples before anti-NOV1401 Fabs were added and coagulation was triggered. Since NOV1401 binds also the zymogen FXI with high affinity, any effect of the anti-NOV1401 Fabs is likely due to replacing FXI from the complex with NOV1401, and likely reflects a true reversal effect.

Figure 7:
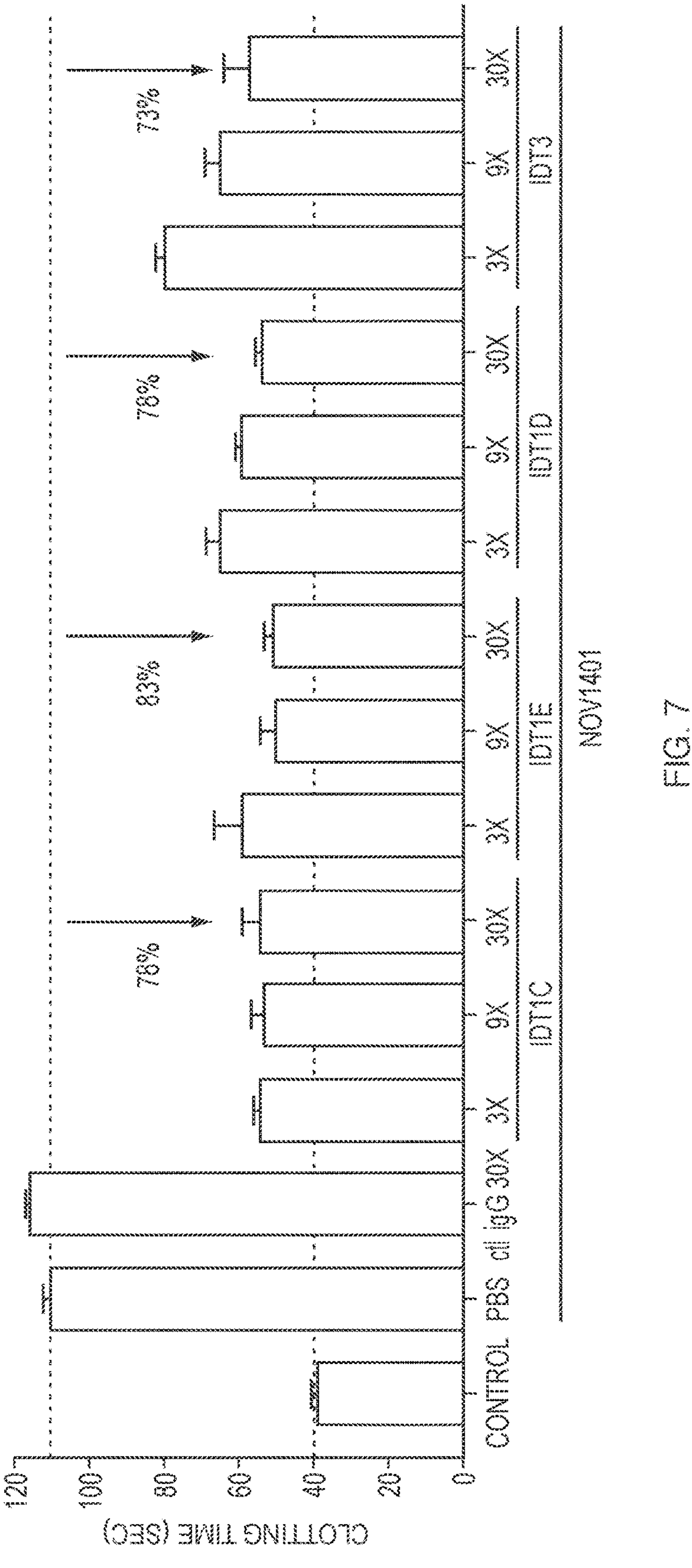
FIG. 7 shows human plasma aPTT assay results for anti-NOV1401 Fabs IDT3, IDT1C, IDT1D and IDT1E. Human plasma samples containing FXI were pre-incubated for 5 minutes with NOV1401 at 0.051 μM before anti-NOV1401 Fabs were added at 3, 9 or 30 times molar excess, and plasma coagulation was triggered after incubating for another 13 minutes. All tested anti-NOV1401 Fabs show a concentration-dependent partial reversal of the effects of NOV1401 on aPTT.

As shown in FIG. 7 and Table 5, all three tested anti-NOV1401 Fabs (IDT1C, IDT1D and IDT1E) reverse the anticoagulant activity of NOV1401 in the human plasma aPTT assay. A three times molar excess of Fab IDT1C versus NOV1401 seemed sufficient to achieve maximal reversal of approximately 80% (e.g., at least 79%), while at least a 30 times molar excess was required for the first generation anti-NOV1401 Fab IDT3 (described in WO 2017/203450) to achieve a maximal reversal effect of approximately 73%. Similarly, a three times molar excess of Fab IDT1E versus NOV1401 was sufficient to achieve maximal reversal of more than 70% (e.g., at least 72%), while at least a 30 times molar excess was required for Fab IDT3 to achieve a comparable maximal reversal effect of approximately 73%. The Fab 1DT1D also seemed to be more efficient in reversal of the anticoagulant activity of NOV1401 in comparison to the first generation Fab IDT3: a three times molar excess of Fab IDT1D versus NOV1401 was sufficient to achieve maximal reversal of more than 60% (e.g., at least 63%), while at least a 9 times molar excess was required for Fab IDT3 to achieve a comparable maximal reversal effect of approximately 64%. At about 30× molar excess of Fab to NOV1401, all three anti-NOV1401 Fabs, IDT1C, IDT1D, and IDT1E, achieved a higher maximal reversal effect (e.g., at least 78% and at least 83%) than the first generation anti-NOV1401 Fab IDT3 (maximal reversal effect of approximately 73%). These results indicate that the higher affinity anti-NOV1401 Fabs exhibited more potent reversal effects than a first generation anti-NOV1401 with lower binding affinity to NOV1401.

TABLE 5

Summary of aPTT reversal data for anti-NOV1401 antibodies

| anti-NOV1401 | NOV1401/anti-NOV1401 ratio (n/n) | | |
|---|---|---|---|
| Fab | 1/30 | 1/9 | 1/3 |
| IDT3 | 73% | 64% | 42% |
| IDT1C | 78% | 80% | 79% |
| IDT1D | 78% | 72% | 63% |
| IDT1E | 83% | 84% | 72% |

INCORPORATION BY REFERENCE

All references cited herein, including patents, patent applications, papers, publications, textbooks, and the like, and the references cited therein, to the extent that they are not already, are hereby incorporated herein by reference in their entirety.

EQUIVALENTS

The foregoing written specification is considered to be sufficient to enable one skilled in the art to practice the present disclosure. The foregoing description and examples detail certain preferred embodiments of the present disclosure and describe the best mode contemplated by the inventors. It will be appreciated, however, that no matter how detailed the foregoing may appear in text, the present disclosure may be practiced in many ways and the present disclosure should be construed in accordance with the appended claims and any equivalents thereof.

The invention claimed is:

1. An antibody or antigen-binding fragment thereof that specifically binds to an anti-FXI/FXIa antibody wherein the antibody or antigen-binding fragment comprises a heavy chain variable region (VH) comprising complementarity determining regions HCDR1, HCDR2, and HCDR3, and a light chain variable region (VL) comprising complementarity determining regions LCDR1, LCDR2, and LCDR3, wherein:

(a) the HCDR1 comprises an amino acid sequence selected from SEQ ID NO: 51, 54, 55 and 57, the HCDR2 comprises an amino acid sequence selected from SEQ ID NO: 121, 122, and 123, the HCDR3 comprises an amino acid sequence selected from SEQ ID NO: 53 and 59, the LCDR1 comprises an amino acid sequence selected from SEQ ID NO: 64, 67 and 70, the LCDR2 comprises an amino acid sequence selected from SEQ ID NO: 65 and 68, and the LCDR3 comprises an amino acid sequence selected from SEQ ID NO: 125 and 126;

(b) the HCDR1 comprises an amino acid sequence selected from SEQ ID NO: 51, 54, 55 and 57, the HCDR2 comprises an amino acid sequence selected from SEQ ID NO: 105, 106 and 107, the HCDR3 comprises an amino acid sequence selected from SEQ ID NO: 53 and 59, the LCDR1 comprises an amino acid sequence selected from SEQ ID NO: 64, 67 and 70, the LCDR2 comprises an amino acid sequence selected from SEQ ID NO: 65 and 68, and the LCDR3 comprises an amino acid sequence selected from SEQ ID NO: 66 and 69;

(c) the HCDR1 comprises an amino acid sequence selected from SEQ ID NO: 51, 54, 55 and 57, the HCDR2 comprises an amino acid sequence selected from SEQ ID NO: 75, 76 and 77, the HCDR3 comprises an amino acid sequence selected from SEQ ID NO: 53 and 59, the LCDR1 comprises an amino acid sequence selected from SEQ ID NO: 64, 67 and 70, the LCDR2 comprises an amino acid sequence selected from SEQ ID NO: 65 and 68, and the LCDR3 comprises an amino acid sequence selected from SEQ ID NO: 94 and 95;

(d) the HCDR1 comprises an amino acid sequence selected from SEQ ID NO: 51, 54, 55 and 57, the HCDR2 comprises an amino acid sequence selected from SEQ ID NO: 52, 56 and 58, the HCDR3 comprises an amino acid sequence selected from SEQ ID NO: 53 and 59, the LCDR1 comprises an amino acid sequence selected from SEQ ID NO: 64, 67 and 70, the LCDR2 comprises an amino acid sequence selected from SEQ ID NO: 65 and 68, and the LCDR3 comprises an amino acid sequence selected from SEQ ID NO: 94 and 95;

(e) the HCDR1 comprises an amino acid sequence selected from SEQ ID NO: 51, 54, 55 and 57, the HCDR2 comprises an amino acid sequence selected from SEQ ID NO: 105, 106 and 107, the HCDR3 comprises an amino acid sequence selected from SEQ ID NO: 53 and 59, the LCDR1 comprises an amino acid sequence selected from SEQ ID NO: 64, 67 and 70, the LCDR2 comprises an amino acid sequence selected from SEQ ID NO: 65 and 68, and the LCDR3 comprises an amino acid sequence selected from SEQ ID NO: 94 and 95; or (f) the HCDR1 comprises an amino acid sequence selected from SEQ ID NO: 51, 54, 55 and 57, the HCDR2 comprises an amino acid sequence selected from SEQ ID NO: 75, 76 and 77, the HCDR3 comprises an amino acid sequence selected from SEQ ID NO: 53 and 59, the LCDR1 comprises an amino acid sequence selected from SEQ ID NO: 64, 67 and 70, the LCDR2 comprises an amino acid sequence selected from SEQ ID NO: 65 and 68, and the LCDR3 comprises an amino acid sequence selected from SEQ ID NO: 66 and 69.

2. The antibody or antigen-binding fragment of claim 1, wherein:

(a) the HCDR1 comprises the amino acid sequence of SEQ ID NO: 51, the HCDR2 comprises the amino acid sequence of SEQ ID NO: 52 or 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94; or (b) the HCDR1 comprises the amino acid sequence of SEQ ID NO: 51, the HCDR2 comprises the amino acid sequence of SEQ ID NO: 75 or 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

3. The antibody or antigen-binding fragment of claim 2, wherein (a) the HCDR1 comprises the amino acid sequence of SEQ ID NO: 51, the HCDR2 comprises the amino acid sequence of SEQ ID NO: 52, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

(b) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

(c) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 94;

(d) the HCDR1 comprises the amino acid sequence of SEQ ID NO: 51, the HCDR2 comprises the amino acid sequence of SEQ ID NO: 75, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66: or (e) the HCDR1 comprises the amino acid sequence of SEQ ID NO: 51, the HCDR2 comprises the amino acid sequence of SEQ ID NO: 105, the HCDR3 comprises the amino acid sequence of SEQ ID NO: 53, the LCDR1 comprises the amino acid sequence of SEQ ID NO: 64, the LCDR2 comprises the amino acid sequence of SEQ ID NO: 65, and the LCDR3 comprises the amino acid sequence of SEQ ID NO: 66.

4. The antibody or antigen-binding fragment of claim 3, wherein:

(a) the HCDR1, HCDR2 and HCDR3 are as set forth in SEQ ID NOs: 51, 52 and 53, respectively, and the LCDR1, LCDR2, and LCDR3 are as set forth in SEQ ID NOs: 64, 65 and 94, respectively;

(b) the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 66, respectively;

(c) the HCDR1, HCDR2 and HCDR3 are as set forth in SEQ ID NOs: 51, 105 and 53, respectively, and the LCDR1, LCDR2, and LCDR3 are as set forth in SEQ ID NOS: 64, 65 and 66, respectively;

(d) the HCDR1, HCDR2 and HCDR3 are as set forth in SEQ ID NOs: 51, 75 and 53, respectively, and the LCDR1, LCDR2, and LCDR3 are as set forth in SEQ ID NOs: 64, 65 and 94, respectively; or (e) the HCDR1, HCDR2 and HCDR3 are as set forth in SEQ ID NOs: 51, 105 and 53, respectively, and the LCDR1, LCDR2, and LCDR3 are as set forth in SEQ ID NOS: 64, 65 and 94, respectively.

5. The antibody or antigen-binding fragment claim 3, wherein the antibody or antigen-binding fragment comprises a heavy chain variable region (VH) and a light chain variable region (VL), wherein:

(a) the VH comprises an amino acid sequence that is at least 90% identical to the amino acid sequence of SEQ ID NO: 124, and the VL comprises an amino acid sequence that is at least 90% identical to the amino acid sequence of SEQ ID NO: 127;

(b) the VH comprises an amino acid sequence that is at least 90% identical to the amino acid sequence of SEQ ID NO: 78 or 85, and the VL comprises an amino acid sequence that is at least 90% identical to the amino acid sequence of SEQ ID NO: 71;

(c) the VH comprises an amino acid sequence that is at least 90% identical to the amino acid sequence of SEQ ID NO: 90 or 60, and the VL comprises an amino acid sequence that is at least 90% identical to the amino acid sequence of SEQ ID NO: 96;

(d) the VH comprises an amino acid sequence that is at least 90% identical to the amino acid sequence of SEQ ID NO: 108 or 112 and the VL comprises an amino acid sequence that is at least 90% identical to the amino acid sequence of SEQ ID NO: 71;

(e) the VH comprises an amino acid sequence that is at least 90% identical to the amino acid sequence of SEQ ID NO: 112 and the VL comprises an amino acid sequence that is at least 90% identical to the amino acid sequence of SEQ ID NO: 96; or (f) the VH comprises an amino acid sequence that is at least 90% identical to the amino acid sequence of SEQ ID NO: 85 and the VL comprises an amino acid sequence that is at least 90% identical to the amino acid sequence of SEQ ID NO: 96.

6. The antibody or antigen-binding fragment of claim 1, wherein the antibody or antigen-binding fragment comprises a heavy chain variable region (VH) and a light chain variable region (VL), wherein:

(a) the VH comprises the amino acid sequence of SEQ ID NO: 124, and the VL comprises the amino acid sequence of SEQ ID NO: 127;

(b) the VH comprises the amino acid sequence of SEQ ID NO: 78 or 85, and the VL comprises the amino acid sequence of SEQ ID NO: 71;

(c) the VH comprises the amino acid sequence of SEQ ID NO: 90 or 60, and the VL comprises the amino acid sequence of SEQ ID NO: 96;

(d) the VH comprises the amino acid sequence of SEQ ID NO: 108 or 112, and the VL comprises the amino acid sequence of SEQ ID NO: 71;

(e) the VH comprises the amino acid sequence of SEQ ID NO: 112 and the VL comprises the amino acid sequence of SEQ ID NO: 96;

(f) the VH comprises the amino acid sequence of SEQ ID NO: 85 and the VL comprises the amino acid sequence of SEQ ID NO: 96;

(g) the VH comprises the amino acid sequence of SEQ ID NO: 116, and the VL comprises the amino acid sequence of SEQ ID NO: 103;

h) the VH comprises the amino acid sequence of SEQ ID NO: 116, and the VL comprises the amino acid sequence of SEQ ID NO: 73; or (i) the VH comprises the amino acid sequence of SEQ ID NO: 119, and the VL comprises the amino acid sequence of SEQ ID NO: 103.

7. The antibody or antigen-binding fragment of claim 1 wherein the antibody or antigen-binding fragment is in a format selected from Fab, Fab', F(ab')2, Fv, and scFv.

8. The antibody or antigen-binding fragment of claim 1, wherein the antibody is an IgG1, IgG2, IgG3 or IgG4 isotype antibody.

9. The antibody or antigen-binding fragment of claim 1, wherein the antibody is an isolated antibody.

10. The antibody or antigen-binding fragment of claim 1, wherein the antibody is a monoclonal human antibody.

11. A polynucleotide comprising one or more nucleotide sequences encoding the antibody or antigen-binding fragment of claim 1.

12. A vector comprising the polynucleotide of claim 11.

13. A host cell comprising the polynucleotide of claim 11.

14. A method of producing a binding agent or an antibody, wherein said method comprises culturing the host cell of claim 13 under suitable conditions for expression of the binding agent or a portion thereof or the antibody, wherein the method optionally comprises purifying the binding agent or the antibody.

15. A pharmaceutical composition comprising the antibody or antigen-binding fragment of claim 1.

16. A method for reversing the anticoagulant effect of an anti-FXI/FXIa antibody in a patient being treated with the anti-FXI/FXIa antibody comprising administering an effective amount of the antibody or antigen-binding fragment of claim 1 to the patient in need thereof.

17. The method of claim 16, wherein the anti-FXI/FXIa antibody comprises (i) a heavy chain variable region (VH) comprising the amino acid sequence of SEQ ID NO: 3 and a light chain variable region (VL) comprising the amino acid sequence of SEQ ID NO: 7; or (ii) a heavy chain comprising the amino acid sequence of SEQ ID NO: 5 and a light chain comprising the amino acid sequence of SEQ ID NO: 9.

18. The method of claim 16, wherein the patient has or is at risk of developing thrombosis.

19. The method of claim 16, wherein the patient has (a) atrial fibrillation;

(b) suspected or confirmed cardiac arrhythmia comprising paroxysmal, persistent or permanent atrial fibrillation or atrial flutter;

(c) Chronic Thromboembolic Pulmonary Hypertension (CTEPH);

(d) valvular heart disease with or without atrial fibrillation;

(e) pulmonary hypertension;

(f) congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intravascular coagulation, paroxysmal nocturnal hemoglobinuria and heparin induced thrombocytopenia; or (g) chronic kidney disease.

* * * * *

SEQUENCE LISTING

```
<160> NUMBER OF SEQ ID NOS: 128

<210> SEQ ID NO 1
<211> LENGTH: 625
<212> TYPE: PRT
```

<213> ORGANISM: Homo sapiens

<400> SEQUENCE: 1

```
Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Ser Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Gly Ile Ser Gly
        355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400
```

```
Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
    450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
        515                 520                 525

Gln Asn Thr Leu Gln Lys Ala Lys Ile Pro Leu Val Thr Asn Glu Glu
    530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
    610                 615                 620

Val
625


<210> SEQ ID NO 2
<211> LENGTH: 3278
<212> TYPE: DNA
<213> ORGANISM: Homo sapiens

<400> SEQUENCE: 2

aggcacacag gcaaaatcaa gttctacatc tgtccctgtg tatgtcactt gtttgaatac     60

gaaataaaat taaaaaaata aattcagtgt attgagaaag caagcaattc tctcaaggta    120

tatttctgac atactaagat tttaacgact ttcacaaata tgctgtactg agagagaatg    180

ttacataaca ttgagaacta gtacaagtaa atattaaagt gaagtgacca tttcctacac    240

aagctcattc agaggaggat gaagaccatt ttggaggaag aaaagcaccc ttattaagaa    300

ttgcagcaag taagccaaca aggtcttttc aggatgattt tcttatatca agtggtacat    360

ttcattttat ttacttcagt ttctggtgaa tgtgtgactc agttgttgaa ggacacctgc    420

tttgaaggag gggacattac tacggtcttc acaccaagcg ccaagtactg ccaggtagtc    480

tgcacttacc acccaagatg tttactcttc actttcacgg cggaatcacc atctgaggat    540

cccacccgat ggtttacttg tgtcctgaaa gacagtgtta cagaaacact gccaagagtg    600

aataggacag cagcgatttc tgggtattct ttcaagcaat gctcacacca aataagcgct    660

tgcaacaaag acatttatgt ggacctagac atgaagggca taaactataa cagctcagtt    720

gccaagagtg ctcaagaatg ccaagaaaga tgcacggatg acgtccactg ccactttttc    780
```

```
acgtacgcca caaggcagtt tcccagcctg gagcatcgta acatttgtct actgaagcac    840
acccaaacag ggacaccaac cagaataacg aagctcgata aagtggtgtc tggattttca    900
ctgaaatcct gtgcactttc taatctggct tgtattaggg acattttccc taatacggtg    960
tttgcagaca gcaacatcga cagtgtcatg gctcccgatg cttttgtctg tggccgaatc   1020
tgcactcatc atcccggttg cttgtttttt accttctttt cccaggaatg gcccaaagaa   1080
tctcaaagaa atctttgtct ccttaaaaca tctgagagtg gattgcccag tacacgcatt   1140
aaaaagagca aagctctttc tggtttcagt ctacaaagct gcaggcacag catcccagtg   1200
ttctgccatt cttcatttta ccatgacact gatttcttgg gagaagaact ggatattgtt   1260
gctgcaaaaa gtcacgaggc ctgccagaaa ctgtgcacca atgccgtccg ctgccagttt   1320
tttacctata ccccagccca agcatcctgc aacgaaggga agggcaagtg ttacttaaag   1380
ctttcttcaa acggatctcc aactaaaata cttcacggga gaggaggcat ctctggatac   1440
acattaaggt tgtgtaaaat ggataatgag tgtaccacca aaatcaagcc caggatcgtt   1500
ggaggaactg cgtctgttcg tggtgagtgg ccgtggcagg tgaccctgca cacaacctca   1560
cccactcaga gacacctgtg tggaggctcc atcattggaa accagtggat attaacagcc   1620
gctcactgtt tctatggggt agagtcacct aagattttgc gtgtctacag tggcatttta   1680
aatcaatctg aaataaaaga ggacacatct ttctttgggg ttcaagaaat aataatccat   1740
gatcagtata aaatggcaga aagcgggtat gatattgcct tgttgaaact ggaaaccaca   1800
gtgaattaca cagattctca acgacccata tgcctgcctt ccaaaggaga tagaaatgta   1860
atatacactg attgctgggt gactggatgg gggtacagaa aactaagaga caaaatacaa   1920
aatactctcc agaaagccaa gataccctta gtgaccaacg aagagtgcca gaagagatac   1980
agaggacata aaataaccca taagatgatc tgtgccggct acagggaagg agggaaggac   2040
gcttgcaagg gagattcggg aggccctctg tcctgcaaac acaatgaggt ctggcatctg   2100
gtaggcatca cgagctgggg cgaaggctgt gctcaaaggg agcggccagg tgtttacacc   2160
aacgtggtcg agtacgtgga ctggattctg gagaaaactc aagcagtgtg aatgggttcc   2220
caggggccat tggagtccct gaaggaccca ggatttgctg ggagagggtg ttgagttcac   2280
tgtgccagca tgcttcctcc acagtaacac gctgaagggg cttggtgttt gtaagaaaat   2340
gctagaagaa aacaaactgt cacaagttgt tatgtccaaa actcccgttc tatgatcgtt   2400
gtagtttgtt tgagcattca gtctctttgt ttttgatcac gcttctatgg agtccaagaa   2460
ttaccataag gcaatatttc tgaagattac tatataggca gatatagcag aaaataacca   2520
agtagtggca gtggggatca ggcagaagaa ctggtaaaag aagccaccat aaatagattt   2580
gttcgatgaa agatgaaaac tggaagaaag gagaacaaag acagtcttca ccattttgca   2640
ggaatctaca ctctgcctat gtgaacacat ttcttttgta aagaaagaaa ttgattgcat   2700
ttaatggcag attttcagaa tagtcaggaa ttcttgtcat ttccatttta aaatatatat   2760
taaaaaaaat cagttcgagt agacacgagc taagagtgaa tgtgaagata acagaatttc   2820
tgtgtggaag aggattacaa gcagcaattt acctggaagt gataccttag ggcaatcttt   2880
gaagatacac tttcctgaaa aatgatttgt gatggattgt atatttattt aaaatatctt   2940
gggaggggag gctgatggag atagggagca tgctcaaacc tccctaagac aagctgctgc   3000
tgtgactatg ggctcccaaa gagctagatc gtatatttat ttgacaaaaa tcaccataga   3060
ctgcatccat actacagaga aaaaacaatt agggcgcaaa tggatagtta cagtaaagtc   3120
ttcagcaagc agctgcctgt attctaagca ctgggatttt ctgtttcgtg caaatattta   3180
```

```
tctcattatt gttgtgatct agttcaataa cctagaattt gaattgtcac cacatagctt   3240

tcaatctgtg ccaacaacta tacaattcat caagtgtg                           3278


<210> SEQ ID NO 3
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120


<210> SEQ ID NO 4
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

caggtgcagc tgctggaatc aggcggcgga ctggtgcagc ctggcggtag cctgagactg     60

agctgcgctg ctagtggctt cacctttagc accgccgcta tgagctgggt tcgacaggcc    120

ccagggaaag gcctcgagtg ggtctcaggg attagcggta gcggctctag cacctactac    180

gccgatagcg tgaagggccg gttcactatc tctagggata actctaagaa caccctgtac    240

ctgcagatga atagcctgag agccgaggac accgccgtct actactgcgc tagagagctg    300

agctacctgt atagcggcta ctacttcgac tactggggtc aaggcaccct ggtcaccgtg    360

tctagc                                                               366


<210> SEQ ID NO 5
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5
```

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
```

```
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 6
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

caggtgcagc tgctggaatc aggcggcgga ctggtgcagc ctggcggtag cctgagactg     60

agctgcgctg ctagtggctt cacctttagc accgccgcta tgagctgggt tcgacaggcc    120

ccagggaaag gcctcgagtg ggtctcaggg attagcggta gcggctctag cacctactac    180

gccgatagcg tgaagggccg gttcactatc tctagggata actctaagaa caccctgtac    240

ctgcagatga atagcctgag agccgaggac accgccgtct actactgcgc tagagagctg    300

agctacctgt atagcggcta ctacttcgac tactggggtc aaggcaccct ggtcaccgtg    360

tctagcgcta gcactaaggg cccctccgtg ttccctctgg ccccttccag caagtctacc    420

tccggcggca cagctgctct gggctgcctg gtcaaggact acttccctga gcctgtgaca    480

gtgtcctgga actctggcgc cctgacctct ggcgtgcaca ccttccctgc cgtgctgcag    540

tcctccggcc tgtactccct gtcctccgtg gtcacagtgc cttcaagcag cctgggcacc    600

cagacctata tctgcaacgt gaaccacaag ccttccaaca ccaaggtgga caagcgggtg    660

gagcctaagt cctgcgacaa gacccacacc tgtcctccct gccctgctcc tgaactgctg    720

ggcggccctt ctgtgttcct gttccctcca aagcccaagg acaccctgat gatctcccgg    780

acccctgaag tgacctgcgt ggtggtggcc gtgtcccacg aggatcctga agtgaagttc    840

aattggtacg tggacggcgt ggaggtgcac aacgccaaga ccaagcctcg ggaggaacag    900

tacaactcca cctaccgggt ggtgtccgtg ctgaccgtgc tgcaccagga ctggctgaac    960

ggcaaagagt acaagtgcaa agtctccaac aaggccctgg ccgcccctat cgaaaagaca   1020

atctccaagg ccaagggcca gcctagggaa ccccaggtgt acaccctgcc acccagccgg   1080

gaggaaatga ccaagaacca ggtgtccctg acctgtctgg tcaagggctt ctacccttcc   1140

gatatcgccg tggagtggga gtctaacggc cagcctgaga acaactacaa gaccacccct   1200

cctgtgctgg actccgacgg ctccttcttc ctgtactcca aactgaccgt ggacaagtcc   1260

cggtggcagc agggcaacgt gttctcctgc tccgtgatgc acgaggccct gcacaaccac   1320

tacacccaga agtccctgtc cctgtctccc ggcaag                              1356


<210> SEQ ID NO 7
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Ser Val Leu Thr Gln Pro Pro Ser Ala Ser Gly Thr Pro Gly Gln
```

```
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110


<210> SEQ ID NO 8
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8

cagtcagtcc tgactcagcc ccctagcgct agtggcaccc ctggtcaaag agtgactatt      60

agctgtagcg gctctagctc taatatcggc tctaacgacg tcagctggta tcagcagctg     120

cccggcaccg cccctaagct gctgatctat aagaactata ataggcctag cggcgtgccc     180

gataggttta gcggatctaa atcagggact tctgctagtc tggctattag cggcctgcag     240

tcagaggacg aggccgacta ctactgtagc gcctgggatc agcgtcagtt cgacgtggtg     300

ttcggcggag gcactaagct gaccgtgctg                                      330


<210> SEQ ID NO 9
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125
```

```
Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 10
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
cagtcagtcc tgactcagcc ccctagcgct agtggcaccc ctggtcaaag agtgactatt     60

agctgtagcg gctctagctc taatatcggc tctaacgacg tcagctggta tcagcagctg    120

cccggcaccg cccctaagct gctgatctat aagaactata ataggcctag cggcgtgccc    180

gataggttta gcggatctaa atcagggact tctgctagtc tggctattag cggcctgcag    240

tcagaggacg aggccgacta ctactgtagc gcctgggatc agcgtcagtt cgacgtggtg    300

ttcggcggag gcactaagct gaccgtgctg ggtcaaccta aggctgcccc cagcgtgacc    360

ctgttccccc ccagcagcga ggagctgcag gccaacaagg ccaccctggt gtgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga aaagaccgtg gccccaaccg agtgcagc                 648
```

<210> SEQ ID NO 11
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120


<210> SEQ ID NO 12
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccggt atctctggtt ctggttcttc tacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctca                                                               366


<210> SEQ ID NO 13
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

```
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 14
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccggt atctctggtt ctggttcttc tacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360
```

```
agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

<210> SEQ ID NO 15
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

<210> SEQ ID NO 16
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta                                     330
```

<210> SEQ ID NO 17
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 18
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
gatatcgtgc tgacccagcc gccgagcgtg agcggtgcac cgggccagcg cgtgaccatt      60

agctgtagcg gcagcagcag caacattggt tctaacgacg tgtcttggta ccagcagctg     120

ccgggcacgg cgccgaaact gctgatctac aaaaactaca accgcccgag cggcgtgccg     180

gatcgcttta gcggatccaa aagcggcacc agcgccagcc tggcgattac cggcctgcaa     240

gcagaagacg aagcggatta ttactgctct gcttgggacc agcgtcagtt cgacgttgtg     300

tttggcggcg gcacgaagtt aaccgtccta ggtcagccca aggctgcccc ctcggtcact     360

ctgttcccgc cctcctctga ggagcttcaa gccaacaagg ccacactggt gtgtctcata     420

agtgacttct acccgggagc cgtgacagtg gcctggaagg cagatagcag ccccgtcaag     480

gcgggagtgg agaccaccac accctccaaa caaagcaaca acaagtacgc ggccagcagc     540

tatctgagcc tgacgcctga gcagtggaag tcccacagaa gctacagctg ccaggtcacg     600

catgaaggga gcaccgtgga gaagacagtg gcccctacag aatgttca                  648


<210> SEQ ID NO 19
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Asp Ser Trp Gly Asp Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120


<210> SEQ ID NO 20
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20

caggtgcaat tgctggaaag cggcggtggc ctggtgcagc cgggtggcag cctgcgtctg      60

agctgcgcgg cgtccggatt caccttttct actgctgcta tgtcttgggt gcgccaggcc     120

ccgggcaaag gtctcgagtg ggtttccact atcgactctt ggggcgacga cactgactat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaactg     300
```

```
tcttacctgt actctggtta ctacttcgat tactggggcc aaggcaccct ggtgactgtt    360

agctca                                                               366


<210> SEQ ID NO 21
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Asp Ser Trp Gly Asp Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 22
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccact atcgactctt ggggcgacga cactgactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260
```

```
aggtggcagc aggggaacgt cttctcatgc tccgtgatgc atgaggctct gcacaaccac   1320

tacacgcaga agagcctctc cctgtctccg ggtaaa                             1356
```

<210> SEQ ID NO 23
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

<210> SEQ ID NO 24
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta                                     330
```

<210> SEQ ID NO 25
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30
```

```
Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 26
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta ggtcagccca aggctgcccc ctcggtcact    360

ctgttcccgc cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tatctgagcc tgacgcctga gcagtggaag tcccacagaa gctacagctg ccaggtcacg    600

catgaaggga gcaccgtgga gaagacagtg gcccctacag aatgttca                648
```

<210> SEQ ID NO 27
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Ser Ile Glu Tyr Tyr Asp Thr Asp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120
```

<210> SEQ ID NO 28
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttcctct atcgaatact acgacactga cactcattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctca                                                               366
```

<210> SEQ ID NO 29
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Ser Ile Glu Tyr Tyr Asp Thr Asp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 30
<211> LENGTH: 1356
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 30

```
caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttcctct atcgaatact acgacactga cactcattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

<210> SEQ ID NO 31
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

```
Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110


<210> SEQ ID NO 32
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

gatatcgtgc tgacccagcc gccgagcgtg agcggtgcac cgggccagcg cgtgaccatt      60

agctgtagcg gcagcagcag caacattggt tctaacgacg tgtcttggta ccagcagctg     120

ccgggcacgg cgccgaaact gctgatctac aaaaactaca accgcccgag cggcgtgccg     180

gatcgcttta gcggatccaa aagcggcacc agcgccagcc tggcgattac cggcctgcaa     240

gcagaagacg aagcggatta ttactgctct gcttgggacc agcgtcagtt cgacgttgtg     300

tttggcggcg gcacgaagtt aaccgtccta                                      330


<210> SEQ ID NO 33
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
```

```
        195                 200                 205

Thr Val Ala Pro Thr Glu Cys Ser
    210                 215


<210> SEQ ID NO 34
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta ggtcagccca aggctgcccc ctcggtcact    360

ctgttcccgc cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tatctgagcc tgacgcctga gcagtggaag tcccacagaa gctacagctg ccaggtcacg    600

catgaaggga gcaccgtgga gaagacagtg gcccctacag aatgttca                648


<210> SEQ ID NO 35
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120


<210> SEQ ID NO 36
<211> LENGTH: 366
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36
caggtgcaat tgctggaaag cggcggtggc ctggtgcagc cgggtggcag cctgcgtctg 60
agctgcgcgg cgtccggatt caccttttct actgctgcta tgtcttgggt gcgccaggcc 120
ccgggcaaag gtctcgagtg ggtttccact atcgaatact ctagccagga aacttactat 180
gcggatagcg tgaaaggccg ctttaccatc agccgcgata attcgaaaaa caccctgtat 240
ctgcaaatga acagcctgcg tgcggaagat acggccgtgt attattgcgc gcgtgaactg 300
tcttacctgt actctggtta ctacttcgat tactggggcc aaggcaccct ggtgactgtt 360
agctca 366

<210> SEQ ID NO 37
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 38
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

```
caggtgcaat tgctggaaag cggcggtggc ctggtgcagc cgggtggcag cctgcgtctg     60

agctgcgcgg cgtccggatt caccttttct actgctgcta tgtcttgggt gcgccaggcc    120

ccgggcaaag gtctcgagtg ggtttccact atcgaatact ctagccagga aacttactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaactg    300

tcttacctgt actctggtta ctacttcgat tactggggcc aaggcaccct ggtgactgtt    360

agctcagcct ccaccaaggg tccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaagcagcg    720

gggggaccgt cagtcttcct cttcccccca aaacccaagg acaccctcat gatctcccgg    780
```

```
acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgggt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

```
<210> SEQ ID NO 39
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

```
<210> SEQ ID NO 40
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta                                     330
```

<210> SEQ ID NO 41
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 42
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42

```
gatatcgtgc tgacccagcc gccgagcgtg agcggtgcac cgggccagcg cgtgaccatt     60

agctgtagcg gcagcagcag caacattggt tctaacgacg tgtcttggta ccagcagctg    120

ccgggcacgg cgccgaaact gctgatctac aaaaactaca accgcccgag cggcgtgccg    180

gatcgcttta gcggatccaa aagcggcacc agcgccagcc tggcgattac cggcctgcaa    240

gcagaagacg aagcggatta ttactgctct gcttgggacc agcgtcagtt cgacgttgtg    300

tttggcggcg gcacgaagtt aaccgtccta ggtcagccca aggctgcccc ctcggtcact    360

ctgttcccgc cctcctctga ggagcttcaa gccaacaagg ccacactggt gtgtctcata    420
```

```
agtgacttct acccgggagc cgtgacagtg gcctggaagg cagatagcag ccccgtcaag    480

gcgggagtgg agaccaccac accctccaaa caaagcaaca acaagtacgc ggccagcagc    540

tatctgagcc tgacgcctga gcagtggaag tcccacagaa gctacagctg ccaggtcacg    600

catgaaggga gcaccgtgga gaagacagtg gcccctacag aatgttca                 648


<210> SEQ ID NO 43
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120


<210> SEQ ID NO 44
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

caagtgcagc tgcttgaatc tggcggcgga ctggtgcagc ctggcggctc cctgagactg     60

tcttgcgccg cctccggctt caccttctcc accgccgcta tgtcctgggt ccgacaggct    120

cccggcaagg gcctggaatg ggtgtccacc attgagtact ccagccagga aacctactac    180

gccgactccg tgaagggccg gttcaccatc tcccgggaca actccaagaa caccctgtac    240

ctgcagatga actccctgcg ggccgaggac accgccgtgt actactgcgc cagagagctg    300

tcctacctgt actccggcta ctacttcgac tactggggcc agggcaccct ggtcaccgtg    360

tcctct                                                               366


<210> SEQ ID NO 45
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 45

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
```

```
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 46
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

caagtgcagc tgcttgaatc tggcggcgga ctggtgcagc ctggcggctc cctgagactg     60

tcttgcgccg cctccggctt caccttctcc accgccgcta tgtcctgggt ccgacaggct    120

cccggcaagg gcctggaatg ggtgtccacc attgagtact ccagccagga aacctactac    180

gccgactccg tgaagggccg gttcaccatc tcccgggaca actccaagaa caccctgtac    240

ctgcagatga actccctgcg ggccgaggac accgccgtgt actactgcgc cagagagctg    300

tcctacctgt actccggcta ctacttcgac tactggggcc agggcaccct ggtcaccgtg    360

tcctctgcta gcaccaaggg cccctccgtg ttccctctgg ccccttccag caagtctacc    420

tccggcggca cagctgctct gggctgcctg gtcaaggact acttccctga gcctgtgaca    480

gtgtcctgga actctggcgc cctgacctct ggcgtgcaca ccttccctgc cgtgctgcag    540

tcctccggcc tgtactccct gtcctccgtg gtcacagtgc cttcaagcag cctgggcacc    600

cagacctata tctgcaacgt gaaccacaag ccttccaaca ccaaggtgga caagcgggtg    660

gagcctaagt cctgcgacaa gacccacacc tgtcctccct gccctgctcc tgaagctgct    720

ggcggccctt ctgtgttcct gttccctcca aagcccaagg acaccctgat gatctcccgg    780

acccctgaag tgacctgcgt ggtggtggac gtgtcccacg aggatcctga agtgaagttc    840

aattggtacg tggacggcgt ggaggtgcac aacgccaaga ccaagcctcg ggaggaacag    900

tacaactcca cctaccgggt ggtgtccgtg ctgaccgtgc tgcaccagga ctggctgaac    960

ggcaaagagt acaagtgcaa agtctccaac aaggccctgc ctgcccctat cgaaaagaca   1020

atctccaagg ccaagggcca gcctagggaa ccccaggtgt acaccctgcc acccagccgg   1080

gaggaaatga ccaagaacca ggtgtccctg acctgtctgg tcaagggctt ctacccttcc   1140

gatatcgccg tggagtggga gtctaacggc cagcctgaga acaactacaa gaccacccct   1200

cctgtgctgg actccgacgg ctccttcttc ctgtactcca aactgaccgt ggacaagtcc   1260

cggtggcagc agggcaacgt gttctcctgc tccgtgatgc acgaggccct gcacaaccac   1320

tacacccaga agtccctgtc cctgtctccc ggcaag                             1356


<210> SEQ ID NO 47
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 47

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

<210> SEQ ID NO 48
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
cagagcgtgc tgacacagcc tccctccgtg tctggcgccc ctggccagag agtgaccatc     60

tcctgctccg gctcctcctc caacatcggc tccaacgacg tgtcctggta tcagcagctg    120

cccggcaccg cccctaagct gctgatctac aagaactaca accggccctc cggcgtgccc    180

gaccggttct ctggctccaa gtctggcacc tccgcctccc tggctatcac cggcctgcag    240

gctgaggacg aggccgacta ctactgctcc gcctgggacc agcggcagtt cgacgtggtg    300

ttcggcggag gcaccaagct gaccgtgctg                                     330
```

<210> SEQ ID NO 49
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110
```

```
Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 50
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

cagagcgtgc tgacacagcc tccctccgtg tctggcgccc ctggccagag agtgaccatc     60

tcctgctccg gctcctcctc caacatcggc tccaacgacg tgtcctggta tcagcagctg    120

cccggcaccg cccctaagct gctgatctac aagaactaca accggccctc cggcgtgccc    180

gaccggttct ctggctccaa gtctggcacc tccgcctccc tggctatcac cggcctgcag    240

gctgaggacg aggccgacta ctactgctcc gcctgggacc agcggcagtt cgacgtggtg    300

ttcggcggag gcaccaagct gaccgtgctg ggccagccta aggctgcccc cagcgtgacc    360

ctgttccccc ccagcagcga ggagctgcag gccaacaagg ccaccctggt gtgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga aaagaccgtg gccccaaccg agtgcagc                 648


<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gly Phe Thr Phe Ser Asp Tyr Ala Met Ser
1               5                   10


<210> SEQ ID NO 52
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"

<400> SEQUENCE: 52

Val Ile Asp Tyr Ser Ser Ser Asn Thr Tyr Tyr Ala Asp Ser Val Lys
1               5                   10                  15

Gly


<210> SEQ ID NO 53
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Glu Gly Tyr Ser Tyr Arg Ser Ile Arg Phe Asp Tyr
1               5                   10


<210> SEQ ID NO 54
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asp Tyr Ala Met Ser
1               5


<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Phe Thr Phe Ser Asp Tyr
1               5


<210> SEQ ID NO 56
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Asp Tyr Ser Ser Ser Asn
1               5


<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 57

Gly Phe Thr Phe Ser Asp Tyr Ala
1 5

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

Ile Asp Tyr Ser Ser Ser Asn Thr
1 5

<210> SEQ ID NO 59
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Ala Arg Glu Gly Tyr Ser Tyr Arg Ser Ile Arg Phe Asp Tyr
1 5 10

<210> SEQ ID NO 60
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Met Ser Trp Val Arg Gln Ala Pro Gly Lys Gly Leu Glu Trp Val
35 40 45

Ser Val Ile Asp Tyr Ser Ser Ser Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Glu Gly Tyr Ser Tyr Arg Ser Ile Arg Phe Asp Tyr Trp Gly
100 105 110

Gln Gly Thr Leu Val Thr Val Ser Ser
115 120

<210> SEQ ID NO 61
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 61

```
caagtgcagc tgctggaatc tggcggcgga ctggtgcagc ctggcggtag tctgagactg     60

tcttgcgccg cctccggctt caccttctcc gactacgcca tgtcctgggt ccgacaggcc    120

cctggcaagg gcctggagtg ggtgtccgtg atcgactact cctcctccaa cacctactac    180

gccgactccg tgaagggccg gttcaccatc tcccgggaca actccaagaa caccctgtac    240

ctgcagatga actccctgcg ggccgaggac accgccgtgt actactgcgc cagagagggc    300

tactcctacc ggtccatcag attcgactac tggggccagg gcaccctggt caccgtgtcc    360

tct                                                                  363
```

<210> SEQ ID NO 62
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Asp Tyr Ser Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

<210> SEQ ID NO 63
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
caagtgcagc tgctggaatc tggcggcgga ctggtgcagc ctggcggtag tctgagactg     60
tcttgcgccg cctccggctt caccttctcc gactacgcca tgtcctgggt ccgacaggcc    120
cctggcaagg gcctggagtg ggtgtccgtg atcgactact cctcctccaa cacctactac    180
gccgactccg tgaagggccg gttcaccatc tcccgggaca actccaagaa caccctgtac    240
ctgcagatga actccctgcg ggccgaggac accgccgtgt actactgcgc cagagagggc    300
tactcctacc ggtccatcag attcgactac tggggccagg gcaccctggt caccgtgtcc    360
tctgctagca ccaagggccc ctccgtgttc cctctggccc cttccagcaa gtctacctct    420
ggcggcaccg ctgctctggg ctgcctggtg aaggactact tccctgagcc tgtgacagtg    480
tcctggaact ctggcgccct gacctccggc gtgcacacct tccctgccgt gctgcagtcc    540
tccggcctgt actccctgtc ctccgtggtg acagtgcctt cctccagcct gggcacccag    600
acctatatct gcaacgtgaa ccacaagcct tccaacacca aggtggacaa gcgggtggag    660
cctaagtcat gc                                                        672
```

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

```
Arg Ala Ser Gln Ser Ile Ser Ser Asn Leu Asn
1               5                   10
```

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

```
Ala Ala Ser Asn Leu Gln Ser
1               5
```

<210> SEQ ID NO 66
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

```
Leu Gln Phe Asp His Thr Pro Phe Thr
1               5
```

<210> SEQ ID NO 67
<211> LENGTH: 7
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 67

Ser Gln Ser Ile Ser Ser Asn
1               5


<210> SEQ ID NO 68
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Ala Ser
1


<210> SEQ ID NO 69
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Phe Asp His Thr Pro Phe
1               5


<210> SEQ ID NO 70
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gln Ser Ile Ser Ser Asn
1               5


<210> SEQ ID NO 71
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp His Thr Pro Phe
                85                  90                  95

Thr Phe Gly Gln Gly Thr Lys Val Glu Ile Lys
            100                 105


<210> SEQ ID NO 72
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72

gacatccaga tgacccagag cccctccagc ctgtccgcct ccgtgggcga cagagtgacc      60

atcacctgtc gggcctccca gtccatctcc tccaacctga actggtatca gcagaagccc     120

ggcaaggccc ctaagctgct gatctacgcc gccagcaacc tgcagtccgg cgtgccctcc     180

agattctccg gctctggctc cggcaccgac ttcaccctga ccatctccag cctgcagccc     240

gaggacttcg ccacctacta ctgcctgcag ttcgaccaca ccccttcac cttcggccag     300

ggcaccaaag tggaaatcaa g                                               321


<210> SEQ ID NO 73
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp His Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 74
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74

gacatccaga tgacccagag cccctccagc ctgtccgcct ccgtgggcga cagagtgacc     60

atcacctgtc gggcctccca gtccatctcc tccaacctga actggtatca gcagaagccc    120

ggcaaggccc ctaagctgct gatctacgcc gccagcaacc tgcagtccgg cgtgccctcc    180

agattctccg gctctggctc cggcaccgac ttcaccctga ccatctccag cctgcagccc    240

gaggacttcg ccacctacta ctgcctgcag ttcgaccaca cccctttcac cttcggccag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642


<210> SEQ ID NO 75
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Thr Ile Ser Tyr Leu Gly Gln Glu Lys His Tyr Ala Asp Ser Val Lys
1               5                   10                  15

Gly


<210> SEQ ID NO 76
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Ser Tyr Leu Gly Gln Glu
1               5


<210> SEQ ID NO 77
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 77

Ile Ser Tyr Leu Gly Gln Glu Lys
1               5


<210> SEQ ID NO 78
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Tyr Leu Gly Gln Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120


<210> SEQ ID NO 79
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79

gaagtgcaat tgctggaaag cggcggtggc ctggtgcagc cgggtggcag cctgcgtctg      60

agctgcgcgg cgtccggatt caccttttct gactacgcta tgtcttgggt gcgccaggcc     120

ccgggcaaag gtctcgagtg ggtttccact atctcttacc tgggccagga aaaacattat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaaggt     300

tactcttacc gttctatccg tttcgattac tggggccaag gcaccctggt gactgttagc     360

tca                                                                   363


<210> SEQ ID NO 80
<211> LENGTH: 242
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 80

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Tyr Leu Gly Gln Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Asp Tyr Lys Asp Asp Asp Asp Lys Gly Ala Pro His His His His
225                 230                 235                 240

His His
```

<210> SEQ ID NO 81
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
gaagtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccact atctcttacc tgggccagga aaaacattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tcagcgtcga ccaaaggccc gagcgtgttt ccgctggccc cgagcagcaa aagcaccagc    420

ggcggcaccg ccgcactggg ctgcctggtg aaagattatt tcccggaacc agtgaccgtg    480
```

```
agctggaaca gcggtgccct gaccagcggc gtgcatacct ttccggcggt gctgcaaagc    540

agcggcctgt atagcctgag cagcgttgtg accgtgccga gcagcagcct gggcacccag    600

acctatattt gcaacgtcaa ccataaaccg agcaacacca aagtcgataa aaaagtcgaa    660

ccgaaaagcg aattcgacta taaagatgac gatgacaaag gcgcgccgca ccatcatcac    720

catcac                                                               726


<210> SEQ ID NO 82
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82

gatatccaga tgacccagag cccgagcagc ctgagcgcca gcgtgggcga tcgcgtgacc     60

attacctgca gagccagcca gtctatttct tctaacctga actggtacca gcagaaaccg    120

ggcaaagcgc cgaaactatt aatctacgct gcttctaacc tgcaaagcgg cgtgccgagc    180

cgctttagcg gcagcggatc cggcaccgat ttcaccctga ccattagctc tctgcaaccg    240

gaagactttg cgacctatta ttgcctgcag ttcgaccata ctccgttcac ctttggccag    300

ggcacgaaag ttgaaattaa a                                              321


<210> SEQ ID NO 83
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp His Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210


<210> SEQ ID NO 84
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

gatatccaga tgacccagag cccgagcagc ctgagcgcca gcgtgggcga tcgcgtgacc     60

attacctgca gagccagcca gtctatttct tctaacctga actggtacca gcagaaaccg    120

ggcaaagcgc cgaaactatt aatctacgct gcttctaacc tgcaaagcgg cgtgccgagc    180

cgctttagcg gcagcggatc cggcaccgat ttcaccctga ccattagctc tctgcaaccg    240

gaagactttg cgacctatta ttgcctgcag ttcgaccata ctccgttcac ctttggccag    300

ggcacgaaag ttgaaattaa acgtacggtg gccgcaccga gcgtgtttat ctttccgccg    360

agcgatgaac agctgaaaag cggcaccgcc agcgtggtgt gcctgctgaa caacttttat    420

ccgcgcgaag ccaaagtgca gtggaaagtg gataacgccc tgcaaagcgg caacagccag    480

gaaagcgtta ccgaacagga tagcaaagat agcacctaca gcctgagcag caccctgacc    540

ctgagcaaag ccgattatga aaaacataaa gtgtatgcct gcgaagtgac ccatcagggc    600

ctgagcagcc cagtgaccaa aagttttaac cgcggcgagg cc                       642


<210> SEQ ID NO 85
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Tyr Leu Gly Gln Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120
```

<210> SEQ ID NO 86
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
caggtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccact atctcttacc tgggccagga aaaacattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tca                                                                  363
```

<210> SEQ ID NO 87
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Tyr Leu Gly Gln Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

210 215 220

<210> SEQ ID NO 88
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88
caggtgcaat tgctggaaag cggcggtggc ctggtgcagc cgggtggcag cctgcgtctg 60
agctgcgcgg cgtccggatt caccttttct gactacgcta tgtcttgggt gcgccaggcc 120
ccgggcaaag gtctcgagtg ggtttccact atctcttacc tgggccagga aaaacattat 180
gcggatagcg tgaaaggccg ctttaccatc agccgcgata attcgaaaaa caccctgtat 240
ctgcaaatga acagcctgcg tgcggaagat acggccgtgt attattgcgc gcgtgaaggt 300
tactcttacc gttctatccg tttcgattac tggggccaag gcaccctggt gactgttagc 360
tcagcgtcga ccaaaggccc gagcgtgttt ccgctggccc cgagcagcaa aagcaccagc 420
ggcggcaccg ccgcactggg ctgcctggtg aaagattatt tcccggaacc agtgaccgtg 480
agctggaaca gcggtgccct gaccagcggc gtgcatacct ttccggcggt gctgcaaagc 540
agcggcctgt atagcctgag cagcgttgtg accgtgccga gcagcagcct gggcacccag 600
acctatattt gcaacgtcaa ccataaaccg agcaacacca aagtcgataa aaaagtcgaa 660
ccgaaaagct gc 672

<210> SEQ ID NO 89
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89
gatatccaga tgacccagag cccgagcagc ctgagcgcca gcgtgggcga tcgcgtgacc 60
attacctgca gagccagcca gtctatttct tctaacctga actggtacca gcagaaaccg 120
ggcaaagcgc cgaaactatt aatctacgct gcttctaacc tgcaaagcgg cgtgccgagc 180
cgctttagcg gcagcggatc cggcaccgat ttcaccctga ccattagctc tctgcaaccg 240
gaagactttg cgacctatta ttgcctgcag ttcgaccata ctccgttcac ctttggccag 300
ggcacgaaag ttgaaattaa acgtacggtg gccgcaccga gcgtgtttat ctttccgccg 360
agcgatgaac agctgaaaag cggcaccgcc agcgtggtgt gcctgctgaa caacttttat 420
ccgcgcgaag ccaaagtgca gtggaaagtg gataacgccc tgcaaagcgg caacagccag 480
gaaagcgtta ccgaacagga tagcaaagat agcacctaca gcctgagcag caccctgacc 540
ctgagcaaag ccgattatga aaaacataaa gtgtatgcct gcgaagtgac ccatcagggc 600
ctgagcagcc cagtgaccaa aagttttaac cgcggcgagt gc 642

<210> SEQ ID NO 90
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Asp Tyr Ser Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120
```

<210> SEQ ID NO 91
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 91

```
gaagtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccgtt atcgactact cttcttctaa cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tca                                                                  363
```

<210> SEQ ID NO 92
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Asp Tyr Ser Ser Ser Asn Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Asp Tyr Lys Asp Asp Asp Asp Lys Gly Ala Pro His His His His
225                 230                 235                 240

His His
```

<210> SEQ ID NO 93
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gaagtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccgtt atcgactact cttcttctaa cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tcagcgtcga ccaaaggccc gagcgtgttt ccgctggccc cgagcagcaa aagcaccagc    420

ggcggcaccg ccgcactggg ctgcctggtg aaagattatt tcccggaacc agtgaccgtg    480

agctggaaca gcggtgccct gaccagcggc gtgcatacct ttccggcggt gctgcaaagc    540

agcggcctgt atagcctgag cagcgttgtg accgtgccga gcagcagcct gggcacccag    600

acctatattt gcaacgtcaa ccataaaccg agcaacacca aagtcgataa aaaagtcgaa    660

ccgaaaagcg aattcgacta taaagatgac gatgacaaag gcgcgccgca ccatcatcac    720

catcac                                                                726
```

<210> SEQ ID NO 94
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 94

Leu Gln Tyr Tyr His Leu Pro Tyr Thr
1 5

<210> SEQ ID NO 95
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 95

Tyr Tyr His Leu Pro Tyr
1 5

<210> SEQ ID NO 96
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 96

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Asn
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Tyr His Leu Pro Tyr
85 90 95

Thr Phe Gly Gln Gly Thr Lys Val Glu Ile Lys
100 105

<210> SEQ ID NO 97
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97
gatatccaga tgacccagag cccgagcagc ctgagcgcca gcgtgggcga tcgcgtgacc 60
attacctgca gagccagcca gtctatttct tctaacctga actggtacca gcagaaaccg 120
ggcaaagcgc cgaaactatt aatctacgct gcttctaacc tgcaaagcgg cgtgccgagc 180
cgctttagcg gcagcggatc cggcaccgat ttcaccctga ccattagctc tctgcaaccg 240
gaagactttg cgacctatta ttgcctgcag tactaccatc tgccgtacac ctttggccag 300
ggcacgaaag ttgaaattaa a 321

<210> SEQ ID NO 98
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Asn
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Tyr His Leu Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Ala
210

<210> SEQ ID NO 99
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99
gatatccaga tgacccagag cccgagcagc ctgagcgcca gcgtgggcga tcgcgtgacc 60
attacctgca gagccagcca gtctatttct tctaacctga actggtacca gcagaaaccg 120
ggcaaagcgc cgaaactatt aatctacgct gcttctaacc tgcaaagcgg cgtgccgagc 180
cgctttagcg gcagcggatc cggcaccgat ttcaccctga ccattagctc tctgcaaccg 240
gaagactttg cgacctatta ttgcctgcag tactaccatc tgccgtacac ctttggccag 300
ggcacgaaag ttgaaattaa acgtacggtg gccgcaccga gcgtgtttat ctttccgccg 360

```
agcgatgaac agctgaaaag cggcaccgcc agcgtggtgt gcctgctgaa caacttttat    420

ccgcgcgaag ccaaagtgca gtggaaagtg gataacgccc tgcaaagcgg caacagccag    480

gaaagcgtta ccgaacagga tagcaaagat agcacctaca gcctgagcag caccctgacc    540

ctgagcaaag ccgattatga aaaacataaa gtgtatgcct gcgaagtgac ccatcagggc    600

ctgagcagcc cagtgaccaa aagttttaac cgcggcgagg cc                        642
```

<210> SEQ ID NO 100
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 100

```
caggtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccgtt atcgactact cttcttctaa cacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tca                                                                  363
```

<210> SEQ ID NO 101
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 101

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Asp Tyr Ser Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220


<210> SEQ ID NO 102
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102

caggtgcaat tgctggaaag cggcggtggc ctggtgcagc cgggtggcag cctgcgtctg      60

agctgcgcgg cgtccggatt caccttttct gactacgcta tgtcttgggt gcgccaggcc     120

ccgggcaaag gtctcgagtg ggtttccgtt atcgactact cttcttctaa cacctactat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaaggt     300

tactcttacc gttctatccg tttcgattac tggggccaag gcaccctggt gactgttagc     360

tcagcgtcga ccaaaggccc gagcgtgttt ccgctggccc cgagcagcaa aagcaccagc     420

ggcggcaccg ccgcactggg ctgcctggtg aaagattatt tcccggaacc agtgaccgtg     480

agctggaaca gcggtgccct gaccagcggc gtgcatacct ttccggcggt gctgcaaagc     540

agcggcctgt atagcctgag cagcgttgtg accgtgccga gcagcagcct gggcacccag     600

acctatattt gcaacgtcaa ccataaaccg agcaacacca aagtcgataa aaaagtcgaa     660

ccgaaaagct gc                                                         672


<210> SEQ ID NO 103
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr His Leu Pro Tyr
                85                  90                  95

Thr Phe Gly Gln Gly Thr Lys Val Glu Ile Lys Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 104
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

gatatccaga tgacccagag cccgagcagc ctgagcgcca gcgtgggcga tcgcgtgacc     60

attacctgca gagccagcca gtctatttct tctaacctga actggtacca gcagaaaccg    120

ggcaaagcgc cgaaactatt aatctacgct gcttctaacc tgcaaagcgg cgtgccgagc    180

cgctttagcg gcagcggatc cggcaccgat ttcaccctga ccattagctc tctgcaaccg    240

gaagactttg cgacctatta ttgcctgcag tactaccatc tgccgtacac ctttggccag    300

ggcacgaaag ttgaaattaa acgtacggtg gccgcaccga gcgtgtttat ctttccgccg    360

agcgatgaac agctgaaaag cggcaccgcc agcgtggtgt gcctgctgaa caacttttat    420

ccgcgcgaag ccaaagtgca gtggaaagtg gataacgccc tgcaaagcgg caacagccag    480

gaaagcgtta ccgaacagga tagcaaagat agcacctaca gcctgagcag caccctgacc    540

ctgagcaaag ccgattatga aaaacataaa gtgtatgcct gcgaagtgac ccatcagggc    600

ctgagcagcc cagtgaccaa aagttttaac cgcggcgagt gc                       642


<210> SEQ ID NO 105
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Thr Ile Ala Tyr Val Gly Ala Pro Thr His Tyr Ala Asp Ser Val Lys
1               5                   10                  15

Gly


<210> SEQ ID NO 106
<211> LENGTH: 6
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic peptide"

<400> SEQUENCE: 106

```
Ala Tyr Val Gly Ala Pro
1               5
```

<210> SEQ ID NO 107
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 107

```
Ile Ala Tyr Val Gly Ala Pro Thr
1               5
```

<210> SEQ ID NO 108
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ala Tyr Val Gly Ala Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120
```

<210> SEQ ID NO 109
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 109

```
gaagtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccact atcgcttacg ttggcgctcc gactcattat    180
```

```
gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tca                                                                  363


<210> SEQ ID NO 110
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ala Tyr Val Gly Ala Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Asp Tyr Lys Asp Asp Asp Asp Lys Gly Ala Pro His His His His
225                 230                 235                 240

His His


<210> SEQ ID NO 111
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111
```

```
gaagtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccact atcgcttacg ttggcgctcc gactcattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tcagcgtcga ccaaaggccc gagcgtgttt ccgctggccc cgagcagcaa aagcaccagc    420

ggcggcaccg ccgcactggg ctgcctggtg aaagattatt tcccggaacc agtgaccgtg    480

agctggaaca gcggtgccct gaccagcggc gtgcatacct ttccggcggt gctgcaaagc    540

agcggcctgt atagcctgag cagcgttgtg accgtgccga gcagcagcct gggcacccag    600

acctatattt gcaacgtcaa ccataaaccg agcaacacca aagtcgataa aaaagtcgaa    660

ccgaaaagcg aattcgacta taaagatgac gatgacaaag gcgcgccgca ccatcatcac    720

catcac                                                               726
```

```
<210> SEQ ID NO 112
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ala Tyr Val Gly Ala Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120
```

```
<210> SEQ ID NO 113
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113

caggtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccact atcgcttacg ttggcgctcc gactcattat    180
```

```
gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tca                                                                   363
```

<210> SEQ ID NO 114
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ala Tyr Val Gly Ala Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 115
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115

```
caggtgcaat tgctggaaag cggcggtggc ctggtgcagc cgggtggcag cctgcgtctg     60

agctgcgcgg cgtccggatt cacctttttct gactacgcta tgtcttgggt gcgccaggcc    120
```

```
ccgggcaaag gtctcgagtg ggtttccact atcgcttacg ttggcgctcc gactcattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tcagcgtcga ccaaaggccc gagcgtgttt ccgctggccc cgagcagcaa aagcaccagc    420

ggcggcaccg ccgcactggg ctgcctggtg aaagattatt tcccggaacc agtgaccgtg    480

agctggaaca gcggtgccct gaccagcggc gtgcatacct ttccggcggt gctgcaaagc    540

agcggcctgt atagcctgag cagcgttgtg accgtgccga gcagcagcct gggcacccag    600

acctatattt gcaacgtcaa ccataaaccg agcaacacca aagtcgataa aaaagtcgaa    660

ccgaaaagct gc                                                        672


<210> SEQ ID NO 116
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ala Tyr Val Gly Ala Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220


<210> SEQ ID NO 117
<211> LENGTH: 672
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 117

caggtgcaat tgctggaaag cggcggtggc ctggtgcagc cgggtggcag cctgcgtctg      60

agctgcgcgg cgtccggatt caccttttct gactacgcta tgtcttgggt gcgccaggcc     120

ccgggcaaag gtctcgagtg ggtttccact atcgcttacg ttggcgctcc gactcattat     180

gcggatagcg tgaaaggccg ctttaccatc agccgcgata attcgaaaaa caccctgtat     240

ctgcaaatga acagcctgcg tgcggaagat acggccgtgt attattgcgc gcgtgaaggt     300

tactcttacc gttctatccg tttcgattac tggggccaag gcaccctggt gactgttagc     360

tcagcgtcga ccaaaggccc gagcgtgttt ccgctggccc cgagcagcaa aagcaccagc     420

ggcggcaccg ccgcactggg ctgcctggtg aaagattatt tcccggaacc agtgaccgtg     480

agctggaaca gcggtgccct gaccagcggc gtgcatacct ttccggcggt gctgcaaagc     540

agcggcctgt atagcctgag cagcgttgtg accgtgccga gcagcagcct gggcacccag     600

acctatattt gcaacgtcaa ccataaaccg agcaacacca aagtcgataa acgagtcgaa     660

ccgaaaagct gc                                                         672


<210> SEQ ID NO 118
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

gatatccaga tgacccagag cccgagcagc ctgagcgcca gcgtgggcga tcgcgtgacc      60

attacctgca gagccagcca gtctatttct tctaacctga actggtacca gcagaaaccg     120

ggcaaagcgc cgaaactatt aatctacgct gcttctaacc tgcaaagcgg cgtgccgagc     180

cgctttagcg gcagcggatc cggcaccgat ttcaccctga ccattagctc tctgcaaccg     240

gaagactttg cgacctatta ttgcctgcag ttcgaccata ctccgttcac ctttggccag     300

ggcacgaaag ttgaaattaa acgtacggtg gccgcaccga gcgtgtttat ctttccgccg     360

agcgatgaac agctgaaaag cggcaccgcc agcgtggtgt gcctgctgaa caacttttat     420

ccgcgcgaag ccaaagtgca gtggaaagtg gataacgccc tgcaaagcgg caacagccag     480

gaaagcgtta ccgaacagga tagcaaagat agcacctaca gcctgagcag caccctgacc     540

ctgagcaaag ccgattatga aaaacataaa gtgtatgcct gcgaagtgac ccatcagggc     600

ctgagcagcc cagtgaccaa aagttttaac cgcggcgagt gt                        642


<210> SEQ ID NO 119
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gln Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Tyr Leu Gly Gln Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

<210> SEQ ID NO 120
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120

```
caggtgcaat tgctggaaag cggcggtggc ctggtgcagc cgggtggcag cctgcgtctg     60

agctgcgcgg cgtccggatt caccttttct gactacgcta tgtcttgggt gcgccaggcc    120

ccgggcaaag gtctcgagtg ggtttccact atctcttacc tgggccagga aaaacattat    180

gcggatagcg tgaaaggccg ctttaccatc agccgcgata attcgaaaaa caccctgtat    240

ctgcaaatga acagcctgcg tgcggaagat acggccgtgt attattgcgc gcgtgaaggt    300

tactcttacc gttctatccg tttcgattac tggggccaag gcaccctggt gactgttagc    360

tcagcgtcga ccaaaggccc gagcgtgttt ccgctggccc cgagcagcaa aagcaccagc    420

ggcggcaccg ccgcactggg ctgcctggtg aaagattatt tcccggaacc agtgaccgtg    480

agctggaaca gcggtgccct gaccagcggc gtgcatacct ttccggcggt gctgcaaagc    540

agcggcctgt atagcctgag cagcgttgtg accgtgccga gcagcagcct gggcacccag    600

acctatattt gcaacgtcaa ccataaaccg agcaacacca aagtcgataa acgagtcgaa    660

ccgaaaagct gc                                                         672
```

<210> SEQ ID NO 121
<211> LENGTH: 17

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (5)..(5)
<223> OTHER INFORMATION: /replace="Leu"
<220> FEATURE:
<221> NAME/KEY: VARIANT
<222> LOCATION: (7)..(7)
<223> OTHER INFORMATION: /replace="Gln"
<220> FEATURE:
<221> NAME/KEY: VARIANT
<222> LOCATION: (8)..(8)
<223> OTHER INFORMATION: /replace="Glu"
<220> FEATURE:
<221> NAME/KEY: VARIANT
<222> LOCATION: (9)..(9)
<223> OTHER INFORMATION: /replace="Lys"
<220> FEATURE:
<221> NAME/KEY: SITE
<222> LOCATION: (1)..(17)
<223> OTHER INFORMATION: /note="Variant residues given in the sequence
      have no preference with respect to those in the annotations
      for variant positions"

<400> SEQUENCE: 121

Thr Ile Ala Tyr Val Gly Ala Pro Thr His Tyr Ala Asp Ser Val Lys
1               5                   10                  15

Gly


<210> SEQ ID NO 122
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (3)..(3)
<223> OTHER INFORMATION: /replace="Leu"
<220> FEATURE:
<221> NAME/KEY: VARIANT
<222> LOCATION: (5)..(5)
<223> OTHER INFORMATION: /replace="Gln"
<220> FEATURE:
<221> NAME/KEY: VARIANT
<222> LOCATION: (6)..(6)
<223> OTHER INFORMATION: /replace="Glu"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 122

Ala Tyr Val Gly Ala Pro
1               5


<210> SEQ ID NO 123
```

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: VARIANT
<222> LOCATION: (6)..(6)
<223> OTHER INFORMATION: /replace="Gln"
<220> FEATURE:
<221> NAME/KEY: VARIANT
<222> LOCATION: (7)..(7)
<223> OTHER INFORMATION: /replace="Glu"
<220> FEATURE:
<221> NAME/KEY: SITE
<222> LOCATION: (1)..(7)
<223> OTHER INFORMATION: /note="Variant residues given in the sequence have no preference with respect to those in the annotations for variant positions"

<400> SEQUENCE: 123

```
Ile Ala Tyr Val Gly Ala Pro
1               5
```

<210> SEQ ID NO 124
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (52)..(52)
<223> OTHER INFORMATION: /replace="Ser"
<220> FEATURE:
<221> NAME/KEY: VARIANT
<222> LOCATION: (54)..(54)
<223> OTHER INFORMATION: /replace="Leu"
<220> FEATURE:
<221> NAME/KEY: VARIANT
<222> LOCATION: (56)..(56)
<223> OTHER INFORMATION: /replace="Gln"
<220> FEATURE:
<221> NAME/KEY: VARIANT
<222> LOCATION: (57)..(57)
<223> OTHER INFORMATION: /replace="Glu"
<220> FEATURE:
<221> NAME/KEY: VARIANT
<222> LOCATION: (58)..(58)
<223> OTHER INFORMATION: /replace="Lys"
<220> FEATURE:
<221> NAME/KEY: SITE
<222> LOCATION: (1)..(121)
<223> OTHER INFORMATION: /note="Variant residues given in the sequence have no preference with respect to those in the annotations for variant positions"

<400> SEQUENCE: 124

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

```
Ala Met Ser Trp Val Arg Gln Ala Pro Gly Lys Gly Leu Glu Trp Val
        35                  40                  45

Ser Thr Ile Ala Tyr Val Gly Ala Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Tyr Arg Ser Ile Arg Phe Asp Tyr Trp Gly
            100                 105                 110

Gln Gly Thr Leu Val Thr Val Ser Ser
        115                 120
```

```
<210> SEQ ID NO 125
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Tyr"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (8)..(8)
<223> OTHER INFORMATION: /replace="Tyr"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 125

Leu Gln Phe Asp His Thr Pro Phe Thr
1               5
```

```
<210> SEQ ID NO 126
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Tyr"
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: VARIANT
<222> LOCATION: (4)..(4)
<223> OTHER INFORMATION: /replace="Leu"
<220> FEATURE:
<221> NAME/KEY: VARIANT
<222> LOCATION: (6)..(6)
```

<223> OTHER INFORMATION: /replace="Tyr"
<220> FEATURE:
<221> NAME/KEY: SITE
<222> LOCATION: (1)..(6)
<223> OTHER INFORMATION: /note="Variant residues given in the sequence have no preference with respect to those in the annotations for variant positions"

<400> SEQUENCE: 126

```
Phe Asp His Thr Pro Phe
1               5
```

<210> SEQ ID NO 127
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (91)..(91)
<223> OTHER INFORMATION: /replace="Tyr"
<220> FEATURE:
<221> NAME/KEY: VARIANT
<222> LOCATION: (92)..(92)
<223> OTHER INFORMATION: /replace="Tyr"
<220> FEATURE:
<221> NAME/KEY: VARIANT
<222> LOCATION: (94)..(94)
<223> OTHER INFORMATION: /replace="Leu"
<220> FEATURE:
<221> NAME/KEY: VARIANT
<222> LOCATION: (96)..(96)
<223> OTHER INFORMATION: /replace="Tyr"
<220> FEATURE:
<221> NAME/KEY: SITE
<222> LOCATION: (1)..(107)
<223> OTHER INFORMATION: /note="Variant residues given in the sequence have no preference with respect to those in the annotations for variant positions"

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp His Thr Pro Phe
                85                  90                  95

Thr Phe Gly Gln Gly Thr Lys Val Glu Ile Lys
            100                 105
```

```
<210> SEQ ID NO 128
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 128

His His His His His His
1               5
```